US008058508B2

(12) United States Patent
Bakker et al.

(10) Patent No.: US 8,058,508 B2
(45) **Date of Patent: *Nov. 15, 2011**

(54) OPTIMIZING GLYCAN PROCESSING IN PLANTS

(75) Inventors: Hendrikus Antonius Cornelis Bakker, Hannover (DE); Hendrik Jan Bosch, Wageningen (NL); Dionisius Elisabeth Antonius Florack, Wageningen (NL); Gerard Johan Adolph Rouwendal, Heteren (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/553,043

(22) Filed: Sep. 2, 2009

(65) Prior Publication Data

US 2010/0122365 A1 May 13, 2010

Related U.S. Application Data

(63) Continuation of application No. 10/508,165, filed as application No. PCT/IB03/01626 on Mar. 18, 2003, now Pat. No. 7,601,891.

(60) Provisional application No. 60/365,735, filed on Mar. 19, 2002.

(51) Int. Cl.

| | |
|---|---|
| *C12N 15/62* | (2006.01) |
| *C12N 15/63* | (2006.01) |
| *C12N 15/82* | (2006.01) |
| *C07H 21/04* | (2006.01) |

(52) U.S. Cl. ..... 800/284; 800/298; 800/288; 435/320.1; 435/468; 536/23.4

(58) Field of Classification Search ........................ None
See application file for complete search history.

(56) References Cited

U.S. PATENT DOCUMENTS

| | | | |
|---|---|---|---|
| 4,956,282 A | 9/1990 | Goodman et al. | |
| 5,202,422 A | 4/1993 | Hiatt et al. | |
| 5,639,947 A | 6/1997 | Hiatt et al. | |
| 5,874,271 A | 2/1999 | Nishikawa et al. | |
| 5,879,912 A | 3/1999 | Roth | |
| 5,939,288 A | 8/1999 | Thornburg | |
| 5,959,177 A | 9/1999 | Hein et al. | |
| 6,046,040 A | 4/2000 | Nishiguchi et al. | |
| 6,054,304 A | 4/2000 | Taniguchi et al. | |
| 6,331,418 B1 | 12/2001 | Roth | |
| 6,344,600 B1 * | 2/2002 | Merot et al. | 800/288 |
| 6,388,068 B1 | 5/2002 | Satoh et al. | |
| 6,602,684 B1 | 8/2003 | Umana et al. | |
| 6,653,459 B1 | 11/2003 | Von Schaewen et al. | |
| 2001/0055584 A1 | 12/2001 | McKenzie et al. | |
| 2002/0174453 A1 | 11/2002 | Danielle et al. | |
| 2004/0072290 A1 | 4/2004 | Umana et al. | |
| 2004/0181827 A1 | 9/2004 | Schaewen | |
| 2007/0214519 A1 | 9/2007 | Fujiyama et al. | |

FOREIGN PATENT DOCUMENTS

| | | |
|---|---|---|
| DE | 19754622 | 6/1999 |
| EP | 0 351 313 A2 | 1/1990 |
| EP | 0 550 756 A1 | 7/1993 |
| EP | 0 737 745 A1 | 10/1996 |
| EP | 1 243 647 | 9/2002 |
| JP | 2000-245470 | 9/2000 |
| JP | 2000-287692 | 10/2000 |
| WO | WO 87/00865 | 2/1987 |
| WO | WO 92/18537 | 10/1992 |
| WO | WO 94/12646 | 6/1994 |
| WO | WO 95/02683 | 1/1995 |
| WO | WO 95/21248 | 8/1995 |
| WO | WO 97/04122 | 2/1997 |
| WO | WO 98/31826 | 7/1998 |
| WO | WO 98/31828 | 7/1998 |
| WO | WO 99/09187 | 2/1999 |
| WO | WO 99/24584 | 5/1999 |
| WO | WO 99/29879 | 6/1999 |
| WO | WO 99/38987 | 8/1999 |
| WO | WO 99/38990 | 8/1999 |
| WO | WO 99/51185 | 10/1999 |
| WO | WO 00/28792 | 5/2000 |
| WO | WO 00/29603 | 5/2000 |
| WO | WO 00/34490 | 6/2000 |
| WO | WO 00/49153 | 8/2000 |
| WO | WO 00/52136 | 9/2000 |
| WO | WO 01/29241 | 4/2001 |
| WO | WO 01/29242 | 4/2001 |
| WO | WO 01/31044 | 5/2001 |
| WO | WO 01/31045 | 5/2001 |
| WO | WO0131045 * | 5/2001 |
| WO | WO 01/49821 | 7/2001 |
| WO | WO 01/49831 | 7/2001 |
| WO | WO 01/62912 | 8/2001 |

(Continued)

OTHER PUBLICATIONS

2000 GenBank Accession AJ277603 Bakker (Provided by Applicant).*

Genbank Submission; NIH/NCBI, Accession No. AJ277603. Bakker et al. Apr. 28, 2000.

Genbank Submission; Accession No. Q92074. Shaper J.H. Nov. 1, 1996.

Genbank Submission; Accession No. U19890. Shaper J. H. Aug. 3, 1996.

Genbank Submission; Accession No. BC124813. Aug. 5, 2006.

Genbank Submission; Accession No. Q08B99. Strausberg et al. Oct. 31, 2006.

Aoki et al. Golgi retention of a trans-Golgi membrane protein, galactosyl-transferase, requires cysteine and histidine residues within the membrane-anchoring domain. (1992) Cell Biology 89, 4319-4323.

(Continued)

*Primary Examiner* — Brent T Page

(74) *Attorney, Agent, or Firm* — Wolf, Greenfield & Sacks, P.C.

(57) ABSTRACT

The invention is directed to methods for optimizing glycan processing in organisms (and in particular, plants) so that a glycoprotein having complex type bi-antennary glycans and thus containing galactose residues on both arms and which are devoid of (or reduce in) xylose and fucose can be obtained. The invention is further directed to said glycoprotein obtained and host system comprising said protein.

18 Claims, 57 Drawing Sheets

FOREIGN PATENT DOCUMENTS

| | | |
|---|---|---|
| WO | WO 01/64901 | 9/2001 |
| WO | WO 01/81591 | 11/2001 |
| WO | WO 01/82912 | 11/2001 |
| WO | WO 02/00879 | 1/2002 |
| WO | WO 02/057468 | 7/2002 |
| WO | WO 02/007067 | 9/2002 |
| WO | WO 03/001187 | 2/2003 |
| WO | WO 03/007661 | 9/2003 |
| WO | WO 03/007861 | 9/2003 |
| WO | WO 03/007863 | 9/2003 |
| WO | WO 2004/005083 | 6/2004 |

OTHER PUBLICATIONS

Asano et al., Growth retardation and early death of beta-1,4-galactosyltransferase knockout mice with augmented proliferation and abnormal differentiation of epithelial cells. EMBO J. Apr. 15, 1997;16(8):1850-7.

Bailey et al. Metabolic engineering of N-linked glycoform synthesis systems in Chinese hamster ovary (CHO) cells (1997) Animal Cell Technology, pp. 489-494.

Bakker et al., Galactose-extended glycans of antibodies produced by transgenic plants. Proc Natl Acad Sci U S A. Feb. 27, 2001;98(5):2899-904.

Bakker et al., An *Arabidopsis thaliana* Cdna complements the N-acetylglucosaminyltransferase I deficiency of CHO Lec1 cells. Biochem Biophys Res Commun. Aug. 11, 1999;261(3):829-32.

Borisjuk et al., Production of Recombinant Proteins in Plant Root Exudates. Nat. Biotechnology 17(5): 466-469 (1999).

Boyd et al. The effect of the removal of sialic acid, galactose and total carbohydrate on the functional activity of Campath-1H (1995) Mol Imm. 32, 1311-8.

Cabanes-Macheteau et al., N-Glycosylation of a mouse IgG expressed in transgenic tobacco plants. Glycobiology. Apr. 1999;9(4):365-72.

Choi et al., Use of combinatorial genetic libraries to humanize N-linked glycosylation in the yeast Pichia pastoris. Proc Natl Acad Sci U S A. Apr. 29, 2003;100(9):5022-7. Epub Apr. 17, 2003.

Chrispeels and Faye, The production of recombinant glycoproteins with defined non-immunogenic glycans. In: Transgenic plants: a production system for industrial and pharmaceutical proteins. John Wiley Pub, UK. 1996:99-113.

Colley "Golgi localization of glycosyltransferases: more questions than answers" (1997) Glycobiology 7(1):1-13.

Cousin et al. "Human variant sex hormone-binding globulin (SHBG) with an additional carbohydrate chain has a reduced clearance rate in rabbit." (1998) J of Clin. Endocrin. and Metab. 83: 245-240.

De Vries et al. Isolation of total and polysomal RNA from plant tissues. (1991) Plant Mol. Biology B6/1-13.

Dieryck et al. Human Haemoglobin from transgenic tobacco (1997) Nature 386, 29-30.

Dinter and Berger, The regulation of cell- and tissue-specific expression of glycans by glycosyltransferases. Adv Exp Med Biol. 1995;376:53-82.

Elbers et al., Influence of growth conditions and developmental stage on N-glycan heterogeneity of transgenic immunoglobulin G and endogenous proteins in tobacco leaves. Plant Physiol. Jul. 2001;126(3):1314-22.

Essl et al., The N-terminal 77 amino acids from tobacco N-acetylglucosaminyltransferase I are sufficient to retain a reporter protein in the Golgi apparatus of *Nicotiana benthamiana* cells. FEBS Lett. Jun. 18, 1999;453(1-2):169-73.

Faye et al Affinity purification of antibodies specific for Asn-linked glycans containing alpha 1—> 3 fucose or beta—> 2 xylose. (1993) Anal Biochem 209, 104-8.

Fischer and Evans, Molecular farming of pharmaceutical proteins. Transgenic Research. 2000;9:279-299.

Fischer et al. Molecular farming of recombinant antibodies in plants. (1999) Biol. Chem. 380:825-839.

Fitchette Laine et al. N-glycans harboring the Lewis a epitope are expressed at the surface of plant cells. (1997) Plan J 12, 1411-7.

Florack et al. Expression of giant silkmoth cecropin B genes in tobacco. (1995) Transgenic Research 4, 132-141.

Fuchs et al., Purification and characterization of microbially expressed neomycin phosphotransferase II (NPTII) protein and its equivalence to the plant expressed protein. Biotechnology (N Y). Dec. 1993;11(13):1537-42.

Fujiyama et al., In vivo conversion of a glycan to human compatible type by transformed tobacco cells. Biochem Biophys Res Commun. Nov. 30, 2001;289(2):553-7.

Gasser and Fraley, Genetically Engineering Plants for Crop Improvement. Science. Jun. 16, 1989;244(4910):1293-1299.

Gleeson "Targeting of proteins to the Golgi apparatus" (1998) Histochem Cell Biol. 109: 517-532.

Gomez and Chrispeels, Complementation of an *Arabidopsis thaliana* mutant that lacks complex asparagine-linked glycans with the human cDNA encoding N-acetylglucosaminyltransferase I. Proc Natl Acad Sci U S A. Mar. 1, 1994:91(5):1829-33.

Grabenhorst and Conradt, The cytoplasmic, transmembrane, and stem regions of glycosyltransferases specify their in vivo functional sublocalization and stability in the Golgi. J Biol Chem. Dec. 17, 1999;274(51):36107-16.

Hamilton et al., Production of complex human glycoproteins in yeast. Science. Aug. 29, 2003;301(5637):1244-6.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Herman and Horvitz, Three proteins involved in *Caenorhabditis elegans* vulval invagination are similar to components of a glycosylation pathway. Proc Natl Acad Sci U S A. Feb. 2, 1999;96(3):974-9.

Hein et al., Evaluation of immunoglobulins from plant cells. Biotechnol Prog. Sep.-Oct. 1991;7(5):455-61.

Hess et al., Transformation experiments by pipetting *Agrobacterium* into the spikelets of wheat (*Triticum aestivum* L.). Plant Science 1990;72:233-44.

Hiei et al., Efficient transformation of rice (*Oryza sativa* L.) mediated by *Agrobacterium* and sequence analysis of the boundaries of the T-DNA. Plant J. Aug. 1994;6(2):271-82.

Hiei et al., Transformation of rice mediated by *Agrobacterium tumefaciens*. Plant Mol Biol. Sep. 1997;35(1-2):205-18.

Hollister et al. Stable expression of mammalian β1,4-galactosyltransferase extends the N-glycosylation pathway in insect cells. (1998) Glycobiology 8(5): 473-480.

Hollister et al., Engineering the protein N-glycosylation pathway in insect cells for production of biantennary, complex N-glycans. Biochemistry. Dec. 17, 2002;41(50):15093-104.

Horsch et al. A simple and general method for transferring genes into plants. (1985) Science 227, 1229-1231.

Ihara et al., cDNA cloning, expression, and chromosomal localization of human N-acetylglucosaminyltransferase III (GnT-III). J Biochem (Tokyo). Jun. 1993;113(6):692-8.

Ihara et al "Ectopic Expression of N-acetylglucosaminyltransferase III in transgenic hepatocytes disrupts apolipoprotein B secretion and induces aberrant cellular morphology with lipid storage." Proc Natl Acad Sci USA 1998 95:2526-2530.

Ioffe and Stanley, Mice lacking N-acetylglucosaminyltransferase I activity die at mid-gestation, revealing an essential role for complex or hybrid N-linked carbohydrates. Proc Natl Acad Sci U S A. Jan. 18, 1994;91(2):728-32.

Ishida et al., High efficiency transformation of maize (*Zea mays* L.) mediated by *Agrobacterium tumefaciens*. Nat Biotechnol. Jun. 1996;14(6):745-50.

Jähne et al., Genetic engineering of ceral crop plants: a review. Euphyica. Kluwer Academic Publishers. 1995:85:35-44.

James et al., Production and characterization of biologically active human GM-CSF secreted by genetically modified plant cells. Protein Expr Purif. Jun. 2000;19(1):131-8.

Jarvis and Finn Modifying the insect cell N-glycosylation pathway with immediate early baculovirus expression vectors. (1996) Nat Biotechnol 14, 1288-92.

Jenkins et al., Getting the glycosylation right: implications for the biotechnology industry. Nat Biotechnol. Aug. 1996;14(8):975-81.

Johnson and Chrispeels Substrate specificities of N-acetylglucosaminyl-, fucosyl-, and xylosyltransferases that modify glycoproteins in the Golgi apparatus of bean cotyledons. (1987) Plant Physiology 84, 1301-1308.
Kang et al. "Salt tolerance of *Arabidopsis thaliana* requires maturation of N-glycosylated proteins in the Golgi apparatus." PNAS 2008 105(15):5933-5938.
Kawar et al., Insect cells encode a class II alpha-mannosidase with unique properties. J Biol Chem. May 11, 2001;276(19):16335-40. Epub Feb. 9, 2001.
Kieliszewski et al., Tandem mass spectrometry and structural elucidation of glycopeptides from a hydroxyproline-rich plant cell wall glycoprotein indicate that contiguous hydroxyproline residues are the major sites of hydroxyproline O-arabinosylation. J Biol Chem. Feb. 10, 1995;270(6):2541-9.
Kihlberg et al. "Glysocylated peptide hormones: pharmacological properties and conformation studies of analogues of [1-Desamino,8-D-arginine]vasopressin." J. Med. Chem.; 38:161-169, 1995.
Kitagawa et al. Molecular cloning and expression of glucuronyltransferase I involved in the biosynthesis of the glycosaminoglycan-protein linkage region of proteoglycans. (1998) JBC 273:6615-6618.
Kleene et al., Expression of soluble active human beta 1,4 galactosyltransferase in *Saccharomyces cerevisiae*. Biochem Biophys Res Commun. May 30, 1994;201(1):160-7.
Krezdorn et al "Human beta 1,4 galactosyltransferase and alpha 2,6 sialyltransferase expressed in *Saccharomyces cerevisiae* are retained as active enzymes in the endoplasmic reticulum" Eur J Biochem. Mar. 15, 1994;220(3):809-17.
Ku et al., High-level expression of maize phosphoenolpyruvate carboxylase in transgenic rice plants. Nat Biotechnol. Jan. 1999;17(1):76-80.
Leiter et al., Purification, cDNA cloning, and expression of GDP-L-Fuc:Asn-linked GlcNAc alphal,3-fucosyltransferase from mung beans. J Biol Chem. Jul. 30, 1999;274(31):21830-9.
Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002;73-109.
Lerouge et al., N-glycoprotein biosynthesis in plants: recent developments and future trends. Plant Mol Biol. Sep. 1998;38(1-2):31-48.
Lerouge et al., N-glycosylation of recombinant pharmaceutical glycoproteins produced in transgenic plants: towards an humanisation of plant N-glycans. Curr Pharm Biotechnol. Dec. 2000;1(4):347-54.
Li et al., Cloning, expression and characterization of a cDNA (6A8) encoding a novel human alpha-mannosidase. Eur J Biochem. Dec. 2000;267(24):7176-83. Erratum in: Eur J Biochem Nov. 2001;268(21):5653.
Ma et al. Generation and assembly of secretory antibodies in plants (1995) Science 268, 716-9.
Madson et al., Altered xyloglucans of *Arabidopsis thaliana*mutants bind normally to cellulose in vivo and in vitro. Poster from Plant Biology(Rockville) Jul. 27, 2001 Abstract #527.
Magnuson et al., Secretion of biologically active human interleukin-2 and interleukin-4 from genetically modified tobacco cells in suspension culture. Protein Expr Purif. Jun. 1998;13(1):45-52.
Magnuson et al., Enhanced recovery of a secreted mammalian protein from suspension culture of genetically modified tobacco cells. Protein Expr Purif. Mar. 1996;7(2):220-8.
Maras et al., In vitro conversion of the carbohydrate moiety of fungal glycoproteins to mammalian-type oligosaccharides—evidence for N-acetylglucosaminyltransferase-I-accepting glycans from *Trichoderma reesei*. Eur J Biochem. Nov. 1, 1997;249(3):701-7.
Masri et al., Identification of the full-length coding sequence for human galactosyltransferase (beta-N-acetylglucosaminide: beta 1,4-galactosyltransferase). Biochem Biophys Res Commun. Dec. 15, 1988;157(2):657-63.
Matsumoto et al. Characterization of a human glycoprotein (erythropoietin) produced in cultured tobacco cells. Mol. Biol. 27, 1163-1172, 1995.
Melo et al. Identification of the human Lewis(a) carbohydrate motif in a secretory peroxidase from a plant cell suspension culture (*Vaccinium myrtillus* L.) FEBS Lett 415, 186-91, 1997.
Milland et al. "The cytoplasmic tail of α1,2-fucosyltransferase contains a sequence for golgi localization" (2001) J. Biol. Chem. 276(15):12012-12018.
Miyake et al., Purification of human erythropoietin. J Biol Chem. Aug. 10, 1977;252(15):5558-64.
Miyoshi et al., The alphal-6-fucosyltransferase gene and its biological significance. Biochim Biophys Acta. Dec. 6, 1999;1473(1):9-20.
Mokrzycki-Issartel et al., A transient tobacco expression system coupled to MALDI-TOF-MS allows validation of the impact of differential targeting on structure and activity of a recombinant therapeutic glycoprotein produced in plants. FEBS Lett. Sep. 25, 2003;552(2-3):170-6.
Munro "Localization of proteins to the Golgi apparatus" (1998) Trends Cell Biol. 8(1): 11-15.
Naigai et al., "N-Glycosylation is Requisite for the Enzyme Activity and Golgi Retention of N-Acetylglucosaminyltransferase III." Glycobiology 7(6):769-776 (1997).
Palacpac et al., Stable expression of human beta1,4-galactosyltransferase in plant cells modifies N-linked glycosylation patterns. Proc Natl Acad Sci U S A. Apr. 13, 1999;96(8):4692-7.
Palacpac et al., Structures of N-linked oligosaccharides of glycoproteins from tobacco BY2 suspension cultured cells. Biosci Biotechnol Biochem. Jan. 1999;63(1):35-9.
Philipp et al., "Characterization of nuclear membranes and endoplasmic reticulum isolated from plant tissue" JCB 1976 68:11-29.
Rayon et al. Characterization of N-Glycans from *Arabidopsis*. Application to a Fucose-Deficient Mutant (1999) Plant Physiology 119, 725-733.
Rayon et al., N-Glycosylation of phytohemagglutinin expressed in bean cotyledons or in transgenic tobacco plants. Plant Physiol Biochem. 1996;34:273-81.
Rishi et al. "Molecular Farming in Plants: A Current Perspective." (2001) J. Plant Biochem. & Biotech 10: 1-12.
Rothman, Protein sorting by selective retention in the endoplasmic reticulum and Golgi stack. Cell. Aug. 14, 1987;50(4):521-2.
Saint-Jore-Dupas et al. "Plant N-Glycan Processing Enzymes Employ Different Targeting Mechanisms for Their Spatial Arrangement along the Secretory Pathway." The Plant Cell 2006 18:3182-3200.
Saito et al. Integration and expression of a rabbit liver cytochrome P-450 gene in transgenic *Nicotiana tabacum* (1991) Proc. Natl. Acad. Sci. 88, 7041-7045.
Sakai et al., Fatty Acid acylation of apoE by human monocyte/marophages and helptocytes. Apr. 1998; 417. Abstract.
Sakai et al., Human glycosyltransferase expression and intracellular/intercellular glycoprotein sugar chain structure in cultured tobacco BY2 cells. Corrected title: Expression of human β 1,4-galactosyltransferase in tobacco BY2 cells modifies glycosylation patterns of intracellular and extracellular glycoproteins. IC Biotech. Osaska, Nara Institute. Mar. 1998. Abstract.
Sakai et al., "Expression of Human β1,4-Galactosyltransferase in Tobacco BY2 Cells Modifies Glycosylation Patterns of Intracellular and Extracellular Glycoproteins," Translation of Abstract from the Ann. Meeting of Japan Society for Bioscience, Biotechnology, and Agrochemistry, Published Mar. 1998. (Additional translation of Sakai et al previously submitted).
Schachter, The 'yellow brick road' to branched complex N-glycans. Glycobiology. Nov. 1991;1(5):453-61.
Scherer et al., "Action and Inhibition of Endogenous Phospholipases during Isolation of Plant Membranes" Plant Physiol 1978 62:933-37.
Schindler et al. Arabinogalactan proteins in maize coleoptiles: developmental relationship to cell death during xylem differentiation but not to extention growth. (1995) Plant JU 7, 25-36.
Seveno et al., Glycoprotein Sialylation in plants? Nat Biotechnol. Nov. 2004;22(11):1351-2.
Shah et al., Sialylated endogenous glycoconjugates in plant cells. Nat Biotechnol. Dec. 2003;21(12):1470-1. Epub Nov. 9, 2003.
Shaper et al. Bovine galactosyltransferase: identification of a clone by direct immunological screening of a cDNA expression library. (1986) Proc Natl Acad Sci USA 83, 1573-7.

Smant et al. Potato root diffusate- induced secretion of soluble, basic proteins originating from the subventral esophageal glands of potato cyst nematodes (1997) Phytopathology 87, 839-845.
Stanley and Ioffe Glycosyltransferase mutants: key to new insights in glycobiology (1995) Faseb j 9, 1436-44.
Stanley et al. CHO cells provide access to novel N-glycans and developmentally regulated glycosyltransferases. (1996) Glycobiology 6, 695-9.
Staudacher E, "Functional purification and characterization of a GDP-fucose: beta-N-acetylglucosamine (Fuc to Asn linked GlcNAc) alpha 1,3-fucosyltransferase from mung beans." Glycoconj J. Dec. 1995;12(6):780-6.
Staudacher E, "Strict order of (Fuc to Asn-linked GlcNAc) fucosyltransferases forming core-difucosylated structures." Glycoconj J. Apr. 1998;15(4):355-60.
Strasser et al., Molecular cloning of cDNA encoding N-acetylglucosaminyltransferase II from *Arabidopsis thaliana*. Glycoconj J. Dec. 1999;16(12):787-91.
Strasser et al., "Molecular cloning and functional expression of beta 1,2-sylosyltransferase cDNA from *Arabidopsis thaliana*[1]" Febs Letters, Elsvier, Amsterdam, NL, Apr. 2000 472(1): 105-108.
Strasser et al. "Molecular basis of N-acetylglucosaminyltransferase I deficiency in *Arabidopsis thaliana* plants lacking complex N-glycans." Biochem J. 2005 387:385-391.
Sturm et al. "Subcellular localization of glycosidases and glycosyltransferases involved in the processing of N-linked oligosaccharides" (1987) Plant Physiol. 85(3):741-745.
Takahashi et al., Xylose-containing common structural unit in N-linked oligosaccharides of laccase from sycamore cells. Biochemistry. 1986;25(2):388-95.
Tang et al., The transmembrane domain of N-glucosaminyltransferase I contains a Golgi retention signal. J Biol Chem. May 15, 1992;267(14):10122-6.
Taniguchi et al., A glycomic approach to the identification and characterization of glycoprotein function in cells transfected with glycosyltransferase genes. Proteomics. Feb. 2001;1(2):239-47.
Terayama et al., Cloning and functional expression of a novel glucuronyltransferase involved in the biosynthesis of the carbohydrate epitope HNK-1. Proc Natl Acad Sci U S A. Jun. 10, 1997;94(12):6093-8.
Terayama et al., "Purification and Characterization of a Glucuronyltransferase Involved in the Biosynthesis of the HNK-1 Epitope on Glycoproteins from Rat Brain." The Journal of Biological Chemistry 273(46):30295-30300 (1998).
Thanavala et al. Immunogenicity of transgenetic plant derived hepatitis B surface antigen. (1995) Proc Natl Acad Sci USA 92, 3358-3361.
Umana et al. Engineered glycoforms of an antineuroblastoma IgG1 with optimize antibody-dependent cellular cytotoxic activity. (1999) Nature Biotech. 17: 176-180.
Van Engelen et al., Coordinate expression of antibody subunit genes yields high levels of functional antibodies in roots of transgenic tobacco. Plant Mol Biol. Dec. 1994;26(6):1701-10.
Van Engelen et al. pBINPLUS: an improved plant transformation vector based on pBIN19. (1995) Transgenetic Res 4, 288-90.
Van Ree et al., Beta(1,2)-xylose and alpha(1,3)-fucose residues have a strong contribution in IgE binding to plant glycoallergens. J Biol Chem. Apr. 14, 2000;275(15):11451-8.
Vitale and Chrispeels, Transient N-acetylglucosamine in the biosynthesis of phytohemagglutinin: attachment in the Golgi apparatus and removal in protein bodies. J Cell Biol. Jul. 1984;99(1 Pt 1):133-40.
Voelker et al., In vitro mutated phytohemagglutinin genes expressed in tobacco seeds: role of glycans in protein targeting and stability. Plant Cell. Jan. 1989;1(1):95-104.
Von Schaewen et al. Isolation of a mutant *Arabidopsis* plant that lacks N-acetyl glucosaminyl transferase I and is unable to synthesize Golgi-modified complex N-linked glycans. (1993) Plant Physiol 102, 1109-18.
Warner, T.G., Metabolic engineering glycosylation: biotechnology's challenge to the glycobiologist in the next millenium; Carbohydrates in chemistry and biology, part II vol. 4. editors Earnst et al. (2000) Wiley-VCH. 1042-64.
Wee et al., Targeting of active sialyltransferase to the plant Golgi apparatus. Plant Cell. Oct. 1998;10(10):1759-68.
Whitelam GC., The production of recombinant proteins in plants. (1995) J. Sci. Food Agric., 68:1-9.
Wiebauer et al., Nuclear pre-mRNA processing in plants: distinct modes of 3'splice-site selection in plants and animals (1988) MCB: vol. 8 pp. 2042-2051.
Wilson et al., Core alphal,3-fucose is a key part of the epitope recognized by antibodies reacting against plant N-linked oligosaccharides and is present in a wide variety of plant extracts. Glycobiology. Jul. 1998;8(7):651-61.
Wilson et al., Cloning and expression of cDNAs encoding alpha1,3-fucosyltransferase homologues from *Arabidopsis thaliana*. Biochim Biophys Acta. Jul. 2, 2001;1527(1-2):88-96.
Wright and Morrison, Effect of glycosylation on antibody function: implications for genetic engineering. Trends Biotechnol. Jan. 1997;15(1):26-32.
Yamaguchi et al., Genomic structure and promoter analysis of the human alphal, 6-fucosyltransferase gene (FUT8). Glycobiology. Jun. 2000;10(6):637-43.
Yamaguchi and Fukuda Golgi retention mechanism of β-1,4-Galactosyltransferase (1995) J of Biol Chemistry 270(20): 12170-12176.
Yin et al., [Obtaining transgenic rice plants and their progenies using *Agrobacterium tumefaciens*] Yi Chuan Xue Bao. Dec. 1998;25(6):517-24. Chinese.
Yoshida et al., Molecular biology and application of plant peroxidase genes. Appl Microbiol Biotechnol. Feb. 2003;60(6):665-70. Epub Dec. 18, 2002.
Yoshida et al., Expression of β1 4 galactosyltransferase in tobacco culture cell. Program for Congress of the Society for Bioscience and Bioengineering of Japan. Sep. 15, 1995;1-5.
Yosida et al., "Challenge for production of human-compatible glycoprotein therapeutics in yeast", Bioscience and Industry, vol. 54, pp. 420-422 (1996).
Zhang et al., Transformation of tobacco using human β-1 , 4 galactosyltransferase gene and regeneration of transgenic plants. Annual reports of IC Biotech. 1995;18:241-7.
Zhang et al., *Agrobacterium*-mediated transformation of elite indica and japonica rice cultivars. Mol Biotechnol. Dec. 1997;8(3):223-31.
Zhang and Wang, Quantitative analysis and process monitoring of site-specific glycosylation microheterogeneity in recombinant human interferon-gamma from Chinese hamster ovary cell culture by hydrophilic interaction chromatography. J Chromatogr B Biomed Sci Appl. Aug. 7, 1998;712(1-2):73-82.
Zhu et al., Beta 1,4 N-acetylgalactosaminyltransferase (GM2/GD2/GA2 synthase) forms homodimers in the endoplasmic reticulum: a strategy to test for dimerization of Golgi membrane proteins. Glycobiology. Oct. 1997;7(7):987-96.

* cited by examiner

<u>At</u>gaggcttcgggagccgctcctgagcggcagcgccgcgatgccaggcgcgtccctacagcgggcctgccgcctgctcgtggccgtctgcgctctgcaccttggcgtcaccctcgtttactacctggctggccg
cgacctgagccgcctgccccaactggtcggagtctccacaccgctgcagggcggctcgaacagtgccgccgccatcgggcagtcctccggggagctccggaccggaggggcccggccgccgcctcctctag
gcgcctcctcccagccgcgcccgggtggcgactccagcccagtcgtggattctggccctggccccgctagcaacttgacctcggtcccagtgccccacaccaccgcactgtcgctgcccgcctgccctgaggag
tccccgctgcttgtgggccccatgctgattgagtttaacatgcctgtggacctggagctcgtggcaaagcagaacccaaatgtgaagatgggcggccgctatgcccccagggactgcgtctctcctcacaaggtgg
ccatcatcattccattccgcaaccggcaggagcacctcaagtactggctatattatttgcacccagtcctgcagcgccagcagctggactatggcatctatgttatcaaccaggcgggagacactatattcaatcgtgct
aagctcctcaatgttggctttcaagaagccttgaaggactatgactacacctgctttgtgtttagtgacgtggacctcattccaatgaatgaccataatgcgtacaggtgtttttcacagccacggcacatttccgttgcaat
ggataagtttggattcagcctaccttatgttcagtattttggaggtgtctctgctctaagtaaacaacagtttctaaccatcaatggatttcctaataattattggggctggggaggagaagatgatgacatttttaacagatta
gtttttagaggcatgtctatatctcgcccaaatgctgtggtcgggaggtgtcgcatgatccgccactcaagagacaagaaaaatgaacccaatcctcagaggtttgaccgaattgcacacacaaaggagacaatgctc
tctgatggtttgaactcactcacctaccaggtgctggatgtacagagatacccattgtatacccaaatcacagtggacatcgggacaccgagc<u>tag</u>

FIG. 5

```
atgaggcttcgggagccgctcctgagcggcagcgccgcgatgccaggcgcgtccctacag
 M  R  L  R  E  P  L  L  S  G  S  A  A  M  P  G  A  S  L  Q
cgggcctgccgcctgctcgtggccgtctgcgctctgcaccttggcgtcaccctcgtttac
 R  A  C  R  L  L  V  A  V  C  A  L  H  L  G  V  T  L  V  Y
tacctggctggccgcgacctgagccgcctgccccaactggtcggagtctccacaccgctg
 Y  L  A  G  R  D  L  S  R  L  P  Q  L  V  G  V  S  T  P  L
cagggcggctcgaacagtgccgccgccatcgggcagtcctccggggagctccggaccgga
 Q  G  G  S  N  S  A  A  A  I  G  Q  S  S  G  E  L  R  T  G
ggggcccggccgccgcctcctctaggcgcctcctcccagccgcgcccgggtggcgactcc
 G  A  R  P  P  P  L  G  A  S  S  Q  P  R  P  G  G  D  S
agcccagtcgtggattctggccctggccccgctagcaacttgacctcggtcccagtgccc
 S  P  V  V  D  S  G  P  G  P  A  S  N  L  T  S  V  P  V  P
cacaccaccgcactgtcgctgcccgcctgccctgaggagtccccgctgcttgtgggcccc
 H  T  T  A  L  S  L  P  A  C  P  E  E  S  P  L  L  V  G  P
atgctgattgagtttaacatgcctgtggacctggagctcgtggcaaagcagaacccaaat
 M  L  I  E  F  N  M  P  V  D  L  E  L  V  A  K  Q  N  P  N
gtgaagatgggcggccgctatgcccccagggactgcgtctctcctcacaaggtggccatc
 V  K  M  G  G  R  Y  A  P  R  D  C  V  S  P  H  K  V  A  I
atcattccattccgcaaccggcaggagcacctcaagtactggctatattatttgcaccca
 I  I  P  F  R  N  R  Q  E  H  L  K  Y  W  L  Y  Y  L  H  P
gtcctgcagcgccagcagctggactatggcatctatgttatcaaccaggcgggagacact
 V  L  Q  R  Q  Q  L  D  Y  G  I  Y  V  I  N  Q  A  G  D  T
atattcaatcgtgctaagctcctcaatgttggctttcaagaagccttgaaggactatgac
 I  F  N  R  A  K  L  L  N  V  G  F  Q  E  A  L  K  D  Y  D
tacacctgctttgtgtttagtgacgtggacctcattccaatgaatgaccataatgcgtac
 Y  T  C  F  V  F  S  D  V  D  L  I  P  M  N  D  H  N  A  Y
aggtgtttttcacagccacggcacatttccgttgcaatggataagtttggattcagccta
 R  C  F  S  Q  P  R  H  I  S  V  A  M  D  K  F  G  F  S  L
Ccttatgttcagtattttggaggtgtctctgctctaagtaaacaacagtttctaaccatc
 P  Y  V  Q  Y  F  G  G  V  S  A  L  S  K  Q  Q  F  L  T  I
aatggatttcctaataattattggggctggggaggagaagatgatgacatttttaacaga
 N  G  F  P  N  N  Y  W  G  W  G  G  E  D  D  D  I  F  N  R
ttagtttttagaggcatgtctatatctcgcccaaatgctgtggtcgggaggtgtcgcatg
 L  V  F  R  G  M  S  I  S  R  P  N  A  V  V  G  R  C  R  M
atccgccactcaagagacaagaaaaatgaacccaatcctcagaggtttgaccgaattgca
 I  R  H  S  R  D  K  K  N  E  P  N  P  Q  R  F  D  R  I  A
cacacaaaggagacaatgctctctgatggtttgaactcactcacctaccaggtgctggat
 H  T  K  E  T  M  L  S  D  G  L  N  S  L  T  Y  Q  V  L  D
gtacagagatacccattgtatacccaaatcacagtggacatcgggacaccgagctag
 V  Q  R  Y  P  L  Y  T  Q  I  T  V  D  I  G  T  P  S  -
```

FIG. 6

MRLREPLLSGAAMPGASLQRACRLLVAVCALHLGVTLVYYLAGRDLSRLPQLVGVSTPLQGGSNSAAAIGQSSGELRTGGARPPPPLG
ASSQPRPGGDSSPVVDSGPGPASNLTSVPVPHTTALSLPACPEESPLLVGPMLIEFNMPVDLELVAKQNPNVKMGGRYAPRDCVSPHKV
AIIIPFRNRQEHLKYWLYYLHPVLQRQQLDYGIYGIYVINQAGDTIFNRAKLLNVGFQEALKDYDYTCFVFSDVDLIPMNDHNAYRCFS
QPRHISVAMDKFGFSLPYVQYFGGVSALSKQQFLTINGFPNNYWGWGGEDDDIFNRLVFRGMSISRPNAVVGRCRMIRHSRDKKNEPN
PQRFDRIAHTKETMLSDGLNSLTYQVLDVQRYPLYTQITVDIGTPS

FIG. 7

ATGAGTAAACGGAATCCGAAGATTCTGAAGATTTTTCTGTATATGTTACTTCTCAACTCTCTCTTTCTCATCATCTACTTCGTTTTT
CACTCATCGTCGTTTTCACCGGAGCAGTCACAGCCTCCTCATATATACCACGTTTCAGTGAATAACCAATCGGCGAtcgggcagtcctccg
gggagctccggaccggaggggcccggccgccgcctcctctaggcgcctcctcccagccgcgcccgggtggcgactccagcccagtcgtggattctggccctggccccgctagcaacttgacctcggtcccagt
gccccacaccaccgcactgtcgctgcccgcctgccctgaggagtccccgctgcttgtgggccccatgctgattgagtttaacatgcctgtggacctggagctcgtggcaaagcagaacccaaatgtgaagatggg
cggccgctatgcccccagggactgcgtctctcctcacaaggtggccatcatcattccattccgcaaccggcaggagcacctcaagtactggctatattatttgcacccagtcctgcagcgccagcagctggactatg
gcatctatgttatcaaccaggcgggagacactatattcaatcgtgctaagctcctcaatgttggctttcaagaagccttgaaggactatgactacacctgctttgtgtttagtgacgtggacctcattccaatgaatgacca
taatgcgtacaggtgtttttcacagccacggcacatttccgttgcaatggataagtttggattcagcctaccttatgttcagtattttggaggtgtctctgctctaagtaaacaacagtttctaaccatcaatggatttcctaata
attattggggctggggaggagaagatgatgacatttttaacagattagtttttagaggcatgtctatatctcgcccaaatgctgtggtcgggaggtgtcgcatgatccgccactcaagagacaagaaaaatgaacccaa
tcctcagaggtttgaccgaattgcacacacaaaggagacaatgctctctgatggtttgaactcactcacctaccaggtgctggatgtacagagatacccattgtatacccaaatcacagtggacatcgggacaccgag
ctag

FIG. 8 atgagtaaacggaatccgaagattctgaagatttttctgtatatgttacttctcaactct
M S K R N P K I L K I F L Y M L L L N S
ctctttctcatcatctacttcgtttttcactcatcgtcgttttcaccggagcagtcacag
L F L I I Y F V F H S S S F S P E Q S Q
cctcctcatatataccacgtttcagtgaataaccaatcggcgatcgggcagtcctccggg
P P H I Y H V S V N N Q S A I G Q S S G
gagctccggaccggagggcccggccgccgcctcctctaggcgcctcctcccagccgcgc
E L R T G G A R P P P P L G A S S Q P R
ccgggtggcgactccagcccagtcgtggattctggccctggccccgctagcaacttgacc
P G G D S S P V V D S G P G P A S N L T
tcggtcccagtgccccacaccaccgcactgtcgctgcccgcctgccctgaggagtccccg
S V P V P H T T A L S L P A C P E E S P
Ctgcttgtgggccccatgctgattgagtttaacatgcctgtggacctggagctcgtggc
L L V G P M L I E F N M P V D L E L V A
Aagcagaacccaaatgtgaagatgggcggccgctatgcccccagggactgcgtctctcct
K Q N P N V K M G G R Y A P R D C V S P
cacaaggtggccatcatcattccattccgcaaccggcaggagcacctcaagtactggcta
H K V A I I I P F R N R Q E H L K Y W L
tattatttgcacccagtcctgcagcgccagcagctggactatggcatctatgttatcaac
Y Y L H P V L Q R Q Q L D Y G I Y V I N
caggcgggagacactatattcaatcgtgctaagctcctcaatgttggctttcaagaagcc
Q A G D T I F N R A K L L N V G F Q E A
ttgaaggactatgactacacctgctttgtgtttagtgacgtggacctcattccaatgaat
L K D Y D Y T C F V F S D V D L I P M N
gaccataatgcgtacaggtgtttttcacagccacggcacatttccgttgcaatggataag
D H N A Y R C F S Q P R H I S V A M D K
tttggattcagcctaccttatgttcagtattttggaggtgtctctgctctaagtaaacaa
F G F S L P Y Y V Q Y F G G V S A L S K Q
cagtttctaaccatcaatggatttcctaataattattggggctggggaggagaagatgat
Q F L T I N G F P N N Y W G W G G E D D
gacattttaacagattagttttagaggcatgtctatatctcgcccaaatgctgtggtc
D I F N R L V F R G M S I S R P N A V V
gggaggtgtcgcatgatccgccactcaagagacaagaaaaatgaacccaatcctcagagg
G R C R M I R H S R D K K N E P N P Q R
tttgaccgaattgcacacacaaaggagacaatgctctctgatggtttgaactcactcacc
F D R I A H T K E T M L S D G L N S L T
taccaggtgctggatgtacagagatacccattgtatacccaaatcacagtggacatcggg
Y Q V L D V Q R Y P L Y T Q I T V D I G
acaccgagctag
T P S -

FIG. 9

MSKRNPKILKIFLYMLLLNSLFLIIYFVFHSSSFSPEQSQPPHIYHVSVNNQSAIGQSSGELRTGGARPPPPLGASSQPRPGGDSSPVVDSG
PGPASNLTSVPVPHTTALSLPACPEESPLLVGPMLIEFNMPVDLELVAKQNPNVKMGGRYAPRDCVSPHKVAIIIPFRNRQEHLKYWLY
YLHPVLQRQQLDYGIYVINQAGDTIFNRAKLLNVGFQEALKDYDYTCFVFSDVDLIPMNDHNAYRCFSQPRHISVAMDKFGFSLPYVQ
YFGGVSALSKQQFLTINGFPNNYWGWGGEDDDIFNRLVFRGMSISRPNAVVGRCRMIRHSRDKKNEPNPQRFDRIAHTKETMLSDGLN
SLTYQVLDVQRYPLYTQITVDIGTPS

FIG. 10

CCATGGTGATGAGACGCTACAAGCTCTTTCTCATGTTCTGTATGGCCGGCCTGTGCCTCATCTCCTTCCTGCACTTCTTCAAGACC
CTGTCCTATGTCACCTTCCCCCGAGAACTGGCCTCCCTCAGCCCTAACCTGGTGTCCAGCTTTTTCTGGAACAATGCCCCGGTCAC
GCCCCAGGCCAGCCCCGAGCCAGGAGGCCCTGACCTGCTGCGTACCCCACTCTACTCCCACTCGCCCCTGCTGCAGCCGCTGCCG
CCCAGCAAGGCGGCCGAGGAGCTCCACCGGGTGGACTTGGTGCTGCCCGAGGACACCACCGAGTATTTCGTGCGCACCAAGGCC
GGCGGCGTCTGCTTCAAACCCGGCACCAAGATGCTGGAGAGGCCGCCCCCGGGACGGCCGGAGGAGAAGCCTGAGGGGGCCAA
CGGCTCCTCGGCCCGGCGGCCACCCCGGTACCTCCTGAGCGCCCGGGAGCGCACGGGGGGCCGAGGCGCCCGGCGCAAGTGGGT
GGAGTGCGTGTGCCTGCCCGGCTGGCACGGACCCAGCTGCGGCGTGCCCACTGTGGTGCAGTACTCCAACCTGCCCACCAAGGA
GCGGCTGGTGCCCAGGGAGGTGCCGCGCCGCGTCATCAACGCCATCAACGTCAACCACGAGTTCGACCTGCTGGACGTGCGCTT
CCACGAGCTGGGCGACGTGGTGGACGCCTTTGTGGTGTGCGAGTCCAACTTCACGGCTTATGGGGAGCCGCGGCCGCTCAAGTTC
CGGGAGATGCTGACCAATGGCACCTTCGAGTACATCCGCCACAAGGTGCTCTATGTCTTCCTGGACCACTTCCCGCCCGGCGGCC
GGCAGGACGGCTGGATCGCCGACGACTACCTGCGCACCTTCCTCACCCAGGACGGCGTCTCGCGGCTGCGCAACCTGCGGCCCG
ACGACGTCTTCATCATTGACGATGCGGACGAGATCCCGGCCCGTGACGGCGTCCTTTTCCTCAAGCTCTACGATGGCTGGACCGA
GCCCTTCGCCTTCCACATGCGCAAGTCGCTCTACGGCTTCTTCTGGAAGCAGCCGGGCACCCTGGAGGTGGTGTCAGGCTGCACG
GTGGACATGCTGCAGGCAGTGTATGGGCTGGACGGCATCCGCCTGCGCCGCCGCCAGTACTACACCATGCCCAACTTCAGACAG
TATGAGAACCGCACCGGCCACATCCTGGTGCAGTGGTCGCTGGGCAGCCCCCTGCACTTCGCCGGCTGGCACTGCTCCTGGTGCT
TCACGCCCGAGGGCATCTACTTCAAGCTCGTGTCCGCCCAGAATGGCGACTTCCCACGCTGGGGTGACTACGAGGACAAGCGGG
ACCTGAACTACATCCGCGGCCTGATCCGCACCGGGGGCTGGTTCGACGGCACGCAGCAGGAGTACCCGCCTGCAGACCCCAGCG
AGCACATGTATGCGCCCAAGTACCTGCTGAAGAACTACGACCGGTTCCACTACCTGCTGGACAACCCCTACCAGGAGCCCAGGA
GCACGGCGGCGGGCGGGTGGCGCCACAGGGGTCCCGAGGGAAGGCCGCCCGCCCGGGGCAAACTGGACGAGGCGGAAGTCGAA
CAAAAACTCATCTCAGAAGAGGATCTGAATTAGGATCC

FIG. 11

```
ccatggtgatgagacgctacaagctctttctcatgttctgtatggccggcctgtgcctcatc
  M  V  M  R  R  Y  K  L  F  L  M  F  C  M  A  G  L  C  L  I
tccttcctgcacttcttcaagaccctgtcctatgtcaccttccccgagaactggcctcc
 S  F  L  H  F  F  K  T  L  S  Y  V  T  F  P  R  E  L  A  S
ctcagccctaacctggtgtccagcttttctggaacaatgccccggtcacgccccaggcc
 L  S  P  N  L  V  S  S  F  F  W  N  N  A  P  V  T  P  Q  A
agccccgagccaggaggccctgacctgctgcgtaccccactctactcccactcgcccctg
 S  P  E  P  G  G  P  D  L  L  R  T  P  L  Y  S  H  S  P  L
ctgcagccgctgccgcccagcaaggcggccgaggagctccaccgggtggacttggtgctg
 L  Q  P  L  P  P  S  K  A  A  E  E  L  H  R  V  D  L  V  L
cccgaggacaccaccgagtatttcgtgcgcaccaaggccggcggcgtctgcttcaaaccc
 P  E  D  T  T  E  Y  F  V  R  T  K  A  G  G  V  C  F  K  P
ggcaccaagatgctggagaggccgcccccgggacggccggaggagaagcctgagggggcc
 G  T  K  M  L  E  R  P  P  P  G  R  P  E  E  K  P  E  G  A
aacggctcctcggcccggcggccaccccggtacctcctgagcgcccgggagcgcacgggg
 N  G  S  S  A  R  R  P  P  R  Y  L  L  S  A  R  E  R  T  G
ggccgaggcgcccggcgcaagtgggtggagtgcgtgtgcctgcccggctggcacggaccc
 G  R  G  A  R  R  K  W  V  E  C  V  C  L  P  G  W  H  G  P
agctgcggcgtgcccactgtggtgcagtactccaacctgcccaccaaggagcggctggtg
 S  C  G  V  P  T  V  V  Q  Y  S  N  L  P  T  K  E  R  L  V
cccagggaggtgccgcgccgcgtcatcaacgccatcaacgtcaaccacgagttcgacctg
 P  R  E  V  P  R  R  V  I  N  A  I  N  V  N  H  E  F  D  L
ctggacgtgcgcttccacgagctgggcgacgtggtggacgcctttgtggtgtgcgagtcc
 L  D  V  R  F  H  E  L  G  D  V  V  D  A  F  V  V  C  E  S
aacttcacggcttatggggagccgcggccgctcaagttccgggagatgctgaccaatggc
 N  F  T  A  Y  G  E  P  R  P  L  K  F  R  E  M  L  T  N  G
accttcgagtacatccgccacaaggtgctctatgtcttcctggaccacttcccgcccggc
 T  F  E  Y  I  R  H  K  V  L  Y  V  F  L  D  H  F  P  P  G
ggccggcaggacggctggatcgccgacgactacctgcgcaccttcctcacccaggacggc
 G  R  Q  D  G  W  I  A  D  D  Y  L  R  T  F  L  T  Q  D  G
gtctcgcggctgcgcaacctgcggcccgacgacgtcttcatcattgacgatgcggacgag
 V  S  R  L  R  N  L  R  P  D  D  V  F  I  I  D  D  A  D  E
atcccggcccgtgacggcgtcctttttcctcaagctctacgatggctggaccgagcccttc
 I  P  A  R  D  G  V  L  F  L  K  L  Y  D  G  W  T  E  P  F
gccttccacatgcgcaagtcgctctacggcttcttctggaagcagccgggcaccctggag
 A  F  H  M  R  K  S  L  Y  G  F  F  W  K  Q  P  G  T  L  E
gtggtgtcaggctgcacggtggacatgctgcaggcagtgtatgggctggacggcatccgc
 V  V  S  G  C  T  V  D  M  L  Q  A  V  Y  G  L  D  G  I  R
ctgcgccgccgccagtactacaccatgcccaacttcagacagtatgagaaccgcaccggc
 L  R  R  R  Q  Y  Y  T  M  P  N  F  R  Q  Y  E  N  R  T  G
cacatcctggtgcagtggtcgctgggcagcccccctgcacttcgccggctggcactgctcc
 H  I  L  V  Q  W  S  L  G  S  P  L  H  F  A  G  W  H  C  S
tggtgcttcacgcccgagggcatctacttcaagctcgtgtccgcccagaatggcgacttc
 W  C  F  T  P  E  G  I  Y  F  K  L  V  S  A  Q  N  G  D  F
ccacgctggggtgactacgaggacaagcgggacctgaactacatccgcggcctgatccgc
 P  R  W  G  D  Y  E  D  K  R  D  L  N  Y  I  R  G  L  I  R
accgggggctggttcgacggcacgcagcaggagtacccgcctgcagaccccagcgagcac
 T  G  G  W  F  D  G  T  Q  Q  E  Y  P  P  A  D  P  S  E  H
atgtatgcgcccaagtacctgctgaagaactacgaccggttccactacctgctggacaac
 M  Y  A  P  K  Y  L  L  K  N  Y  D  R  F  H  Y  L  L  D  N
ccctaccaggagcccaggagcacggcggcgggcgggtggcgccacaggggtcccgaggga
 P  Y  Q  E  P  R  S  T  A  A  G  G  W  R  H  R  G  P  E  G
aggccgcccgcccggggcaaactggacgaggcggaagtcgaacaaaaactcatctcagaa
 R  P  P  A  R  G  K  L  D  E  A  E  V  E  Q  K  L  I  S  E
gaggatctgaattaggatcc
 E  D  L  N  -  D
```

FIG. 12

MVMRRYKLFL MFCMAGLCLI SFLHFFKTLS YVTFPRELAS LSPNLVSSFF WNNAPVTPQA SPEPGGPDLL RTPLYSHSPL
LQPLPPSKAA EELHRVDLVL PEDTTEYFVR TKAGGVCFKP GTKMLERPPP GRPEEKPEGA NGSSARRPPR YLLSARERTG
GRGARRKWVE CVCLPGWHGP SCGVPTVVQY SNLPTKERLV PREVPRRVIN AINVNHEFDL LDVRFHELGD VVDAFVVCES
NFTAYGEPRP LKFREMLTNG TFEYIRHKVL YVFLDHFPPG GRQDGWIADD YLRTFLTQDG VSRLRNLRPD DVFIIDDADE
IPARDGVLFL KLYDGWTEPF AFHMRKSLYG FFWKQPGTLE VVSGCTVDML QAVYGLDGIR LRRRQYYTMP NFRQYENRTG
HILVQWSLGS PLHFAGWHCS WCFTPEGIYF KLVSAQNGDF PRWGDYEDKR DLNYIRGLIR TGGWFDGTQQ EYPPADPSEH
MYAPKYLLKN YDRFHYLLDN PYQEPRSTAA GGWRHRGPEG RPPARGKLDE AEVEQKLISE EDLN

FIG. 13

CATGAGTAAACGGAATCCGAAGATTCTGAAGATTTTTCTGTATATGTTACTTCTCAACTCTCTCTTTCTCATCATCTACTTCGTTTT
TCACTCATCGTCGTTTTCACCGGAGCAGTCACAGCCTCCTCATATATACCACGTTTCAGTGAATAACCAATCGGCACATGGAGGC
CCTGACCTGCTGCGTACCCCACTCTACTCCCACTCGCCCCTGCTGCAGCCGCTGCCGCCCAGCAAGGCGGCCGAGGAGCTCCACC
GGGTGGACTTGGTGCTGCCCGAGGACACCACCGAGTATTTCGTGCGCACCAAGGCCGGCGGCGTCTGCTTCAAACCCGGCACCA
AGATGCTGGAGAGGCCGCCCCCGGGACGGCCGGAGGAGAAGCCTGAGGGGGCCAACGGCTCCTCGGCCCGGCGGCCACCCCGG
TACCTCCTGAGCGCCCGGGAGCGCACGGGGGGCCGAGGCGCCCGGCGCAAGTGGGTGGAGTGCGTGTGCCTGCCCGGCTGGCAC
GGACCCAGCTGCGGCGTGCCCACTGTGGTGCAGTACTCCAACCTGCCCACCAAGGAGCGGCTGGTGCCCAGGGAGGTGCCGCGC
CGCGTCATCAACGCCATCAACGTCAACCACGAGTTCGACCTGCTGGACGTGCGCTTCCACGAGCTGGGCGACGTGGTGGACGCCT
TTGTGGTGTGCGAGTCCAACTTCACGGCTTATGGGGAGCCGCGGCCGCTCAAGTTCCGGGAGATGCTGACCAATGGCACCTTCGA
GTACATCCGCCACAAGGTGCTCTATGTCTTCCTGGACCACTTCCCGCCCGGCGGCCGGCAGGACGGCTGGATCGCCGACGACTAC
CTGCGCACCTTCCTCACCCAGGACGGCGTCTCGCGGCTGCGCAACCTGCGGCCCGACGACGTCTTCATCATTGACGATGCGGACG
AGATCCCGGCCCGTGACGGCGTCCTTTTCCTCAAGCTCTACGATGGCTGGACCGAGCCCTTCGCCTTCCACATGCGCAAGTCGCT
CTACGGCTTCTTCTGGAAGCAGCCGGGCACCCTGGAGGTGGTGTCAGGCTGCACGGTGGACATGCTGCAGGCAGTGTATGGGCT
GGACGGCATCCGCCTGCGCCGCCGCCAGTACTACACCATGCCCAACTTCAGACAGTATGAGAACCGCACCGGCCACATCCTGGT
GCAGTGGTCGCTGGGCAGCCCCCTGCACTTCGCCGGCTGGCACTGCTCCTGGTGCTTCACGCCCGAGGGCATCTACTTCAAGCTC
GTGTCCGCCCAGAATGGCGACTTCCCACGCTGGGGTGACTACGAGGACAAGCGGGACCTGAACTACATCCGCGGCCTGATCCGC
ACCGGGGGCTGGTTCGACGGCACGCAGCAGGAGTACCCGCCTGCAGACCCCAGCGAGCACATGTATGCGCCCAAGTACCTGCTG
AAGAACTACGACCGGTTCCACTACCTGCTGGACAACCCCTACCAGGAGCCCAGGAGCACGGCGGCGGGCGGGTGGCGCCACAG
GGGTCCCGAGGGAAGGCCGCCCGCCCGGGGCAAACTGGACGAGGCGGAAGTCGAACAAAAACTCATCTCAGAAGAGGATCTGA
ATTAGGATCC

FIG. 14

```
catgagtaaacggaatccgaagattctgaagatttttctgtatatgttacttctcaactct
 M  S  K  R  N  P  K  I  L  K  I  F  L  Y  M  L  L  L  N  S
ctctttctcatcatctacttcgtttttcactcatcgtcgttttcaccggagcagtcacag
 L  F  L  I  I  Y  F  V  F  H  S  S  S  F  S  P  E  Q  S  Q
cctcctcatatataccacgtttcagtgaataaccaatcggcacatggaggccctgacctg
 P  P  H  I  Y  H  V  S  V  N  N  Q  S  A  H  G  G  P  D  L
ctgcgtaccccactctactcccactcgcccctgctgcagccgctgccgcccagcaaggcg
 L  R  T  P  L  Y  S  H  S  P  L  L  Q  P  L  P  P  S  K  A
gccgaggagctccaccgggtggacttggtgctgcccgaggacaccaccgagtatttcgtg
 A  E  E  L  H  R  V  D  L  V  L  P  E  D  T  T  E  Y  F  V
cgcaccaaggccggcggcgtctgcttcaaacccggcaccaagatgctggagaggccgccc
 R  T  K  A  G  G  V  C  F  K  P  G  T  K  M  L  E  R  P  P
ccgggacggccggaggagaagcctgagggggccaacggctcctcggcccggcggccaccc
 P  G  R  P  E  E  K  P  E  G  A  N  G  S  S  A  R  R  P  P
cggtacctcctgagcgcccgggagcgcacggggggccgaggcgcccggcgcaagtgggtg
 R  Y  L  L  S  A  R  E  R  T  G  G  R  G  A  R  R  K  W  V
gagtgcgtgtgcctgcccggctggcacggacccagctgcggcgtgcccactgtggtgcag
 E  C  V  C  L  P  G  W  H  G  P  S  C  G  V  P  T  V  V  Q
tactccaacctgcccaccaaggagcggctggtgcccagggaggtgccgcgccgcgtcatc
 Y  S  N  L  P  T  K  E  R  L  V  P  R  E  V  P  R  R  V  I
aacgccatcaacgtcaaccacgagttcgacctgctggacgtgcgcttccacgagctgggc
 N  A  I  N  V  N  H  E  F  D  L  L  D  V  R  F  H  E  L  G
gacgtggtggacgcctttgtggtgtgcgagtccaacttcacggcttatggggagccgcgg
 D  V  V  D  A  F  V  V  C  E  S  N  F  T  A  Y  G  E  P  R
ccgctcaagttccgggagatgctgaccaatggcaccttcgagtacatccgccacaaggtg
 P  L  K  F  R  E  M  L  T  N  G  T  F  E  Y  I  R  H  K  V
ctctatgtcttcctggaccacttcccgcccggcggccggcaggacggctggatcgccgac
 L  Y  V  F  L  D  H  F  P  P  G  G  R  Q  D  G  W  I  A  D
gactacctgcgcaccttcctcacccaggacggcgtctcgcggctgcgcaacctgcggccc
 D  Y  L  R  T  F  L  T  Q  D  G  V  S  R  L  R  N  L  R  P
gacgacgtcttcatcattgacgatgcggacgagatcccggcccgtgacggcgtcctttc
 D  D  V  F  I  I  D  D  A  D  E  I  P  A  R  D  G  V  L  F
Ctcaagctctacgatggctggaccgagcccttcgccttccacatgcgcaagtcgctctac
 L  K  L  Y  D  G  W  T  E  P  F  A  F  H  M  R  K  S  L  Y
ggcttcttctggaagcagccgggcaccctggaggtggtgtcaggctgcacggtggacatg
 G  F  F  W  K  Q  P  G  T  L  E  V  V  S  G  C  T  V  D  M
ctgcaggcagtgtatgggctggacggcatccgcctgcgccgccgccagtactacaccatg
 L  Q  A  V  Y  G  L  D  G  I  R  L  R  R  R  Q  Y  Y  T  M
cccaacttcagacagtatgagaaccgcaccggccacatcctggtgcagtggtcgctgggc
 P  N  F  R  Q  Y  E  N  R  T  G  H  I  L  V  Q  W  S  L  G
agcccccctgcacttcgccggctggcactgctcctggtgcttcacgcccgagggcatctac
 S  P  L  H  F  A  G  W  H  C  S  W  C  F  T  P  E  G  I  Y
ttcaagctcgtgtccgcccagaatggcgacttcccacgctggggtgactacgaggacaag
 F  K  L  V  S  A  Q  N  G  D  F  P  R  W  G  D  Y  E  D  K
cgggacctgaactacatccgcggcctgatccgcaccggggggctggttcgacggcacgcag
 R  D  L  N  Y  I  R  G  L  I  R  T  G  G  W  F  D  G  T  Q
caggagtacccgcctgcagaccccagcgagcacatgtatgcgcccaagtacctgctgaag
 Q  E  Y  P  P  A  D  P  S  E  H  M  Y  A  P  K  Y  L  L  K
aactacgaccggttccactacctgctggacaacccctaccaggagcccaggagcacggcg
 N  Y  D  R  F  H  Y  L  L  D  N  P  Y  Q  E  P  R  S  T  A
gcgggcgggtggcgccacaggggtcccgagggaaggccgcccgcccggggcaaactggac
 A  G  G  W  R  H  R  G  P  E  G  R  P  P  A  R  G  K  L  D
gaggcggaagtcgaacaaaaactcatctcagaagaggatctgaattaggatcc
 E  A  E  V  E  Q  K  L  I  S  E  E  D  L  N  -  D
```

FIG. 15

MSKRNPKILK IFLYMLLLNS LFLIIYFVFH SSSFSPEQSQ PPHIYHVSVN NQSAHGGPDL LRTPLYSHSP LLQPLPPSKA
AEELHRVDLV LPEDTTEYFV RTKAGGVCFK PGTKMLERPP PGRPEEKPEG ANGSSARRPP RYLLSARERT GGRGARRKWV
ECVCLPGWHG PSCGVPTVVQ YSNLPTKERL VPREVPRRVI NAINVNHEFD LLDVRFHELG DVVDAFVVCE SNFTAYGEPR
PLKFREMLTN GTFEYIRHKV LYVFLDHFPP GGRQDGWIAD DYLRTFLTQD GVSRLRNLRP DDVFIIDDAD EIPARDGVLF
LKLYDGWTEP FAFHMRKSLY GFFWKQPGTL EVVSGCTVDM LQAVYGLDGI RLRRRQYYTM PNFRQYENRT GHILVQWSLG
SPLHFAGWHC SWCFTPEGIY FKLVSAQNGD FPRWGDYEDK RDLNYIRGLI RTGGWFDGTQ QEYPPADPSE HMYAPKYLLK
NYDRFHYLLD NPYQEPRSTA AGGWRHRGPE GRPPARGKLD EAEVEQKLIS EEDLN

FIG. 16

GGCGCGCCTCGAGGCGATCGCAGATCTAATCTAACCAATTACGATACGCTTTGGGTACACTTGATTTTTGTTTCAG
TGGTTACATATATCTTGTTTTATATGCTATCTTTAAGGATCTGCACAAAGATTATTTGTTGATGTTCTTGATGGGG
CTCAGAAGATTTGATATGATACACTCTAATCTTTAGGAGATACCAGCCAGGATTATATTCAGTAAGACAATCAAAT
TTTACGTGTTCAAACTCGTTATCTTTTCATTCAAAGGATGAGCCAGAATCTTTATAGAATGATTGCAATCGAGAAT
ATGTTCGGCCGATATGCCTTTGTTGGCTTCAATATTCTACATATCACACAAGAATCGACCGTATTGTACCCTCTTT
CCATAAAGGAAAACACAATATGCAGATGCTTTTTCCCACATGCAGTAACATATAGGTATTCAAAAATGGCTAAAA
GAAGTTGGATAACAAATTGACAACTATTTCCATTTCTGTTATATAAATTTCACAACACACAAAAGCCCGTAATCAA
GAGTCTGCCCATGTACGAAATAACTTCTATTATTTGGTATTGGGCCTAAGCCCAGCTCAGAGTACGTGGGGGTACC
ACATATAGGAAGGTAACAAAATACTGCAAGATAGCCCCATAACGTACCAGCCTCTCCTTACCACGAAGAGATAAGA
TATAAGACCCACCCTGCCACGTGTCACATCGTCATGGTGGTTAATGATAAGGGATTACATCCTTCTATGTTTGTGG
ACATGATGCATGTAATGTCATGAGCCACAGGATCCAATGGCCACAGGAACGTAAGAATGTAGATAGATTTGATTTT
GTCCGTTAGATAGCAAACAACATTATAAAAGGTGTGTATCAATAGGAACTAATTCACTCATTGGATTCATAGAAGT
CCATTCCTCCTAAGTATCTAGAAACCATGGCGAGGATCTCGTGTGACTTGAGATTTCTTCTCATCCCGGCAGCTTT
CATGTTCATCTACATCCAGATGAGGCTTTTCCAGACGCAATCACAGTATGCAGATCGCCTCAGTTCCGCTATCGAA
TCTGAGAACCATTGCACTAGTCAAATGCGAGGCCTCATAGATGAAGTTAGCATCAAACAGTCGCGGATTGTTGCCC
TCGAAGATATGAAGAACCGCCAGGACGAAGAACTTGTGCAGCTTAAGGATCTAATCCAGACGTTTGAAAAAAAAGG
AATAGCAAAACTCACTCAAGGTGGAGCCATGGATTCCAATTCAGGCGCCGTCGTTGATATCACAACTAAAGATCTA
TACGATAGGATTGAGTTTCTTGATACAGATGGTGGTCCATGGAAACAAGGTTGGAGAGTTACGTATAAAGACGATG
AGTGGGAGAAAGAGAAGCTCAAAATCTTCGTTGTTCCTCATTCTCATAACGATCCTGGTTGGAAATTGACTGTAGA
GGAGTATTATCAGAGACAATCCAGACATATTCTTGACACCATTGTTGAGACTTTATCTAAGGTATGACGAAAGTTT
TTGCTTTTGGTTTTAATATTTTAATTCTCTCCCATGGTTATCCCGTGAACAATCTTAAATGTCTTAAAATTCTCAT
GACGTCATTAAACTCTATAACCAAACTTCTTTGCTGGGTTCTGTTTTTTTTAGTTTCGTGATGAAACAGAGTTCT
AGAAGTTCGTTCTTTTGGAAAATTTGAAGTCTTTGGAGCTAAAGTTTGTTTTTTATTACTGGGTTTTGAGATTGA
AGGATAGCTAGAATCTTATTTGTGTGGGGGTTTGTTTTGAATATGTTTAATAGGATTCAAGAAGAAAGTTTATATG
GGAGGAGATGTCATATCTGGAGAGATGGTGGAGAGACGCTTCACCTAATAAACAAGAAGCTTTGACTAAATTGGTT

FIG. 17

AAGGATGGGCAGCTAGAGATTGTTGGAGGTGGCTGGGTTATGAATGATGAGGCTAATTCACATTATTTTGCCATAA
TTGAACAGATAGCAGAGGGTAATATGTGGCTGAATGACACAATTGGGGTTATTCCTAAGAATTCTTGGGCTATAGA
TCCCTTTGGCTATTCATCAACCATGGCTTATCTTCTCCGGCGTATGGGTTTTGAAAACATGCTTATTCAAAGGACT
CATTACGAGCTCAAGAAAGACCTTGCCCAGCATAAGAATCTTGAATATATTTGGCGTCAGAGCTGGGATGCTATGG
AAACCACAGATATCTTTGTTCATATGATGCCGTTTTATTCATACGATATCCCACACACTTGTGGACCAGAGCCTGC
AATTTGCTGTCAGTTTGATTTCGCTCGGATGCGGGGATTTAAGTATGAACTTTGTCCATGGGGAAAGCACCCAGTG
GAGACCACACTAGAAAATGTGCAGGAGAGGGCATTAAAGCTTCTGGATCAATACAGGAAAAAATCCACTCTATATC
GAACTAATACACTTCTTATACCTCTTGGAGATGATTTTAGGTACATTAGTATCGATGAAGCCGAGGCTCAGTTCCG
TAACTACCAGATGTTGTTTGATCACATCAACTCTAATCCTAGTCTAAACGCAGAAGCAAAGTTTGGTACTTTGGAG
GATTATTTCAGAACAGTCCGAGAAGAAGCAGACAGAGTGAATTATTCTCGTCCTGGTGAGGTTGGCTCTGGTCAGG
TTGTTGGTTTCCCTTCTCTGTCAGGTGACTTCTTTACATATGCAGATAGGCAACAAGACTATTGGAGTGGTTATTA
TGTTTCAAGACCTTTCTTCAAAGCTGTTGATCGTGTGCTCGAGCATACCCTTCGTGGAGCTGAGATCATGATGTCA
TTTCTGCTAGGTTATTGCCATCGAATTCAATGTGAGAAATTTCCAACAAGTTTTACGTATAAGTTGACTGCTGCAA
GAAGAAATCTGGCTCTTTTCCAGCACCATGATGGGGTAACTGGAACTGCTAAGGATTATGTGGTACAAGATTACGG
CACCCGGATGCATACTTCATTGCAAGACCTTCAGATCTTTATGTCTAAAGCAATCGAAGTTCTTCTTGGGATCCGC
CACGAGAAAGAAAAATCTGATCAATCCCCATCATTTTTCGAGGCAGAGCAAATGAGATCAAAGTATGATGCTCGGC
CAGTTCACAAGCCAATTGCTGCCCGGGAAGGAAATTCGCACACAGTTATACTCTTCAATCCATCAGAACAGACGAG
AGAGGAGGTGGTGACGGTTGTTGTTAACCGCGCTGAAATCTCGGTTTTGGACTCAAACTGGACTTGTGTCCCTAGC
CAAATTTCTCCTGAAGTGCAGCATGACGATACCAAACTATTCACCGGCAGACATCGCCTTTACTGGAAAGCTTCCA
TCCCAGCTCTTGGTCTGAGAACATATTTCATTGCTAATGGGAATGTCGAGTGTGAGAAAGCTACTCCGTCTAAACT
CAAATACGCTTCTGAGTTTGACCCATTTCCTTGTCCTCCTCCATATTCCTGCTCCAAACTGGACAACGACGTTACT
GAGATCCGAAATGAACATCAGACTCTTGTGTTTGATGTGAAGAACGGATCACTGCGGAAGATAGTCCATAGAAACG
GATCAGAGACTGTTGTGGGAGAAGAGATAGGTATGTACTCTAGTCCAGAGAGTGGAGCTTACCTGTTCAAACCAGA
TGGTGAAGCTCAGCCAATTGTTCAACCTGATGGACATGTAGTCACCTCTGAGGGTCTGCTGGTTCAAGAAGTCTTC
TCTTACCCTAAAACCAAATGGGAGAAATCACCCCTCTCTCAGAAAACTCGTCTTTACACTGGAGGTAATACGCTTC
AGGATCAAGTGGTCGAGATAGAATATCATGTTGAGCTTCTTGGTAATGATTTTGATGACCGGGAATTGATTGTCCG
GTACAAGACTGATGTTGACAACAAGAAGGTCTTCTATTCAGATCTCAATGGTTTCCAAATGAGCAGGAGAGAAACT

FIG. 17 Cont.

TATGATAAGATCCCTCTTCAAGGAAACTACTACCCAATGCCATCTCTCGCATTTATCCAAGGATCCAATGGTCAGA
GATTCTCCGTGCACTCTCGTCAATCTCTCGGTGTTGCAAGCCTCAAAGAGGGTTGGTTGGAGATTATGCTGGACAG
ACGGTTGGTTCGTGATGACGGACGGGGTCTAGGGCAAGGTGTGATGGATAACCGCGCAATGACCGTGGTATTTCAC
CTTCTTGCGGAATCTAACATTTCTCAAGCAGACCCTGCTTCCAACACTAACCCGAGGAACCCTTCGCTTCTCTCTC
ACCTCATAGGTGCTCACTTAAACTACCCCATAAACACATTCATTGCCAAGAAACCGCAAGACATATCTGTGCGTGT
TCCACAATACGGTTCCTTTGCTCCTTTAGCCAAACCGTTACCATGTGACCTCCACATTGTAAATTTCAAGGTTCCT
CGTCCATCCAAATACTCTCAGCAATTGGAAGAAGACAAGCCAAGGTTCGCTCTTATCCTCAATAGACGAGCTTGGG
ATTCAGCTTATTGCCATAAAGGAAGACAAGTAAACTGCACAAGCATGGCTAATGAACCAGTAAACTTTTCCGACAT
GTTCAAAGATCTTGCAGCTTCAAAGGTAAAACCAACTTCACTGAATCTCTTGCAAGAAGATATGGAGATTCTTGGG
TACGATGACCAAGAGCTACCTCGAGATAGTTCACAGCCACGGGAAGGACGTGTCTCGATCTCTCCCATGGAAATAC
GAGCTTATAAGCTTGAACTGCGACCTCACAAGTGAACCTGCTGAAGATCCGCTAGAGTCCGCAAAAATCACCAGTC
TCTCTCTACAAATCTATCTCTCTCTATTTTTCTCCAGAATAATGTGTGAGTAGTTCCCAGATAAGGGAATTAGGGT
TCTTATAGGGTTTCGCTCATGTGTTGAGCATATAAGAAACCCTTAGTATGTATTTGTATTTGTAAAATACTTCTAT
CAATAAAATTTCTAATCCTAAAACCAAAATCCCGCGCGCGCCTCGAGGCGATCGCAGATCTCATTATACCGTTAGA
AGCATAGTTAAAATCTAAAGCTTGTCGTTAATTCTAGTCATTTTACATTGTTGGGTTCTACATTATTAATGAATTT
TCTAATGCAAATACAGAATTTAAATCAAAATTGTTGAATTATGCTAAACATGTAACATACGTATATCTCCGCCTTG
TGTGTTGTATTAACTTGAAGTTATCATAAGAACCACAAATACACTAGTAAATCTATGAGAAGGCAGGTGGCAACAC
AAACAAGAGTATCTAAGATTTTCATTTGTGACTATAGGAATATAATATCTCTTATCTGATTTAATGAATCCACATG
TTCACTTCTCATTTGTCCACAAGATCACAACTTTATCTTCAATATTCACAACTTGTTATATCCACCACAATTTCAT
TCTTTTCACTTAGCCCCACAAAATACTTTGTCCCCTTATTTGCCACCTTTTGTATTTAATTTATTCTTGTGGAGCT
AAGTGTTCATATTATTCTTCTTCTCAAAAAAACAAAAACAAAAAAAAAGAGAAGAAAACCATGGCGAGGATCTCGT
GTGACTTGAGATTTCTTCTCATCCCGGCAGCTTTCATGTTCATCTACATCCAGATGAGGCTTTTCCAGACGCAATC
ACAGTATGCAGATCGCCTCAGTTCCGCTATCGAATCTGAGAACCATTGCACTAGTCAAATGCGAGGCCTCATAGAT
GAAGTTAGCATCAAACAGTCGCGGATTGTTGCCCTCGAAGATATGAAGAACCGCCAGGACGAAGAACTTGTGCAGC
TTAAGGATCTAATCCAGACGTTTGAAAAAAAAGGAATAGCAAAACTCACTCAAGGTGGAGCCATGGCTCTAAGGTT
GCATAGAAGGAACCATTTTTCGCCTAGAAATACGGATCTGTTCCCGGATTTGGCAAAAGATCGTGTGGTTATCGTC
TTGTATGTGCATAATCGGGCTCAGTATTTTCGAGTCACAGTGGAAAGTTTGTCGAAGGTTAAAGGTATAAGTGAGA
CATTGTTGATTGTTAGTCATGATGGTTACTTTGAAGAGATGAATAGGATTGTGGAGAGTATTAAGTTTTGTCAAGT

FIG. 17 Cont.

GAAACAGATTTTCTCGCCTTATTCGCCTCATATATATCGTACTAGCTTCCCGGGTGTGACCCTGAATGATTGTAAG
AACAAGGGTGATGAGGCAAAGGGGCATTGTGAAGGTAATCCTGATCAGTATGGGAATCATCGGTCTCCGAAGATTG
TATCTTTGAAGCATCACTGGTGGTGGATGATGAACACTGTATGGGATGGGTTGGAAGAGACTAAAGGACATGAGGG
GCATATCCTTTTCATTGAAGAAGATCATTTTCTGTTTCCTAATGCCTATCGTAACATACAGACTCTTACGAGGCTG
AAACCCGCAAAGTGTCCTGACTGTTTTGCTGCTAATTTAGCACCGTCTGATGTGAAGTCAAGAGGAGAAGGGCTTG
AAAGTTTGGTTGCAGAGAGAATGGGAAATGTTGGGTATTCTTTTAATAGAAGTGTGTGGGAGAATATTCATCAGAA
GGCAAGAGAGTTTTGTTTCTTTGATGATTACAACTGGGATATAACGATGTGGGCAACGGTTTTCCCGTCGTTTGGT
TCCCCGGTGTACACATTGCGAGGGCCTAGGACTAGTGCGGTACACTTTGGAAAATGTGGGTTGCATCAAGGTAGAG
GAGATGAGGGTGATTGCATCGATAATGGGGTCGTAAACATAGAAGTTAAGGAAACAGATAAAGTTGTGAACATAAA
AGAAGGATGGGGAGTTCGGGTGTATAAGCATCAAGCGGGTTATAAAGCCGGTTTCGAAGGTTGGGGAGGTTGGGGC
GATGATAGGGACCGACATTTATGTTTGGATTTTGCCACTATGTATCGTTACAGCAGTAGCAGTGCATCTCCATGAA
ACGGATCCGCTAGAGTCCGCAAAAATCACCAGTCTCTCTCTACAAATCTATCTCTCTCTATTTTTCTCCAGAATAA
TGTGTGAGTAGTTCCCAGATAAGGGAATTAGGGTTCTTATAGGGTTTCGCTCATGTGTTGAGCATATAAGAAACCC
TTAGTATGTATTTGTATTTGTAAAATACTTCTATCAATAAAATTTCTAATCCTAAAACCAAAATCCCGCGAGAGAC
CTCTTAATTAA

FIG. 17 Cont.

GGCGCGCCTCGAGGCGATCGCAGATCTAATCTAACCAATTACGATACGCTTTGGGTACACTTGATTTTTGTTTCAG
TGGTTACATATATCTTGTTTTATATGCTATCTTTAAGGATCTGCACAAAGATTATTTGTTGATGTTCTTGATGGGG
CTCAGAAGATTTGATATGATACACTCTAATCTTTAGGAGATACCAGCCAGGATTATATTCAGTAAGACAATCAAAT
TTTACGTGTTCAAACTCGTTATCTTTTCATTCAAAGGATGAGCCAGAATCTTTATAGAATGATTGCAATCGAGAAT
ATGTTCGGCCGATATGCCTTTGTTGGCTTCAATATTCTACATATCACACAAGAATCGACCGTATTGTACCCTCTTT
CCATAAAGGAAAACACAATATGCAGATGCTTTTTCCCACATGCAGTAACATATAGGTATTCAAAAATGGCTAAAA
GAAGTTGGATAACAAATTGACAACTATTTCCATTTCTGTTATATAAATTTCACAACACACAAAAGCCCGTAATCAA
GAGTCTGCCCATGTACGAAATAACTTCTATTATTTGGTATTGGGCCTAAGCCCAGCTCAGAGTACGTGGGGGTACC
ACATATAGGAAGGTAACAAAATACTGCAAGATAGCCCCATAACGTACCAGCCTCTCCTTACCACGAAGAGATAAGA
TATAAGACCCACCCTGCCACGTGTCACATCGTCATGGTGGTTAATGATAAGGGATTACATCCTTCTATGTTTGTGG
ACATGATGCATGTAATGTCATGAGCCACAGGATCCAATGGCCACAGGAACGTAAGAATGTAGATAGATTTGATTTT
GTCCGTTAGATAGCAAACAACATTATAAAAGGTGTGTATCAATAGGAACTAATTCACTCATTGGATTCATAGAAGT
CCATTCCTCCTAAGTATCTAGAAACCATGGCGAGGATCTCGTGTGACTTGAGATTTCTTCTCATCCCGGCAGCTTT
CATGTTCATCTACATCCAGATGAGGCTTTTCCAGACGCAATCACAGTATGCAGATCGCCTCAGTTCCGCTATCGAA
TCTGAGAACCATTGCACTAGTCAAATGCGAGGCCTCATAGATGAAGTTAGCATCAAACAGTCGCGGATTGTTGCCC
TCGAAGATATGAAGAACCGCCAGGACGAAGAACTTGTGCAGCTTAAGGATCTAATCCAGACGTTTGAAAAAAAAGG
AATAGCAAAACTCACTCAAGGTGGAGCCATGGATTCCAATTCAGGCGCCGTCGTTGATATCACAACTAAAGATCTA
TACGATAGGATTGAGTTTCTTGATACAGATGGTGGTCCATGGAAACAAGGTTGGAGAGTTACGTATAAAGACGATG
AGTGGGAGAAAGAGAAGCTCAAAATCTTCGTTGTTCCTCATTCTCATAACGATCCTGGTTGGAAATTGACTGTAGA
GGAGTATTATCAGAGACAATCCAGACATATTCTTGACACCATTGTTGAGACTTTATCTAAGGTATGACGAAAGTTT
TTGCTTTTGGTTTTAATATTTTAATTCTCTCCCATGGTTATCCCGTGAACAATCTTAAATGTCTTAAAATTCTCAT
GACGTCATTAAACTCTATAACCAAACTTCTTTGCTGGGTTCTGTTTTTTTTTAGTTTCGTGATGAAACAGAGTTCT
AGAAGTTCGTTCTTTTGGAAAATTTGAAGTCTTTGGAGCTAAAGTTTGTTTTTTTATTACTGGGTTTTGAGATTGA
AGGATAGCTAGAATCTTATTTGTGTGGGGGTTTGTTTTGAATATGTTTAATAGGATTCAAGAAGAAAGTTTATATG
GGAGGAGATGTCATATCTGGAGAGATGGTGGAGAGACGCTTCACCTAATAAACAAGAAGCTTTGACTAAATTGGTT
AAGGATGGGCAGCTAGAGATTGTTGGAGGTGGCTGGGTTATGAATGATGAGGCTAATTCACATTATTTTGCCATAA

FIG. 18

TTGAACAGATAGCAGAGGGTAATATGTGGCTGAATGACACAATTGGGGTTATTCCTAAGAATTCTTGGGCTATAGA
TCCCTTTGGCTATTCATCAACCATGGCTTATCTTCTCCGGCGTATGGGTTTTGAAAACATGCTTATTCAAAGGACT
CATTACGAGCTCAAGAAAGACCTTGCCCAGCATAAGAATCTTGAATATATTTGGCGTCAGAGCTGGGATGCTATGG
AAACCACAGATATCTTTGTTCATATGATGCCGTTTTATTCATACGATATCCCACACACTTGTGGACCAGAGCCTGC
AATTTGCTGTCAGTTTGATTTCGCTCGGATGCGGGGATTTAAGTATGAACTTTGTCCATGGGAAAGCACCCAGTG
GAGACCACACTAGAAAATGTGCAGGAGAGGGCATTAAAGCTTCTGGATCAATACAGGAAAAAATCCACTCTATATC
GAACTAATACACTTCTTATACCTCTTGGAGATGATTTTAGGTACATTAGTATCGATGAAGCCGAGGCTCAGTTCCG
TAACTACCAGATGTTGTTTGATCACATCAACTCTAATCCTAGTCTAAACGCAGAAGCAAAGTTTGGTACTTTGGAG
GATTATTTCAGAACAGTCCGAGAAGAAGCAGACAGAGTGAATTATTCTCGTCCTGGTGAGGTTGGCTCTGGTCAGG
TTGTTGGTTTCCCTTCTCTGTCAGGTGACTTCTTTACATATGCAGATAGGCAACAAGACTATTGGAGTGGTTATTA
TGTTTCAAGACCTTTCTTCAAAGCTGTTGATCGTGTGCTCGAGCATACCCTTCGTGGAGCTGAGATCATGATGTCA
TTTCTGCTAGGTTATTGCCATCGAATTCAATGTGAGAAATTTCCAACAAGTTTTACGTATAAGTTGA[illegible]GCTGCAA
GAAGAAATCTGGCTCTTTTCCAGCACCATGATGGGGTAACTGGAACTGCTAAGGATTATGTGGTACAAGATTACGG
CACCCGGATGCATACTTCATTGCAAGACCTTCAGATCTTTATGTCTAAAGCAATCGAAGTTCTTCTTGGGATCCGC
CACGAGAAAGAAAAATCTGATCAATCCCCATCATTTTTCGAGGCAGAGCAAATGAGATCAAAGTATGATGCTCGGC
CAGTTCACAAGCCAATTGCTGCCCGGGAAGGAAATTCGCACACAGTTATACTCTTCAATCCATCAGAACAGACGAG
AGAGGAGGTGGTGACGGTTGTTGTTAACCGCGCTGAAATCTCGGTTTTGGACTCAAACTGGACTTGTGTCCCTAGC
CAAATTTCTCCTGAAGTGCAGCATGACGATACCAAACTATTCACCGGCAGACATCGCCTTTACTGGAAAGCTTCCA
TCCCAGCTCTTGGTCTGAGAACATATTTCATTGCTAATGGGAATGTCGAGTGTGAGAAAGCTACTCCGTCTAAACT
CAAATACGCTTCTGAGTTTGACCCATTTCCTTGTCCTCCTCCATATTCCTGCTCCAAACTGGACAACGACGTTACT
GAGATCCGAAATGAACATCAGACTCTTGTGTTTGATGTGAAGAACGGATCACTGCGGAAGATAGTCCATAGAAACG
GATCAGAGACTGTTGTGGGAGAAGAGATAGGTATGTACTCTAGTCCAGAGAGTGGAGCTTACCTGTTCAAACCAGA
TGGTGAAGCTCAGCCAATTGTTCAACCTGATGGACATGTAGTCACCTCTGAGGGTCTGCTGGTTCAAGAAGTCTTC
TCTTACCCTAAAACCAAATGGGAGAAATCACCCCTCTCTCAGAAAACTCGTCTTTACACTGGAGGTAATACGCTTC
AGGATCAAGTGGTCGAGATAGAATATCATGTTGAGCTTCTTGGTAATGATTTTGATGACCGGGAATTGATTGTCCG
GTACAAGACTGATGTTGACAACAAGAAGGTCTTCTATTCAGATCTCAATGGTTTCCAAATGAGCAGGAGAGAAACT
TATGATAAGATCCCTCTTCAAGGAAACTACTACCCAATGCCATCTCTCGCATTTATCCAAGGATCCAATGGTCAGA

FIG. 18 Cont.

GATTCTCCGTGCACTCTCGTCAATCTCTCGGTGTTGCAAGCCTCAAAGAGGGTTGGTTGGAGATTATGCTGGACAG
ACGGTTGGTTCGTGATGACGGACGGGGTCTAGGGCAAGGTGTGATGGATAACCGCGCAATGACCGTGGTATTTCAC
CTTCTTGCGGAATCTAACATTTCTCAAGCAGACCCTGCTTCCAACACTAACCCGAGGAACCCTTCGCTTCTCTCTC
ACCTCATAGGTGCTCACTTAAACTACCCCATAAACACATTCATTGCCAAGAAACCGCAAGACATATCTGTGCGTGT
TCCACAATACGGTTCCTTTGCTCCTTTAGCCAAACCGTTACCATGTGACCTCCACATTGTAAATTTCAAGGTTCCT
CGTCCATCCAAATACTCTCAGCAATTGGAAGAAGACAAGCCAAGGTTCGCTCTTATCCTCAATAGACGAGCTTGGG
ATTCAGCTTATTGCCATAAAGGAAGACAAGTAAACTGCACAAGCATGGCTAATGAACCAGTAAACTTTTCCGACAT
GTTCAAAGATCTTGCAGCTTCAAAGGTAAAACCAACTTCACTGAATCTCTTGCAAGAAGATATGGAGATTCTTGGG
TACGATGACCAAGAGCTACCTCGAGATAGTTCACAGCCACGGGAAGGACGTGTCTCGATCTCTCCCATGGAAATAC
GAGCTTATAAGCTTGAACTGCGACCTCACAAGTGAACCTGCTGAAGATCCGCTAGAGTCCGCAAAAATCACCAGTC
TCTCTCTACAAATCTATCTCTCTCTATTTTTCTCCAGAATAATGTGTGAGTAGTTCCCAGATAAGGGAATTAGGGT
TCTTATAGGGTTTCGCTCATGTGTTGAGCATATAAGAAACCCTTAGTATGTATTTGTATTTGTAAAATACTTCTAT
CAATAAAATTTCTAATCCTAAAACCAAAATCCCGCGAGAGACCTCTTAATTAA

FIG. 18 Cont.

CCATGGCGAGGATCTCGTGTGACTTGAGATTTCTTCTCATCCCGGCAGCTTTCATGTTCATCTACATCCAGATGAG
GCTTTTCCAGACGCAATCACAGTATGCAGATCGCCTCAGTTCCGCTATCGAATCTGAGAACCATTGCACTAGTCAA
ATGCGAGGCCTCATAGATGAAGTTAGCATCAAACAGTCGCGGATTGTTGCCCTCGAAGATATGAAGAACCGCCAGG
ACGAAGAACTTGTGCAGCTTAAGGATCTAATCCAGACGTTTGAAAAAAAGGAATAGCAAAACTCACTCAAGGTGG
AGCCATGGATTCCAATTCAGGCGCCGTCGTTGATATCACAACTAAAGATCTATACGATAGGATTGAGTTTCTTGAT
ACAGATGGTGGTCCATGGAAACAAGGTTGGAGAGTTACGTATAAAGACGATGAGTGGGAGAAAGAGAAGCTCAAAA
TCTTCGTTGTTCCTCATTCTCATAACGATCCTGGTTGGAAATTGACTGTAGAGGAGTATTATCAGAGACAATCCAG
ACATATTCTTGACACCATTGTTGAGACTTTATCTAAGGTATGACGAAAGTTTTTGCTTTTGGTTTTAATATTTTAA
TTCTCTCCCATGGTTATCCCGTGAACAATCTTAAATGTCTTAAAATTCTCATGACGTCATTAAACTCTATAACCAA
ACTTCTTTGCTGGGTTCTGTTTTTTTTAGTTTCGTGATGAAACAGAGTTCTAGAAGTTCGTTCTTTTGGAAAATT
TGAAGTCTTTGGAGCTAAAGTTTGTTTTTTTATTACTGGGTTTTGAGATTGAAGGATAGCTAGAATCTTATTTGTG
TGGGGGTTTGTTTTGAATATGTTTAATAGGATTCAAGAAGAAAGTTTATATGGAGGAGATGTCATATCTGGAGAG
ATGGTGGAGAGACGCTTCACCTAATAAACAAGAAGCTTTGACTAAATTGGTTAAGGATGGGCAGCTAGAGATTGTT
GGAGGTGGCTGGGTTATGAATGATGAGGCTAATTCACATTATTTTGCCATAATTGAACAGATAGCAGAGGGTAATA
TGTGGCTGAATGACACAATTGGGGTTATTCCTAAGAATTCTTGGGCTATAGATCCCTTTGGCTATTCATCAACCAT
GGCTTATCTTCTCCGGCGTATGGGTTTTGAAAACATGCTTATTCAAAGGACTCATTACGAGCTCAAGAAAGACCTT
GCCCAGCATAAGAATCTTGAATATATTTGGCGTCAGAGCTGGGATGCTATGGAAACCACAGATATCTTTGTTCATA
TGATGCCGTTTTATTCATACGATATCCCACACACTTGTGGACCAGAGCCTGCAATTTGCTGTCAGTTTGATTTCGC
TCGGATGCGGGGATTTAAGTATGAACTTTGTCCATGGGGAAAGCACCCAGTGGAGACCACACTAGAAAATGTGCAG
GAGAGGGCATTAAAGCTTCTGGATCAATACAGGAAAAAATCCACTCTATATCGAACTAATACACTTCTTATACCTC
TTGGAGATGATTTTAGGTACATTAGTATCGATGAAGCCGAGGCTCAGTTCCGTAACTACCAGATGTTGTTTGATCA
CATCAACTCTAATCCTAGTCTAAACGCAGAAGCAAAGTTTGGTACTTTGGAGGATTATTTCAGAACAGTCCGAGAA
GAAGCAGACAGAGTGAATTATTCTCGTCCTGGTGAGGTTGGCTCTGGTCAGGTTGTTGGTTTCCCTTCTCTGTCAG
GTGACTTCTTTACATATGCAGATAGGCAACAAGACTATTGGAGTGGTTATTATGTTTCAAGACCTTTCTTCAAAGC
TGTTGATCGTGTGCTCGAGCATACCCTTCGTGGAGCTGAGATCATGATGTCATTTCTGCTAGGTTATTGCCATCGA
ATTCAATGTGAGAAATTTCCAACAAGTTTTACGTATAAGTTGACTGCTGCAAGAAGAAATCTGGCTCTTTTCCAGC

FIG. 19

ACCATGATGGGGTAACTGGAACTGCTAAGGATTATGTGGTACAAGATTACGGCACCCGGATGCATACTTCATTGCA
AGACCTTCAGATCTTTATGTCTAAAGCAATCGAAGTTCTTCTTGGGATCCGCCACGAGAAAGAAAAATCTGATCAA
TCCCCATCATTTTTCGAGGCAGAGCAAATGAGATCAAAGTATGATGCTCGGCCAGTTCACAAGCCAATTGCTGCCC
GGGAAGGAAATTCGCACACAGTTATACTCTTCAATCCATCAGAACAGACGAGAGAGGAGGTGGTGACGGTTGTTGT
TAACCGCGCTGAAATCTCGGTTTTGGACTCAAACTGGACTTGTGTCCCTAGCCAAATTTCTCCTGAAGTGCAGCAT
GACGATACCAAACTATTCACCGGCAGACATCGCCTTTACTGGAAAGCTTCCATCCCAGCTCTTGGTCTGAGAACAT
ATTTCATTGCTAATGGGAATGTCGAGTGTGAGAAAGCTACTCCGTCTAAACTCAAATACGCTTCTGAGTTTGACCC
ATTTCCTTGTCCTCCTCCATATTCCTGCTCCAAACTGGACAACGACGTTACTGAGATCCGAAATGAACATCAGACT
CTTGTGTTTGATGTGAAGAACGGATCACTGCGGAAGATAGTCCATAGAAACGGATCAGAGACTGTTGTGGGAGAAG
AGATAGGTATGTACTCTAGTCCAGAGAGTGGAGCTTACCTGTTCAAACCAGATGGTGAAGCTCAGCCAATTGTTCA
ACCTGATGGACATGTAGTCACCTCTGAGGGTCTGCTGGTTCAAGAAGTCTTCTCTTACCCTAAAACCAAATGGGAG
AAATCACCCCTCTCTCAGAAAACTCGTCTTTACACTGGAGGTAATACGCTTCAGGATCAAGTGGTCGAGATAGAAT
ATCATGTTGAGCTTCTTGGTAATGATTTTGATGACCGGGAATTGATTGTCCGGTACAAGACTGATGTTGACAACAA
GAAGGTCTTCTATTCAGATCTCAATGGTTTCCAAATGAGCAGGAGAGAAACTTATGATAAGATCCCTCTTCAAGGA
AACTACTACCCAATGCCATCTCTCGCATTTATCCAAGGATCCAATGGTCAGAGATTCTCCGTGCACTCTCGTCAAT
CTCTCGGTGTTGCAAGCCTCAAAGAGGGTTGGTTGGAGATTATGCTGGACAGACGGTTGGTTCGTGATGACGGACG
GGGTCTAGGGCAAGGTGTGATGGATAACCGCGCAATGACCGTGGTATTTCACCTTCTTGCGGAATCTAACATTTCT
CAAGCAGACCCTGCTTCCAACACTAACCCGAGGAACCCTTCGCTTCTCTCTCACCTCATAGGTGCTCACTTAAACT
ACCCCATAAACACATTCATTGCCAAGAAACCGCAAGACATATCTGTGCGTGTTCCACAATACGGTTCCTTTGCTCC
TTTAGCCAAACCGTTACCATGTGACCTCCACATTGTAAATTTCAAGGTTCCTCGTCCATCCAAATACTCTCAGCAA
TTGGAAGAAGACAAGCCAAGGTTCGCTCTTATCCTCAATAGACGAGCTTGGGATTCAGCTTATTGCCATAAAGGAA
GACAAGTAAACTGCACAAGCATGGCTAATGAACCAGTAAACTTTTCCGACATGTTCAAAGATCTTGCAGCTTCAAA
GGTAAAACCAACTTCACTGAATCTCTTGCAAGAAGATATGGAGATTCTTGGGTACGATGACCAAGAGCTACCTCGA
GATAGTTCACAGCCACGGGAAGGACGTGTCTCGATCTCTCCCATGGAAATACGAGCTTATAAGCTTGAACTGCGAC
CTCACAAGTGAACCTGCTGAAGATC

FIG. 19 Cont.

GGCGCGCCTCGAGGCGATCGCAGATCTCATTATACCGTTAGAAGCATAGTTAAAATCTAAAGCTTGTCGTTAATTC
TAGTCATTTTACATTGTTGGGTTCTACATTATTAATGAATTTTCTAATGCAAATACAGAATTTAAATCAAAATTGT
TGAATTATGCTAAACATGTAACATACGTATATCTCCGCCTTGTGTGTTGTATTAACTTGAAGTTATCATAAGAACC
ACAAATACACTAGTAAATCTATGAGAAGGCAGGTGGCAACACAAACAAGAGTATCTAAGATTTTCATTTGTGACTA
TAGGAATATAATATCTCTTATCTGATTTAATGAATCCACATGTTCACTTCTCATTTGTCCACAAGATCACAACTTT
ATCTTCAATATTCACAACTTGTTATATCCACCACAATTTCATTCTTTTCACTTAGCCCCACAAAATACTTTGTCCC
CTTATTTGCCACCTTTTGTATTTAATTTATTCTTGTGGAGCTAAGTGTTCATATTATTCTTCTTCTCAAAAAAACA
AAAACAAAAAAAAAGAGAAGAAAACCATGGCGAGGATCTCGTGTGACTTGAGATTTCTTCTCATCCCGGCAGCTTT
CATGTTCATCTACATCCAGATGAGGCTTTTCCAGACGCAATCACAGTATGCAGATCGCCTCAGTTCCGCTATCGAA
TCTGAGAACCATTGCACTAGTCAAATGCGAGGCCTCATAGATGAAGTTAGCATCAAACAGTCGCGGATTGTTGCCC
TCGAAGATATGAAGAACCGCCAGGACGAAGAACTTGTGCAGCTTAAGGATCTAATCCAGACGTTTGAAAAAAAAGG
AATAGCAAAACTCACTCAAGGTGGAGCCATGGCTCTAAGGTTGCATAGAAGGAACCATTTTTCGCCTAGAAATACG
GATCTGTTCCCGGATTTGGCAAAAGATCGTGTGGTTATCGTCTTGTATGTGCATAATCGGGCTCAGTATTTTCGAG
TCACAGTGGAAAGTTTGTCGAAGGTTAAAGGTATAAGTGAGACATTGTTGATTGTTAGTCATGATGGTTACTTTGA
AGAGATGAATAGGATTGTGGAGAGTATTAAGTTTTGTCAAGTGAAACAGATTTTCTCGCCTTATTCGCCTCATATA
TATCGTACTAGCTTCCCGGGTGTGACCCTGAATGATTGTAAGAACAAGGGTGATGAGGCAAAGGGGCATTGTGAAG
GTAATCCTGATCAGTATGGGAATCATCGGTCTCCGAAGATTGTATCTTTGAAGCATCACTGGTGGTGGATGATGAA
CACTGTATGGGATGGGTTGGAAGAGACTAAAGGACATGAGGGGCATATCCTTTTCATTGAAGAAGATCATTTTCTG
TTTCCTAATGCCTATCGTAACATACAGACTCTTACGAGGCTGAAACCCGCAAAGTGTCCTGACTGTTTTGCTGCTA
ATTTAGCACCGTCTGATGTGAAGTCAAGAGGAGAAGGGCTTGAAAGTTTGGTTGCAGAGAGAATGGGAAATGTTGG
GTATTCTTTTAATAGAAGTGTGTGGGAGAATATTCATCAGAAGGCAAGAGAGTTTTGTTTCTTTGATGATTACAAC
TGGGATATAACGATGTGGGCAACGGTTTTCCCGTCGTTTGGTTCCCCGGTGTACACATTGCGAGGGCCTAGGACTA
GTGCGGTACACTTTGGAAAATGTGGGTTGCATCAAGGTAGAGGAGATGAGGGTGATTGCATCGATAATGGGGTCGT
AAACATAGAAGTTAAGGAAACAGATAAAGTTGTGAACATAAAAGAAGGATGGGGAGTTCGGGTGTATAAGCATCAA
GCGGGTTATAAAGCCGGTTTCGAAGGTTGGGGAGGTTGGGGCGATGATAGGGACCGACATTTATGTTTGGATTTTG
CCACTATGTATCGTTACAGCAGTAGCAGTGCATCTCCATGAAACGGATCCGCTAGAGTCCGCAAAAATCACCAGTC
TCTCTCTACAAATCTATCTCTCTCTATTTTTCTCCAGAATAATGTGTGAGTAGTTCCCAGATAAGGGAATTAGGGT
TCTTATAGGGTTTCGCTCATGTGTTGAGCATATAAGAAACCCTTAGTATGTATTTGTATTTGTAAAATACTTCTAT
CAATAAAATTTCTAATCCTAAAACCAAAATCCCGCGAGAGACCTCTTAATTAA

FIG. 20

CCATGGCGAGGATCTCGTGTGACTTGAGATTTCTTCTCATCCCGGCAGCTTTCATGTTCATCTACATCCAGATGAG
GCTTTTCCAGACGCAATCACAGTATGCAGATCGCCTCAGTTCCGCTATCGAATCTGAGAACCATTGCACTAGTCAA
ATGCGAGGCCTCATAGATGAAGTTAGCATCAAACAGTCGCGGATTGTTGCCCTCGAAGATATGAAGAACCGCCAGG
ACGAAGAACTTGTGCAGCTTAAGGATCTAATCCAGACGTTTGAAAAAAAAGGAATAGCAAAACTCACTCAAGGTGG
AGCCATGGCTCTAAGGTTGCATAGAAGGAACCATTTTTCGCCTAGAAATACGGATCTGTTCCCGGATTTGGCAAAA
GATCGTGTGGTTATCGTCTTGTATGTGCATAATCGGGCTCAGTATTTTCGAGTCACAGTGGAAAGTTTGTCGAAGG
TTAAAGGTATAAGTGAGACATTGTTGATTGTTAGTCATGATGGTTACTTTGAAGAGATGAATAGGATTGTGGAGAG
TATTAAGTTTTGTCAAGTGAAACAGATTTTCTCGCCTTATTCGCCTCATATATATCGTACTAGCTTCCCGGGTGTG
ACCCTGAATGATTGTAAGAACAAGGGTGATGAGGCAAAGGGGCATTGTGAAGGTAATCCTGATCAGTATGGGAATC
ATCGGTCTCCGAAGATTGTATCTTTGAAGCATCACTGGTGGTGGATGATGAACACTGTATGGGATGGGTTGGAAGA
GACTAAAGGACATGAGGGGCATATCCTTTTCATTGAAGAAGATCATTTTCTGTTTCCTAATGCCTATCGTAACATA
CAGACTCTTACGAGGCTGAAACCCGCAAAGTGTCCTGACTGTTTTGCTGCTAATTTAGCACCGTCTGATGTGAAGT
CAAGAGGAGAAGGGCTTGAAAGTTTGGTTGCAGAGAGAATGGGAAATGTTGGGTATTCTTTTAATAGAAGTGTGTG
GGAGAATATTCATCAGAAGGCAAGAGAGTTTTGTTTCTTTGATGATTACAACTGGGATATAACGATGTGGGCAACG
GTTTTCCCGTCGTTTGGTTCCCCGGTGTACACATTGCGAGGGCCTAGGACTAGTGCGGTACACTTTGGAAAATGTG
GGTTGCATCAAGGTAGAGGAGATGAGGGTGATTGCATCGATAATGGGGTCGTAAACATAGAAGTTAAGGAAACAGA
TAAAGTTGTGAACATAAAAGAAGGATGGGGAGTTCGGGTGTATAAGCATCAAGCGGGTTATAAAGCCGGTTTCGAA
GGTTGGGGAGGTTGGGGCGATGATAGGGACCGACATTTATGTTTGGATTTTGCCACTATGTATCGTTACAGCAGTA
GCAGTGCATCTCCATGAAACGGATCC

FIG. 21

CCATGGCGAGGATCTCGTGTGACTTGAGATTTCTTCTCATCCCGGCAGCTTTCATGTTCATCTACATCCAGATGAG
GCTTTTCCAGACGCAATCACAGTATGCAGATCGCCTCAGTTCCGCTATCGAATCTGAGAACCATTGCACTAGTCAA
ATGCGAGGCCTCATAGATGAAGTTAGCATCAAACAGTCGCGGATTGTTGCCCTCGAAGATATGAAGAACCGCCAGG
ACGAAGAACTTGTGCAGCTTAAGGATCTAATCCAGACGTTTGAAAAAAAAGGAATAGCAAAACTCACTCAAGGTGG
AGCCATGG

FIG. 22A

CCATGGCGAGAGGGAGCAGATCAGTGGGTAGCAGCAGCAGCAAATGGAGGTACTGCAACCCTTCCTATTACTTGAA
GCGCCCAAAGCGTCTTGCTCTGCTCTTCATCGTTTTCGTTTGTGTCTCTTTCGTTTTCTGGGACCGTCAAACTCTC
GTCAGAGAGCACCAGGTTGAAATTTCTGAGCTGCAGAAAGAAGTGACTGATTTGAAAAATTTGGTGGATGATTTAA
ATAACAAACAAGGTGGTACCTCTGGGAAAACTGACTTGGGGACCATGG

FIG. 22B

GGCGCGCCTCGAGGCGATCGCAGATCCGATATAACAAAATTTGAATCGCACAGATCGATCTCTTTGGAGATTCTAT
ACCTAGAAAATGGAGACGATTTTCAAATCTCTGTAAAAATTCTGGTTTCTTCTTGACGGAAGAAGACGACGACTCC
AATATTTCGGTTAGTACTGAACCGGAAAGTTTGACTGGTGCAACCAATTTAATGTACCGTACGTAACGCACCAATC
GGATTTTGTATTCAATGGGCCTTATCTGTGAGCCCATTAATTGATGTGACGGCCTAAACTAAATCCGAACGGTTTA
TTTCAGCGATCCGCGACGGTTTGTATTCAGCCAATAGCAATCAATTATGTAGCAGTGGTGATCCTCGTCAAACCAG
TAAAGCTAGATCTGGACCGTTGAATTGGTGCAAGAAAGCACATGTTGTGATATTTTTACCCGTACGATTAGAAAAC
TTGAGAAACACATTGATAATCGATAAAAACCGTCCGATCATATAAATCCGCTTTACCATCGTTGCCTATAAATTAA
TATCAATAGCCGTACACGCGTGAAGACTGACAATATTATCTTTTTCGAATTCGGAGCTCAAGTTTGAAATTCGGAG
AAGCTAGAGAGTTTTCTGATAACCATGGCGAGAGGGAGCAGATCAGTGGGTAGCAGCAGCAGCAAATGGAGGTACT
GCAACCCTTCCTATTACTTGAAGCGCCCAAAGCGTCTTGCTCTGCTCTTCATCGTTTTCGTTTGTGTCTCTTTCGT
TTTCTGGGACCGTCAAACTCTCGTCAGAGAGCACCAGGTTGAAATTTCTGAGCTGCAGAAAGAAGTGACTGATTTG
AAAAATTTGGTGGATGATTTAAATAACAAACAAGGTGGTACCTCTGGGAAAACTGACTTGGGGACCATGGGACAGA
TGCCTGTGGCTGCTGTAGTGGTTATGGCCTGCAGTCGTGCAGACTATCTTGAAAGGACTGTTAAATCAGTTTTAAC
ATATCAAACTCCCGTTGCTTCAAAATATCCTCTATTTATATCTCAGGATGGATCTGATCAAGCTGTCAAGAGCAAG
TCATTGAGCTATAATCAATTAACATATATGCAGCACTTGGATTTTGAACCAGTGGTCACTGAAAGGCCTGGCGAAC
TGACTGCGTACTACAAGATTGCACGTCACTACAAGTGGGCACTGGACCAGTTGTTTTACAAACACAAATTTAGTCG
AGTGATTATACTAGAAGATGATATGGAAATTGCTCCAGACTTCTTTGATTACTTTGAGGCTGCAGCTAGTCTCATG
GATAGGGATAAAACCATTATGGCTGCTTCATCATGGAATGATAATGGACAGAAGCAGTTTGTGCATGATCCCTATG
CGCTATACCGATCAGATTTTTTCCTGGCCTTGGGTGGATGCTCAAGAGATCGACTTGGGATGAGTTATCACCAAA
GTGGCCAAAGGCTTACTGGGATGATTGGCTGAGACTAAAGGAAAACCATAAAGGCCGCCAATTCATTCGACCGGAA
GTCTGTAGAACATACAATTTTGGTGAACATGGGTCTAGTTTGGGACAGTTTTTCAGTCAGTATCTGGAACCTATAA
AGCTAAACGATGTGACGGTTGACTGGAAAGCAAAGGACCTGGGATACCTGACAGAGGGAAACTATACCAAGTACTT
TTCTGGCTTAGTGAGACAAGCACGACCAATTCAAGGTTCTGACCTTGTCTTAAAGGCTCAAAACATAAAGGATGAT
GTTCGTATCCGGTATAAAGACCAAGTAGAGTTTGAACGCATTGCAGGGGAATTTGGTATATTTGAAGAATGGAAGG
ATGGTGTGCCTCGAACAGCATATAAAGGAGTAGTGGTGTTTCGAATCCAGACAACAAGACGTGTATTCCTGGTTGG
GCCAGATTCTGTAATGCAGCTTGGAATTCGAAATTCCTGATGCGGATCCGCTAGAGTCCGCAAAAATCACCAGTCT
CTCTCTACAAATCTATCTCTCTCTATTTTTCTCCAGAATAATGTGTGAGTAGTTCCCAGATAAGGGAATTAGGGTT

FIG. 23

CTTATAGGGTTTCGCTCATGTGTTGAGCATATAAGAAACCCTTAGTATGTATTTGTATTTGTAAAATACTTCTATC
AATAAAATTTCTAATCCTAAAACCAAAATCCCGCGCCTCGAGGCGATCGCAGATCTAATCTAACCAATTACGATAC
GCTTTGGGTACACTTGATTTTTGTTTCAGTGGTTACATATATCTTGTTTTATATGCTATCTTTAAGGATCTGCACA
AAGATTATTTGTTGATGTTCTTGATGGGGCTCAGAAGATTTGATATGATACACTCTAATCTTTAGGAGATACCAGC
CAGGATTATATTCAGTAAGACAATCAAATTTTACGTGTTCAAACTCGTTATCTTTTCATTCAAAGGATGAGCCAGA
ATCTTTATAGAATGATTGCAATCGAGAATATGTTCGGCCGATATGCCTTTGTTGGCTTCAATATTCTACATATCAC
ACAAGAATCGACCGTATTGTACCCTCTTTCCATAAAGGAAAACACAATATGCAGATGCTTTTTTCCCACATGCAGT
AACATATAGGTATTCAAAAATGGCTAAAAGAAGTTGGATAACAAATTGACAACTATTTCCATTTCTGTTATATAAA
TTTCACAACACACAAAAGCCCGTAATCAAGAGTCTGCCCATGTACGAAATAACTTCTATTATTTGGTATTGGGCCT
AAGCCCAGCTCAGAGTACGTGGGGGTACCACATATAGGAAGGTAACAAAATACTGCAAGATAGCCCCATAACGTAC
CAGCCTCTCCTTACCACGAAGAGATAAGATATAAGACCCACCCTGCCACGTGTCACATCGTCATGGTGGTTAATGA
TAAGGGATTACATCCTTCTATGTTTGTGGACATGATGCATGTAATGTCATGAGCCACAGGATCCAATGGCCACAGG
AACGTAAGAATGTAGATAGATTTGATTTTGTCCGTTAGATAGCAAACAACATTATAAAAGGTGTGTATCAATAGGA
ACTAATTCACTCATTGGATTCATAGAAGTCCATTCCTCCTAAGTATCTAGAAACCATGGCGAGAGGGAGCAGATCA
GTGGGTAGCAGCAGCAGCAAATGGAGGTACTGCAACCCTTCCTATTACTTGAAGCGCCCAAAGCGTCTTGCTCTGC
TCTTCATCGTTTTCGTTTGTGTCTCTTTCGTTTTCTGGGACCGTCAAACTCTCGTCAGAGAGCACCAGGTTGAAAT
TTCTGAGCTGCAGAAAGAAGTGACTGATTTGAAAAATTTGGTGGATGATTTAAATAACAAACAAGGTGGTACCTCT
GGGAAAACTGACTTGGGGACCATGGATTCCAATTCAGGCGCCGTCGTTGATATCACAACTAAAGATCTATACGATA
GGATTGAGTTTCTTGATACAGATGGTGGTCCATGGAAACAAGGTTGGAGAGTTACGTATAAAGACGATGAGTGGGA
GAAAGAGAAGCTCAAAATCTTCGTTGTTCCTCATTCTCATAACGATCCTGGTTGGAAATTGACTGTAGAGGAGTAT
TATCAGAGACAATCCAGACATATTCTTGACACCATTGTTGAGACTTTATCTAAGGTATGACGAAAGTTTTTGCTTT
TGGTTTTAATATTTTAATTCTCTCCCATGGTTATCCCGTGAACAATCTTAAATGTCTTAAAATTCTCATGACGTCA
TTAAACTCTATAACCAAACTTCTTTGCTGGGTTCTGTTTTTTTTAGTTTCGTGATGAAACAGAGTTCTAGAAGTT
CGTTCTTTTGGAAAATTTGAAGTCTTTGGAGCTAAAGTTTGTTTTTTTATTACTGGGTTTTGAGATTGAAGGATAG
CTAGAATCTTATTTGTGTGGGGGTTTGTTTTGAATATGTTTAATAGGATTCAAGAAGAAAGTTTATATGGGAGGAG
ATGTCATATCTGGAGAGATGGTGGAGAGACGCTTCACCTAATAAACAAGAAGCTTTGACTAAATTGGTTAAGGATG
GGCAGCTAGAGATTGTTGGAGGTGGCTGGGTTATGAATGATGAGGCTAATTCACATTATTTTGCCATAATTGAACA

FIG. 23 Cont.

GATAGCAGAGGGTAATATGTGGCTGAATGACACAATTGGGGTTATTCCTAAGAATTCTTGGGCTATAGATCCCTTT
GGCTATTCATCAACCATGGCTTATCTTCTCCGGCGTATGGGTTTTGAAAACATGCTTATTCAAAGGACTCATTACG
AGCTCAAGAAAGACCTTGCCCAGCATAAGAATCTTGAATATATTTGGCGTCAGAGCTGGGATGCTATGGAAACCAC
AGATATCTTTGTTCATATGATGCCGTTTTATTCATACGATATCCCACACACTTGTGGACCAGAGCCTGCAATTTGC
TGTCAGTTTGATTTCGCTCGGATGCGGGGATTTAAGTATGAACTTTGTCCATGGGAAAGCACCCAGTGGAGACCA
CACTAGAAAATGTGCAGGAGAGGGCATTAAAGCTTCTGGATCAATACAGGAAAAAATCCACTCTATATCGAACTAA
TACACTTCTTATACCTCTTGGAGATGATTTTAGGTACATTAGTATCGATGAAGCCGAGGCTCAGTTCCGTAACTAC
CAGATGTTGTTTGATCACATCAACTCTAATCCTAGTCTAAACGCAGAAGCAAAGTTTGGTACTTTGGAGGATTATT
TCAGAACAGTCCGAGAAGAAGCAGACAGAGTGAATTATTCTCGTCCTGGTGAGGTTGGCTCTGGTCAGGTTGTTGG
TTTCCCTTCTCTGTCAGGTGACTTCTTTACATATGCAGATAGGCAACAAGACTATTGGAGTGGTTATTATGTTTCA
AGACCTTTCTTCAAAGCTGTTGATCGTGTGCTCGAGCATACCCTTCGTGGAGCTGAGATCATGATGTCATTTCTGC
TAGGTTATTGCCATCGAATTCAATGTGAGAAATTTCCAACAAGTTTTACGTATAAGTTGACTGCTGCAAGAAGAAA
TCTGGCTCTTTTCCAGCACCATGATGGGGTAACTGGAACTGCTAAGGATTATGTGGTACAAGATTACGGCACCCGG
ATGCATACTTCATTGCAAGACCTTCAGATCTTTATGTCTAAAGCAATCGAAGTTCTTCTTGGGATCCGCCACGAGA
AAGAAAAATCTGATCAATCCCCATCATTTTTCGAGGCAGAGCAAATGAGATCAAAGTATGATGCTCGGCCAGTTCA
CAAGCCAATTGCTGCCCGGGAAGGAAATTCGCACACAGTTATACTCTTCAATCCATCAGAACAGACGAGAGAGGAG
GTGGTGACGGTTGTTGTTAACCGCGCTGAAATCTCGGTTTTGGACTCAAACTGGACTTGTGTCCCTAGCCAAATTT
CTCCTGAAGTGCAGCATGACGATACCAAACTATTCACCGGCAGACATCGCCTTTACTGGAAAGCTTCCATCCCAGC
TCTTGGTCTGAGAACATATTTCATTGCTAATGGGAATGTCGAGTGTGAGAAAGCTACTCCGTCTAAACTCAAATAC
GCTTCTGAGTTTGACCCATTTCCTTGTCCTCCTCCATATTCCTGCTCCAAACTGGACAACGACGTTACTGAGATCC
GAAATGAACATCAGACTCTTGTGTTTGATGTGAAGAACGGATCACTGCGGAAGATAGTCCATAGAAACGGATCAGA
GACTGTTGTGGGAGAAGAGATAGGTATGTACTCTAGTCCAGAGAGTGGAGCTTACCTGTTCAAACCAGATGGTGAA
GCTCAGCCAATTGTTCAACCTGATGGACATGTAGTCACCTCTGAGGGTCTGCTGGTTCAAGAAGTCTTCTCTTACC
CTAAAACCAAATGGGAGAAATCACCCCTCTCTCAGAAAACTCGTCTTTACACTGGAGGTAATACGCTTCAGGATCA
AGTGGTCGAGATAGAATATCATGTTGAGCTTCTTGGTAATGATTTTGATGACCGGGAATTGATTGTCCGGTACAAG
ACTGATGTTGACAACAAGAAGGTCTTCTATTCAGATCTCAATGGTTTCCAAATGAGCAGGAGAGAAACTTATGATA
AGATCCCTCTTCAAGGAAACTACTACCCAATGCCATCTCTCGCATTTATCCAAGGATCCAATGGTCAGAGATTCTC

FIG. 23 Cont.

CGTGCACTCTCGTCAATCTCTCGGTGTTGCAAGCCTCAAAGAGGGTTGGTTGGAGATTATGCTGGACAGACGGTTG
GTTCGTGATGACGGACGGGGTCTAGGGCAAGGTGTGATGGATAACCGCGCAATGACCGTGGTATTTCACCTTCTTG
CGGAATCTAACATTTCTCAAGCAGACCCTGCTTCCAACACTAACCCGAGGAACCCTTCGCTTCTCTCTCACCTCAT
AGGTGCTCACTTAAACTACCCCATAAACACATTCATTGCCAAGAAACCGCAAGACATATCTGTGCGTGTTCCACAA
TACGGTTCCTTTGCTCCTTTAGCCAAACCGTTACCATGTGACCTCCACATTGTAAATTTCAAGGTTCCTCGTCCAT
CCAAATACTCTCAGCAATTGGAAGAAGACAAGCCAAGGTTCGCTCTTATCCTCAATAGACGAGCTTGGGATTCAGC
TTATTGCCATAAAGGAAGACAAGTAAACTGCACAAGCATGGCTAATGAACCAGTAAACTTTTCCGACATGTTCAAA
GATCTTGCAGCTTCAAAGGTAAAACCAACTTCACTGAATCTCTTGCAAGAAGATATGGAGATTCTTGGGTACGATG
ACCAAGAGCTACCTCGAGATAGTTCACAGCCACGGGAAGGACGTGTCTCGATCTCTCCCATGGAAATACGAGCTTA
TAAGCTTGAACTGCGACCTCACAAGTGAACCTGCTGAAGATCCGCTAGAGTCCGCAAAAATCACCAGTCTCTCTCT
ACAAATCTATCTCTCTCTATTTTTCTCCAGAATAATGTGTGAGTAGTTCCCAGATAAGGGAATTAGGGTTCTTATA
GGGTTTCGCTCATGTGTTGAGCATATAAGAAACCCTTAGTATGTATTTGTATTTGTAAAATACTTCTATCAATAAA
ATTTCTAATCCTAAAACCAAAATCCCGCGCGCCTCGAGGCGATCGCAGATCTCATTATACCGTTAGAAGCATAG
TTAAAATCTAAAGCTTGTCGTTAATTCTAGTCATTTTACATTGTTGGGTTCTACATTATTAATGAATTTTCTAATG
CAAATACAGAATTTAAATCAAAATTGTTGAATTATGCTAAACATGTAACATACGTATATCTCCGCCTTGTGTGTTG
TATTAACTTGAAGTTATCATAAGAACCACAAATACACTAGTAAATCTATGAGAAGGCAGGTGGCAACACAAACAAG
AGTATCTAAGATTTTCATTTGTGACTATAGGAATATAATATCTCTTATCTGATTTAATGAATCCACATGTTCACTT
CTCATTTGTCCACAAGATCACAACTTTATCTTCAATATTCACAACTTGTTATATCCACCACAATTTCATTCTTTTC
ACTTAGCCCCACAAAATACTTTGTCCCCTTATTTGCCACCTTTTGTATTTAATTTATTCTTGTGGAGCTAAGTGTT
CATATTATTCTTCTTCTCAAAAAAACAAAAACAAAAAAAAAGAGAAGAAAACCATGGCGAGAGGGAGCAGATCAGT
GGGTAGCAGCAGCAGCAAATGGAGGTACTGCAACCCTTCCTATTACTTGAAGCGCCCAAAGCGTCTTGCTCTGCTC
TTCATCGTTTTCGTTTGTGTCTCTTTCGTTTTCTGGGACCGTCAAACTCTCGTCAGAGAGCACCAGGTTGAAATTT
CTGAGCTGCAGAAAGAAGTGACTGATTTGAAAAATTTGGTGGATGATTTAAATAACAAACAAGGTGGTACCTCTGG
GAAAACTGACTTGGGGACCATGGCTCTAAGGTTGCATAGAAGGAACCATTTTTCGCCTAGAAATACGGATCTGTTC
CCGGATTTGGCAAAAGATCGTGTGGTTATCGTCTTGTATGTGCATAATCGGGCTCAGTATTTTCGAGTCACAGTGG
AAAGTTTGTCGAAGGTTAAAGGTATAAGTGAGACATTGTTGATTGTTAGTCATGATGGTTACTTTGAAGAGATGAA
TAGGATTGTGGAGAGTATTAAGTTTTGTCAAGTGAAACAGATTTTCTCGCCTTATTCGCCTCATATATATCGTACT

FIG. 23 Cont.

AGCTTCCCGGGTGTGACCCTGAATGATTGTAAGAACAAGGGTGATGAGGCAAAGGGGCATTGTGAAGGTAATCCTG
ATCAGTATGGGAATCATCGGTCTCCGAAGATTGTATCTTTGAAGCATCACTGGTGGTGGATGATGAACACTGTATG
GGATGGGTTGGAAGAGACTAAAGGACATGAGGGGCATATCCTTTTCATTGAAGAAGATCATTTTCTGTTTCCTAAT
GCCTATCGTAACATACAGACTCTTACGAGGCTGAAACCCGCAAAGTGTCCTGACTGTTTTGCTGCTAATTTAGCAC
CGTCTGATGTGAAGTCAAGAGGAGAAGGGCTTGAAAGTTTGGTTGCAGAGAGAATGGGAAATGTTGGGTATTCTTT
TAATAGAAGTGTGTGGGAGAATATTCATCAGAAGGCAAGAGAGTTTTGTTTCTTTGATGATTACAACTGGGATATA
ACGATGTGGGCAACGGTTTTCCCGTCGTTTGGTTCCCCGGTGTACACATTGCGAGGGCCTAGGACTAGTGCGGTAC
ACTTTGGAAAATGTGGGTTGCATCAAGGTAGAGGAGATGAGGGTGATTGCATCGATAATGGGGTCGTAAACATAGA
AGTTAAGGAAACAGATAAAGTTGTGAACATAAAAGAAGGATGGGGAGTTCGGGTGTATAAGCATCAAGCGGGTTAT
AAAGCCGGTTTCGAAGGTTGGGGAGGTTGGGGCGATGATAGGGACCGACATTTATGTTTGGATTTTGCCACTATGT
ATCGTTACAGCAGTAGCAGTGCATCTCCATGAAACGGATCCGCTAGAGTCCGCAAAAATCACCAGTCTCTCTCTAC
AAATCTATCTCTCTCTATTTTTCTCCAGAATAATGTGTGAGTAGTTCCCAGATAAGGGAATTAGGGTTCTTATAGG
GTTTCGCTCATGTGTTGAGCATATAAGAAACCCTTAGTATGTATTTGTATTTGTAAAATACTTCTATCAATAAAAT
TTCTAATCCTAAAACCAAAATCCCGCGAGAGACCTCTTAATTAA

FIG. 23 Cont.

GGCGCGCCTCGAGGCGATCGCAGATCCGATATAACAAAATTTGAATCGCACAGATCGATCTCTTTGGAGATTCTAT
ACCTAGAAAATGGAGACGATTTTCAAATCTCTGTAAAAATTCTGGTTTCTTCTTGACGGAAGAAGACGACGACTCC
AATATTTCGGTTAGTACTGAACCGGAAAGTTTGACTGGTGCAACCAATTTAATGTACCGTACGTAACGCACCAATC
GGATTTTGTATTCAATGGGCCTTATCTGTGAGCCCATTAATTGATGTGACGGCCTAAACTAAATCCGAACGGTTTA
TTTCAGCGATCCGCGACGGTTTGTATTCAGCCAATAGCAATCAATTATGTAGCAGTGGTGATCCTCGTCAAACCAG
TAAAGCTAGATCTGGACCGTTGAATTGGTGCAAGAAAGCACATGTTGTGATATTTTTACCCGTACGATTAGAAAAC
TTGAGAAACACATTGATAATCGATAAAAACCGTCCGATCATATAAATCCGCTTTACCATCGTTGCCTATAAATTAA
TATCAATAGCCGTACACGCGTGAAGACTGACAATATTATCTTTTTCGAATTCGGAGCTCAAGTTTGAAATTCGGAG
AAGCTAGAGAGTTTTCTGATAACCATGGCGAGAGGGAGCAGATCAGTGGGTAGCAGCAGCAGCAAATGGAGGTACT
GCAACCCTTCCTATTACTTGAAGCGCCCAAAGCGTCTTGCTCTGCTCTTCATCGTTTTCGTTTGTGTCTCTTTCGT
TTTCTGGGACCGTCAAACTCTCGTCAGAGAGCACCAGGTTGAAATTTCTGAGCTGCAGAAAGAAGTGACTGATTTG
AAAAATTTGGTGGATGATTTAAATAACAAACAAGGTGGTACCTCTGGGAAAACTGACTTGGGGACCATGGGACAGA
TGCCTGTGGCTGCTGTAGTGGTTATGGCCTGCAGTCGTGCAGACTATCTTGAAAGGACTGTTAAATCAGTTTTAAC
ATATCAAACTCCCGTTGCTTCAAAATATCCTCTATTTATATCTCAGGATGGATCTGATCAAGCTGTCAAGAGCAAG
TCATTGAGCTATAATCAATTAACATATATGCAGCACTTGGATTTTGAACCAGTGGTCACTGAAAGGCCTGGCGAAC
TGACTGCGTACTACAAGATTGCACGTCACTACAAGTGGGCACTGGACCAGTTGTTTACAAACACAAATTTAGTCG
AGTGATTATACTAGAAGATGATATGGAAATTGCTCCAGACTTCTTTGATTACTTTGAGGCTGCAGCTAGTCTCATG
GATAGGGATAAAACCATTATGGCTGCTTCATCATGGAATGATAATGGACAGAAGCAGTTTGTGCATGATCCCTATG
CGCTATACCGATCAGATTTTTTTCCTGGCCTTGGGTGGATGCTCAAGAGATCGACTTGGGATGAGTTATCACCAAA
GTGGCCAAAGGCTTACTGGGATGATTGGCTGAGACTAAAGGAAAACCATAAAGGCCGCCAATTCATTCGACCGGAA
GTCTGTAGAACATACAATTTTGGTGAACATGGGTCTAGTTTGGGACAGTTTTTCAGTCAGTATCTGGAACCTATAA
AGCTAAACGATGTGACGGTTGACTGGAAAGCAAAGGACCTGGGATACCTGACAGAGGGAAACTATACCAAGTACTT
TTCTGGCTTAGTGAGACAAGCACGACCAATTCAAGGTTCTGACCTTGTCTTAAAGGCTCAAAACATAAAGGATGAT
GTTCGTATCCGGTATAAAGACCAAGTAGAGTTTGAACGCATTGCAGGGGAATTTGGTATATTTGAAGAATGGAAGG
ATGGTGTGCCTCGAACAGCATATAAAGGAGTAGTGGTGTTTCGAATCCAGACAACAAGACGTGTATTCCTGGTTGG
GCCAGATTCTGTAATGCAGCTTGGAATTCGAAATTCCTGATGCGGATCCGCTAGAGTCCGCAAAAATCACCAGTCT
CTCTCTACAAATCTATCTCTCTCTATTTTTCTCCAGAATAATGTGTGAGTAGTTCCCAGATAAGGGAATTAGGGTT
CTTATAGGGTTTCGCTCATGTGTTGAGCATATAAGAAACCCTTAGTATGTATTTGTATTTGTAAAATACTTCTATC

FIG. 24

GGATCCGATATAACAAAATTTGAATCGCACAGATCGATCTCTTTGGAGATTCTATACCTAGAAAATGGAGACGATT
TTCAAATCTCTGTAAAAATTCTGGTTTCTTCTTGACGGAAGAAGACGACGACTCCAATATTTCGGTTAGTACTGAA
CCGGAAAGTTTGACTGGTGCAACCAATTTAATGTACCGTACGTAACGCACCAATCGGATTTTGTATTCAATGGGCC
TTATCTGTGAGCCCATTAATTGATGTGACGGCCTAAACTAAATCCGAACGGTTTATTTCAGCGATCCGCGACGGTT
TGTATTCAGCCAATAGCAATCAATTATGTAGCAGTGGTGATCCTCGTCAAACCAGTAAAGCTAGATCTGGACCGTT
GAATTGGTGCAAGAAAGCACATGTTGTGATATTTTTACCCGTACGATTAGAAAACTTGAGAAACACATTGATAATC
GATAAAAACCGTCCGATCATATAAATCCGCTTTACCATCGTTGCCTATAAATTAATATCAATAGCCGTACACGCGT
GAAGACTGACAATATTATCTTTTTCGAATTCGGAGCTCAAGTTTGAAATTCGGAGAAGCTAGAGAGTTTTCTGATA
ACCATGG

FIG. 25

CCATGGCGAGAGGGAGCAGATCAGTGGGTAGCAGCAGCAGCAAATGGAGGTACTGCAACCCTTCCTATTACTTGAA
GCGCCCAAAGCGTCTTGCTCTGCTCTTCATCGTTTTCGTTTGTGTCTCTTTCGTTTTCTGGGACCGTCAAACTCTC
GTCAGAGAGCACCAGGTTGAAATTTCTGAGCTGCAGAAAGAAGTGACTGATTTGAAAAATTTGGTGGATGATTTAA
ATAACAAACAAGGTGGTACCTCTGGGAAAACTGACTTGGGGACCATGGGACAGATGCCTGTGGCTGCTGTAGTGGT
TATGGCCTGCAGTCGTGCAGACTATCTTGAAAGGACTGTTAAATCAGTTTTAACATATCAAACTCCCGTTGCTTCA
AAATATCCTCTATTTATATCTCAGGATGGATCTGATCAAGCTGTCAAGAGCAAGTCATTGAGCTATAATCAATTAA
CATATATGCAGCACTTGGATTTTGAACCAGTGGTCACTGAAAGGCCTGGCGAACTGACTGCGTACTACAAGATTGC
ACGTCACTACAAGTGGGCACTGGACCAGTTGTTTTACAAACACAAATTTAGTCGAGTGATTATACTAGAAGATGAT
ATGGAAATTGCTCCAGACTTCTTTGATTACTTTGAGGCTGCAGCTAGTCTCATGGATAGGGATAAAACCATTATGG
CTGCTTCATCATGGAATGATAATGGACAGAAGCAGTTTGTGCATGATCCCTATGCGCTATACCGATCAGATTTTTT
TCCTGGCCTTGGGTGGATGCTCAAGAGATCGACTTGGGATGAGTTATCACCAAAGTGGCCAAAGGCTTACTGGGAT
GATTGGCTGAGACTAAAGGAAAACCATAAAGGCCGCCAATTCATTCGACCGGAAGTCTGTAGAACATACAATTTTG
GTGAACATGGGTCTAGTTTGGGACAGTTTTTCAGTCAGTATCTGGAACCTATAAAGCTAAACGATGTGACGGTTGA
CTGGAAAGCAAAGGACCTGGGATACCTGACAGAGGGAAACTATACCAAGTACTTTTCTGGCTTAGTGAGACAAGCA
CGACCAATTCAAGGTTCTGACCTTGTCTTAAAGGCTCAAAACATAAAGGATGATGTTCGTATCCGGTATAAAGACC
AAGTAGAGTTTGAACGCATTGCAGGGGAATTTGGTATATTTGAAGAATGGAAGGATGGTGTGCCTCGAACAGCATA
TAAAGGAGTAGTGGTGTTTCGAATCCAGACAACAAGACGTGTATTCCTGGTTGGGCCAGATTCTGTAATGCAGCTT
GGAATTCGAAATTCCTGATGCGGATCC

FIG. 26

GGCGCGCCTCGAGGCGATCGCAGATCTAATCTAACCAATTACGATACGCTTTGGGTACACTTGATTTTTGTTTCAG
TGGTTACATATATCTTGTTTTATATGCTATCTTTAAGGATCTGCACAAAGATTATTTGTTGATGTTCTTGATGGGG
CTCAGAAGATTTGATATGATACACTCTAATCTTTAGGAGATACCAGCCAGGATTATATTCAGTAAGACAATCAAAT
TTTACGTGTTCAAACTCGTTATCTTTTCATTCAAAGGATGAGCCAGAATCTTTATAGAATGATTGCAATCGAGAAT
ATGTTCGGCCGATATGCCTTTGTTGGCTTCAATATTCTACATATCACACAAGAATCGACCGTATTGTACCCTCTTT
CCATAAAGGAAAACACAATATGCAGATGCTTTTTCCCACATGCAGTAACATATAGGTATTCAAAAATGGCTAAAA
GAAGTTGGATAACAAATTGACAACTATTTCCATTTCTGTTATATAAATTTCACAACACACAAAAGCCCGTAATCAA
GAGTCTGCCCATGTACGAAATAACTTCTATTATTTGGTATTGGGCCTAAGCCCAGCTCAGAGTACGTGGGGGTACC
ACATATAGGAAGGTAACAAAATACTGCAAGATAGCCCCATAACGTACCAGCCTCTCCTTACCACGAAGAGATAAGA
TATAAGACCCACCCTGCCACGTGTCACATCGTCATGGTGGTTAATGATAAGGGATTACATCCTTCTATGTTTGTGG
ACATGATGCATGTAATGTCATGAGCCACAGGATCCAATGGCCACAGGAACGTAAGAATGTAGATAGATTTGATTTT
GTCCGTTAGATAGCAAACAACATTATAAAAGGTGTGTATCAATAGGAACTAATTCACTCATTGGATTCATAGAAGT
CCATTCCTCCTAAGTATCTAGAAACCATGGCGAGAGGGAGCAGATCAGTGGGTAGCAGCAGCAGCAAATGGAGGTA
CTGCAACCCTTCCTATTACTTGAAGCGCCCAAAGCGTCTTGCTCTGCTCTTCATCGTTTCGTTTGTGTCTCTTTC
GTTTTCTGGGACCGTCAAACTCTCGTCAGAGAGCACCAGGTTGAAATTTCTGAGCTGCAGAAAGAAGTGACTGATT
TGAAAAATTTGGTGGATGATTTAAATAACAAACAAGGTGGTACCTCTGGGAAAACTGACTTGGGGACCATGGATTC
CAATTCAGGCGCCGTCGTTGATATCACAACTAAAGATCTATACGATAGGATTGAGTTTCTTGATACAGATGGTGGT
CCATGGAAACAAGGTTGGAGAGTTACGTATAAAGACGATGAGTGGGAGAAAGAGAAGCTCAAAATCTTCGTTGTTC
CTCATTCTCATAACGATCCTGGTTGGAAATTGACTGTAGAGGAGTATTATCAGAGACAATCCAGACATATTCTTGA
CACCATTGTTGAGACTTTATCTAAGGTATGACGAAAGTTTTTGCTTTTGGTTTTAATATTTTAATTCTCTCCCATG
GTTATCCCGTGAACAATCTTAAATGTCTTAAAATTCTCATGACGTCATTAAACTCTATAACCAAACTTCTTTGCTG
GGTTCTGTTTTTTTTTAGTTTCGTGATGAAACAGAGTTCTAGAAGTTCGTTCTTTTGGAAAATTTGAAGTCTTTGG
AGCTAAAGTTTGTTTTTTTATTACTGGGTTTTGAGATTGAAGGATAGCTAGAATCTTATTTGTGTGGGGGTTTGTT
TTGAATATGTTTAATAGGATTCAAGAAGAAAGTTTATATGGGAGGAGATGTCATATCTGGAGAGATGGTGGAGAGA
CGCTTCACCTAATAAACAAGAAGCTTTGACTAAATTGGTTAAGGATGGGCAGCTAGAGATTGTTGGAGGTGGCTGG

FIG. 27

GTTATGAATGATGAGGCTAATTCACATTATTTTGCCATAATTGAACAGATAGCAGAGGGTAATATGTGGCTGAATG
ACACAATTGGGGTTATTCCTAAGAATTCTTGGGCTATAGATCCCTTTGGCTATTCATCAACCATGGCTTATCTTCT
CCGGCGTATGGGTTTTGAAAACATGCTTATTCAAAGGACTCATTACGAGCTCAAGAAAGACCTTGCCCAGCATAAG
AATCTTGAATATATTTGGCGTCAGAGCTGGGATGCTATGGAAACCACAGATATCTTTGTTCATATGATGCCGTTTT
ATTCATACGATATCCCACACACTTGTGGACCAGAGCCTGCAATTTGCTGTCAGTTTGATTTCGCTCGGATGCGGGG
ATTTAAGTATGAACTTTGTCCATGGGGAAAGCACCCAGTGGAGACCACACTAGAAAATGTGCAGGAGAGGGCATTA
AAGCTTCTGGATCAATACAGGAAAAAATCCACTCTATATCGAACTAATACACTTCTTATACCTCTTGGAGATGATT
TTAGGTACATTAGTATCGATGAAGCCGAGGCTCAGTTCCGTAACTACCAGATGTTGTTTGATCACATCAACTCTAA
TCCTAGTCTAAACGCAGAAGCAAAGTTTGGTACTTTGGAGGATTATTTCAGAACAGTCCGAGAAGAAGCAGACAGA
GTGAATTATTCTCGTCCTGGTGAGGTTGGCTCTGGTCAGGTTGTTGGTTTCCCTTCTCTGTCAGGTGACTTCTTTA
CATATGCAGATAGGCAACAAGACTATTGGAGTGGTTATTATGTTTCAAGACCTTTCTTCAAAGCTGTTGATCGTGT
GCTCGAGCATACCCTTCGTGGAGCTGAGATCATGATGTCATTTCTGCTAGGTTATTGCCATCGAATTCAATGTGAG
AAATTTCCAACAAGTTTTACGTATAAGTTGACTGCTGCAAGAAGAAATCTGGCTCTTTTCCAGCACCATGATGGGG
TAACTGGAACTGCTAAGGATTATGTGGTACAAGATTACGGCACCCGGATGCATACTTCATTGCAAGACCTTCAGAT
CTTTATGTCTAAAGCAATCGAAGTTCTTCTTGGGATCCGCCACGAGAAAGAAAAATCTGATCAATCCCCATCATTT
TTCGAGGCAGAGCAAATGAGATCAAAGTATGATGCTCGGCCAGTTCACAAGCCAATTGCTGCCCGGGAAGGAAATT
CGCACACAGTTATACTCTTCAATCCATCAGAACAGACGAGAGAGGAGGTGGTGACGGTTGTTGTTAACCGCGCTGA
AATCTCGGTTTTGGACTCAAACTGGACTTGTGTCCCTAGCCAAATTTCTCCTGAAGTGCAGCATGACGATACCAAA
CTATTCACCGGCAGACATCGCCTTTACTGGAAAGCTTCCATCCCAGCTCTTGGTCTGAGAACATATTTCATTGCTA
ATGGGAATGTCGAGTGTGAGAAAGCTACTCCGTCTAAACTCAAATACGCTTCTGAGTTTGACCCATTTCCTTGTCC
TCCTCCATATTCCTGCTCCAAACTGGACAACGACGTTACTGAGATCCGAAATGAACATCAGACTCTTGTGTTTGAT
GTGAAGAACGGATCACTGCGGAAGATAGTCCATAGAAACGGATCAGAGACTGTTGTGGGAGAAGAGATAGGTATGT
ACTCTAGTCCAGAGAGTGGAGCTTACCTGTTCAAACCAGATGGTGAAGCTCAGCCAATTGTTCAACCTGATGGACA
TGTAGTCACCTCTGAGGGTCTGCTGGTTCAAGAAGTCTTCTCTTACCCTAAAACCAAATGGGAGAAATCACCCCTC
TCTCAGAAAACTCGTCTTTACACTGGAGGTAATACGCTTCAGGATCAAGTGGTCGAGATAGAATATCATGTTGAGC
TTCTTGGTAATGATTTTGATGACCGGGAATTGATTGTCCGGTACAAGACTGATGTTGACAACAAGAAGGTCTTCTA
TTCAGATCTCAATGGTTTCCAAATGAGCAGGAGAGAAACTTATGATAAGATCCCTCTTCAAGGAAACTACTACCCA
ATGCCATCTCTCGCATTTATCCAAGGATCCAATGGTCAGAGATTCTCCGTGCACTCTCGTCAATCTCTCGGTGTTG

FIG. 27 Cont.

CAAGCCTCAAAGAGGGTTGGTTGGAGATTATGCTGGACAGACGGTTGGTTCGTGATGACGGACGGGGTCTAGGGCA
AGGTGTGATGGATAACCGCGCAATGACCGTGGTATTTCACCTTCTTGCGGAATCTAACATTTCTCAAGCAGACCCT
GCTTCCAACACTAACCCGAGGAACCCTTCGCTTCTCTCTCACCTCATAGGTGCTCACTTAAACTACCCCATAAACA
CATTCATTGCCAAGAAACCGCAAGACATATCTGTGCGTGTTCCACAATACGGTTCCTTTGCTCCTTTAGCCAAACC
GTTACCATGTGACCTCCACATTGTAAATTTCAAGGTTCCTCGTCCATCCAAATACTCTCAGCAATTGGAAGAAGAC
AAGCCAAGGTTCGCTCTTATCCTCAATAGACGAGCTTGGGATTCAGCTTATTGCCATAAAGGAAGACAAGTAAACT
GCACAAGCATGGCTAATGAACCAGTAAACTTTTCCGACATGTTCAAAGATCTTGCAGCTTCAAAGGTAAAACCAAC
TTCACTGAATCTCTTGCAAGAAGATATGGAGATTCTTGGGTACGATGACCAAGAGCTACCTCGAGATAGTTCACAG
CCACGGGAAGGACGTGTCTCGATCTCTCCCATGGAAATACGAGCTTATAAGCTTGAACTGCGACCTCACAAGTGAA
CCTGCTGAAGATCCGCTAGAGTCCGCAAAAATCACCAGTCTCTCTCTACAAATCTATCTCTCTCTATTTTTCTCCA
GAATAATGTGTGAGTAGTTCCCAGATAAGGGAATTAGGGTTCTTATAGGGTTTCGCTCATGTGTTGAGCATATAAG
AAACCCTTAGTATGTATTTGTATTTGTAAAATACTTCTATCAATAAAATTTCTAATCCTAAAACCAAAATCCCGCG
AGAGACCTCTTAATTAA

FIG. 27 Cont.

AGATCTAATCTAACCAATTACGATACGCTTTGGGTACACTTGATTTTTGTTTCAGTGGTTACATATATCTTGTTTT
ATATGCTATCTTTAAGGATCTGCACAAAGATTATTTGTTGATGTTCTTGATGGGGCTCAGAAGATTTGATATGATA
CACTCTAATCTTTAGGAGATACCAGCCAGGATTATATTCAGTAAGACAATCAAATTTTACGTGTTCAAACTCGTTA
TCTTTTCATTCAAAGGATGAGCCAGAATCTTTATAGAATGATTGCAATCGAGAATATGTTCGGCCGATATGCCTTT
GTTGGCTTCAATATTCTACATATCACACAAGAATCGACCGTATTGTACCCTCTTTCCATAAAGGAAAACACAATAT
GCAGATGCTTTTTTCCCACATGCAGTAACATATAGGTATTCAAAAATGGCTAAAAGAAGTTGGATAACAAATTGAC
AACTATTTCCATTTCTGTTATATAAATTTCACAACACACAAAAGCCCGTAATCAAGAGTCTGCCCATGTACGAAAT
AACTTCTATTATTTGGTATTGGGCCTAAGCCCAGCTCAGAGTACGTGGGGGTACCACATATAGGAAGGTAACAAAA
TACTGCAAGATAGCCCCATAACGTACCAGCCTCTCCTTACCACGAAGAGATAAGATATAAGACCCACCCTGCCACG
TGTCACATCGTCATGGTGGTTAATGATAAGGGATTACATCCTTCTATGTTTGTGGACATGATGCATGTAATGTCAT
GAGCCACAGGATCCAATGGCCACAGGAACGTAAGAATGTAGATAGATTTGATTTTGTCCGTTAGATAGCAAACAAC
ATTATAAAAGGTGTGTATCAATAGGAACTAATTCACTCATTGGATTCATAGAAGTCCATTCCTCCTAAGTATCTAG
AAACCATGG

FIG. 28

CCATGGCGAGAGGGAGCAGATCAGTGGGTAGCAGCAGCAAATGGAGGTACTGCAACCCTTCCTATTACTTGAA
GCGCCCAAAGCGTCTTGCTCTGCTCTTCATCGTTTTCGTTTGTGTCTCTTTCGTTTTCTGGGACCGTCAAACTCTC
GTCAGAGAGCACCAGGTTGAAATTTCTGAGCTGCAGAAAGAAGTGACTGATTTGAAAAATTTGGTGGATGATTTAA
ATAACAAACAAGGTGGTACCTCTGGGAAAACTGACTTGGGGACCATGGATTCCAATTCAGGCGCCGTCGTTGATAT
CACAACTAAAGATCTATACGATAGGATTGAGTTTCTTGATACAGATGGTGGTCCATGGAAACAAGGTTGGAGAGTT
ACGTATAAAGACGATGAGTGGGAGAAAGAGAAGCTCAAAATCTTCGTTGTTCCTCATTCTCATAACGATCCTGGTT
GGAAATTGACTGTAGAGGAGTATTATCAGAGACAATCCAGACATATTCTTGACACCATTGTTGAGACTTTATCTAA
GGTATGACGAAAGTTTTTGCTTTTGGTTTTAATATTTTAATTCTCTCCCATGGTTATCCCGTGAACAATCTTAAAT
GTCTTAAAATTCTCATGACGTCATTAAACTCTATAACCAAACTTCTTTGCTGGGTTCTGTTTTTTTTAGTTTCGT
GATGAAACAGAGTTCTAGAAGTTCGTTCTTTTGGAAAATTTGAAGTCTTTGGAGCTAAAGTTTGTTTTTTATTAC
TGGGTTTTGAGATTGAAGGATAGCTAGAATCTTATTTGTGTGGGGGTTTGTTTTGAATATGTTTAATAGGATTCAA
GAAGAAAGTTTATATGGGAGGAGATGTCATATCTGGAGAGATGGTGGAGAGACGCTTCACCTAATAAACAAGAAGC
TTTGACTAAATTGGTTAAGGATGGGCAGCTAGAGATTGTTGGAGGTGGCTGGGTTATGAATGATGAGGCTAATTCA
CATTATTTTGCCATAATTGAACAGATAGCAGAGGGTAATATGTGGCTGAATGACACAATTGGGGTTATTCCTAAGA
ATTCTTGGGCTATAGATCCCTTTGGCTATTCATCAACCATGGCTTATCTTCTCCGGCGTATGGGTTTTGAAAACAT
GCTTATTCAAAGGACTCATTACGAGCTCAAGAAAGACCTTGCCCAGCATAAGAATCTTGAATATATTTGGCGTCAG
AGCTGGGATGCTATGGAAACCACAGATATCTTTGTTCATATGATGCCGTTTTATTCATACGATATCCCACACACTT
GTGGACCAGAGCCTGCAATTTGCTGTCAGTTTGATTTCGCTCGGATGCGGGGATTTAAGTATGAACTTTGTCCATG
GGGAAAGCACCCAGTGGAGACCACACTAGAAAATGTGCAGGAGAGGGCATTAAAGCTTCTGGATCAATACAGGAAA
AAATCCACTCTATATCGAACTAATACACTTCTTATACCTCTTGGAGATGATTTTAGGTACATTAGTATCGATGAAG
CCGAGGCTCAGTTCCGTAACTACCAGATGTTGTTTGATCACATCAACTCTAATCCTAGTCTAAACGCAGAAGCAAA
GTTTGGTACTTTGGAGGATTATTTCAGAACAGTCCGAGAAGAAGCAGACAGAGTGAATTATTCTCGTCCTGGTGAG
GTTGGCTCTGGTCAGGTTGTTGGTTTCCCTTCTCTGTCAGGTGACTTCTTTACATATGCAGATAGGCAACAAGACT
ATTGGAGTGGTTATTATGTTTCAAGACCTTTCTTCAAAGCTGTTGATCGTGTGCTCGAGCATACCCTTCGTGGAGC
TGAGATCATGATGTCATTTCTGCTAGGTTATTGCCATCGAATTCAATGTGAGAAATTTCCAACAAGTTTTACGTAT
AAGTTGACTGCTGCAAGAAGAAATCTGGCTCTTTTCCAGCACCATGATGGGGTAACTGGAACTGCTAAGGATTATG

FIG. 29

TGGTACAAGATTACGGCACCCGGATGCATACTTCATTGCAAGACCTTCAGATCTTTATGTCTAAAGCAATCGAAGT
TCTTCTTGGGATCCGCCACGAGAAAGAAAAATCTGATCAATCCCCATCATTTTTCGAGGCAGAGCAAATGAGATCA
AAGTATGATGCTCGGCCAGTTCACAAGCCAATTGCTGCCCGGGAAGGAAATTCGCACACAGTTATACTCTTCAATC
CATCAGAACAGACGAGAGAGGAGGTGGTGACGGTTGTTGTTAACCGCGCTGAAATCTCGGTTTTGGACTCAAACTG
GACTTGTGTCCCTAGCCAAATTTCTCCTGAAGTGCAGCATGACGATACCAAACTATTCACCGGCAGACATCGCCTT
TACTGGAAAGCTTCCATCCCAGCTCTTGGTCTGAGAACATATTTCATTGCTAATGGGAATGTCGAGTGTGAGAAAG
CTACTCCGTCTAAACTCAAATACGCTTCTGAGTTTGACCCATTTCCTTGTCCTCCTCCATATTCCTGCTCCAAACT
GGACAACGACGTTACTGAGATCCGAAATGAACATCAGACTCTTGTGTTTGATGTGAAGAACGGATCACTGCGGAAG
ATAGTCCATAGAAACGGATCAGAGACTGTTGTGGGAGAAGAGATAGGTATGTACTCTAGTCCAGAGAGTGGAGCTT
ACCTGTTCAAACCAGATGGTGAAGCTCAGCCAATTGTTCAACCTGATGGACATGTAGTCACCTCTGAGGGTCTGCT
GGTTCAAGAAGTCTTCTCTTACCCTAAAACCAAATGGGAGAAATCACCCCTCTCTCAGAAAACTCGTCTTTACACT
GGAGGTAATACGCTTCAGGATCAAGTGGTCGAGATAGAATATCATGTTGAGCTTCTTGGTAATGATTTTGATGACC
GGGAATTGATTGTCCGGTACAAGACTGATGTTGACAACAAGAAGGTCTTCTATTCAGATCTCAATGGTTTCCAAAT
GAGCAGGAGAGAAACTTATGATAAGATCCCTCTTCAAGGAAACTACTACCCAATGCCATCTCTCGCATTTATCCAA
GGATCCAATGGTCAGAGATTCTCCGTGCACTCTCGTCAATCTCTCGGTGTTGCAAGCCTCAAAGAGGGTTGGTTGG
AGATTATGCTGGACAGACGGTTGGTTCGTGATGACGGACGGGGTCTAGGGCAAGGTGTGATGGATAACCGCGCAAT
GACCGTGGTATTTCACCTTCTTGCGGAATCTAACATTTCTCAAGCAGACCCTGCTTCCAACACTAACCCGAGGAAC
CCTTCGCTTCTCTCTCACCTCATAGGTGCTCACTTAAACTACCCCATAAACACATTCATTGCCAAGAAACCGCAAG
ACATATCTGTGCGTGTTCCACAATACGGTTCCTTTGCTCCTTTAGCCAAACCGTTACCATGTGACCTCCACATTGT
AAATTTCAAGGTTCCTCGTCCATCCAAATACTCTCAGCAATTGGAAGAAGACAAGCCAAGGTTCGCTCTTATCCTC
AATAGACGAGCTTGGGATTCAGCTTATTGCCATAAAGGAAGACAAGTAAACTGCACAAGCATGGCTAATGAACCAG
TAAACTTTTCCGACATGTTCAAAGATCTTGCAGCTTCAAAGGTAAAACCAACTTCACTGAATCTCTTGCAAGAAGA
TATGGAGATTCTTGGGTACGATGACCAAGAGCTACCTCGAGATAGTTCACAGCCACGGGAAGGACGTGTCTCGATC
TCTCCCATGGAAATACGAGCTTATAAGCTTGAACTGCGACCTCACAAGTGAACCTGCTGAAGATC

FIG. 29 Cont.

GGCGCGCCTCGAGGCGATCGCAGATCTCATTATACCGTTAGAAGCATAGTTAAAATCTAAAGCTTGTCGTTAATTC
TAGTCATTTTACATTGTTGGGTTCTACATTATTAATGAATTTTCTAATGCAAATACAGAATTTAAATCAAAATTGT
TGAATTATGCTAAACATGTAACATACGTATATCTCCGCCTTGTGTGTTGTATTAACTTGAAGTTATCATAAGAACC
ACAAATACACTAGTAAATCTATGAGAAGGCAGGTGGCAACACAAACAAGAGTATCTAAGATTTTCATTTGTGACTA
TAGGAATATAATATCTCTTATCTGATTTAATGAATCCACATGTTCACTTCTCATTTGTCCACAAGATCACAACTTT
ATCTTCAATATTCACAACTTGTTATATCCACCACAATTTCATTCTTTTCACTTAGCCCCACAAAATACTTTGTCCC
CTTATTTGCCACCTTTTGTATTTAATTTATTCTTGTGGAGCTAAGTGTTCATATTATTCTTCTTCTCAAAAAAACA
AAAACAAAAAAAAAGAGAAGAAAACCATGGCGAGAGGGAGCAGATCAGTGGGTAGCAGCAGCAGCAAATGGAGGTA
CTGCAACCCTTCCTATTACTTGAAGCGCCCAAAGCGTCTTGCTCTGCTCTTCATCGTTTTCGTTTGTGTCTCTTTC
GTTTTCTGGGACCGTCAAACTCTCGTCAGAGAGCACCAGGTTGAAATTTCTGAGCTGCAGAAAGAAGTGACTGATT
TGAAAAATTTGGTGGATGATTTAAATAACAAACAAGGTGGTACCTCTGGGAAAACTGACTTGGGGACCATGGCTCT
AAGGTTGCATAGAAGGAACCATTTTTCGCCTAGAAATACGGATCTGTTCCCGGATTTGGCAAAAGATCGTGTGGTT
ATCGTCTTGTATGTGCATAATCGGGCTCAGTATTTTCGAGTCACAGTGGAAAGTTTGTCGAAGGTTAAAGGTATAA
GTGAGACATTGTTGATTGTTAGTCATGATGGTTACTTTGAAGAGATGAATAGGATTGTGGAGAGTATTAAGTTTTG
TCAAGTGAAACAGATTTTCTCGCCTTATTCGCCTCATATATATCGTACTAGCTTCCCGGGTGTGACCCTGAATGAT
TGTAAGAACAAGGGTGATGAGGCAAAGGGGCATTGTGAAGGTAATCCTGATCAGTATGGGAATCATCGGTCTCCGA
AGATTGTATCTTTGAAGCATCACTGGTGGTGGATGATGAACACTGTATGGGATGGGTTGGAAGAGACTAAAGGACA
TGAGGGGCATATCCTTTTCATTGAAGAAGATCATTTTCTGTTTCCTAATGCCTATCGTAACATACAGACTCTTACG
AGGCTGAAACCCGCAAAGTGTCCTGACTGTTTTGCTGCTAATTTAGCACCGTCTGATGTGAAGTCAAGAGGAGAAG
GGCTTGAAAGTTTGGTTGCAGAGAGAATGGGAAATGTTGGGTATTCTTTTAATAGAAGTGTGTGGGAGAATATTCA
TCAGAAGGCAAGAGAGTTTTGTTTCTTTGATGATTACAACTGGGATATAACGATGTGGGCAACGGTTTTCCCGTCG
TTTGGTTCCCCGGTGTACACATTGCGAGGGCCTAGGACTAGTGCGGTACACTTTGGAAAATGTGGGTTGCATCAAG

FIG. 30

GTAGAGGAGATGAGGGTGATTGCATCGATAATGGGGTCGTAAACATAGAAGTTAAGGAAACAGATAAAGTTGTGAA
CATAAAAGAAGGATGGGGAGTTCGGGTGTATAAGCATCAAGCGGGTTATAAAGCCGGTTTCGAAGGTTGGGGAGGT
TGGGGCGATGATAGGGACCGACATTTATGTTTGGATTTTGCCACTATGTATCGTTACAGCAGTAGCAGTGCATCTC
CATGAAACGGATCCGCTAGAGTCCGCAAAAATCACCAGTCTCTCTCTACAAATCTATCTCTCTCTATTTTTCTCCA
GAATAATGTGTGAGTAGTTCCCAGATAAGGGAATTAGGGTTCTTATAGGGTTTCGCTCATGTGTTGAGCATATAAG
AAACCCTTAGTATGTATTTGTATTTGTAAAATACTTCTATCAATAAAATTTCTAATCCTAAAACCAAAATCCCGCG
AGAGACCTCTTAATTAA

FIG. 30 Cont.

AGATCTCATTATACCGTTAGAAGCATAGTTAAAATCTAAAGCTTGTCGTTAATTCTAGTCATTTTACATTGTTGGG
TTCTACATTATTAATGAATTTTCTAATGCAAATACAGAATTTAAATCAAAATTGTTGAATTATGCTAAACATGTAA
CATACGTATATCTCCGCCTTGTGTGTTGTATTAACTTGAAGTTATCATAAGAACCACAAATACACTAGTAAATCTA
TGAGAAGGCAGGTGGCAACACAAACAAGAGTATCTAAGATTTTCATTTGTGACTATAGGAATATAATATCTCTTAT
CTGATTTAATGAATCCACATGTTCACTTCTCATTTGTCCACAAGATCACAACTTTATCTTCAATATTCACAACTTG
TTATATCCACCACAATTTCATTCTTTTCACTTAGCCCCACAAAATACTTTGTCCCCTTATTTGCCACCTTTTGTAT
TTAATTTATTCTTGTGGAGCTAAGTGTTCATATTATTCTTCTTCTCAAAAAAACAAAAACAAAAAAAAAGAGAAGA
AAACCATGG

FIG. 31

CCATGGCGAGAGGGAGCAGATCAGTGGGTAGCAGCAGCAGCAAATGGAGGTACTGCAACCCTTCCTATTACTTGAA
GCGCCCAAAGCGTCTTGCTCTGCTCTTCATCGTTTTCGTTTGTGTCTCTTTCGTTTTCTGGGACCGTCAAACTCTC
GTCAGAGAGCACCAGGTTGAAATTTCTGAGCTGCAGAAAGAAGTGACTGATTTGAAAAATTTGGTGGATGATTTAA
ATAACAAACAAGGTGGTACCTCTGGGAAAACTGACTTGGGGACCATGGCTCTAAGGTTGCATAGAAGGAACCATTT
TTCGCCTAGAAATACGGATCTGTTCCCGGATTTGGCAAAAGATCGTGTGGTTATCGTCTTGTATGTGCATAATCGG
GCTCAGTATTTTCGAGTCACAGTGGAAAGTTTGTCGAAGGTTAAAGGTATAAGTGAGACATTGTTGATTGTTAGTC
ATGATGGTTACTTTGAAGAGATGAATAGGATTGTGGAGAGTATTAAGTTTTGTCAAGTGAAACAGATTTTCTCGCC
TTATTCGCCTCATATATATCGTACTAGCTTCCCGGGTGTGACCCTGAATGATTGTAAGAACAAGGGTGATGAGGCA
AAGGGGCATTGTGAAGGTAATCCTGATCAGTATGGGAATCATCGGTCTCCGAAGATTGTATCTTTGAAGCATCACT
GGTGGTGGATGATGAACACTGTATGGGATGGGTTGGAAGAGACTAAAGGACATGAGGGGCATATCCTTTTCATTGA
AGAAGATCATTTTCTGTTTCCTAATGCCTATCGTAACATACAGACTCTTACGAGGCTGAAACCCGCAAAGTGTCCT
GACTGTTTTGCTGCTAATTTAGCACCGTCTGATGTGAAGTCAAGAGGAGAAGGGCTTGAAAGTTTGGTTGCAGAGA
GAATGGGAAATGTTGGGTATTCTTTTAATAGAAGTGTGTGGGAGAATATTCATCAGAAGGCAAGAGAGTTTTGTTT
CTTTGATGATTACAACTGGGATATAACGATGTGGGCAACGGTTTTCCCGTCGTTTGGTTCCCCGGTGTACACATTG
CGAGGGCCTAGGACTAGTGCGGTACACTTTGGAAAATGTGGGTTGCATCAAGGTAGAGGAGATGAGGGTGATTGCA
TCGATAATGGGGTCGTAAACATAGAAGTTAAGGAAACAGATAAAGTTGTGAACATAAAAGAAGGATGGGGAGTTCG
GGTGTATAAGCATCAAGCGGGTTATAAAGCCGGTTTCGAAGGTTGGGGAGGTTGGGGCGATGATAGGGACCGACAT
TTATGTTTGGATTTTGCCACTATGTATCGTTACAGCAGTAGCAGTGCATCTCCATGAAACGGATCC

FIG. 32

GGATCCGCTAGAGTCCGCAAAAATCACCAGTCTCTCTCTACAAATCTATCTCTCTCTATTTTTCTCCAGAATAATG
TGTGAGTAGTTCCCAGATAAGGGAATTAGGGTTCTTATAGGGTTTCGCTCATGTGTTGAGCATATAAGAAACCCTT
AGTATGTATTTGTATTTGTAAAATACTTCTATCAATAAAATTTCTAATCCTAAAACCAAAATCCCGCGAGAGACCT
CTTAATTAA

FIG. 33

Lanes: 25μg total protein each

1, MGR48-plantibody control

2, TmXyl-GalT

3, GalT

4, SSNN control

Lanes 1, 2 & 3: 300 ng MGR48 IgG
1, MGR48 hybridoma
2, MGR48 tobacco
3, MGR48 TmXyl-GalT

```
ATGGGCATCAAGATGGAGACACATTCTCAGGTCTTTGTATACATGTTGCTGTGGTTGTCTGGTGTCGACATGAAGCACTTCAAATCTTCCCTCACT
CACACCGTCAAGAGCCGAGACGAGCCAACTCCGGATCAATGCCCTGCATTGAAGGAAAGCGAAGCGGACATCGACACCGTGGCGATATACCCAACT
TTTGATTTTCAGCCGAGCTGGTTGCGTACAAAGGAATTTTGGGACAAGTCCTTCGAGGATCGGTATGAAAGAATTCATAACGACACTACACGGCCT
AGACTGAAGGTAATCGTGGTTCCTCACTCACACAACGACCCGGGATGGCTGAAGACGTTTGAACAGTACTTCGAGTGGAAGACCAAGAACATTATC
AACAACATAGTGAACAAACTGCACCAGTACCCCAACATGACCTTCATTTGGACCGAGATATCGTTTCTGAATGCCTGGTGGGAAAGGTCGCACCCT
GTCAAACAAAAGGCATTGAAAAAACTTATCAAAGAAGGTCGTCTCGAGATCACGACGGGCGGCTGGGTGATGCCGGACGAAGCCTGCACGCATATC
TATGCGCTAATTGACCAGTTTATTGAAGGACATCACTGGGTGAAAACTAATCTCGGCGTCATCCCGAAGACAGGATGGTCTATTGACCCCTTCGGC
CACGGGGCCACTGTGCCTTACCTGCTAGACCAGAGCGGCCTTGAGGGAACCATTATACAGAGAATCCATTATGCGTGGAAACAGTGGCTGGCGGAG
CGACAGATTGAGGAGTTTTACTGGCTGGCGAGTTGGGCTACTACGAAGCCGTCCATGATAGTGCACAATCAGCCGTTTGATATTTATTCAATAAAA
AGCACGTGTGGCCCGCACCCTTCAATTTGTCTCAGTTTCGACTTCAGGAAGATTCCCGGCGAATATTCTGAATACACAGCTAAGCACGAAGACATC
ACGGAACACAACTTGCACAGCAAGGCAAAGACTTTGATAGAGGAGTACGACCGTATCGGGTCCCTGACTCCACACAACGTGGTGCTGGTGCCGCTC
GGAGACGACTTCAGATACGAGTACAGCGTCGAGTTTGATGCCCAATACGTCAATTATATGAAAATGTTTAACTACATCAATGCTCACAAGGAAATC
TTCAACGCTGACGTACAGTTCGGAACTCCTCTCGATTACTTTAACGCCATGAAAGAAAGACATCAAAATATACCCAGCTTAAAGGGAGATTTCTTC
GTTTACTCCGATATTTTCAGCGAAGGTAAACCAGCGTACTGGTCAGGTTACTACACTACTAGACCCTACCAAAAAATCCTCGCCCGTCAGTTCGAA
CACCAACTGCGATCGGCAGAGATTTTATTCACCCTTGTATCGAACTACATCAGACAGATGGGTCGCCAAGGAGAGTTCGGAGCTTCTGAGAAAAAG
TTAGAAAAATCTTACGAGCAGCTTATCTATGCTCGACGGAACTTGGGTCTGTTTCAACATCACGATGCGATTACTGGAACATCAAAGTCCAGTGTG
ATGCAAGATTACGGAACCAAACTGTTCACAAGTCTGTATCACTGCATCCGCCTGCAGGAGGCCGCGCTCACCACCATCATGTTGCCTGACCAGTCG
TTGCACTCGCAGAGCATTATACAAAGCGAGGTTGAGTGGGAAACTTACGGAAAACCGCCCAAGAAGCTGCAAGTGTCCTTCATTGACAAGAAGAAA
GTTATACTTTTTAATCCGTTGGCTGAGACTCGAACTGAAGTGGTCACGGTTAGATCCAACACGTCCAACATCCGGGTGTACGATACACACAAGAGG
AAGCACGTCTTGTATCAGATAATGCCCAGCATCACAATCCAAGACAACGGCAAGAGTATCGTAAGCGACACCACGTTCGACATAATGTTCGTGGCC
ACCATCCCGCCCCTCACCTCCATCTCGTACAAGCTGCAGGAGCACACCAACACTTCCCACCACTGCGTCATTTTCTGCAACAACTGCGAACAATAC
CAGAAATCCAATGTGTTCCAAATTAAGAAAATGATGCCTGGTGACATACAATTAGAAAATGCAGTGCTAAAACTTCTCGTTAATAGGAACACCGGC
TTTCTGAGACAAGTCTATAGAAAGGACATCCGGAAGAGAACTGTCGTTGACGTACAATTCGGCGCATATCAAAGTGCCCAAAGACATTCTGGTGCT
TACCTCTTCATGCCTCATTACGACTCACCTGAGAAGAATGTTCTGCATCCCTACACTAATCAGAACAACATGCAAGATGATAACATAATCATAGTG
TCCGGACCTATTTCTACGGAAATCACGACCATGTACTTGCCCTTCTTGGTGCACACTATTAGGATATACAACGTGCCGGACCCGGTACTGTCGCGT
GCTATTCTATTAGAGACCGATGTAGATTTCGAGGCGCCACCTAAGAACAGAGAGACTGAGTTATTTATGAGATTACAGACTGATATACAAAACGGT
GACATTCCCGAATTTTACACCGATCAGAACGGATTCCAGTACCAAAAGAGGGTCAAAGTGAATAAACTAGGAATAGAAGCTAATTACTACCCGATC
ACTACCATGGCGTGCCTGCAAGACGAGGAGACCCGGCTCACTCTGCTGACGAACCACGCTCAAGGCGCTGCTGCATACGAACCAGGACGCTTAGAA
```

FIG. 37

GTCATGCTCGATCGTCGAACTCTTTATGATGACTTCAGAGGAATCGGTGAAGGAGTAGTCGATAACAAACCGACGACTTTCCAGAACTGGATTTTA
ATTGAATCCATGCCAGGCGTGACGCGAGCCAAGAGAGACACTAGTGAACCAGGTTTCAAATTTGTTAATGAACGTCGTTTTGGCCCCGGCCAGAAG
GAAAGCCCTTACCAAGTACCGTCGCAGACTGCGGACTACCTGAGCAGGATGTTCAATTACCCGGTGAACGTGTACCTGGTGGACACTAGCGAGGTT
GGCGAGATCGAGGTGAAGCCGTACCAGTCGTTCCTGCAGAGCTTCCCGCCCGGCATCCACCTGGTCACCCTGCGCACCATCACCGACGACGTGCTC
GAACTCTTCCCCAGCAACGAAAGCTACATGGTACTGCACCGACCAGGATACAGCTGCGCTGTCGGAGAGAAGCCAGTCGCCAAGTCTCCCAAGTTT
TCGTCCAAAACCAGGTTCAATGGTCTGAACATTCAGAACATCACTGCAGTCAGCCTGACCGGCCTGAAGTCACTCCGACCTCTCACAGGTCTGAGT
GACATCCACCTGAACGCTATGGAGGTAAAAACTTACAAGATCAGGTTTAAGGACGAGCTTTAA

FIG. 37 Cont.

MGIKMETHSQVFVYMLLWLSGVDMKHFKSSLTHTVKSRDEPTPDQCPALKESEADIDTVAIYPTFDFQPSWLRTKEFWDKSFEDRYERIHNDTTRP
RLKVIVVPHSHNDPGWLKTFEQYFEWKTKNIINNIVNKLHQYPNMTFIWTEISFLNAWWERSHPVKQKALKKLIKEGRLEITTGGWVMPDEACTHI
YALIDQFIEGHHWVKTNLGVIPKTGWSIDPFGHGATVPYLLDQSGLEGTIIQRIHYAWKQWLAERQIEEFYWLASWATTKPSMIVHNQPFDIYSIK
STCGPHPSICLSFDFRKIPGEYSEYTAKHEDITEHNLHSKAKTLIEEYDRIGSLTPHNVVLVPLGDDFRYEYSVEFDAQYVNYMKMFNYINAHKEI
FNADVQFGTPLDYFNAMKERHQNIPSLKGDFFVYSDIFSEGKPAYWSGYYTTRPYQKILARQFEHQLRSAEILFTLVSNYIRQMGRQGEFGASEKK
LEKSYEQLIYARRNLGLFQHHDAITGTSKSSVMQDYGTKLFTSLYHCIRLQEAALTTIMLPDQSLHSQSIIQSEVEWETYGKPPKKLQVSFIDKKK
VILFNPLAETRTEVVTVRSNTSNIRVYDTHKRKHVLYQIMPSITIQDNGKSIVSDTTFDIMFVATIPPLTSISYKLQEHTNTSHHCVIFCNNCEQY
QKSNVFQIKKMMPGDIQLENAVLKLLVNRNTGFLRQVYRKDIRKRTVVDVQFGAYQSAQRHSGAYLFMPHYDSPEKNVLHPYTNQNNMQDDNIIIV
SGPISTEITTMYLPFLVHTIRIYNVPDPVLSRAILLETDVDFEAPPKNRETELFMRLQTDIQNGDIPEFYTDQNGFQYQKRVKVNKLGIEANYYPI
TTMACLQDEETRLTLLTNHAQGAAAYEPGRLEVMLDRRTLYDDFRGIGEGVVDNKPTTFQNWILIESMPGVTRAKRDTSEPGFKFVNERRFGPGQK
ESPYQVPSQTADYLSRMFNYPVNVYLVDTSEVGEIEVKPYQSFLQSFPPGIHLVTLRTITDDVLELFPSNESYMVLHRPGYSCAVGEKPVAKSPKF
SSKTRFNGLNIQNITAVSLTGLKSLRPLTGLSDIHLNAMEVKTYKIRFKDEL

FIG. 38

ATGGGCATCAAGATGGAGACACATTCTCAGGTCTTTGTATACATGTTGCTGTGGTTGTCTGGTGTCGACATGCAGTCCTCCGGGGAGCTCCGGACC
GGAGGGGCCCGGCCGCCGCCTCCTCTAGGCGCCTCCTCCCAGCCGCGCCCGGGTGGCGACTCCAGCCCAGTCGTGGATTCTGGCCCTGGCCCCGCT
AGCAACTTGACCTCGGTCCCAGTGCCCCACACCACCGCACTGTCGCTGCCCGCCTGCCCTGAGGAGTCCCCGCTGCTTGTGGGCCCCATGCTGATT
GAGTTTAACATGCCTGTGGACCTGGAGCTCGTGGCAAAGCAGAACCCAAATGTGAAGATGGGCGGCCGCTATGCCCCCAGGGACTGCGTCTCTCCT
CACAAGGTGGCCATCATCATTCCATTCCGCAACCGGCAGGAGCACCTCAAGTACTGGCTATATTATTTGCACCCAGTCCTGCAGCGCCAGCAGCTG
GACTATGGCATCTATGTTATCAACCAGGCGGGAGACACTATATTCAATCGTGCTAAGCTCCTCAATGTTGGCTTTCAAGAAGCCTTGAAGGACTAT
GACTACACCTGCTTTGTGTTTAGTGACGTGGACCTCATTCCAATGAATGACCATAATGCGTACAGGTGTTTTTCACAGCCACGGCACATTTCCGTT
GCAATGGATAAGTTTGGATTCAGCCTACCTTATGTTCAGTATTTTGGAGGTGTCTCTGCTCTAAGTAAACAACAGTTTCTAACCATCAATGGATTT
CCTAATAATTATTGGGGCTGGGGAGGAGAAGATGATGACATTTTTAACAGATTAGTTTTTAGAGGCATGTCTATATCTCGCCCAAATGCTGTGGTC
GGGAGGTGTCGCATGATCCGCCACTCAAGAGACAAGAAAAATGAACCCAATCCTCAGAGGTTTGACCGAATTGCACACACAAAGGAGACAATGCTC
TCTGATGGTTTGAACTCACTCACCTACCAGGTGCTGGATGTACAGAGATACCCATTGTATACCCAAATCACAGTGGACATCGGGACACCGAGCAAG
GACGAGCTTTAG

FIG. 39

MGIKMETHSQVFVYMLLWLSGVDMQSSGELRTGGARPPPPLGASSQPRPGGDSSPVVDSGPGPASNLTSVPVPHTTALSLPACPEESPLLVGPMLI
EFNMPVDLELVAKQNPNVKMGGRYAPRDCVSPHKVAIIIPFRNRQEHLKYWLYYLHPVLQRQQLDYGIYVINQAGDTIFNRAKLLNVGFQEALKDY
DYTCFVFSDVDLIPMNDHNAYRCFSQPRHISVAMDKFGFSLPYVQYFGGVSALSKQQFLTINGFPNNYWGWGGEDDDIFNRLVFRGMSISRPNAVV
GRCRMIRHSRDKKNEPNPQRFDRIAHTKETMLSDGLNSLTYQVLDVQRYPLYTQITVDIGTPSKDEL

FIG. 40

ATGGGCATCAAGATGGAGACACATTCTCAGGTCTTTGTATACATGTTGCTGTGGTTGTCTGGTGTCGACATGGGACAGATGCCTGTGGCTGCTGTA
GTGGTTATGGCCTGCAGTCGTGCAGACTATCTTGAAAGGACTGTTAAATCAGTTTTAACATATCAAACTCCCGTTGCTTCAAAATATCCTCTATTT
ATATCTCAGGATGGATCTGATCAAGCTGTCAAGAGCAAGTCATTGAGCTATAATCAATTAACATATATGCAGCACTTGGATTTTGAACCAGTGGTC
ACTGAAAGGCCTGGCGAACTGACTGCGTACTACAAGATTGCACGTCACTACAAGTGGGCACTGGACCAGTTGTTTTACAAACACAAATTTAGTCGA
GTGATTATACTAGAAGATGATATGGAAATTGCTCCAGACTTCTTTGATTACTTTGAGGCTGCAGCTAGTCTCATGGATAGGGATAAAACCATTATG
GCTGCTTCATCATGGAATGATAATGGACAGAAGCAGTTTGTGCATGATCCCTATGCGCTATACCGATCAGATTTTTTTCCTGGCCTTGGGTGGATG
CTCAAGAGATCGACTTGGGATGAGTTATCACCAAAGTGGCCAAAGGCTTACTGGGATGATTGGCTGAGACTAAAGGAAAACCATAAAGGCCGCCAA
TTCATTCGACCGGAAGTCTGTAGAACATACAATTTTGGTGAACATGGGTCTAGTTTGGGACAGTTTTTCAGTCAGTATCTGGAACCTATAAAGCTA
AACGATGTGACGGTTGACTGGAAAGCAAAGGACCTGGGATACCTGACAGAGGGAAACTATACCAAGTACTTTTCTGGCTTAGTGAGACAAGCACGA
CCAATTCAAGGTTCTGACCTTGTCTTAAAGGCTCAAAACATAAAGGATGATGTTCGTATCCGGTATAAAGACCAAGTAGAGTTTGAACGCATTGCA
GGGGAATTTGGTATATTTGAAGAATGGAAGGATGGTGTGCCTCGAACAGCATATAAAGGAGTAGTGGTGTTTCGAATCCAGACAACAAGACGTGTA
TTCCTGGTTGGGCCAGATTCTGTAATGCAGCTTGGAATTCGAAATTCCAAGGACGAGCTTTGA

FIG. 41

MGIKMETHSQVFVYMLLWLSGVDMGQMPVAAVVVMACSRADYLERTVKSVLTYQTPVASKYPLFISQDGSDQAVKSKSLSYNQLTYMQHLDFEPVV
TERPGELTAYYKIARHYKWALDQLFYKHKFSRVIILEDDMEIAPDFFDYFEAAASLMDRDKTIMAASSWNDNGQKQFVHDPYALYRSDFFPGLGWM
LKRSTWDELSPKWPKAYWDDWLRLKENHKGRQFIRPEVCRTYNFGEHGSSLGQFFSQYLEPIKLNDVTVDWKAKDLGYLTEGNYTKYFSGLVRQAR
PIQGSDLVLKAQNIKDDVRIRYKDQVEFERIAGEFGIFEEWKDGVPRTAYKGVVVFRIQTTRRVFLVGPDSVMQLGIRNSKDEL

FIG. 42

ATGGGCATCAAGATGGAGACACATTCTCAGGTCTTTGTATACATGTTGCTGTGGTTGTCTGGTGTCGACATGGCTCTAAGGTTGCATAGAAGGAAC
CATTTTTCGCCTAGAAATACGGATCTGTTCCCGGATTTGGCAAAAGATCGTGTGGTTATCGTCTTGTATGTGCATAATCGGGCTCAGTATTTTCGA
GTCACAGTGGAAAGTTTGTCGAAGGTTAAAGGTATAAGTGAGACATTGTTGATTGTTAGTCATGATGGTTACTTTGAAGAGATGAATAGGATTGTG
GAGAGTATTAAGTTTTGTCAAGTGAAACAGATTTTCTCGCCTTATTCGCCTCATATATATCGTACTAGCTTCCCGGGTGTGACCCTGAATGATTGT
AAGAACAAGGGTGATGAGGCAAAGGGGCATTGTGAAGGTAATCCTGATCAGTATGGGAATCATCGGTCTCCGAAGATTGTATCTTTGAAGCATCAC
TGGTGGTGGATGATGAACACTGTATGGGATGGGTTGGAAGAGACTAAAGGACATGAGGGGCATATCCTTTTCATTGAAGAAGATCATTTTCTGTTT
CCTAATGCCTATCGTAACATACAGACTCTTACGAGGCTGAAACCCGCAAAGTGTCCTGACTGTTTTGCTGCTAATTTAGCACCGTCTGATGTGAAG
TCAAGAGGAGAAGGGCTTGAAAGTTTGGTTGCAGAGAGAATGGGAAATGTTGGGTATTCTTTTAATAGAAGTGTGTGGGAGAATATTCATCAGAAG
GCAAGAGAGTTTTGTTTCTTTGATGATTACAACTGGGATATAACGATGTGGGCAACGGTTTTCCCGTCGTTTGGTTCCCCGGTGTACACATTGCGA
GGGCCTAGGACTAGTGCGGTACACTTTGGAAAATGTGGGTTGCATCAAGGTAGAGGAGATGAGGGTGATTGCATCGATAATGGGGTCGTAAACATA
GAAGTTAAGGAAACAGATAAAGTTGTGAACATAAAAGAAGGATGGGGAGTTCGGGTGTATAAGCATCAAGCGGGTTATAAAGCCGGTTTCGAAGGT
TGGGGAGGTTGGGGCGATGATAGGGACCGACATTTATGTTTGGATTTTGCCACTATGTATCGTTACAGCAGTAGCAGTGCATCTCCAAAGGACGAG
CTTTGA

FIG. 43

MGIKMETHSQVFVYMLLWLSGVDMALRLHRRNHFSPRNTDLFPDLAKDRVVIVLYVHNRAQYFRVTVESLSKVKGISETLLIVSHDGYFEEMNRIV
ESIKFCQVKQIFSPYSPHIYRTSFPGVTLNDCKNKGDEAKGHCEGNPDQYGNHRSPKIVSLKHHWWWMMNTVWDGLEETKGHEGHILFIEEDHFLF
PNAYRNIQTLTRLKPAKCPDCFAANLAPSDVKSRGEGLESLVAERMGNVGYSFNRSVWENIHQKAREFCFFDDYNWDITMWATVFPSFGSPVYTLR
GPRTSAVHFGKCGLHQGRGDEGDCIDNGVVNIEVKETDKVVNIKEGWGVRVYKHQAGYKAGFEGWGGWGDDRDRHLCLDFATMYRYSSSSASPKDE
L

FIG. 44

ATGCTGAAGAAGCAGTCTGCAGGGCTTGTGCTGTGGGGCGCTATCCTCTTTGTGGCCTGGAATGCCCTGCTGCTCCTCTTCTTCTGGACGCGCCCA
GCACCTGGCAGGCCACCCTCAGTCAGCGCTCTCGATGGCGACCCCGCCAGCCTCACCCGGGAAGTCGACATGCAGTCCTCCGGGGAGCTCCGGACC
GGAGGGGCCCGGCCGCCGCCTCCTCTAGGCGCCTCCTCCCAGCCGCGCCCGGGTGGCGACTCCAGCCCAGTCGTGGATTCTGGCCCTGGCCCCGCT
AGCAACTTGACCTCGGTCCCAGTGCCCCACACCACCGCACTGTCGCTGCCCGCCTGCCCTGAGGAGTCCCCGCTGCTTGTGGGCCCCATGCTGATT
GAGTTTAACATGCCTGTGGACCTGGAGCTCGTGGCAAAGCAGAACCCAAATGTGAAGATGGGCGGCCGCTATGCCCCCAGGGACTGCGTCTCTCCT
CACAAGGTGGCCATCATCATTCCATTCCGCAACCGGCAGGAGCACCTCAAGTACTGGCTATATTATTTGCACCCAGTCCTGCAGCGCCAGCAGCTG
GACTATGGCATCTATGTTATCAACCAGGCGGGAGACACTATATTCAATCGTGCTAAGCTCCTCAATGTTGGCTTTCAAGAAGCCTTGAAGGACTAT
GACTACACCTGCTTTGTGTTTAGTGACGTGGACCTCATTCCAATGAATGACCATAATGCGTACAGGTGTTTTTCACAGCCACGGCACATTTCCGTT
GCAATGGATAAGTTTGGATTCAGCCTACCTTATGTTCAGTATTTTGGAGGTGTCTCTGCTCTAAGTAAACAACAGTTTCTAACCATCAATGGATTT
CCTAATAATTATTGGGGCTGGGGAGGAGAAGATGATGACATTTTTAACAGATTAGTTTTTAGAGGCATGTCTATATCTCGCCCAAATGCTGTGGTC
GGGAGGTGTCGCATGATCCGCCACTCAAGAGACAAGAAAAATGAACCCAATCCTCAGAGGTTTGACCGAATTGCACACACAAAGGAGACAATGCTC
TCTGATGGTTTGAACTCACTCACCTACCAGGTGCTGGATGTACAGAGATACCCATTGTATACCCAAATCACAGTGGACATCGGGACACCGAGCTAG

FIG. 45

MLKKQSAGLVLWGAILFVAWNALLLLFFWTRPAPGRPPSVSALDGDPASLTREVDMQSSGELRTGGARPPPPLGASSQPRPGGDSSPVVDSGPGPA
SNLTSVPVPHTTALSLPACPEESPLLVGPMLIEFNMPVDLELVAKQNPNVKMGGRYAPRDCVSPHKVAIIIPFRNRQEHLKYWLYYLHPVLQRQQL
DYGIYVINQAGDTIFNRAKLLNVGFQEALKDYDYTCFVFSDVDLIPMNDHNAYRCFSQPRHISVAMDKFGFSLPYVQYFGGVSALSKQQFLTINGF
PNNYWGWGGEDDDIFNRLVFRGMSISRPNAVVGRCRMIRHSRDKKNEPNPQRFDRIAHTKETMLSDGLNSLTYQVLDVQRYPLYTQITVDIGTPS

FIG. 46

OPTIMIZING GLYCAN PROCESSING IN PLANTS

RELATED APPLICATIONS

This application is a continuation of U.S. application Ser. No. 10/508,165, filed on Sep. 17, 2004, which is a national stage filing under 35 U.S.C. 371 of International Application PCT/IB03/001626, filed Mar. 18, 2003, which claims priority from Application No. 60/365,735, filed Mar. 19, 2002, the entire contents of each of which are incorporated by reference herein.

FIELD OF THE INVENTION

The invention is directed to methods for optimizing glycan processing of cell or an organism containing glycoproteins with N-glycans, in particular plants so that a glycoprotein having an N-glycan, high mannose type, hybrid or preferably complex type N-glycans, including but not limited to bi-antennary N-glycans, and containing a galactose residue on at least one arm of the N-glycan and which are devoid of (or reduced in) xylose and fucose residues can be obtained. The invention is further directed to said glycoprotein obtained and in particular a plant host system comprising said protein.

BACKGROUND OF THE INVENTION

N-linked glycans, specific oligosaccharide structures attached to asparagine residues of glycoproteins, can contribute significantly to the properties of the protein and, in turn, to the properties of the organism. Plant proteins can carry N-linked glycans but in marked contrast to mammals only few biological processes are known to which they contribute.

Biogenesis of N-linked glycans begins with the synthesis of a lipid linked oligosaccharide moiety (Glc3Man9GlcNAc2-) which is transferred en bloc to the nascent polypeptide chain in the endoplasmic reticulum (ER). Through a series of trimming reactions by exoglycosidases in the ER and cis-Golgi compartments, the so-called "high mannose" (Man9GlcNAc2 to Man5GlcNAc2) glycans are formed. Subsequently, the formation of complex type glycans starts with the transfer of the first GlcNAc onto Man5GlcNAc2 by GnTI and further trimming by mannosidase II (ManII) to form GlcNAcMan3GlcNAc2. Complex glycan biosynthesis continues while the glycoprotein is progressing through the secretory pathway with the transfer in the Golgi apparatus of the second GlcNAc residue by GnTII as well as other monosaccharide residues onto the GlcNAcMan3GlcNAc2 under the action of several other glycosyl transferases.

Plants and mammals differ with respect to the formation of complex glycans (see FIG. 1, which compares the glycosylation pathway of glycoproteins in plants and mammals). In plants, complex glycans are characterized by the presence of β(1,2)-xylose residues linked to the Man-3 and/or an α(1,3)-fucose residue linked to GlcNAc-1, instead of an α(1,6)-fucose residue linked to the GlcNAc-1. Genes encoding the corresponding xylosyl (XylT) and fucosyl (FucT) transferases have been isolated [Strasser et al., "Molecular cloning and functional expression of beta1,2-xylosyltransferase cDNA from *Arabidopsis thaliana," FEBS Lett.* 472:105 (2000); Leiter et al., "Purification, cDNA cloning, and expression of GDP-L-Fuc:Asn-linked GlcNAc alpha 1,3-fucosyltransferase from mung beans," *J. Biol. Chem.* 274:21830 (1999)]. Plants do not possess β(1,4)-galactosyltransferases nor α(2,6)sialyltransferases and consequently plant glycans lack the β(1,4)-galactose and terminal α(2,6) NeuAc residues often found on mammalian glycans.

The final glycan structures are not only determined by the mere presence of enzymes involved in their biosynthesis and transport but to a large extent by the specific sequence of the various enzymatic reactions. The latter is controlled by discrete sequestering and relative position of these enzymes throughout the ER and Golgi, which is mediated by the interaction of determinants of the transferase and specific characteristics of the sub-Golgi compartment for which the transferase is destined. A number of studies using hybrid molecules have identified that the transmembrane domains of several glycosyltransferases, including that of β(1,4)-galactosyltransferases, play a central role in their sub-Golgi sorting [Grabenhorst et al., *J. Biol. Chem* 274:36107 (1999); Colley, K., *Glycobiology* 7:1 (1997); Munro, *S., Trends Cell Biol.* 8:11 (1998); Gleeson, P. A., *Histochem. Cell Biol.* 109:517 (1998)].

Although plants and mammals have diverged a relatively long time ago, N-linked glycosylation seems at least partly conserved. This is evidenced by the similar though not identical glycan structures and by the observation that a mammalian GlcNAcTI gene complements a *Arabidopsis* mutant that is deficient in GlcNAcTI activity, and vice versa. The differences in glycan structures can have important consequences. For example, xylose and α(1,3)-fucose epitopes are known to be highly immunogenic and possibly allergenic in some circumstances, which may pose a problem when plants are used for the production of therapeutic glycoproteins. Moreover, blood serum of many allergy patients contains IgE directed against these epitopes but also 50% of non-allergic blood donors contains in their sera antibodies specific for core-xylose whereas 25% have antibodies for core-alpha 1,3-fucose (Bardor et al., 2002, in press, *Glycobiology*) (Advance Access published Dec. 17, 2002) which make these individuals at risk to treatments with recombinant proteins produced in plants containing fucose and/or xylose. In addition, this carbohydrate directed IgE in sera might cause false positive reaction in in vitro tests using plant extracts since there is evidence that these carbohydrate specific IgE's are not relevant for the allergenic reaction. In sum, a therapeutic failure with a glycoprotein produced in plants might be the result of accelerated clearance of the recombinant glycoprotein having xylose and/or fucose.

Accordingly, there is a need to better control glycosylation in plants, and particularly, glycosylation of glycoproteins intended for therapeutic use.

DEFINITIONS

To facilitate understanding of the invention, a number of terms as used in this specification are defined below.

The term "vector" refers to any genetic element, such as a plasmid, phage, transposon, cosmid, chromosome, retrovirus, virion, or similar genetic element, which is capable of replication when associated with the proper control elements and which can transfer gene sequences into cells and/or between cells. Thus, this term includes cloning and expression vehicles, as well as viral vectors.

The term "expression vector" as used herein refers to a recombinant DNA molecule containing a desired coding sequence (or coding sequences)—such as the coding sequence(s) for the hybrid enzyme(s) described in more detail below—and appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. It is not intended that the present invention be limited to particular expression vectors or expression vectors with particular elements.

The term "transgenic" when used in reference to a cell refers to a cell which contains a transgene, or whose genome has been altered by the introduction of a transgene. The term "transgenic" when used in reference to a cell, tissue or to a plant refers to a cell, tissue or plant, respectively, which comprises a transgene, where one or more cells of the tissue contain a transgene (such as a gene encoding the hybrid enzyme(s) of the present invention), or a plant whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, or other like modifications) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), or other similar elements.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, or other like modifications) relative to the naturally-occurring gene.

The term "fusion protein" refers to a protein wherein at least one part or portion is from a first protein and another part or portion is from a second protein. The term "hybrid enzyme" refers to a fusion protein which is a functional enzyme, wherein at least one part or portion is from a first species and another part or portion is from a second species. Preferred hybrid enzymes of the present invention are functional glycosyltransferases (or portions thereof) wherein at least one part or portion is from a plant and another part or portion is from a mammal (such as human).

The term "introduction into a cell" or "introduction into a host cell" in the context of nucleic acid (e.g., vectors) is intended to include what the art calls "transformation" or "transfection" or "transduction." Transformation of a cell may be stable or transient—and the present invention contemplates introduction of vectors under conditions where, on the one hand, there is stable expression, and on the other hand, where there is only transient expression. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., antigen binding of an antibody) encoded by the transgene (e.g., the antibody gene). The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction (PCR) of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "host cell" includes both mammalian (e.g. human B cell clones, Chinese hamster ovary cells, hepatocytes) and non-mammalian cells (e.g. insect cells, bacterial cells, plant cells). In one embodiment, the host cells are mammalian cells and the introduction of a vector expressing a hybrid protein of the present invention (e.g. TmGnTII-GalT) inhibits (or at least reduces) fucosylation in said mammalian cells.

The term "nucleotide sequence of interest" refers to any nucleotide sequence, the manipulation of which may be deemed desirable for any reason (e.g., confer improved qualities, use for production of therapeutic proteins), by one of ordinary skill in the art. Such nucleotide sequences include, but are not limited to, coding sequences of structural genes (e.g., reporter genes, selection marker genes, oncogenes, antibody genes, drug resistance genes, growth factors, and other like genes), and non-coding regulatory sequences which do not encode an mRNA or protein product, (e.g., promoter sequence, polyadenylation sequence, termination sequence, enhancer sequence, and other like sequences). The present invention contemplates host cells expressing a heterologous protein encoded by a nucleotide sequence of interest along with one or more hybrid enzymes.

The term "isolated" when used in relation to a nucleic acid, as in "an isolated nucleic acid sequence" refers to a nucleic acid sequence that is identified and separated from one or more other components (e.g., separated from a cell containing the nucleic acid, or separated from at least one contaminant nucleic acid, or separated from one or more proteins, one or more lipids) with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising SEQ ID NO:1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free, from other components with which they are naturally associated. The present invention contemplates both purified (including substantially purified) and unpurified hybrid enzyme(s) (which are described in more detail below).

As used herein, the terms "complementary" or "complementarity" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

A "complement" of a nucleic acid sequence as used herein refers to a nucleotide sequence whose nucleic acids show total complementarity to the nucleic acids of the nucleic acid sequence. For example, the present invention contemplates the complements of SEQ ID NOS: 1, 3, 5, 9, 27, 28, 29, 30, 31, 32, 33, 34, 35, 37, 38, 40, 41 and 43.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

When used in reference to a single-stranded nucleic acid sequence, the term "substantially homologous" refers to any probe which can hybridize to the single-stranded nucleic acid sequence under conditions of low stringency as described infra.

The term "hybridization" as used herein includes "any process by which a strand of nucleic acid joins with a complementary strand through base pairing." [Coombs J (1994) *Dictionary of Biotechnology*, Stockton Press, New York N.Y.]. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\%\ G+C)$, when a nucleic acid is in aqueous solution at 1 M NaCl [see e.g., Anderson and Young, Quantitative Filter Hybridization, in: *Nucleic Acid Hybridization* (1985)]. Other references include more sophisticated computations which take structural as well as sequence characteristics into account for the calculation of $T_m$.

Low stringency conditions when used in reference to nucleic acid hybridization comprise conditions equivalent to binding or hybridization at 68° C. in a solution consisting of 5×SSPE (Saline, Sodium Phosphate, EDTA) (43.8 g/l NaCl, 6.9 g/l $NaH_2PO_4.H_2O$ and 1.85 g/l EDTA (Ethylenediaminetetracetic Acid), pH adjusted to 7.4 with NaOH), 0.1% SDS (Sodium dodecyl sulfate), 5×Denhardt's reagent [50×Denhardt's contains the following per 500 ml: 5 g Ficoll (Type 400, Pharmacia), 5 g BSA (Bovine Serum Albumin) (Fraction V; Sigma)] and 100 μg/ml denatured salmon sperm DNA followed by washing in a solution comprising between 0.2× and 2.0×SSPE, and 0.1% SDS at room temperature when a DNA probe of about 100 to about 1000 nucleotides in length is employed.

High stringency conditions when used in reference to nucleic acid hybridization comprise conditions equivalent to binding or hybridization at 68° C. in a solution consisting of 5×SSPE, 1% SDS, 5×Denhardt's reagent and 100 μg/ml denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be tissue specific or cell specific. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, or similar stimuli). Typically, constitutive promoters are capable of directing expression of a transgene in substantially any cell and any tissue. In contrast, a "regulatable" promoter is one which is capable of directing a level of transcription of an operably linked nuclei acid sequence in the presence of a stimulus (e.g., heat shock, chemicals, light, or similar stimuli) which is different from the level of transcription of the operably linked nucleic acid sequence in the absence of the stimulus.

The terms "infecting" and "infection" with a bacterium refer to co-incubation of a target biological sample, (e.g., cell, tissue, plant part) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, butt not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine) by the infected cell. Thus, *Agrobacterium* strains which cause production of nopaline (e.g., strain LBA4301, C58, A208) are referred to as "nopaline-type" *Agrobacteria; Agrobacterium* strains which cause production of octopine (e.g., strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" *Agrobacteria*.

The terms "bombarding, "bombardment," and "biolistic bombardment" refer to the process of accelerating particles towards a target biological sample (e.g., cell, tissue, plant part—such as a leaf, or intact plant) to effect wounding of the cell membrane of a cell in the target biological sample and/or entry of the particles into the target biological sample. Methods for biolistic bombardment are known in the art (e.g., U.S. Pat. Nos. 5,584,807 and 5,141,131, the contents of both are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle bombardment as described herein. The present invention specifically contemplates schemes for introducing nucleic acid which employ microwounding.

The term "organism" as used herein refers to all organisms and in particular organisms, containing glycoproteins with n-linked glycans.

The term "plant" as used herein refers to a plurality of plant cells which are largely differentiated into a structure that is present at any stage of a plant's development. Such structures include, but are not limited to, a fruit, shoot, stem, root, leaf, seed, flower petal, or similar structure. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, and other types of cells). Plant tissue may be in planta, in organ culture, tissue culture, or cell culture. Similarly, "plant cells" may be cells in culture or may be part of a plant.

Glycosyltransferases are enzymes that catalyze the processing reactions that determine the structures of cellular oligosaccharides, including the oligosaccharides on glycoproteins. As used herein, "glycosyltransferase" is meant to include mannosidases, even though these enzymes trim glycans and do not "transfer" a monosaccharide. Glycosyltransferases share the feature of a type II membrane orientation. Each glycosyltransferase is comprised of an amino terminal cytoplasmic tail (shown for illustration purposes below as a made up of a string of amino acids arbitrarily labeled "X"—without intending to suggest the actual size of the region), a signal anchor domain (shown below as made up of a string of amino acids labeled "H" for hydrophobic—without intending to suggest the actual size of the domain and without intending to suggest that the domain is only made up of hydrophobic amino acids) that spans the membrane (referred to herein as a "transmembrane domain"), followed by a luminal stem (shown below as made up of a string of amino acids arbitrarily labeled "S"—without intended to suggest the actual size of the region) or stalk region, and a carboxy-terminal catalytic domain (shown below as made up of a string of amino acids arbitrarily labeled "C"—without intending to suggest the actual size of the domain:

$NH_2$-$\underline{\text{XXXXXXHHHHHHHHSSSSSSSS}}$CCCCCCCC

Collectively, The Cytoplasmic Tail-Transmembrane-Stem Region or "CTS" (which has been underlined in the above schematic for clarity) can be used (or portions thereof) in embodiments contemplated by the present invention wherein the catalytic domain is exchanged or "swapped" with a corresponding catalytic domain from another molecule (or portions of such regions/domains) to create a hybrid protein.

For example, in a preferred embodiment, the present invention contemplates nucleic acid encoding a hybrid enzyme (as well as vectors containing such nucleic acid, host cells containing such vectors, and the hybrid enzyme itself), said hybrid enzyme comprising at least a portion of a CTS region [e.g., the cytoplasmic tail ("C"), the transmembrane domain ("T"), the cytoplasmic tail together with the transmembrane domain ("CT"), the transmembrane domain together with the stem ("TS"), or the complete CTS region] of a first glycosyltransferase (e.g. plant glycosyltransferase) and at least a portion of a catalytic region of a second glycosyltransferase (e.g. mammalian glycosyltransferase). To create such an embodiment, the coding sequence for the entire CTS region (or portion thereof) may be deleted from nucleic acid coding for the mammalian glycosyltransferase and replaced with the coding sequence for the entire CTS region (or portion thereof) of a plant glycosyltransferase. On the other hand, a different approach might be taken to create this embodiment; for example, the coding sequence for the entire catalytic domain (or portion thereof) may be deleted from the coding sequence for the plant glycosyltransferase and replaced with the coding sequence for the entire catalytic domain (or portion thereof) of the mammalian glycosyltransferase. In such a case, the resulting hybrid enzyme would have the amino-terminal cytoplasmic tail of the plant glycosyltransferase linked to the plant glycosyltransferase transmembrane domain linked to the stem region of the plant glycosyltransferase in the normal manner of the wild-type plant enzyme—but the stem region would be linked to the catalytic domain of the mammalian glycosyltransferase (or portion thereof).

It is not intended that the present invention be limited only to the two approaches outlined above. Other variations in the approach are contemplated. For example, to create nucleic acid encoding a hybrid enzyme, said hybrid enzyme comprising at least a portion of a transmembrane region of a plant glycosyltransferase and at least a portion of a catalytic region of a mammalian glycosyltransferase, one might use less than the entire coding sequence for the CTS region (e.g., only the transmembrane domain of the plant glycosytransferase, or the complete cytoplasmic tail together with all or a portion of the transmembrane domain, or the complete cytoplasmic tail together with all of the transmembrane domain together with a portion of the stem region). One might delete the mammalian coding sequence for the entire cytoplasmic tail together with the coding sequence for the transmembrane domain (or portion thereof)—followed by replacement with the corresponding coding sequence for the cytoplasmic tail and transmembrane domain (or portion thereof) of the plant glycosyltransferase. In such a case, the resulting hybrid enzyme would have the stem region of the mammalian glycosyltransferase linked to the plant glycosyltransferase transmembrane domain (or portion thereof) which in turn would be linked to the amino-terminal cytoplasmic tail of the plant glycosyltransferase, with the stem region being linked to the catalytic domain of the mammalian glycosyltransferase (i.e. two of the four regions/domains would be of plant origin and two would be of mammalian origin).

In other embodiments, the present invention contemplates nucleic acid encoding a hybrid enzyme (along with vectors, host cells containing the vectors, plants—or plant parts—containing the host cells), said hybrid enzyme comprising at least a portion of an amino-terminal cytoplasmic tail of a plant glycosyltransferase and at least a portion of a catalytic region of a mammalian glycosyltransferase. In this embodiment, the hybrid enzyme encoded by the nucleic acid might or might not contain other plant sequences (e.g., the transmembrane domain or portion thereof, the stem region or portion thereof). For example, to create such an embodiment, the coding sequence for the entire cytoplasmic tail (or portion thereof) may be deleted from nucleic acid coding for the mammalian glycosyltransferase and replaced with the coding sequence for the entire cytoplasmic domain (or portion thereof) of a plant glycosyltransferase. In such a case, the resulting hybrid enzyme would have the amino-terminal cytoplasmic tail (or portion thereof) of the plant glycosyltransferase linked to the mammalian glycosyltransferase transmembrane domain, which in turn is linked to stem region of the mammalian glycosyltransferase, the stem region being linked to the catalytic domain of the mammalian glycosyltransferase. On the other hand, a different approach might be taken to create this embodiment; for example, the coding sequence for the entire catalytic domain (or portion thereof) may be deleted from the coding sequence for the plant glycosyltransferase and replaced with the coding sequence for the entire catalytic domain (or portion thereof) of the mammalian glycosyltransferase. In such a case, the resulting hybrid enzyme would have the amino-terminal cytoplasmic tail of the plant glycosyltransferase linked to the plant glycosyltransferase transmembrane domain linked to the stem region of the plant glycosyltransferase in the normal manner of the wild-type plant enzyme—but the stem region would be linked to the catalytic domain of the mammalian glycosyltransferase (or portion thereof).

In the above discussion, the use of the phrase "or portion thereof" was used to expressly indicate that less than the entire region/domain might be employed in the particular case (e.g., a fragment might be used). For example, the cytoplasmic tail of glycosyltransferases ranges from approximately 5 to 50 amino acids in length, and more typically 15 to 30 amino acids, depending on the particular transferase. A "portion" of the cytoplasmic tail region is herein defined as no fewer than four amino acids and can be as large as up to the full length of the region/domain less one amino acid. It is desired that the portion function in a manner analogous to the full length region/domain—but need not function to the same degree. For example, to the extent the full-length cytoplasmic tail functions as a Golgi retention region or ER retention signal, it is desired that the portion employed in the above-named embodiments also function as a Golgi or ER retention region, albeit perhaps not as efficiently as the full-length region. Similarly, the transmembrane domain is typically 15-25 amino acids in length and made up of primarily hydrophobic amino acids. A "portion" of the transmembrane domain is herein defined as no fewer than ten amino acids and can be as large as up to the full length of the region/domain (for the particular type of transferase) less one amino acid. It is desired that the portion function in a manner analogous to the full length region/domain—but need not function to the same degree. For example, to the extent the full-length transmembrane domain functions as the primary Golgi retention region or ER retention signal, it is desired that the portion employed in the above-named embodiments also function as a Golgi or ER retention region, albeit perhaps not as efficiently as the full-length region. The present invention specifically contemplates conservative substitutions to create variants of the wild-type transmembrane domain or portions thereof. For example, the present invention contemplates replacing one or more hydrophobic amino acids (shown as "H" in the schematic above) of the wild-type sequence with one or more different amino acids, preferably also hydrophobic amino acids.

A portion of the catalytic domain can be as large as the full length of the domain less on amino acid. Where the catalytic domain is from a beta1,4-galactosyltransferase, it is preferred that the portion include at a minimum residues 345-365 which are believed to be involved in the conformation conferring an oligosaccharide acceptor binding site (it is preferred that the portion include this region at a minimum and five to ten amino acids on either side to permit the proper conformation).

The present invention also includes synthetic CTS regions and portions thereof. A "portion" of a CTS region must include at least one (and may include more than one) entire domain (e.g., the entire transmembrane domain) but less than the entire CTS region.

Importantly, by using the term "CTS region" or "transmembrane domain" it is not intended that only wild type sequences be encompassed. Indeed, this invention is not limited to natural glycosyltransferases and enzymes involved in glycosylation, but also includes the use of synthetic enzymes exhibit the same or similar function. In one embodiment, wild type domains are changed (e.g. by deletion, insertion, replacement and the like).

Finally, by using the indicator "Tm" when referring to a particular hybrid (e.g., "TmXyl-), entire transmembrane/CTS domains (with or without changes to the wild-type sequence) as well as portions (with or without changes to the wild-type sequence) are intended to be encompassed.

SUMMARY OF THE INVENTION

The present invention contemplates nucleic acid (whether DNA or RNA) encoding hybrid enzymes (or "fusion proteins"), vectors containing such nucleic acid, host cells (including but not limited to cells in plant tissue and whole plants) containing such vectors an expressing the hybrid enzymes, and the isolated hybrid enzyme(s) themselves. In one embodiment, expression of said hybrid enzymes (or "fusion proteins") results in changes in glycosylation, such as, but not limited to, reduction of sugar moieties such as xylose, fucose, Lewis$^{A/B/X}$ or other sugar structures that interfere with desired glycoform accumulation. In one embodiment, the present invention contemplates nucleic acid encoding a hybrid enzyme, said hybrid enzyme comprising a CTS region (or portion thereof) of a glycosyltransferase (including but not limited to a plant glycosyltransferase) and a catalytic region (or portion thereof) of a non-plant glycosyltransferase (e.g., mammalian, fish, amphibian, fungal). It is preferred that, when expressed, the CTS region (or portion thereof) is linked (directly or indirectly) in operable combination to said catalytic region (or portion thereof). The linking is preferably covalent and the combination is operable in that the catalytic region exhibits catalytic function (even if said catalytic function is reduced as compared to the wild-type enzyme). The linking can be direct in the sense that there are no intervening amino acids or other regions/domains. On the other hand, the linking can be indirect in that there are intervening amino acids (or other chemical groups) and/or other regions/domains between them. Of course, the nucleic acid used to make the nucleic acid encoding the above-described hybrid enzyme(s) can be obtained enzymatically from a physical sequence (e.g. genomic DNA, a cDNA, and the like) or alternatively, made synthetically using a reference sequence (e.g. electronic or hardcopy sequence) as a guide.

In a particular embodiment, the present invention contemplates nucleic acid encoding a hybrid enzyme, said hybrid enzyme comprising a transmembrane region (e.g., at least a transmembrane region and optionally more of the CTS region) of a plant glycosyltransferase and a catalytic region (or portion thereof) of a non-plant (such as a mammalian) glycosyltransferase. Again, it is preferred that, when expressed, these regions are linked (directly or indirectly) in operable combination. In yet another embodiment, the present invention contemplates nucleic acid encoding a hybrid enzyme, said hybrid enzyme comprising a transmembrane domain (or portion thereof) of a plant glycosyltransferase and a catalytic region (or portion thereof) of a mammalian glycosyltransferase. Again, it is preferred that, when expressed, these regions are linked (directly or indirectly) in operable combination.

It is not intended that the present invention be limited to particular transferases. In one embodiment, the plant glycosyltransferase is a xylosyltransferase. In another embodiment, the plant glycosyltransferase is a N-acetylglucosaminyltransferase. In another embodiment, the plant glycosyltransferase is a fucosyltransferase. In a preferred embodiment, the mammalian glycosyltransferase is a human galactosyltransferase (such as the human beta 1,4-galactosyltransferase encoded by SEQ ID NO:1 wherein the nucleotides encoding the transmembrane domain are deleted and replaced).

It is not intended that the present invention is limited to the use of a plant-derived glycosyltransferase CTS-domain and a human glycosyltransferase catalytic domain but also vice versa and the use of any CTS-domain of a glycosyltransferase in combination with the catalytic fragment of at least one other glycosyltransferase. Indeed, the present invention broadly contemplates, in one embodiment, nucleic acid encoding a hybrid enzyme, said hybrid enzyme comprising a transmembrane region of a first glycosyltransferase and a catalytic region of a second glycosyltransferase. It is preferred that said first and second glycosyltransferases are from different species (and can be from a different genus or even from a different phylum). In one embodiment, said first glycosyltransferase comprises a plant glycosyltransferase. In another embodiment, said plant glycosyltransferase is a xylosyltransferase. In yet another embodiment, said plant glycosyltransferase is a fucosyltransferase. In a preferred embodiment said second glycosyltransferase comprises a mammalian glycosyltransferase. In a particularly preferred embodiment, said mammalian glycosyltransferase is a human galactosyltransferase.

It is not intended that the present invention be limited to circumstances where the first and second glycosyltransferases are plant and non-plant, respectively. In one embodiment, said first glycosyltransferase comprises a first mammalian glycosyltransferase and said second glycosyltransferase comprises a second mammalian glycosyltransferase. In a preferred embodiment, said first mammalian glycosyltransferase is a non-human glycosyltransferase and said second mammalian glycosyltransferase is a human glycosyltransferase.

It is not intended that the present invention be limited to the type of vector. In one embodiment, the present invention contemplates an expression vector, comprising the nucleic acid encoding the above-described hybrid enzyme.

It is also not intended that the present invention be limited to the type of host cells. A variety of prokaryotic and eukaryotic host cells are commercially available for expressing proteins. In one embodiment, the present invention contemplates a host cell containing the vector comprising the nucleic acid encoding the above-described hybrid enzyme (with or without other vectors or other nucleic acid encoding other hybrid enzymes or glycosyltransferases). In a preferred embodiment, the host cell is a plant cell. In a particularly preferred embodiment, the present invention contemplates a plant comprising such a host cell.

It is not intended that the present invention be limited by the method by which host cells are made to express the hybrid enzymes of the present invention. In one embodiment, the present invention contemplates a method, comprising: a) providing: i) a host cell (such as a plant cell, whether in culture or as part of plant tissue or even as part of an intact growing plant), and ii) an expression vector comprising nucleic acid encoding a hybrid enzyme, said hybrid enzyme comprising at least a portion of a CTS region of a plant glycosyltransferase (e.g. the transmembrane domain) and at least a portion of a catalytic region of a mammalian glycosyltransferase; and b) introducing said expression vector into said plant cell under conditions such that said hybrid enzyme is expressed. Again, it is not intended that the present invention be limited to particular transferases. In one embodiment, the plant glycosyltransferase used in the above-described method is a xylosyltransferase. In another embodiment, the plant glycosyltransferase is a N-acetylglucosaminyltransferase. In another embodiment, the plant glycosyltransferase is a fucosyltransferase. In a preferred embodiment, the mammalian glycosyltransferase used in the above-described method is a human galactosyltransferase (such as the human beta 1,4-galactosyltransferase encoded by SEQ ID NO:1 wherein the nucleotides encoding the transmembrane domain are deleted and replaced) (or simply where the nucleotides of SEQ ID NO:1 encoding the catalytic domain, or portion thereof, are taken and linked to nucleotides encoding the CTS region, or portion thereof, of a plant glycosyltransferase.).

It is not intended that the present invention be limited to a particular scheme for controlling glycosylation of a heterologous protein using the hybrid enzymes described above. In one embodiment, the present invention contemplates a method, comprising: a) providing: i) a host cell (such as a plant cell), ii) a first expression vector comprising nucleic acid encoding a hybrid enzyme, said hybrid enzyme comprising at least a portion of a CTS region (e.g. at least a transmembrane domain) of a first (such as a plant) glycosyltransferase and at least a portion of a catalytic region of a second (such as a mammalian) glycosyltransferase, and iii) a second expression vector comprising nucleic acid encoding a heterologous glycoprotein; (or portion thereof; and b) introducing said first and second expression vectors into said plant cell under conditions such that said hybrid enzyme and said heterologous protein are expressed. Alternatively, a single vector with nucleic acid encoding both the hybrid enzyme (or hybrid enzymes) and the heterologous glycoprotein might be used. Regardless of which method is used, the invention contemplates, in one embodiment, the additional step (c) of isolating the heterologous protein—as well as the isolated protein itself as a composition.

On the other hand, the present invention also contemplates introducing different vectors into different plant cells (whether they are cells in culture, part of plant tissue, or even part of an intact growing plant). In one embodiment, the present invention contemplates a method, comprising: a) providing: i) a first plant comprising a first expression vector, said first vector comprising nucleic acid encoding a hybrid enzyme (or encoding two or more hybrid enzymes), said hybrid enzyme comprising at least a portion of a CTS region (e.g. the first approximately 40-60 amino acids of the N-terminus) of a plant glycosyltransferase and at least a portion of a catalytic region of a mammalian glycosyltransferase, and ii) a second plant comprising a second expression vector, said second vector comprising nucleic acid encoding a heterologous protein (or portion thereof); and crossing said first plant and said second plant to produce progeny expressing said hybrid enzyme and said heterologous protein. Of course, such progeny can be isolated, grown up, and analyzed for the presence of each (or both) of the proteins. Indeed, the heterologous protein can be used (typically first purified substantially free of plant cellular material) therapeutically (e.g., administered to a human or animal, whether orally, by intravenous, transdermally or by some other route of administration) to treat or prevent disease.

It is not intended that the present invention be limited to a particular heterologous protein. In one embodiment, any peptide or protein that is not endogenous to the host cell (or organism) is contemplated. In one embodiment, the heterologous protein is an antibody or antibody fragment. In a particularly preferred embodiment, the antibody is a human antibody or "humanized" antibody expressed in a plant in high yield. "Humanized" antibodies are typically prepared from non-human antibodies (e.g. rodent antibodies) by taking the hypervariable regions (the so-called CDRs) of the non-human antibodies and "grafting" them on to human frameworks. The entire process can be synthetic (provided that the sequences are known) and frameworks can be selected from a database of common human frameworks. Many times, there is a loss of affinity in the process unless either the framework sequences are modified or the CDRs are modified. Indeed, increases in affinity can be revealed when the CDRs are systematically mutated (for example, by randomization procedures) and tested.

While the present invention is particularly useful in the context of heterologous proteins, in one embodiment, the hybrid enzymes of the present invention are used to change the glycosylation of endogenous proteins, i.e. proteins normally expressed by the host cell or organism.

The present invention specifically contemplates the plants themselves. In one embodiment, the present invention contemplates a plant, comprising first and second expression vectors, said first vector comprising nucleic acid encoding a hybrid enzyme, said hybrid enzyme comprising at least a portion of a CTS region (e.g. the cytoplasmic tail together with at least a portion of the transmembrane domain) of a plant glycosyltransferase and at least a portion of a catalytic region of a mammalian glycosyltransferase, said second expression vector, said second vector comprising nucleic acid encoding a heterologous protein (or portion thereof). In a preferred embodiment, by virtue of being expressed along with the hybrid enzyme (or hybrid enzymes) of the present invention, the heterologous protein displays reduced (10% to 99%) alpha 1,3-fucosylation (or even no fucosylation), as compared to when the heterologous protein is expressed in the plant in the absence of the hybrid enzyme (or enzymes). In a preferred embodiment, by virtue of being expressed along with the hybrid enzyme (or hybrid enzymes) of the present invention, the heterologous protein displays reduced (10% to 99%) xylosylation (or even no xylose), as compared to when the heterologous protein is expressed in the plant in the absence of the hybrid enzyme (or enzymes). In a preferred embodiment, by virtue of being expressed along with the hybrid enzyme (or hybrid enzymes) of the present invention, the heterologous protein displays both reduced fucose and xylose, as compared to when the heterologous protein is expressed in the plant in the absence of the hybrid enzyme (or enzymes).

It is not intended that the present invention be limited to a particular theory by which reduced fucose and/or xylose is achieved. Very little is known about the sub-Golgi sorting mechanism in plants. The mammalian specific β(1,4)-galactosyltransferase (GalT) has been used (see the Examples below) as an excellent first marker to study this phenomenon since it generates glycan structures not normally found in plants. The glycan structures of plants that express galactosyltransferase has been compared with glycan structures from plants that express a chimeric galactosyltransferase of which the CTS domain is exchanged for that of a plant xylosyltransferase (or portion thereof). The change in observed glycan structures show that the galactosyltransferase is, as in mammals, confined to a specific sub-compartment of the plant Golgi. Without limiting the invention to any particular mechanism, the sorting mechanism of plants and mammals are apparently conserved even to the extent that glycosyltransferases unknown to plants are routed to specific analogous location in the Golgi. This location is later in the Golgi than where the endogenous xylosyl-, fucosyl- and GlcNAc-TII (GnTII) transferases are located.

The finding that N-glycans in these plants that express relocalised variants of GalT containing significantly less xylose and fucose is also of biotechnological relevance. For glycoproteins intended for therapeutic use in mammals, such as humans, the approach of certain embodiments of the present invention provides methods and compositions for controlling N-linked glycosylation of glycoproteins in plants so that glycoprotein essentially free of xylose and fucose and containing at least a bi-antennary N-glycans (but not limited to bi-antennary, also include tri-antennary, and the like) and (at least one) galactose residue on at least one of the arms of the N-glycan can be obtained. Hence, it is not intended that the present invention is limited to bi-antennary N-glycans but also includes bisected bi-antennary N-glycans, tri-antennary N-glycans, and the like. Furthermore, the invention is not limited to complex-type N-glycans but also includes hybrid-type N-glycans and other type N-glycans. The present invention contemplates such resulting glyco-proteins. In addition, the methods and compositions of the present invention may be applicable for plants and non-plant systems where besides xylose, fucose, Lewis$^{A/B/X}$ type N-glycan modifications (β1-3-GalT, α1-4-FucT, other) or other sugars, "interfere" with desired glycoform accumulation.

In one embodiment, the invention is directed to controlling N-linked glycosylation of plants by modulating the localization of enzymes involved in glycan biosynthesis in the Golgi apparatus. Specifically, embodiments of the invention are directed to a method of producing in a plant host system a glycoprotein having bi-antennary glycans and containing at least one galactose residues on at least one of the arms and which are devoid (or reduced in) of xylose and fucose, comprising: (a) preventing (or inhibiting) addition of xylose and fucose on the core of the glycan of said glycoprotein and (b) adding one or preferably two galactose residues to said arms.

Addition of xylose and fucose to said heterologous glycoprotein may be reduced or even prevented by introducing to said plant host system a nucleic acid encoding a hybrid enzyme comprising a CTS region (or portion thereof) of a protein, particularly an enzyme such as plant xylosyltransferase and catalytic region (or portion thereof) of a galactosyltransferase not normally found in a plant, or a modified galactosyltransferase where its transmembrane portion has been removed and endoplasmic reticulum retention signal have been inserted, wherein said protein or enzyme acts earlier in the Golgi apparatus of a plant cell in said plant host system than said galactosyltransferase. It is preferred that the galactosyltransferase is a mammalian galactosyltransferase and in particular, a human galactosyltransferase. In a most specific embodiment, said galactosyltransferase is human β1,4 galactosyltransferase (GalT). In a preferred embodiment, said xylosyltransferase is a β1,2-xylosyltransferase. The exchange of the CTS region or CTS fragment of a mammalian glycosyltransferase (such as a galactosyltransferase) by one from the group of enzymes that act earlier in the Golgi apparatus than galactosyltransferase including but not limited to those from of XylT, FucT, GnTI, GnTII, GnTIII, GnTIV, GnTV, GnTVI, ManI, Mann and ManIII results in strongly reduced amounts of glycans that contain the undesired xylose and fucose residues (see FIG. 2). In addition, galactosylation is improved and the diversity in glycans is reduced. While not limited to any particular mechanism, the increase in galactosylated glycans that carry neither xylose nor fucose is believed to be mainly attributed to the accumulation of GalGNMan5, GNMan5 or GalGNMan4. Also, galactosylation occurs on one glycan arm only. Apparently, the galactosylation earlier in the Golgi inhibits trimming of the said glycoforms by Mannosidase II (ManII) to GalGNMan3. Also addition of the second GlcNAc by GlcNAcTII (GnTII) is inhibited.

Therefore, in one embodiment, a further step is contemplated to obtain the desired glycoprotein that has both arms galactosylated and yet is essentially devoid of xylose and fucose. Thus, in one embodiment, the method of the invention as noted above further comprises adding galactose residues to the arms of said glycoprotein (see FIG. 3). In one embodiment of the invention, galactose residues are added onto both arms by introducing to said plant host system (a) a nucleic acid sequence encoding a first hybrid enzyme comprising the CTS region (or fragment, such as one including the transmembrane domain) of GnTI and the active domain (or portion thereof) of GnTII; (b) a nucleic acid sequence encoding the second hybrid enzyme comprising the CTS region (or fragment, such as one including the transmembrane of GnTI and the active domain of ManII and (c) a nucleic acid sequence encoding a third hybrid enzyme comprising the CTS region (or fragment, such as one including the transmembrane domain) of XylT and the active domain (or portion thereof) of human galactosyltransferse (TmXyl-GalT). In another embodiment of the invention, galactose residues are added onto both arms by introducing to said plant host system (a) a nucleic acid sequence encoding a first hybrid enzyme comprising the CTS region (or fragment, such as one including the transmembrane domain) of ManI and the active domain (or portion thereof) of GnTI; (b) a nucleic acid sequence encoding the second hybrid enzyme comprising the CTS region (or fragment, such as one including the transmembrane domain) of ManI and the active domain (or portion thereof) of GnTII; (c) a nucleic acid sequence encoding the third hybrid enzyme comprising the CTS region (or fragment, such as one including the transmembrane domain) of ManI and the active domain (or portion thereof) of ManII, and (d) a nucleic acid sequence encoding a fourth hybrid enzyme comprising the CTS region (or fragment, such as one including the transmembrane domain) of XylT and the active domain (or portion thereof) of human galactosyltransferse (TmXyl-GlT).

It is not intended that the present invention be limited to particular combinations of hybrid enzymes or the number of such hybrid enzymes employed in a single cell, plant tissue or plant. In a preferred embodiment, the present invention contemplates host cells expressing TmXyl-GalT plus TmGnTI-GnTII plus TmGnTI-ManII. In one embodiment of the invention, galactose residues are added to said arms by introducing to said plant host system (a) a nucleic acid sequence encoding a first hybrid enzyme comprising a CTS region (or fragment thereof) of a protein, particularly an enzyme, including but not limited to N-acetylglucosaminyltransferase I (GnTI) and a catalytic region (or portion thereof) of a mannosidase II (ManII), wherein said enzyme acts earlier in the Golgi apparatus of a plant cell in said plant host system than said mannosidase II or modified mannosidase II where its transmembrane portion has been deleted and endoplasmic reticulum retention signal have been inserted and (b) a nucleic acid sequence encoding a second hybrid enzyme comprising a CTS region (or fragment, such as one including the transmembrane domain) of an enzyme including but not limited to N-acetyl-glucosaminyltransferase I (GnTI) and a catalytic region (or portion thereof) of a N-acetylglucosaminyl-transferase II (GnTII), wherein said enzyme acts earlier in the Golgi apparatus of a plant cell in said plant host system than said N acetylglucosaminyl-transferaseII (GnTII) or modified N-acetylglucosaminyltransferase II (GnTII) where its transmembrane portion has been deleted and an endoplasmic reticulum retention signal have been inserted. The sequences encoding N-acetylglucosaminyltransferases or mannosidase II or the said transmembrane fragments can originate form plants or from eukaryotic non-plant organisms (e.g., mammals).

In yet another preferred embodiment, the present invention contemplates a host cell expressing TmXyl-GalT plus TmManI-GnTI plus TmManI-ManII plus TmManI-GnTII. In another embodiment of the invention, galactose residues are added to said arms by introducing to said plant host system (a) a nucleic acid sequence encoding a first hybrid enzyme comprising a CTS region (or fragment, such as one including the transmembrane domain) of a protein, particularly an enzyme, including but not limited to Mannosidase I (ManI) and a catalytic region (or portion thereof) of a N acetylglucosaminyltransferase I (GnTI), wherein said enzyme acts earlier in the Golgi apparatus of a plant cell in said plant host system than said N-acetylglucosaminyl-transferase I (GnTI) or modified N acetylglucosaminyltransferase I (GnTI) where its transmembrane portion has been deleted and endoplasmic reticulum retention signal have been inserted and (b) a nucleic acid sequence encoding a second hybrid enzyme comprising a CTS region (or fragment, such as one including the transmembrane domain) of an enzyme including but not limited to Mannosidase I (ManI) and a catalytic region (or portion thereof) of a Mannosidase II (ManII), wherein said enzyme acts earlier in the Golgi apparatus of a plant cell in said plant host system than said Mannosidase II (ManII) or modified Mannosidase II (ManII) where its transmembrane portion has been deleted and an endoplasmic reticulum retention signal have been inserted and (c) a nucleic acid sequence encoding a third hybrid enzyme comprising a CTS region (or fragment, such as one including the transmembrane domain) of an enzyme including but not limited to Mannosidase I (ManI) and a catalytic region (or portion thereof) of a N-acetylglucos-aminyltransferase II (GnTII), wherein said enzyme acts earlier in the Golgi apparatus of a plant cell in said plant host system than said N-acetylglucosaminyltransferase II (GnTII) or modified N-acetylglucosaminyltransferase II (GnTII) where its transmembrane portion has been deleted and an endoplasmic reticulum retention signal have been inserted. The sequences encoding N-acetylglucosaminyltransferases or mannosidases or the said transmembrane fragments can originate from plants or from eukaryotic non-plant organisms (e.g., mammals).

In still another preferred embodiment, the present invention contemplates host cells expressing TmXyl-GalT plus ManIII. In another embodiment of the invention, galactose residues are added to said arms by introducing to said plant host system (a) a nucleic acid sequence encoding a Mannosidase III (MannI, wildtype gene sequence but not limited to: also ManIII with endoplasmic reticulum retention signal; MannIII with transmembrane fragment of early (cis-) Golgi apparatus glycosyltransferase (GnTI, ManI, GnTIII). The sequences encoding Mannosidase III can originate form insects, preferably from *Spodoptera frugiperda* or *Drosophila melanogaster* (but not limited to), human or from other organisms.

In still another preferred embodiment, the present invention contemplates a host cell expressing TmXyl-GalT plus ManIII plus TmGnTI-GnTII. In yet another preferred embodiment, the present invention contemplates a host cell expressing TmXyl-GalT plus MannIII plus TmManI-GnTI plus TmManI-GnTII.

The method of the invention may optionally comprise, in one embodiment, introducing into said plant host system a mammalian N-acetylglucosaminyltransferase GnTIII, particularly a human GnTIII or hybrid protein comprising a catalytic portion of mammalian GnTIII and a transmembrane portion of a protein, said protein residing in the ER or earlier compartment of the Golgi apparatus of a eukaryotic cell. For example, in one embodiment, the hybrid enzyme TmXyl-GnTIII is contemplated (along with nucleic acid coding for such a hybrid enzyme, vectors containing such nucleic acid, host cells containing such vectors, and plants—or plant parts—containing such host cells). In another embodiment, the hybrid enzyme TmFuc-GnTIII is contemplated (along with nucleic acid coding for such a hybrid enzyme, vectors containing such nucleic acid, host cells containing such vectors, and plants—or plant parts—containing such host cells). The present invention specifically contemplates host cells expressing such hybrid enzymes (with or without additional hybrid enzymes or other glycosyltransferases).

The invention is further directed to said hybrid and modified enzymes, nucleic acid sequences encoding said hybrid enzymes, vectors comprising said nucleic acid sequences and methods for obtaining said hybrid enzymes. Furthermore, the invention is directed to a plant host system comprising a heterologous glycoprotein having preferably complex type bi-antennary glycans and containing at least one galactose residue on at least one of the arms and are devoid of xylose and fucose. A "heterologous glycoprotein" is a glycoprotein originating from a species other than the plant host system. The glycoprotein may include but is not limited to antibodies, hormones, growth factors and growth factor receptors and antigens.

Indeed, the present invention is particularly useful for controlling the glycosylation of heterologous glycoproteins, such as antibodies or antibody fragments (single chain antibodies, Fab fragments, $Fab_2$ fragments, Fv fragments, and the like). To control the glycosylation of an antibody, the gene construct encoding a hybrid enzyme of the present invention (e.g., the TmXyl-GalT gene construct) can be introduced in transgenic plants expressing an antibody (e.g., monoclonal antibody) or antibody fragment. On the other hand, the gene(s) encoding the antibody (or antibody fragment) can be introduced by retransformation of plant expressing TmXyl-GalT gene construct. In still another embodiment, the binary vector harbouring the TmXyl-GalT expression cassette can be co-transformed to plants together with a plant binary vector harbouring the expression cassettes comprising both light and heavy chain sequences of a monoclonal antibody on a single T-DNA or with binary vectors harbouring the expression cassettes for light and heavy chain sequences both separately on independent T-DNA's but both encoding a monoclonal antibody. The present invention specifically contemplates, in one embodiment, crossing plants expressing antibodies with plant expressing the hybrid glycosyltransferase(s) of the present invention.

A "host system" may include but is not limited to any organism containing glycoproteins with N-glycans.

A "plant host system" may include but is not limited to a plant or portion thereof, which includes but is not limited to a plant cell, plant organ and/or plant tissue. The plant may be a monocotyledon (monocot) which is a flowering plant whose embryos have one cotyledon or seed leaf and includes but is not limited to lilies, grasses, corn (*Zea mays*), rice, grains including oats, wheat and barley, orchids, irises, onions and palms. Alternatively, the plant may be a dicotyledenon (dicot) which includes but is not limited to tobacco (*Nicotiana*), tomatoes, potatoes, legumes (e.g., alfalfa and soybeans), roses, daises, cacti, violets and duckweed. The plant may also be a moss which includes but is not limited to *Physcomitrella patens*.

The invention is further directed to a method for obtaining said plant host system. The method comprises crossing a plant expressing a heterologous glycoprotein with a plant comprising (a) a hybrid enzyme comprising a catalytic region (or portion thereof) of a galactosyltransferase not normally found in a plant and a CTS region (or fragment, such as one including the transmembrane domain) of a protein, wherein said protein acts earlier in the Golgi apparatus of a plant cell in said plant host system than said galactosyltransferase or a modified galactosyltransferase where its transmembrane portion has been deleted and endoplasmic reticulum retention signal has been inserted; (b) a hybrid enzyme comprising a CTS region (or portion thereof, such as one including the transmembrane domain) of a protein, particularly an enzyme, including but not limited to N-acetylglucosaminyltransferase I (GnTI) and a catalytic region (or portion thereof) of a mannosidase II (ManII), wherein said enzyme acts earlier in the Golgi apparatus of a plant cell in said plant host system than said mannosidase II or modified mannosidase II where its transmembrane portion has been deleted and endoplasmic reticulum retention signal have been inserted and (c) a hybrid enzyme comprising at least a transmembrane region of an enzyme (such as the first 40-60 amino acids of the N-terminus) of a glycosyltransferase including but not limited to N-acetylglucosaminyltransferase I (GnTI) and a catalytic region of a N-acetylglucos-aminyltransferase II (GnTII), wherein said enzyme acts earlier in the Golgi apparatus of a plant cell in said plant host system than said N acetylglucosaminyltransferase II (GnTII) or modified N-acetylglucosaminyl-transferase II (GnTII) where its transmembrane portion has been deleted and an endoplasmic reticulum retention signal have been inserted, harvesting progeny from said crossing and selecting a desired progeny plant expressing said heterologous glycoprotein.

The invention is further directed to said plant or portion thereof which would constitute a plant host system. Said plant host system may further comprise a mammalian GnTIII enzyme or hybrid protein comprising a catalytic portion of mammalian GnTIII and a transmembrane portion of a protein, said protein residing in the ER or earlier compartment of the Golgi apparatus of a eukaryotic cell.

Additionally, the invention also provides the use of a plant host system to produce a desired glycoprotein or functional fragment thereof. The invention additionally provides a method for obtaining a desired glycoprotein or functional fragment thereof comprising cultivating a plant according to the invention until said plant has reached a harvestable stage, for example when sufficient biomass has grown to allow profitable harvesting, followed by harvesting said plant with established techniques known in the art and fractionating said plant with established techniques known in the art to obtain fractionated plant material and at least partly isolating said glycoprotein from said fractionated plant material.

Alternatively, said plant host cell system comprising said heterologous glycoprotein may also be obtained by introducing into a plant host cell system or portion thereof (a) a nucleic acid sequence encoding a hybrid enzyme comprising a catalytic region of a galactosyltransferase not normally found in a plant and at least the transmembrane region (or more of the CTS) of a protein, wherein said protein acts earlier in the Golgi apparatus of a plant cell in said plant host system than said galactosyltransferase or a modified galactosyltransferase where its transmembrane portion has been deleted and endoplasmic reticulum retention signal have been inserted; (b) a nucleic acid sequence encoding a first hybrid enzyme comprising at least the transmembrane region (or more of the CTS if desired) of a protein, particularly an enzyme, including but not limited to N-acetylglucosaminyltransferase I (GnTI) and a catalytic region of a mannosidase II (Mann), wherein said enzyme acts earlier in the Golgi apparatus of a plant cell in said plant host system than said mannosidase II, or modified mannosidase II where its transmembrane portion has been deleted and endoplasmic reticulum retention signal have been inserted and (c) a nucleic acid sequence encoding a second hybrid enzyme comprising at least a transmembrane region (more of the CTS if desired) of an enzyme including but not limited to N-acetylglucosaminyl-transferase I (GnTI) and a catalytic region of a N-acetylglucosaminyltransferase II (GnTII), wherein said enzyme acts earlier in the Golgi apparatus of a plant cell in said plant host system than said N-acetylglucos-aminyltransferase-II (GnTII) or modified N-acetylglucosaminyltransferase II (GnTII) where its transmembrane portion has been deleted and an endoplasmic reticulum retention signal have been inserted, and isolating a plant or portion thereof expressing said heterologous glycoprotein (or portion thereof). In one embodiment, one vector comprising all of the nucleic acid sequences is introduced into said plant host system. In another embodiment, each nucleic acid sequence is inserted into separate vectors and these vectors are introduced into said plant host system. In another embodiment combinations of two or more nucleic acid sequences are inserted into separate vectors which are than combined into said plant host system by retransformation or co-transformation or by crossing.

The invention also provides use of such a plant-derived glycoprotein or functional fragment thereof according to the invention for the production of a composition, particularly, pharmaceutical composition, for example for the treatment of a patient with an antibody, a hormone, a vaccine, antigen, an enzyme, or the like. Such a pharmaceutical composition comprising a glycoprotein or functional fragment thereof is now also provided.

Finally, it is contemplated that the above-described approach may be useful in reducing the overall diversity in glycans in plants expressing one or more of the hybrid enzymes of the present invention (as compared to wild-type plants or plants simply transformed with only mammalian GalT).

BRIEF DESCRIPTION OF THE FIGURES

FIG. 5 shows the nucleic acid sequence (SEQ ID NO:1) for a human galactosyltransferase (human B1,4-galactosyltransferase GalT).

FIG. 6 shows the nucleic acid sequence of FIG. 5 along with the corresponding amino acid sequence (SEQ ID NO:2).

FIG. 7 shows an illustrative mutated sequence (SEQ ID NO:59) derived the wild type amino acid sequence (SEQ ID NO:2) for a human galactosyltransferase, wherein a serine has been deleted from the cytoplasmic tail and a G-I-Y motif has been repeated. Of course, such changes are merely illustrative of the many possible changes within the scope of the present invention. For example, in one embodiment, the present invention contemplates mutated sequences wherein only deletions (one or more) are employed (e.g. deletions in the cytoplasmic tail domain or the stem domain)—with no insertions or repeats. Similarly, in one embodiment, the present invention contemplates mutated sequences wherein only (one or more) insertions or replacements (e.g. in the transmembrane domain) are employed—with no deletions.

FIG. 8 shows the nucleic acid sequence (SEQ ID NO:3) encoding a hybrid enzyme comprising human galactosyltransferase (human B1,4-galactosyltransferase—GalT). The upper case letters are nucleotides of *Arabidopsis thaliana* mRNA for beta 1,2-xylosyltransferase (database entry: EMBL:ATH277603, the TmXyl-fragment used involves nucleotides 135-297 of this database sequence).

FIG. 9 shows the nucleic acid sequence of FIG. 8 along with the corresponding amino acid sequence (SEQ ID NO:4).

FIG. 10 shows the amino acid sequence (SEQ ID NO:4) for the hybrid enzyme encoded by the nucleic acid shown in FIG. 8.

FIG. 11 shows the nucleic acid sequence (SEQ ID NO:5) for the human glycosyltransferase GnTIII (along with additional sequence encoding a myc-tag) (primary accession number Q09327 GNT3 HUMAN).

FIG. 12 shows the nucleic acid sequence of FIG. 11 along with the corresponding amino acid sequence (SEQ ID NO:6).

FIG. 13 shows the amino acid sequence (SEQ ID NO:6) for a human GnTIII (along with additional amino acid sequence of the myc epitope tag SEQ ID NO:7).

FIG. 14 shows the nucleic acid sequence (SEQ ID NO:9) encoding one embodiment of a hybrid enzyme of the present invention, said hybrid enzyme comprising the transmembrane domain of a plant xylosyltransferase (TmXyl-) and the catalytic domain (along with other regions) for human GnTIII (TmXyl-GnTIII) (along with additional sequence encoding a myc-tag).

FIG. 15 shows the nucleic acid sequence of FIG. 14 along with the corresponding amino acid sequence (SEQ ID NO:10).

FIG. 16 shows the amino acid sequence (SEQ ID NO:10) for hybrid enzyme encoded by the nucleic acid of FIG. 14 (along with additional sequence for the myc epitope tag SEQ ID NO:7).

FIG. 17 shows the complete nucleic acid sequence (SEQ ID NO:27) for a cassette encoding the hybrid enzymes TmXyl-GalT plus TmGnTI-GnTII plus TmGnTI-ManII).

FIG. 18 shows the complete nucleic acid sequence (SEQ ID NO:28) for a cassette encoding the hybrid enzyme TmGnTI-ManII (with the RbcS1 promoter sequence SEQ ID NO:39 shown).

FIG. 19 shows the nucleic acid sequence (SEQ ID NO:29) encoding the hybrid enzyme TmGnTI-ManII.

FIG. 20 shows the nucleic acid sequence (SEQ ID NO:30) encoding the hybrid enzyme TmGnTI-GnTII.

FIG. 21 shows the nucleic acid sequence (SEQ ID NO:31) encoding the hybrid enzyme TmGnTI-GnTII, wherein the transmembrane fragment used (designated TmGntI) has the nucleic acid sequence set forth in SEQ ID NO:32.

FIG. 22A shows the nucleic acid sequence (SEQ ID NO:32) encoding one embodiment of a transmembrane domain fragment (TmGnTI). FIG. 22B shows the nucleic acid sequence (SEQ ID NO:33) encoding another embodiment of a transmembrane domain fragment (TmManI).

FIG. 23 shows the complete nucleic acid sequence (SEQ ID NO:34) for a triple cassette embodiment of the present invention.

FIG. 24 shows the nucleic acid sequence (SEQ ID NO:35) for a hybrid gene expression cassette (TmManI-GnTI).

FIG. 25 shows the nucleic acid sequence (SEQ ID NO:36) for the histone 3.1 promoter.

FIG. 26 shows the nucleic acid sequence (SEQ ID NO:37) for the hybrid gene fusion (TmManI-TmGnTI).

FIG. 27 shows the nucleic acid sequence (SEQ ID NO:38) for the hybrid gene fusion TmManI-ManII (with the RbcS1 promoter sequence SEQ ID NO:39 shown).

FIG. 28 shows the nucleic acid sequence (SEQ ID NO:39) for the RbcS1 promoter.

FIG. 29 shows the nucleic acid sequence (SEQ ID NO:40) for the hybrid gene TmManI-ManII wherein the nucleic acid sequence (SEQ ID NO:33) encoding the transmembrane fragment is shown.

FIG. 30 shows the nucleic acid sequence (SEQ ID NO:41) for the hybrid gene TmManI-GnTII.

FIG. 31 shows the nucleic acid sequence (SEQ ID NO:42) for the Lhca promoter.

FIG. 32 shows the nucleic acid sequence (SEQ ID NO:43) for the hybrid gene TmManI-GnTII wherein the nucleic acid sequence (SEQ ID NO:33) encoding the transmembrane fragment is shown FIG. 33 shows the nucleic acid sequence (SEQ ID NO:44) for the terminator sequence used (see below).

FIG. 37 shows the nucleic acid sequence (SEQ ID NO:49) of a hybrid gene wherein the aminoterminal CTS region of an insect Mannosidase III gene is replaced by a mouse signal peptide and a carboxyterminal endoplasmic reticulum retention signal (KDEL) was added.

FIG. 38 shows the corresponding amino acid sequence (SEQ ID NO:50) for the nucleic acid sequence of FIG. 37.

FIG. 39 shows the nucleic acid sequence (SEQ ID NO:51) of a hybrid gene wherein the aminoterminal CTS region of a human beta-1,4-galactosyltransferase (GalT) gene is replaced by a mouse signal peptide and a carboxyterminal endoplasmic reticulum retention signal (KDEL) was added.

FIG. 40 shows the corresponding amino acid sequence (SEQ ID NO:52) for the nucleic acid sequence of FIG. 39.

FIG. 41 shows the nucleic acid sequence (SEQ ID NO:53) of a hybrid gene wherein the aminoterminal CTS region of an *Arabidopsis thaliana* GnTI gene is replaced by a mouse signal peptide and a carboxyterminal endoplasmic reticulum retention signal (KDEL) was added.

FIG. 42 shows the corresponding amino acid sequence (SEQ ID NO:54) for the nucleic acid sequence of FIG. 41.

FIG. 43 shows the nucleic acid sequence (SEQ ID NO:55) of a hybrid gene wherein the aminoterminal CTS region of an *Arabidopsis thaliana* GnTII gene is replaced by a mouse signal peptide and a carboxyterminal endoplasmic reticulum retention signal (KDEL) was added.

FIG. 44 shows the corresponding amino acid sequence (SEQ ID NO:56) for the nucleic acid sequence of FIG. 43.

FIG. 45 shows the nucleic acid sequence (SEQ ID NO:57) of a hybrid gene wherein the aminoterminal CTS region of a human beta-1,4-galactosyltransferase (GalT) gene is replaced by the CTS region of the human gene for GnTI.

FIG. 46 shows the corresponding amino acid sequence (SEQ ID NO:58) for the nucleic acid sequence of FIG. 45.

DETAILED DESCRIPTION OF THE INVENTION

Hybrid Enzymes

Figure 1:
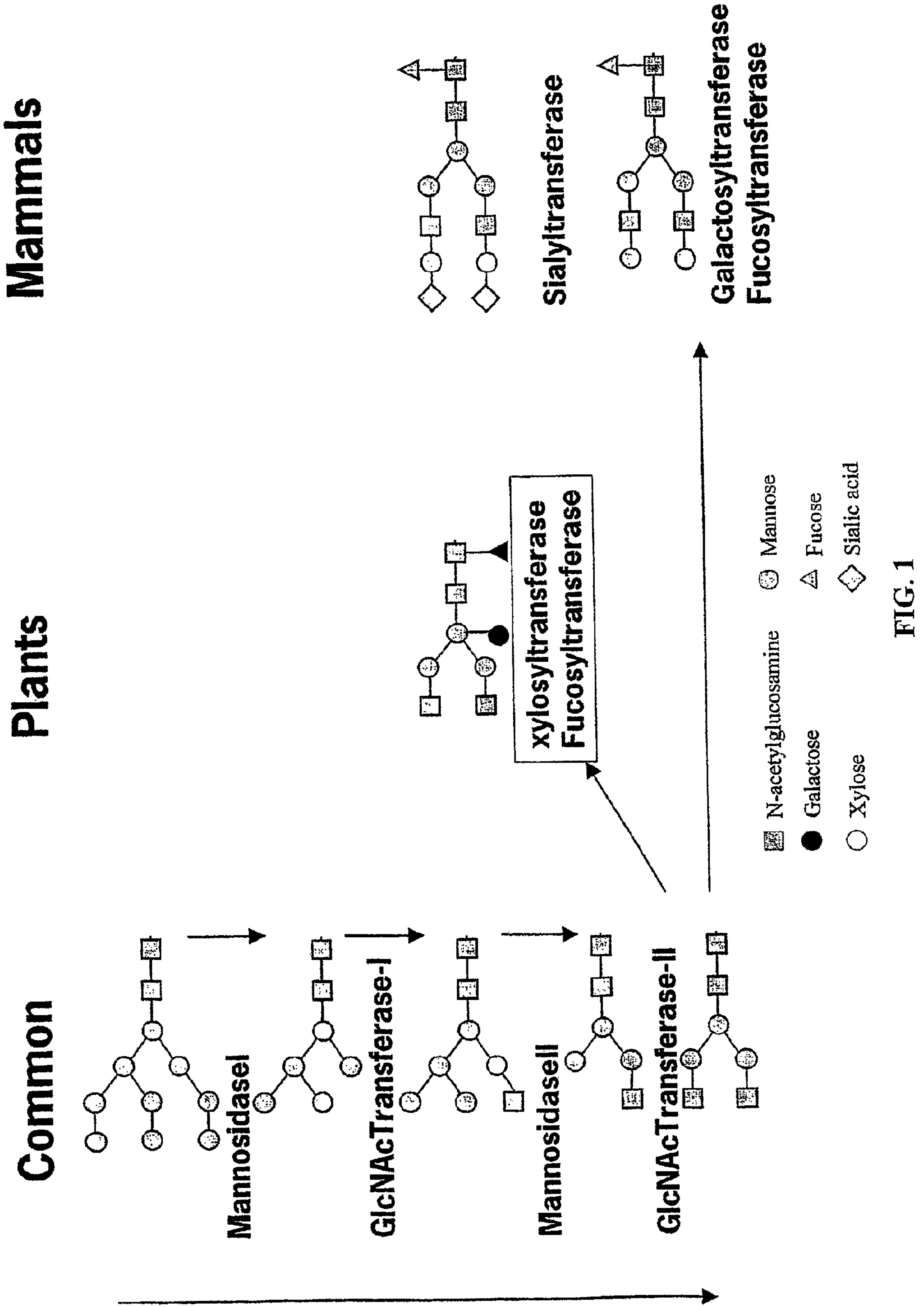
FIG. 1 compares the glycosylation pathway of glycoproteins in plants and in mammals.
Figure 2:
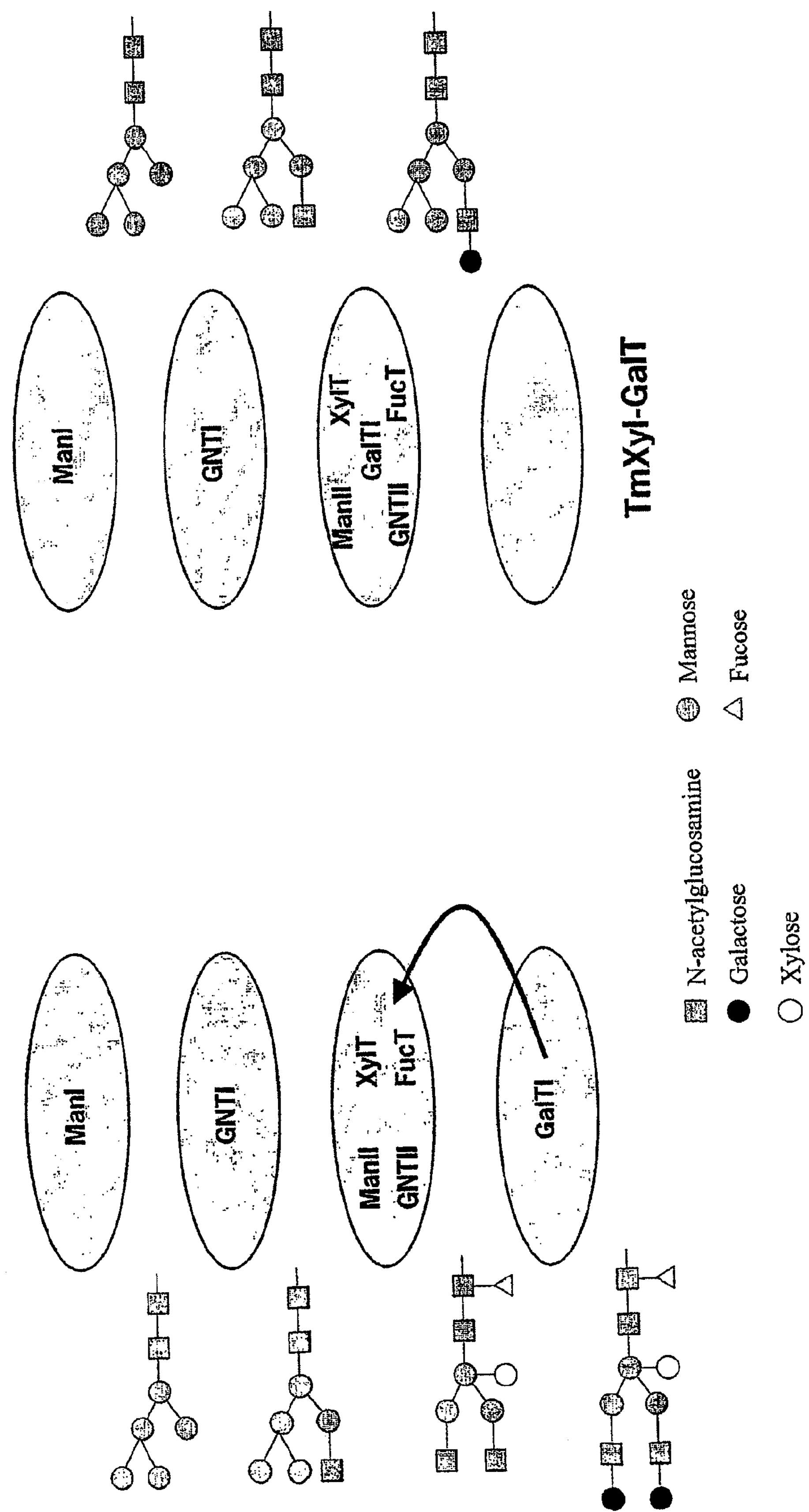
FIG. 2 shows the effect of exchanging the CTS fragment of galactosyltransferase with xylosyltransferase
Figure 3:
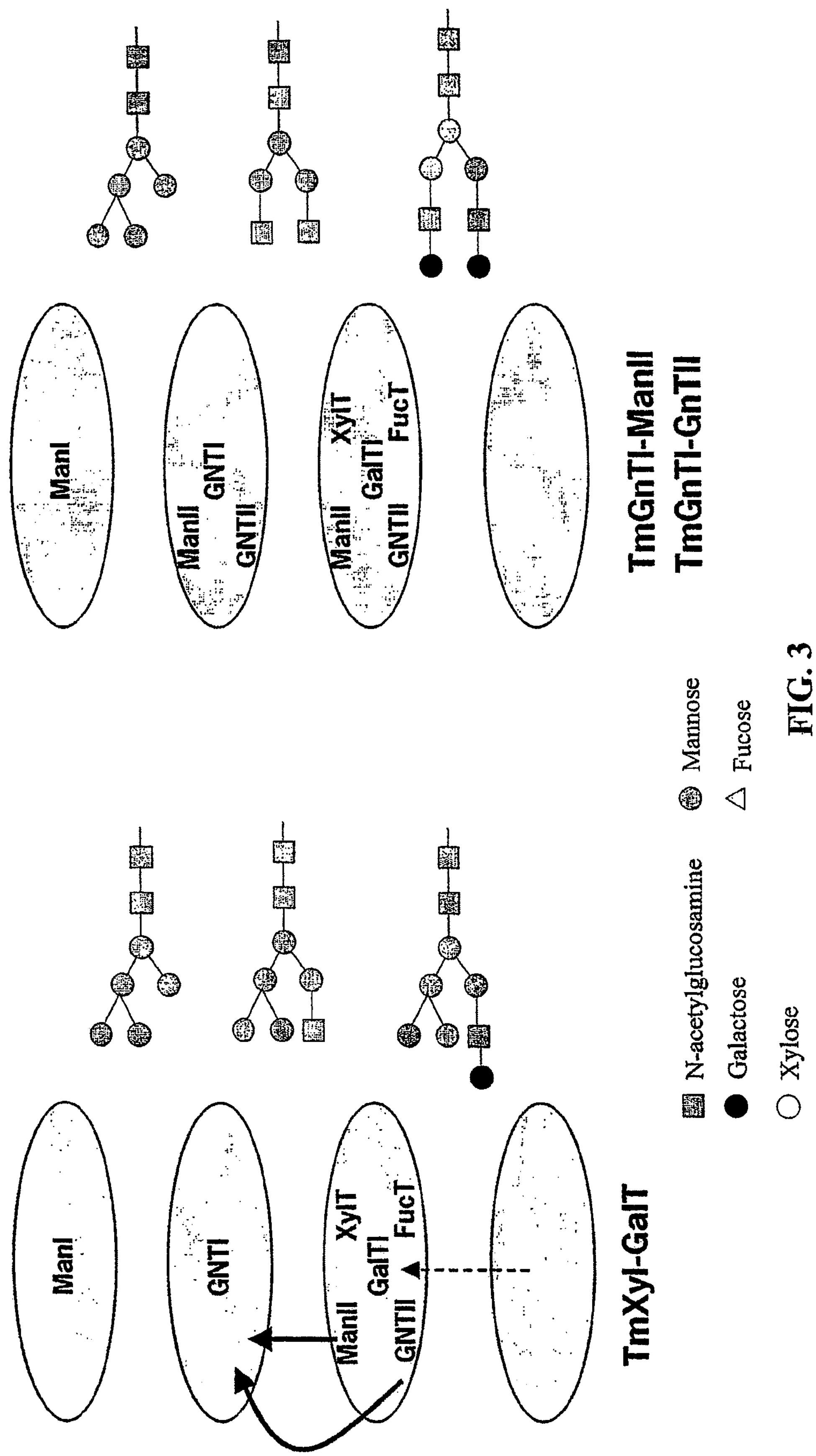
FIG. 3 shows the further effect of relocalizing mannosidase II and GlcNAcTII.
Figure 4:
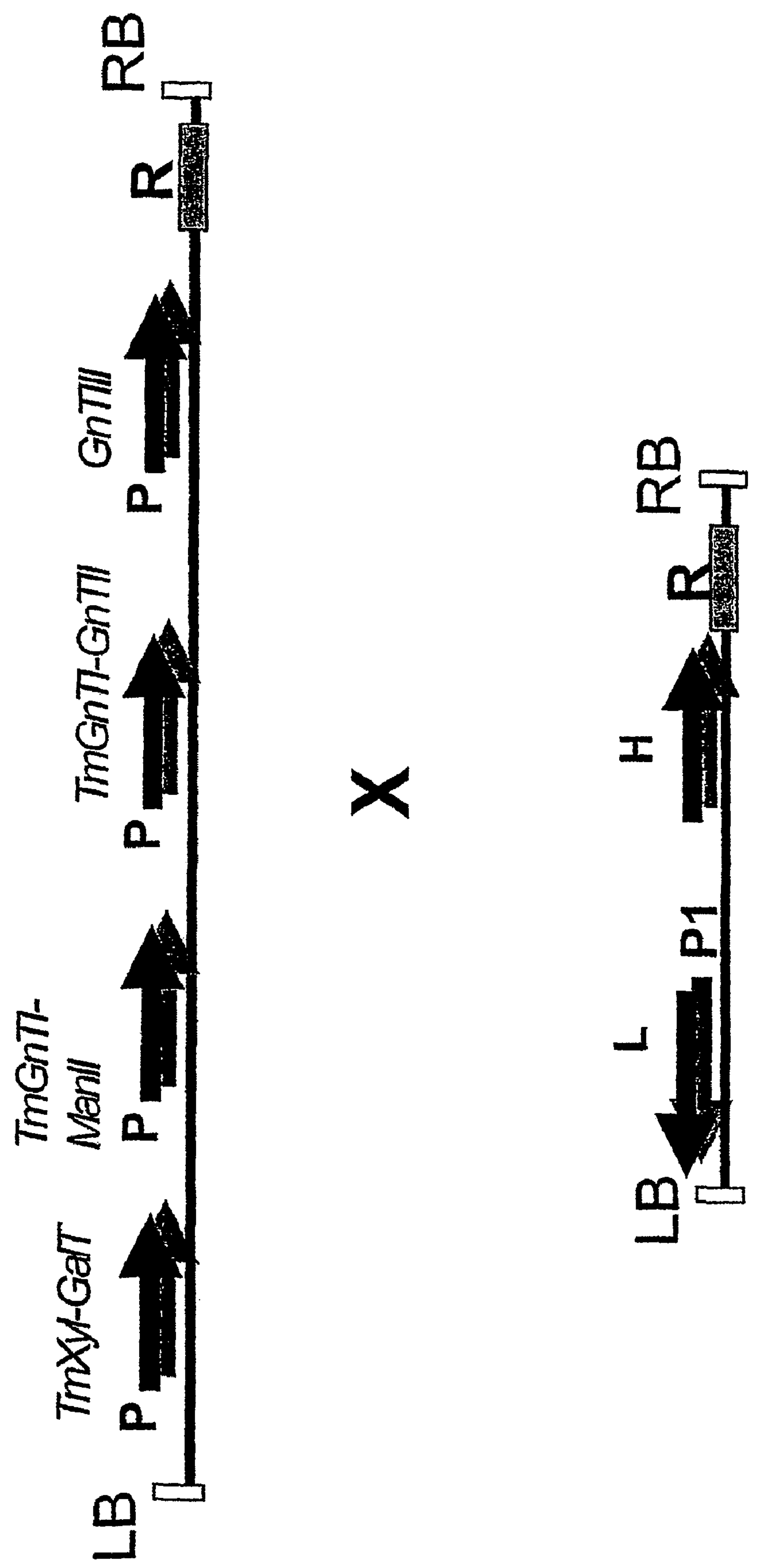
FIG. 4 top panel shows a T-DNA construct carrying the genes encoding glycan modifying enzymes to produce efficiently galactosylated glycans that are devoid of immunogenic xylose and fucose and the bottom panel shows a T-DNA construct carrying antibody light chain and heavy chain genes.

The nucleic acid sequences encoding the various glycosylation enzymes such as mannosidases, GlcNAcTs, galactosyltransferases may be obtained using various recombinant DNA procedures known in the art, such as polymerase chain reaction (PCR) or screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used.

Once the DNA fragments are generated, identification of the specific DNA fragment containing the desired gene may be accomplished in a number of ways. For example, if an amount of a portion of a gene or its specific RNA, or a fragment thereof is available and can be purified and labeled, the generated DNA fragments may be screened by nucleic acid hybridization to the labeled probe [Benton and Davis, *Science* 196:180 (1977); Grunstein and Hogness, *Proc. Natl. Acad. Sci. U.S.A.* 72:3961 (1975)]. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the protein of interest.

A nucleic acid sequence encoding a hybrid enzyme comprising a transmembrane portion of a first enzyme and a catalytic portion of a second enzyme may be obtained as follows. The sequence encoding the transmembrane portion is removed from the second enzyme, leaving a nucleic acid sequence comprising a nucleic acid sequence encoding the C-terminal portion of the second enzyme, which encompasses the catalytic site. The sequence encoding the transmembrane portion of the first enzyme is isolated or obtained via PCR and ligated to the sequence encoding a sequence comprising the C-terminal portion of the second enzyme.

Modified Enzymes

A nucleic acid sequence encoding a protein, particularly enzymes such as galactosyltransferases, mannosidases and N-acetylglucosamine transferases that are retained in the ER may be obtained by removing the sequence encoding the transmembrane fragment and substituting it for a methionine (initiation of translation) codon and by inserting between the last codon and the stop codon of galactosyltransferase the nucleic acid sequence encoding an ER retention signal such as the sequence encoding KDEL (amino acid residue sequence: lysine-aspartic acid-glutamic acid-leucine) [Rothman *Cell* 50:521 (1987)].

Using Domains and Portions Thereof

As noted above, the phrases "at least a portion of" or a "fragment of" refers to the minimal amino acid sequence necessary for a protein or a peptide to retain its natural or native function. For example, the function of an enzyme could refer to its enzymatic or catalytic role, its ability to anchor a protein in the Golgi apparatus, or as a signal peptide. Thus, the phrases "at least a portion of a transmembrane domain" or "a fragment of a transmembrane domain" each refer to the smallest amino acid segment of a larger transmembrane domain that still retains at least part of the native transmembrane functionality (for example, the function may be evident, albeit decreased). As another example, the phrases "at least a portion of a catalytic region" or "a fragment of a catalytic region" each refer to the smallest amino acid segment of a larger catalytic region that still retains at least part of the native catalytic functionality (again, even if somewhat decreased). As discussed herein, one skilled in the art will know the minimal amino acid segment that is necessary for a protein or a peptide to retain at least some of the functionality of the native protein or peptide.

The glycosyltransferase enzymes are typically grouped into families based on the type of sugar they transfer (galactosyltransferases, sialyltransferases, etc.). Based on amino-acid sequence similarity and the stereochemical course of the reaction, glycosyltransferases can be classified into at least 27 and perhaps as many as 47 different families [Campbell et al.,

*Biochem. J.* 326:929-939 (1997), *Biochem. J.* 329:719 (1998)]. The majority of glycosyltransferases cloned to date are type II transmembrane proteins (i.e., single transmembrane domain with the $NH_2$ terminus in the cytosol and the COOH terminus in the lumen of the Golgi apparatus). Regardless of how they are classified, all glycosyltransferases share some common structural features: a short $NH_2$-terminal cytoplasmic tail, a 16-20 amino acid signal-anchor or transmembrane domain, and an extended stem region which is followed by the large COOH-terminal catalytic domain. The cytoplasmic tail appears to be involved in the specific localization of some types of glycosyltransferases to the Golgi [Milland et al., *J. Biol. Chem.* 277:10374-10378]. The signal anchor domains can act as both uncleavable signal peptides and as membrane-spanning regions that orient the catalytic domains of the glycosyltransferases within the lumen of the Golgi apparatus.

In one embodiment of the present invention, a portion defined by the N-terminal 77 amino acids of *Nicotiana benthamiana* (tobacco) acetylglucosaminyltransferase I are contemplated for use in the hybrid enzyme(s), since this portion has been found to be sufficient to target to and to retain a reporter protein in the plant Golgi apparatus [Essl et al., *FEBS Lett* 453:169-173 (1999)]. Subcellular localization in tobacco of various fusion proteins between the putative cytoplasmic, transmembrane and stem domains revealed that the cytoplasmic-transmembrane domains alone were sufficient to sustain Golgi retention of β 1,2-xylosyltransferase without the contribution of any luminal sequences [Dimberger et al., *Plant Mol. Biol.* 50:273-281 (2002)]. Thus, as noted above, certain embodiments of the present invention utilize portions of the CTS region which involve only the cytoplasmic-transmembrane domains (or portions thereof) without utilizing the stem region of the CTS region. However, while some types of glycosyltransferases rely primarily on their transmembrane domain for Golgi retention, other types require their transmembrane region and sequences flanking one or both sides of this region [Colley, *Glycobiology* 7:1-13 (1997)]. For example, the N-terminal peptide encompassing amino acids 1 to 32 appears to be the minimal targeting signal sufficient to localize β 1,6 N-acetylglucosaminyltransferase to the Golgi. This peptide makes up the cytoplasmic and transmembrane domains of this enzyme [Zerfaoui et al., *Glycobiology* 12:15-24].

A great deal of information is available on the amino acid sequences of the domains for specific glycosyltransferases. For example, the amino acid sequence of the mammalian galactosyltransferase provided in GenBank Accession No. AAM17731 has the "stem" and "catalytic" domains spanning residues 19 to 147 and residues 148 to 397, respectively [U.S. Pat. No. 6,416,988, hereby incorporated by reference]—and the present invention, in certain embodiments, specifically contemplates such portions for use in the hybrid enzyme(s). The amino acid sequence of the rat liver sialyltransferase provided in GenBank Accession No. AAC91156 has a 9-amino acid $NH_2$-terminal cytoplasmic tail, a 17-amino acid signal-anchor domain, and a luminal domain that includes an exposed stem region followed by a 41 kDa catalytic domain [Hudgin et al., *Can. J. Biochem.* 49:829-837 (1971); U.S. Pat. Nos. 5,032,519 and 5,776,772, hereby incorporated by reference]. Known human and mouse β 1,3-galactosyltransferases have a catalytic domain with eight conserved regions [Kolbinger et al., *J. Biol. Chem.* 273:433-440 (1998); Hennet et al., *J. Biol. Chem.* 273:58-65 (1998); U.S. Pat. No. 5,955,282, hereby incorporated by reference]. For example, the amino acid sequence of mouse UDP-galactose: β-N-acetylglucosamine β 1,3-galactosyltransferase-I provided in GenBank Accession No. NM020026 has the following catalytic regions: region 1 from residues 78-83; region 2 from residues 93-102; region 3 from residues 116-119; region 4 from residues 147-158; region 5 from residues 172-183; region 6 from residues 203-206; region 7 from amino acid residues 236-246; and region 8 from residues 264-275. [Hennet et al., supra.]—all of which are contemplated in certain embodiments of the present invention as useful portions in the context of the hybrid enzyme(s) discussed above.

While earlier comparisons amongst known cDNA clones of glycosyltransferases had revealed very little sequence homology between the enzymes [Paulson et al., *J. Biol. Chem.* 264:17615-618 (1989)], more recent advances have made it possible to deduce conserved domain structures in glycosyltransferases of diverse specificity [Kapitonov et al., *Glycobiology* 9:961-978 (1999)]. For example, the nucleic acid and amino acid sequences of a number of glycosyltransferases have been identified using sequence data provided by the complete genomic sequences obtained for such diverse organisms as *Homo sapiens* (humans), *Caenorhabditis elegans* (soil nematode), *Arabidopsis thaliana* (thale cress, a mustard) and *Oryza sativa* (rice).

As a result of extensive studies, common amino acid sequences have been deduced for homologous binding sites of various families of glycosyltransferases. For example, sialyltransferases have sialyl motifs that appear to participate in the recognition of the donor substrate, CMP-sialic acid [Paulson et al., *J. Biol. Chem.,* 264:17615-17618 (1989); Datta et al., *J. Biol. Chem.,* 270:1497-1500 (1995); Katsutoshi, *Trends Glycosci. Glycotech.* 8:195-215 (1996)]. The hexapeptide RDKKND in Gal α1-3 galactosyltransferase and RDKKNE in GlcNAc β1-4 galactosyltransferase have been suggested as the binding site for UDP-Gal [(Joziasse et al., *J. Biol. Chem.,* 260:4941-4951 (1985), *J. Biol. Chem.,* 264:14290-14297 (1989); Joziasse, *Glycobiology,* 2:271-277 (1992)].

A small, highly-conserved motif formed by two aspartic acid residues (DXD), which is frequently surrounded by a hydrophobic region, has been identified in a large number of different eukaryotic transferases, including α-1,3-mannosyltransferase, β1,4-galactosyltransfereases, α-1,3-galactosyltransferases, glucuronyltransferases, fucosyltransferases, glycogenins and others [Wiggins et al., *Proc. Natl. Acad. Sci. U.S.A.* 95:7945-7950 (1998)]. Mutation studies indicate that this motif is necessary for enzymatic activity [Busch et al., *J. Biol. Chem.* 273:19566-19572 (1998); Wang et al., *J. Biol. Chem.* 277:18568-18573 (2002)]. Multiple peptide alignment showed several motifs corresponding to putative catalytic domains that are conserved throughout all members of the β 3-galactosyltransferase family, namely, a type II transmembrane domain, a conserved DxD motif, an N-glycosylation site and five conserved cysteines [Gromova et al., *Mol. Carcinog.* 32:61-72 (2001)].

Through the use of BLAST searches and multiple alignments, the E-$X_7$-E motif was found to be a highly conserved among the members of four families of retaining glycosyltransferases [Cid et al., *J. Biol. Chem.* 275:33614-33621 (2000)]. The O-linked acetylglucosaminyltransferases (GlcNAc) add a single β-N-acetylglucosamine moiety to specific serine or threonine hydroxyls. BLAST analyses, consensus secondary structure predictions and fold recognition studies indicate that a conserved motif in the second Rossmann domain points to the UDP-GlcNAc donor-binding site [Wrabl et al., *J. Mol. Biol.* 314:365-374 (2001)]. The β1,3-glycosyltransferase enzymes identified to date share several conserved regions and conserved cysteine residues, all being located in the putative catalytic domain. Site-directed mutagenesis of the murine β3GatT-I gene (Accession No.

AF029790) indicate that the conserved residues W101 and W162 are involved in the binding of the UDP-galactose donor, the residue W315 in the binding of the N-acetylglucosamine-β-p-nitrophenol acceptor, and the domain including E264 appears to participate in the binding of both substrates [Malissard et al., *Eur. J. Biochem.* 269:233-239 (2002)].

Expression of Proteins of Interest in Plant Host System

The nucleic acid encoding the hybrid or modified enzymes or other heterologous proteins, such as a heterologous glycoprotein may be inserted according to certain embodiments of the present invention into an appropriate expression vector, i.e., a vector which contains the necessary elements for the transcription and translation of the inserted coding sequence, or in the case of an RNA viral vector, the necessary elements for replication and translation, as well as selectable markers. These include but are not limited to a promoter region, a signal sequence, 5' untranslated sequences, initiation codon (depending upon whether or not the structural gene comes equipped with one), and transcription and translation termination sequences. Methods for obtaining such vectors are known in the art (see WO 01/29242 for review).

Promoter sequences suitable for expression in plants are described in the art, e.g., WO 91/198696. These include non-constitutive promoters or constitutive promoters, such as, the nopaline synthetase and octopine synthetase promoters, cauliflower mosaic virus (CaMV) 19S and 35S promoters and the figwort mosaic virus (FMV) 35 promoter (see U.S. Pat. Nos. 5,352,605 and 6,051,753, both of which are hereby incorporated by reference). Promoters used may also be tissue specific promoters targeted for example to the endosperm, aleurone layer, embryo, pericarp, stem, leaves, tubers, roots, and the like.

A signal sequence allows processing and translocation of a protein where appropriate. The signal can be derived from plants or could be non-plant signal sequences. The signal peptides direct the nascent polypeptide to the endoplasmic reticulum, where the polypeptide subsequently undergoes post-translational modification. Signal peptides can routinely be identified by those of skill in the art. They typically have a tripartite structure, with positively charged amino acids at the N-terminal end, followed by a hydrophobic region and then the cleavage site within a region of reduced hydrophobicity.

The transcription termination is routinely at the opposite end from the transcription initiation regulatory region. It may be associated with the transcriptional initiation region or from a different gene and may be selected to enhance expression. An example is the NOS terminator from *Agrobacterium* Ti plasmid and the rice alpha-amylase terminator. Polyadenylation tails may also be added. Examples include but are not limited to *Agrobacterium* octopine synthetase signal, [Gielen et al., *EMBO J.* 3:835-846 (1984)] or nopaline synthase of the same species [Depicker et al., *Mol. Appl. Genet.* 1:561-573 (1982)].

Enhancers may be included to increase and/or maximize transcription of the heterologous protein. These include, but are not limited to peptide export signal sequence, codon usage, introns, polyadenylation, and transcription termination sites (see WO 01/29242).

Markers include preferably prokaryote selectable markers. Such markers include resistance toward antibiotics such as ampicillin, tetracycline, kanamycin, and spectinomycin. Specific examples include but are not limited to streptomycin phosphotransferase (spt) gene coding for streptomycin resistance, neomycin phosphotransferase (nptII) gene encoding kanamycin or geneticin resistance, hygromycin phosphotransferase (hpt) gene encoding resistance to hygromycin.

The vectors constructed may be introduced into the plant host system using procedures known in the art (reviewed in WO 01/29242 and WO 01/31045). The vectors may be modified to intermediate plant transformation plasmids that contain a region of homology to an *Agrobacterium tumefaciens* vector, a T-DNA border region from *A. tumefaciens*. Alternatively, the vectors used in the methods of the present invention may be *Agrobacterium vectors*. Methods for introducing the vectors include but are not limited to microinjection, velocity ballistic penetration by small particles with the nucleic acid either within the matrix of small beads or particles, or on the surface and electroporation. The vector may be introduced into a plant cell, tissue or organ. In a specific embodiment, once the presence of a heterologous gene is ascertained, a plant may be regenerated using procedures known in the art. The presence of desired proteins may be screened using methods known in the art, preferably using screening assays where the biologically active site is detected in such a way as to produce a detectable signal. This signal may be produced directly or indirectly. Examples of such assays include ELISA or a radioimmunoassay.

Transient Expression

The present invention specifically contemplates both stable and transient expression of the above-described hybrid enzymes. Techniques for transforming a wide variety of higher plant species for transient expression of an expression cassette are well known [see, for example, Weising et al., *Ann. Rev. Genet.* 22:421-477 (1988)]. Variables of different systems include type nucleic acid transferred (DNA, RNA, plasmid, viral), type of tissue transformed, means of introducing transgene(s), and conditions of transformation. For example, a nucleic acid construct may be introduced directly into a plant cell using techniques ranging from electroporation, PEG poration, particle bombardment, silicon fiber delivery, microinjection of plant cell protoplasts or embryogenic callus or other plant tissue, or *Agrobacterium*-mediated transformation [Hiei et al., *Plant J.* 6:271-282 (1994)]. Because transformation efficiencies are variable, internal standards (e.g., 35S-Luc) are often used to standardize transformation efficiencies.

Expression constructs for transient assays include plasmids and viral vectors. A variety of plant viruses that can be employed as vectors are known in the art and include cauliflower mosaic virus (CaMV), geminivirus, brome mosaic virus, and tobacco mosaic virus.

Plant tissues suitable for transient expression include cultured cells, either intact or as protoplasts (in which the cell wall is removed), cultured tissue, cultured plants, and plant tissue such as leaves.

Some transient expression methods utilize gene transfer into plant cell protoplasts mediated by electroporation or polyethylene glycol (PEG). These methods require the preparation and culture of plant protoplasts, and involve creating pores in the protoplast through which nucleic acid is transferred into the interior of the protoplast.

Exemplary electroporation techniques are described in Fromm et al., *Proc. Natl. Acad. Sci.* 82: 5824 (1985). The introduction of DNA constructs using polyethylene glycol precipitation is described in Paszkowski et al., *EMBO J.* 3: 2717-2722 (1984). PEG-mediated transformation of tobacco protoplasts, which includes the steps of isolation, purification, and transformation of the protoplasts, are described in Lyck et al., (1997) *Planta* 202: 117-125 and Scharf et al., (1998) *Mol Cell Biol* 18: 2240-2251, and Kirschner et al., (2000) *The Plant J* 24(3): 397-411. These methods have been used, for example, to identify cis-acting elements in promoters activated by external stimuli, Abel and Theologis (1994)

*Plant J* 5: 421-427; Hattori et al., (1992) *Genes Dev* 6: 609-618; Sablowski et al., (1994) *EMBO J* 13: 128-137; and Solano et al., (1995) *EMBO J* 14: 1773-1784), as well as for other gene expression studies (U.S. Pat. No. 6,376,747, hereby incorporated by reference).

Ballistic transformation techniques are described in Klein et al., (1987) *Nature* 327: 70-73. Biolistic transient transformation is used with suspension cells or plant organs. For example, it has been developed for use in *Nicotiana tabacum* leaves, Godon et al (1993) *Biochimie* 75(7): 591-595. It has also been used in investigating plant promoters, (Baum et al., (1997) *Plant J* 12: 463-469; Stromvik et al., (1999) *Plant Mol Biol* 41(2): 217-31, Tuerck and Fromm (1994) *Plant Cell* 6: 1655-1663; and U.S. Pat. No. 5,847,102, hereby incorporated by reference), and to characterize transcription factors (Goff et al., (1990) *EMBO J* 9: 2517-2522; Gubler et al., (1999) *Plant J* 17: 1-9; and Sainz et al., (1997) *Plant Cell* 9: 611-625).

Other methods allow visualization of transient expression of genes in situ, such as with onion epidermal peels, in which GFP expression in various cellular compartments was observed (Scott et al., (1999) *Biotechniques* 26(6): 1128-1132

Nucleic acids can also be introduced into plants by direct injection. Transient gene expression can be obtained by injection of the DNA into reproductive organs of a plant (see, for example, Pena et al., (1987) Nature, 325:274), such as by direct DNA transfer into pollen (see, for example, Zhou et al., (1983) *Methods in Enzymology,* 101:433; D. Hess (1987) *Intern Rev. Cytol.,* 107:367; Luo et al., (1988) *Plant Mol. Biol. Reporter,* 6:165. DNA can also be injected directly into the cells of immature embryos (see, for example, Neuhaus et al., (1987) *Theor. Appl. Genet:* 75:30; and Benbrook et al., (1986) in *Proceedings Bio Expo* 1986, Butterworth, Stoneham, Mass., pp. 27-54).

*Agrobacterium*-mediated transformation is applicable to both dicots and monocots. Optimized methods and vectors for *Agrobacterium*-mediated transformation of plants in the family Graminae, such as rice and maize have been described (see, for example, Heath et al., (1997) *Mol. Plant-Microbe Interact.* 10:221-227; Hiei et al., (1994) *Plant J.* 6:271-282 and Ishida et al., (1996) *Nat. Biotech.* 14:745-750). The efficiency of maize transformation is affected by a variety of factors including the types and stages of tissue infected, the concentration of *Agrobacterium*, the tissue culture media, the Ti vectors and the maize genotype.

Another useful basic transformation protocol involves a combination of wounding by particle bombardment, followed by use of *Agrobacterium* for DNA delivery (see, for example, Bidney et al., (1992) *Plant Mol. Biol.* 18:301-313). Both intact meristem transformation and a split meristem transformation methods are also known (U.S. Pat. No. 6,300,545, hereby incorporated by reference).

Additional methods utilizing *Agrobacteria* include agroinfection and agroinfiltration. By inserting a viral genome into the T-DNA, *Agrobacterium* can be used to mediate the viral infection of plants (see, for example, U.S. Pat. No. 6,300,545, hereby incorporated by reference). Following transfer of the T-DNA to the plant cell, excision of the viral genome from the T-DNA (mobilization) is required for successful viral infection. This *Agrobacterium*-mediated method for introducing a virus into a plant host is known as agroinfection (see, for example, Grimsley, "Agroinfection" pp. 325-342, in *Methods in Molecular Biology*, vol 44: *Agrobacterium* Protocols, ed. Gartland and Davey, Humana Press, Inc., Totowa, N.J.; and Grimsley (1990) *Physiol. Plant.* 79:147-153).

The development of plant virus gene vectors for expression of foreign genes in plants provides a means to provide high levels of gene expression within a short time. Suitable viral replicons include double-stranded DNA from a virus having a double stranded DNA genome or replication intermediate. The excised viral DNA is capable of acting as a replicon or replication intermediate, either independently, or with factors supplied in trans. The viral DNA may or may not encode infectious viral particles and furthermore may contain insertions, deletions, substitutions, rearrangements or other modifications. The viral DNA may contain heterologous DNA, which is any non-viral DNA or DNA from a different virus. For example, the heterologous DNA may comprise an expression cassette for a protein or RNA of interest.

Super binary vectors carrying the vir genes of *Agrobacterium* strains A281 and A348 are useful for high efficiency transformation of monocots. However, even without the use of high efficiency vectors, it has been demonstrated that T-DNA is transferred to maize at an efficiency that results in systemic infection by viruses introduced by agroinfection, although tumors are not formed (Grimsley et al., (1989) *Mol. Gen. Genet.* 217:309-316). This is because integration of the T-DNA containing the viral genome is not required for viral multiplication, since the excised viral genome acts as an independent replicon.

Another *Agrobacteria*-mediated transient expression assay is based on *Agrobacterium*-mediated transformation of tobacco leaves in planta (Yang et al., (2000) *The Plant J* 22(6): 543-551). The method utilizes infiltration of agrobacteria carrying plasmid constructs into tobacco leaves, and is referred to as agroinfiltration; it has been utilized used to analyze in vivo expression of promoters and transcription factors in as little as 2-3 days. It also allows examination of effects of external stimuli such as pathogen infections and environmental stresses on promoter activity in situ.

Example 1

An *Arabidopsis thaliana* cDNA encoding β1,2-xylosyltransferase was isolated from a cDNA library by a previously described PCR based sibling selection procedure [Bakker et al., *BBRC* 261:829 (1999)]. Xylosyltransferase activity was confirmed by immunostaining of transfected CHO cells with a xylose specific antibody purified from rabbit-anti-horseradish-peroxidase antiserum. A DNA fragment covering the N-terminal part of the xylosyltransferase was amplified using primers:

```
XylTpvuF:
ATACTCGAGTTAACAATGAGTAAACGGAATC    (SEQ ID NO: 45)
and

XylTpvuR:
TTCTCGATCGCCGATTGGTTATTC           (SEQ ID NO: 46)
```

XhoI and HpaI restriction sites were introduced in front of the start codon and a PvuI was introduced at the reverse end. A C-terminal fragment from Human β1,4galactosyltransferase (acc.no. x55415, Aoki 1992) was amplified using primers

```
GalTpvuF:
GCCGCCGCGATCGGGCAGTCCTCC           (SEQ ID NO: 47)
and

GalTrev:
AACGGATCCACGCTAGCTCGGTGTCCCGAT     (SEQ ID NO: 48)
```

thus introducing PvuI and BamHI sites. The XhoI/PvuI and PvuI/BamHI digested PCR fragments were ligated in XhoI/BamHI digested pBluescriptSK+ and sequenced. The resulting open reading frame encodes a fusion protein containing the first 54 amino acids of *A. thaliana* β1,2-xylosyltransferase fused with amino acid 69 to 398 of human β1,4galactosyltransferase and is designated as TmXyl-GalT. The fragment was cloned into a plant expression vector between the CaMV35S promoter and Nos terminator, using HpaI/BamHI. The clone was introduced into *Nicotiana tabacum* (samsun NN) as described for native human β1,4galactosyltransferase [Bakker et al., *Proc. Nat. Acad. Sci. USA* 98:2899 (2001)].

Protein extract of transgenic plants and Western Blots were made as described [Bakker et al., *Proc. Nat. Acad. Sci. USA* 98:2899 (2001)]. Based on reaction with the lectin RCA, a transgenic plant expressing TmXylGalT was selected for further glycan analysis by MALDI-TOF [Elbers et al., *Plant Physiology* 126:1314 (2001] and compared with glycans isolated from plants expressing native β1,4galactosyltransferase and with glycans from wild-type plants. Relative peak areas of the MALDI-TOF spectrum are given in Table 1. That is to say, Table 1 is a comparison of the results of mass spec (MALDI-TOF) analysis of N-glycans of endogenous glycoproteins of control tobacco ("Tobacco"), transgenic tobacco expressing human beta-1,4-galactosyltransferase ("GalT") and transgenic tobacco plants expressing the beta-1,4-galactosyltransferase gene of which the CTS region has been replaced with that of beta-1,2-xylosyltransferase ("TmXyl-GalT").

TABLE 1

| m/z | Type | Tobacco | GalT | TmXyl-GalT |
|---|---|---|---|---|
| 933 | M3 | | 3 | 7 |
| 1065 | XM3 | 10 | 16 | 3 |
| 1079 | FM3 | | | 4 |
| 1095 | M4 | | | 9 |
| 1211 | FXM3 | 41 | 27 | |
| 1257 | M5 | 4 | 5 | 23 |
| 1268 | GNXM3 | | 4 | |
| 1298 | GalGNM3 | | | 6 |
| 1298 | GNM4 | | | |
| 1414 | GNFXM3 | 27 | 13 | 5 |
| 1419 | M6 | 7 | 8 | 10 |
| 1460 | GalGNM4 | | | 11 |
| 1460 | GNM5 | | | |
| 1485 | GN2FM3 | | 4 | |
| 1576 | GalGNFXM3 | | 5 | |
| 1576 | GNFXM4 | | | |
| 1581 | M7 | 3 | | 4 |
| 1606 | GNFM5 | | | 3 |
| 1606 | GalGNFM4 | | | |
| 1617 | GN2FXM3 | 8 | 9 | |
| 1622 | GalGNM5 | | | 9 |
| 1622 | GNM6 | | | |
| 1743 | M8 | | 2 | 3 |
| 1768 | GalGNFM5 | | | 3 |
| 1768 | GNFM6 | | | |
| 1779 | GalGN2FXM3 | | 2 | |
| 1905 | M9 | | | 1 |
| 1941 | Gal2GN2FXM3 | | 2 | |
| | TOTAL | 100 | 100 | 101 |

These data show that:

1. In TmXylGalT plants, xylosylation and fucosylation of the glycans is dramatically reduced: 82% of the glycans do not carry xylose nor fucose as compared to 14% in wild-type plants.
2. Galactosylation has increased from 9% in Gall plants to 32% in TmXylGalT plants.

Example 2

Figure 34:
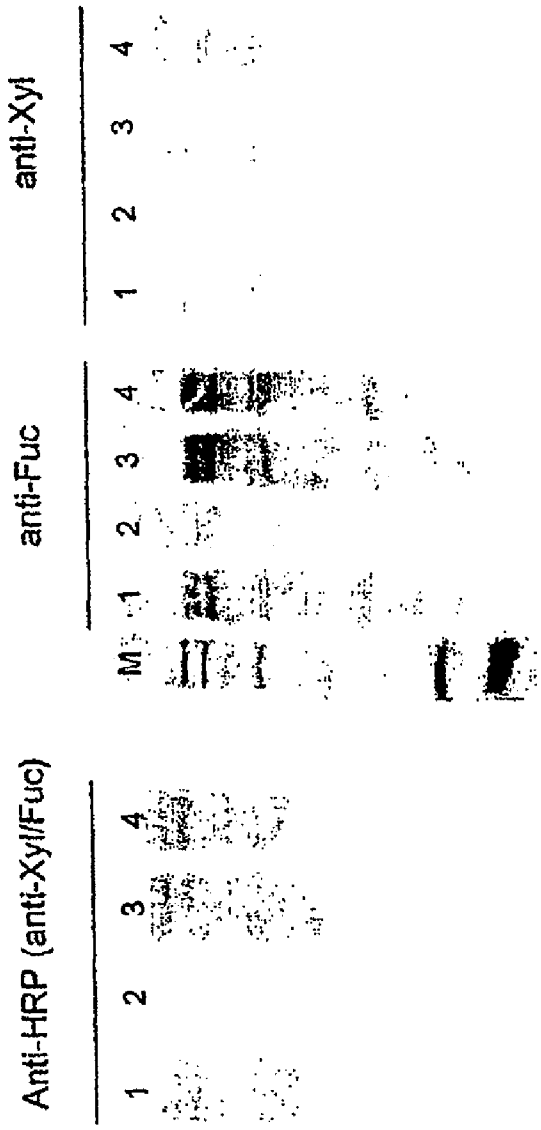
FIG. 34 is a Western Blot which examines total protein glycosylation of plants of the present invention compared to control plants.

A transgenic plant expressing said TmXyl-GalT gene (TmXyl-GalT-12 plant) was selected (above) based on lectin blotting using biotin-labelled RCA (Vector Laboratories, Burlingame, Calif.). Comparison of protein extracts of MGR48 transgenic (control) plant, a selected transgenic plant expressing the unmodified human β1,4-galactosyltransferase gene and TmXyl-GalT-12 plant for the presence of xylose and fucose using anti-HRP (horseradish peroxidase) polyclonal antibody (known for high anti-xylose and anti-fucose reactivity) clearly showed reduced xylose and fucose (FIG. 34: "Anti-HRP"). Western blotting using an anti-xylose fraction of the anti-HRP and an anti-fucose fraction (each of which can be prepared by affinity chromatography over the appropriate ligand) showed that especially xylose was reduced compared to control plants (FIG. 34: anti-Fuc" and "anti-Xyl").

Example 3

Figure 35:
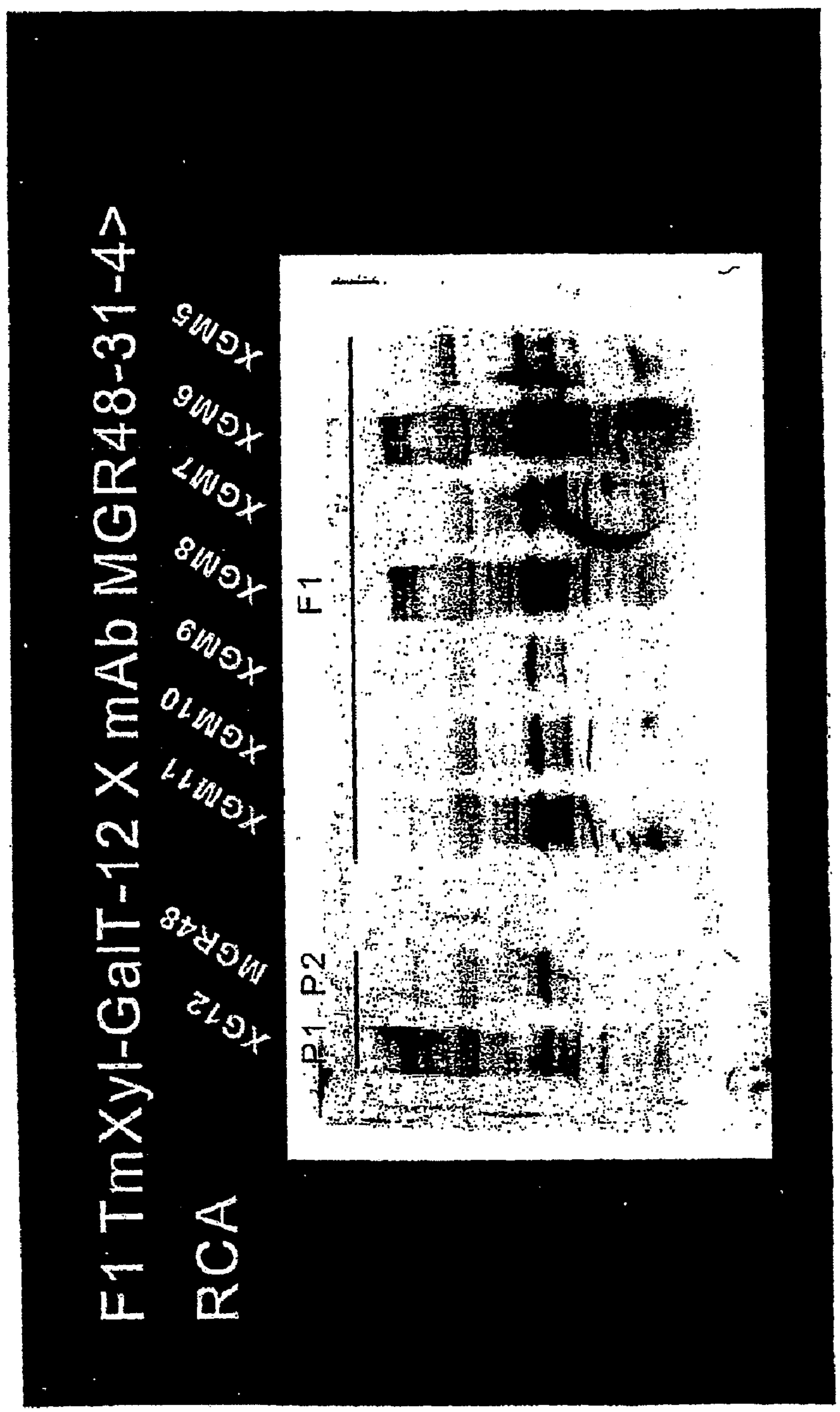
FIG. 35 is a lectin blot with RCA on F1 progeny of crossed plants, said progeny made according to one embodiment of the present invention

The TmXyl-GalT-12 plant was crossed with a transgenic plant expressing the monoclonal antibody MGR48 from a single T-DNA integration event (MGR48-31) and which was first made homozygous by selecting offspring plants not segregating for the kanamycin resistance marker and antibody production (MGR48-31-4). Pollen of MGR48-31-4 was used for pollination of emasculated TmXyl-GalT-12 plants. Vice versa, pollen of TmXyl-GalT-12 plant was used for fertilization on emasculated MGR48-31-4 plants. A number of F1 plants were analyzed for the presence of MGR48 by western blotting and for galactosylation of endogenous glycoproteins by lectin blotting using RCA (FIG. 35). One plant expressing MGR48 and showing galactosylation of endogenous glycoproteins was selected for further analysis. This plant was identified as XGM8.

Seeds from TmXyl-GalT-12 (♀) x MGR48-31-4 (♂) were sown and F1 offspring plants (XGM) were analysed for antibody production by Western blotting and for galactosylation by lectin blotting using biotinylated RCA120 (Vector Labs., Burlingame, Calif.) using standard techniques as described before. All plants as expected expressed the monoclonal antibody MGR48 and the majority also had galactosylated glycans as depicted from lectin blotting using RCA120. A single plant expressing both antibody MGR48 and having galactosylated N-glycans was chosen for further analysis (XGM8) (TmXyl-GalT-12 X MGR48-31-4 offpring plant 8). The monoclonal recombinant MGR48 antibody was purified from this plant as described before and submitted to N-glycan analysis by MALDI-TOF.

Briefly, XGM8 plant was grown in greenhouse for antibody production under optimal conditions [Elbers et al., *Plant Physiology* 126:1314 (2001)]. Protein extract of leaves of transgenic XGM8 plant was made and monoclonal antibody was purified using protein G chromatography as described [Bakker et al, *Proc. Nat. Acad. Sci. USA* 98:2899 (2001)]. MALDI-TOF of N-glycans of purified monoclonal antibody was as described (Elbers et al., 2001, supra). The presence of galactose on glycans was established by enzyme sequencing using bovine testis β-galactosidase as described (Bakker et al., 2001, supra; Table 2). Table 2 (below) is a comparison of the results of mass spec (MALDI-TOF) analysis of N-glycans of endogenous glycoproteins ("Xyl-GalT Endo") of a F1 hybrid of TmXyl-GalT-12plant and plant producing rec-mAb (MGR48) and of N-glycans of rec-mAB purified by protein G chromatography from said F1 hybrid.

TABLE 2

| m/z | Type | Xyl-GalT Endo | Xyl-GalT IgG |
|---|---|---|---|
| 933 | M3 | 6 | 4 |
| 1065 | XM3 | 2 | 2 |
| 1079 | FM3 | 2 | 3 |
| 1095 | M4 | 5 | 5 |
| 1136 | GNM3 | 1 | 2 |
| 1211 | FXM3 | 6 | 3 |
| 1241 | FM4 | 3 | 2 |
| 1257 | M5 | 17 | 12 |
| 1268 | GNXM3 | 1 | 2 |
| 1282 | GNFM3 | 2 | 3 |
| 1298 | GalGNM3 | 3 | 4 |
| 1403 | FM5 | 4 | 3 |
| 1414 | GNFXM3 | 2 | 4 |
| 1419 | M6 | 5 | 4 |
| 1430 | GNXM4 | 2 | 2 |
| 1430 | GalGNXM3 | | |
| 1444 | GNFM4 | 1 | 3 |
| 1444 | GalGNFM3 | | |
| 1460 | GalGNM4 | 8 | 10 |
| 1460 | GNM5 | | |
| 1471 | GN2XM3 | 1 | |
| 1485 | GN2FM3 | 1 | 1 |
| 1501 | GalGN2M3 | 1 | 1 |
| 1576 | GalGNFXM3 | 2 | 3 |
| 1576 | GNFXM4 | | |
| 1581 | M7 | 2 | 2 |
| 1593 | GalGNXM4 | 1 | 2 |
| 1593 | GNXM5 | | |
| 1606 | GNFM5 | 3 | 4 |
| 1606 | GalGNFM4 | | |
| 1617 | GN2FXM3 | 2 | 1 |
| 1622 | GalGNM5 | 6 | 6 |
| 1622 | GNM6 | | |
| 1647 | GalGN2FM3 | 1 | 1 |
| 1663 | Gal2GN2M3 | 1 | 1 |
| 1738 | GNFXM5 | 1 | 2 |
| 1738 | GalGNFXM4 | | |
| 1743 | M8 | 1 | 2 |
| 1754 | GalGNXM5 | 1 | 2 |
| 1768 | GalGNFM5 | 2 | 3 |
| 1768 | GNFM6 | | |
| 1784 | GNM7 | 1 | 1 |
| 1784 | GalGNM6 | | |
| 1809 | Gal2GN2FM3 | 2 | 1 |
| 1900 | GNFXM6 | 1 | |
| 1900 | GalGNFXM5 | | |
| 1905 | M9 | 1 | 1 |
| | TOTAL | 101 | 102 |

Figure 36:
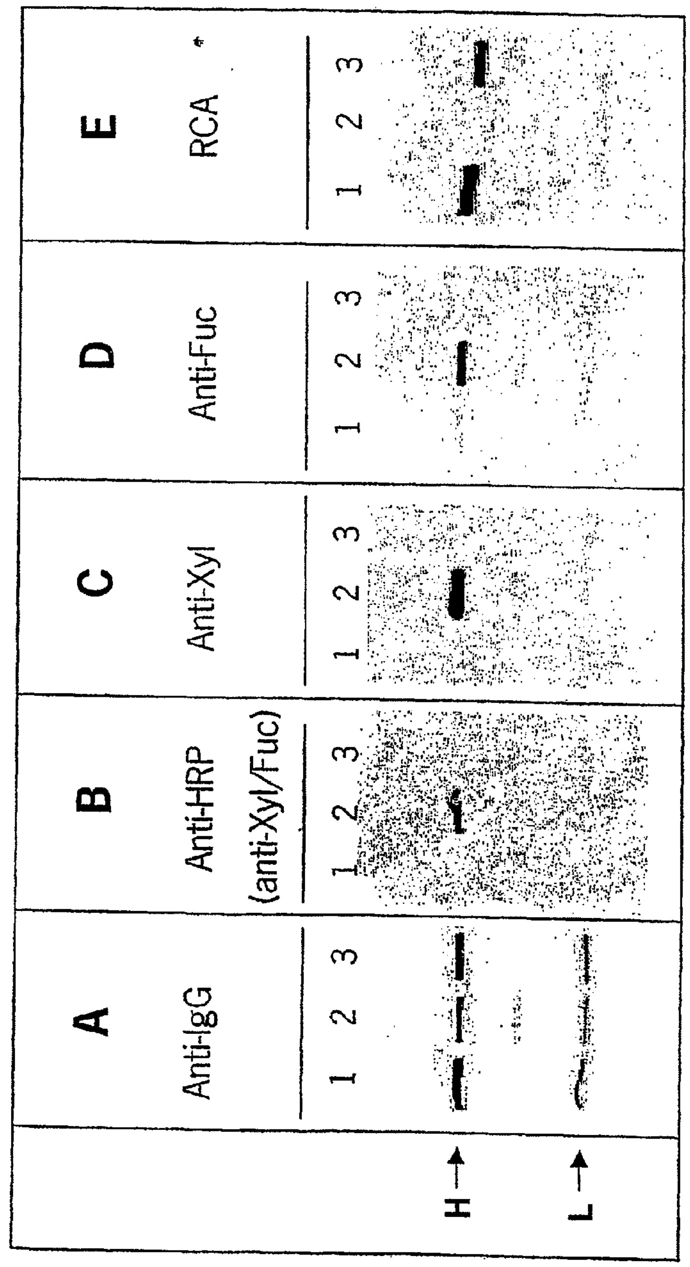
FIG. 36 is a Western Blot. Panel A was assayed with anti-IgG antibody. Panel B was assayed with an anti-HRP antibody. Panel C was assayed with a specific anti-Xyl antibody fraction. Panel D was assayed with a specific anti-Fucose antibody fraction. Panel E was assayed with the lectin RCA.

These data show that:

1. In the F1 hybrid, xylosylation and fucosylation of the glycans is dramatically reduced: 43% of the glycans of endogenous glycoproteins lack xylose and fucose as compared to only 14% in wild-type tobacco plants.
2. The glycans of purified mAb of this F1 hybrid have reduced xylose and fucose, 47% compared to 14% for wildtype tobacco. See also FIG. 36, panels B-D.
3. Galactosylation of endogenous glycoproteins of F1 hybrid has increased from 9% in GalT plants to 37% in F1 TmXyl-GalT X MGR48 plant. See also FIG. 35.
4. Purified rec-mAb from said F1 (see FIG. 36, panel A) shows increased galactosylation; that is to say, 46% has galactose. See also FIG. 36, panel E.

It should however be noted that the observed quantities (MALDI-TOF) do not necessarily reflect the molar rations of said glycoforms in vivo. Quantification based on MALDI-TOF can be under- or overestimated depending on the specific glycoform under study. Also, since there is no molecular weight difference between Gal and Man, some peaks can not be annotated unambiguously unless there are clear differences in relative height of specific molecules before and after galactosidase treatment.

Example 4

A more direct comparison of xylose, fucose and galactose content was done by examining the MGR48 IgG antibodies from hybridoma, transgenic tobacco and TmXyl-GalT transgenic tobacco. As mentioned above, the TmXyl-GalT-12 plant was crossed with tobacco plant expressing MGR48 IgG (MGR48 tobacco) resulting in an F1 hybrid harbouring MGR48 TmXyl-GalT. An F1 plant was chosen for extraction and purification of MGR48 IgG. Antibodies from said plants (tobacco and TmXyl-GalT) were isolated and purified using protein G chromatography (Fibers et al., 2001. *Plant Physiology* 126: 1314-1322). 300 nanograms amounts of each, hybridoma MGR48 and plant-derived recMGR48, were loaded on precast 12% SDS-PAGE gels (BioRad) and run. The contents of each lane were as follows: Lane 1, MGR48 from hybridoma; Lane 2, purified recMGR48 from normal transgenic tobacco plant; and Lane 3, purified recMGR48 from TmXyl-GalT transgenic plant. Following SDS-PAGE proteins were transferred to nitrocellulose using CAPS buffer. Blots were incubated with A, anti-mouse IgG; B, polyclonal rabbit anti-HRP (anti-xylose/(alpha 1,3-fucose); C, anti-xylose; D, anti-(alpha 1,3-) fucose antibodies; and E, biotinylated RCA. Detection was with LumiLight on Lumi Imager following incubation with HRP-labelled sheep anti-mouse (panel A) or goat-anti-rabbit (panels B-D) antibodies and HRP-labeled streptavidin (E).

Panel A shows that approximately similar amounts of the MGR48 IgG was loaded for all lanes (1-3). L refers to Light chain and H, heavy chain of MGR48 IgG. Panel B shows that the heavy chain of MGR48 antibody in lane 2 (tobacco) strongly reacts with anti-HRP as expected, whereas the heavy chain of hybridoma derived MGR48 (lane 1) does not (as expected). Hybridoma derived antibodies do not carry xylose and alpha 1,3-fuctose residues. Remarkably, MGR48 antibodies from TmXyl-GalT tobacco plant also do not react, suggesting that the heavy chain of antibody from this plant have significantly reduced (perhaps by 90% or more) the amounts of xylose and fucose residues on the N-glycans. This is confirmed by experiments depicted in panels C (anti-xylose) and D (anti-fucose). Panel E shows that the heavy chain of MGR48 antibody of hybridoma (lane 1) has a galactosylated N-glycan, whereas tobacco-derived MGR48 (lane 2) has not, both as expected. Heavy chain of MGR48 from the TmXyl-GalT plant (lane 3) also has galactosylated N-glycan due to the presence of the construct expressing the hybrid enzyme.

These data are in agreement with the data obtained from similar experiments using total protein extracts from similar plants (tobacco and TmXyl-GalT-12 plant) as shown previously and confirm that the novel trait introduced in tobacco from expression of TmXyl-GalT gene can be stably transmitted to offspring and a recombinant monoclonal antibody.

Example 5

Further characterization of the above-described F1 hybrid was performed by treatment with beta-galactosidase. Table 3 is a comparison of the results of mass spec (MALDI-TOF) analysis of N-glycans of rec-mAbs purified by protein G chromatography from an F1 hybrid of TmXyl-GalT and MGR48 plant before and after treatment of the glycans with beta-galactosidase.

TABLE 3

| m/z | Type | Xyl-GalT IgG- | Xyl-GalT IgG + beta-galactosidase |
|---|---|---|---|
| 933 | M3 | 4 | 4 |
| 1065 | XM3 | 2 | 2 |
| 1079 | FM3 | 3 | 3 |
| 1095 | M4 | 5 | 4 |
| 1136 | GNM3 | 2 | 3 |
| 1211 | FXM3 | 3 | 4 |
| 1241 | FM4 | 2 | 2 |
| 1257 | M5 | 12 | 13 |
| 1268 | GNXM3 | 2 | 3 |
| 1282 | GNFM3 | 3 | 3 |
| 1298 | GalGNM3 | 4 | 4 |
| 1403 | FM5 | 3 | 2 |
| 1414 | GNFXM3 | 4 | 5 |
| 1419 | M6 | 4 | 3 |
| 1430 | GNXM4 | 2 | 2 |
| 1430 | GalGNXM3 | | |
| 1444 | GNFM4 | 3 | 3 |
| 1444 | GalGNFM3 | | |
| 1460 | GalGNM4 | 10 | 14 |
| 1460 | GNM5 | | |
| 1471 | GN2XM3 | | 1 |
| 1485 | GN2FM3 | 1 | 1 |
| 1501 | GalGN2M3 | 1 | |
| 1576 | GalGNFXM3 | 3 | 3 |
| 1576 | GNFXM4 | | |
| 1581 | M7 | 2 | 2 |
| 1593 | GalGNXM4 | 2 | 2 |
| 1593 | GNXM5 | | |
| 1606 | GNFM5 | 4 | 6 |
| 1606 | GalGNFM4 | | |
| 1617 | GN2FXM3 | 1 | 1 |
| 1622 | GalGNM5 | 6 | 1 |
| 1622 | GNM6 | | |
| 1647 | GalGN2FM3 | 1 | |
| 1663 | Gal2GN2M3 | 1 | |
| 1738 | GNFXM5 | 2 | 2 |
| 1738 | GalGNFXM4 | | |
| 1743 | M8 | 2 | 2 |
| 1754 | GalGNXM5 | 2 | 1 |
| 1768 | GalGNFM5 | 3 | 1 |
| 1768 | GNFM6 | | |
| 1784 | GNM7 | 1 | 1 |
| 1784 | GalGNM6 | | |
| 1809 | Gal2GN2FM3 | 1 | |
| 1900 | GNFXM6 | | 1 |
| 1900 | GalGNFXM5 | | |
| 1905 | M9 | 1 | 1 |
| | TOTAL | 102 | 100 |

These data show that:

1. Rec-mAbs from F1 hybrid contain galactose which can be deduced from the observed reduction of specific (galactose-containing) glycoforms after beta-galactosidase treatment and increase of glycoforms lacking galactose. Note the observed reduction of m/z 1622 from 6 to 1% and simultaneous increase of m/z 1460 from 10 to 14% which is the result of the removal of galactose from GalGNM5 to give rise to GNM5. The same is true for m/z 1768 (3 to 1% decrease) and corresponding m/z 1606 peak (4 to 6% increase). See also FIG. 36, panel E.
2. Similarly a number of peaks that can be attributed to galactose containing glycans vanish upon treatment with galactosidase, especially m/z 1501, 1647 and 1663 confirming the presence of galactose.

Example 6

In another embodiment, the aminoterminal CTS region of an insect Mannosidase III gene (accession number: AF005034; mistakenly annotated as a Mannosidase II gene!) is replaced by a mouse signal peptide coding sequence for import into the endoplasmic reticulum (see FIG. 37). The signal peptide sequence encodes a fully active signal peptide normally present at the aminoterminus of IgG sequences and has been used successfully in plants and other organisms before. Furthermore a synthetic sequence coding for a so-called endoplasmic reticulum retention sequence (KDEL) is added to the carboxyterminus of the gene part encoding the catalytic fragment for ER retention. The hybrid Mannosidase III protein encoded by this gene sequence will hence accumulate preferentially in the endoplasmic reticulum.

Example 7

In another embodiment, the aminoterminal CTS region of the human beta-1,4-galactosyltransferase (GalT) gene (accession A52551) is replaced by a mouse signal peptide coding sequence for import into the endoplasmic reticulum (see FIG. 39). The signal peptide sequence encodes a fully active signal peptide normally present at the aminoterminus of IgG sequences and has been used successfully in plants and other organisms before. Furthermore a synthetic sequence coding for a so-called endoplasmic reticulum retention sequence (KDEL) is added to the carboxyterminus of the gene part encoding the catalytic fragment for ER retention. The hybrid beta-1,4-galactosyl-transferase protein encoded by this gene sequence will hence accumulate preferentially in the endoplasmic reticulum.

Example 8

In another embodiment, the aminoterminal CTS region of *Arabidopsis thaliana* GnTI (acc. AJ243198) is replaced by a mouse signal peptide coding sequence for import into the endoplasmic reticulum (see FIG. 41). The signal peptide sequence encodes a fully active signal peptide normally present at the aminoterminus of IgG sequences and has been used successfully in plants and other organisms before. Furthermore a synthetic sequence coding for a so-called endoplasmic reticulum retention sequence (KDEL) is added to the carboxyterminus of the gene part encoding the catalytic fragment for ER retention. The hybrid GnTI protein encoded by this gene sequence will hence accumulate preferentially in the endoplasmic reticulum.

Example 9

In another embodiment, the aminoterminal CTS region of an *Arabidopsis thaliana* GnTII (acc. AJ249274) is replaced by a mouse signal peptide coding sequence for import into the endoplasmic reticulum (see FIG. 43). The signal peptide sequence encodes a fully active signal peptide normally present at the aminoterminus of IgG sequences and has been used successfully in plants and other organisms before. Furthermore a synthetic sequence coding for a so-called endoplasmic reticulum retention sequence (KDEL) is added to the carboxyterminus of the gene part encoding the catalytic fragment for ER retention. The hybrid GnTII protein encoded by this gene sequence will hence accumulate preferentially in the endoplasmic reticulum.

Example 10

In another embodiment, the aminoterminal CTS region of the human gene for beta-1,4-galactosyltransferase (GalT) gene is replaced by the CTS region of the human gene for GnTI (TmhuGnTI-GalT) (see FIG. 45).

Figure 47:
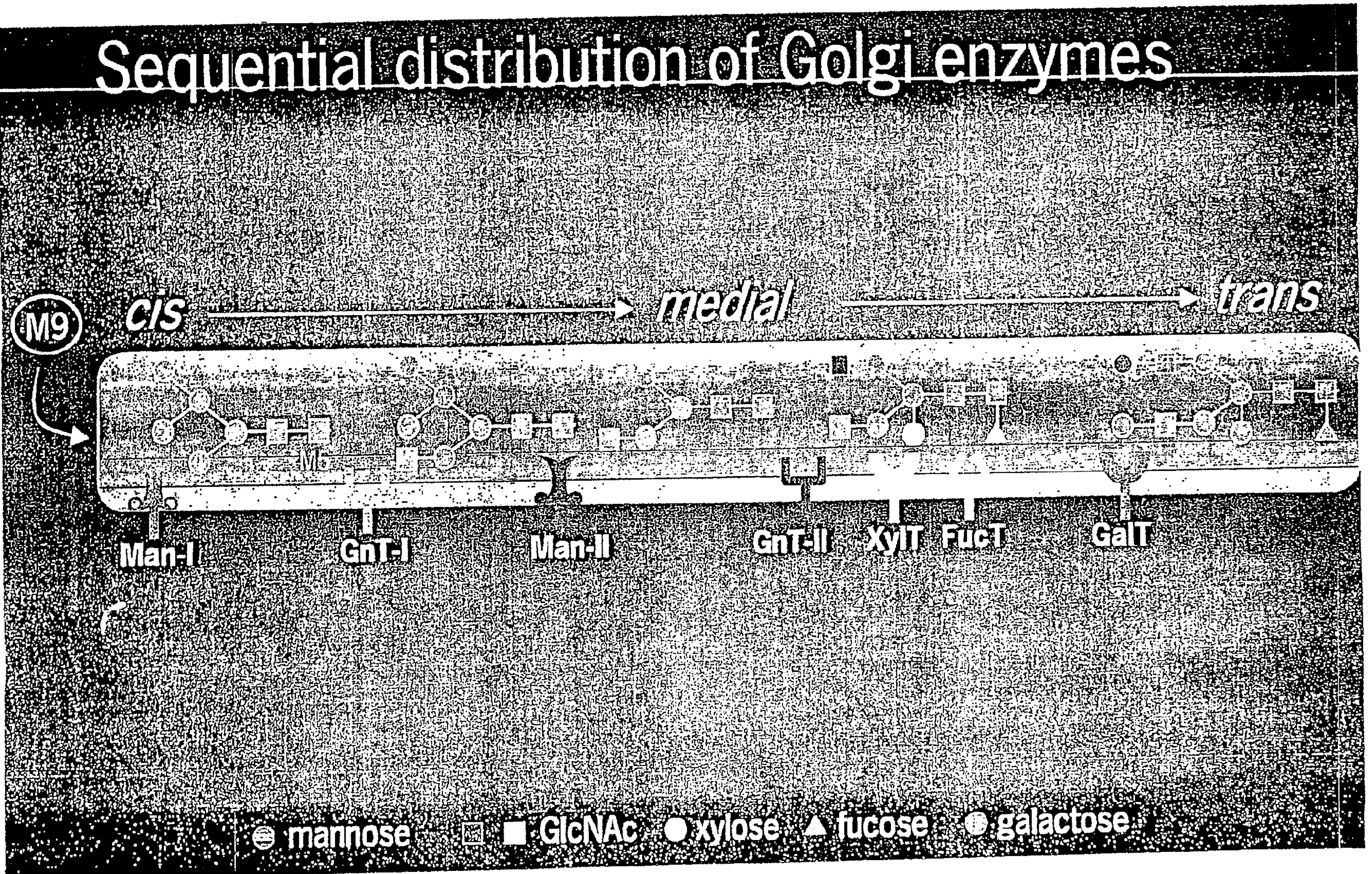
FIG. 47 is a schematic of how enzymes might be localized to the Golgi.
Figure 48:
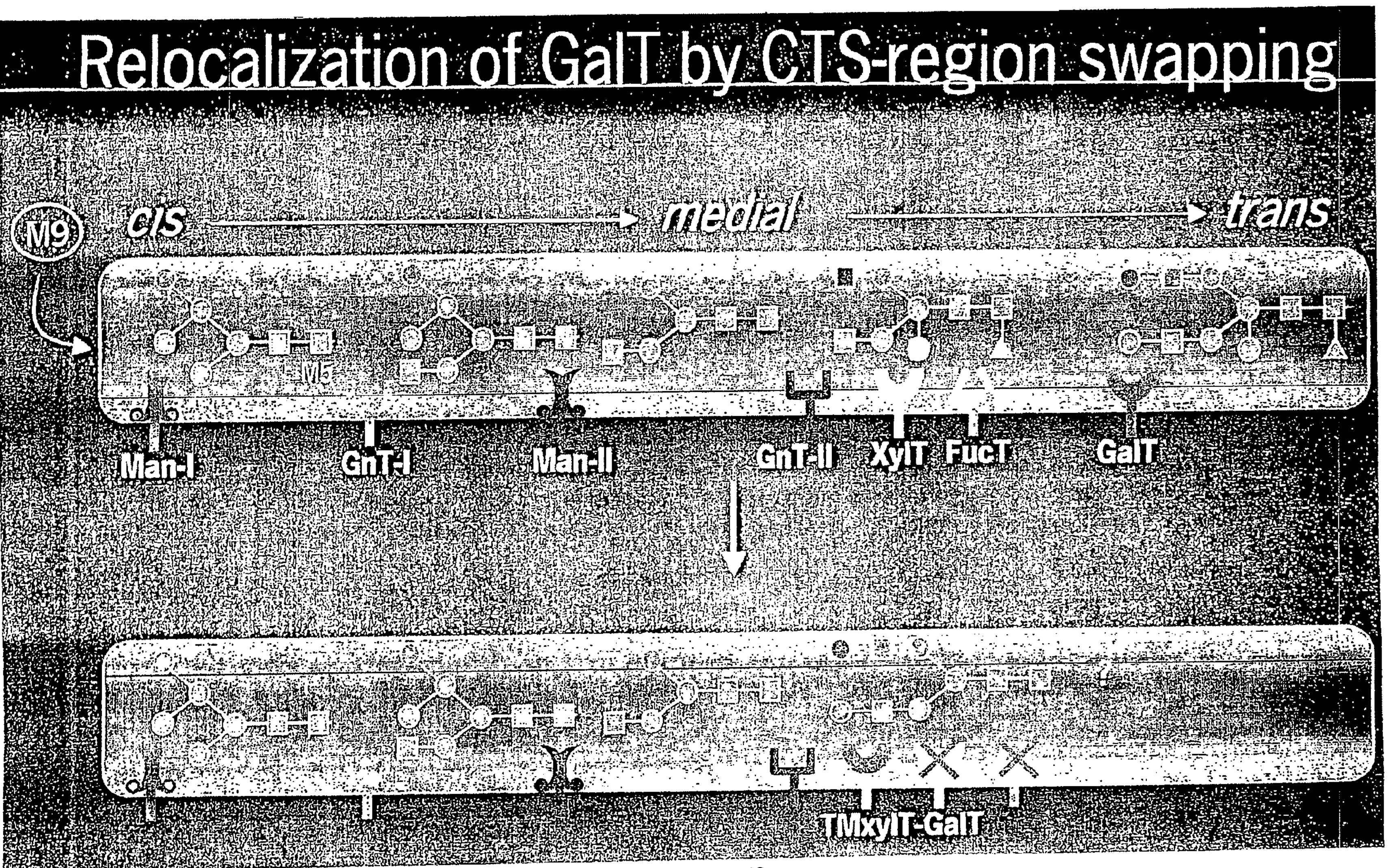
FIG. 48 is a non-limiting speculative schematic of how the "swapping" of regions of transferases might cause relocalization.

It is understood that the present invention is not limited to any particular mechanism. Nor is it necessary to understand the mechanism in order to successfully use the various embodiments of the invention. Nonetheless, it is believed that there is a sequential distribution of Golgi enzymes (FIG. 47) and that the swapping in of transmembrane domains of plant glycosyltransferases causes relocalization (FIG. 48).

It is understood that the present invention is not limited to the particular methodology, protocols, cell lines, vectors, and reagents described herein, as these may vary. It is also to be understood that the terminology used herein is used for the purpose of describing particular embodiments only, and is not intend to limit the scope of the present invention. It must be noted that as used herein and in the appended claims, the singular forms “a”, “an”, and “the” include plural reference unless the context clearly dictates otherwise. Unless defined otherwise, all technical and scientific terms used herein have the same meanings as commonly understood by one of ordinary skill in the art to which this invention belongs.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A nucleic acid encoding a hybrid enzyme, said hybrid enzyme comprising a transmembrane region of a plant xylosyltransferase and a catalytic region of a human galactosyltransferase, wherein the hybrid enzyme comprises the amino acid sequence set forth in SEQ ID NO: 4.

2. An expression vector, comprising the nucleic acid of claim 1.

3. A plant host cell transfected with the vector of claim 2.

4. A cell suspension comprising the host cell of claim 3.

5. A hybrid enzyme expressed by the plant host cell of claim 3.

6. A plant comprising the host cell of claim 3.

7. A method, comprising: a. providing: i) a plant cell, and ii) an expression vector comprising a nucleic acid encoding a hybrid enzyme that comprises a transmembrane region of a plant xylosyltransferase and a catalytic region of a human galactosyltransferase, the hybrid enzyme comprising the amino acid sequence set forth in SEQ ID NO:4; and b. introducing said expression vector into said plant cell under conditions such that said hybrid enzyme is expressed.

8. A method, comprising: a. providing: i) a plant cell, ii) a first expression vector comprising a first nucleic acid encoding a hybrid enzyme that comprises a transmembrane region of a plant glycosyltransferase and a catalytic region of a mammalian glycosyltransferase, the hybrid enzyme comprising the amino acid sequence set forth in SEQ ID NO:4, and iii) a second expression vector comprising a second nucleic acid encoding a heterologous glycoprotein; and b. introducing said first and second expression vectors into said plant cell under conditions such that said hybrid enzyme and said heterologous protein are expressed.

9. The method of claim 8, wherein said heterologous protein is an antibody or antibody fragment.

10. A method, comprising: a) providing: i) a first plant comprising a first expression vector, said first vector comprising a first nucleic acid encoding a hybrid enzyme that comprises at least a portion of a transmembrane region of a plant glycosyltransferase and at least a portion of a catalytic region of a mammalian glycosyltransferase, the hybrid enzyme comprising the amino acid sequence set forth in SEQ ID NO:4, and ii) a second plant comprising a second expression vector, said second vector comprising a second nucleic acid encoding a heterologous protein; and b) crossing said first plant and said second plant to produce progeny expressing said hybrid enzyme and said heterologous protein.

11. A nucleic acid, encoding a hybrid enzyme comprising a catalytic region of a human galactosyltransferase and an endoplasmic reticulum retention signal, wherein the hybrid enzyme comprises the amino acid sequence set forth in SEQ ID NO: 52.

12. The nucleic acid of claim 1, wherein the nucleic acid comprises the nucleic acid sequence set forth in SEQ ID NO: 3.

13. The expression vector of claim 2 comprising the nucleic acid set forth in SEQ ID NO: 3.

14. The hybrid enzyme of claim 5, wherein the hybrid enzyme is encoded by the nucleotide sequence set forth in SEQ ID NO: 3.

15. The nucleic acid of claim 11, wherein the nucleic acid comprises the nucleic acid sequence set forth in SEQ ID NO: 51.

16. The method of claim 7, wherein the nucleic acid comprises the nucleotide sequence set forth in SEQ ID NO:3.

17. The method of claim 8, wherein the first nucleic acid comprises the nucleotide sequence set forth in SEQ ID NO:3.

18. The method of claim 10, wherein the first nucleic acid comprises the nucleotide sequence set forth in SEQ ID NO:3.

* * * * *

SEQUENCE LISTING

<160> NUMBER OF SEQ ID NOS: 59

<210> SEQ ID NO 1
<211> LENGTH: 1197
<212> TYPE: DNA
<213> ORGANISM: Homo sapiens

<400> SEQUENCE: 1
atgaggcttc gggagccgct cctgagcggc agcgccgcga tgccaggcgc gtccctacag 60
cgggcctgcc gcctgctcgt ggccgtctgc gctctgcacc ttggcgtcac cctcgtttac 120
tacctggctg gccgcgacct gagccgcctg ccccaactgg tcggagtctc cacaccgctg 180
cagggcggct cgaacagtgc cgccgccatc gggcagtcct ccggggagct ccggaccgga 240
ggggcccggc cgccgcctcc tctaggcgcc tcctcccagc cgcgcccggg tggcgactcc 300
agcccagtcg tggattctgg ccctggcccc gctagcaact tgacctcggt cccagtgccc 360
cacaccaccg cactgtcgct gcccgcctgc cctgaggagt ccccgctgct tgtgggcccc 420
atgctgattg agtttaacat gcctgtggac ctggagctcg tggcaaagca gaacccaaat 480
gtgaagatgg gcggccgcta tgcccccagg gactgcgtct ctcctcacaa ggtggccatc 540
atcattccat tccgcaaccg gcaggagcac ctcaagtact ggctatatta tttgcaccca 600
gtcctgcagc gccagcagct ggactatggc atctatgtta tcaaccaggc gggagacact 660
atattcaatc gtgctaagct cctcaatgtt ggctttcaag aagccttgaa ggactatgac 720
tacacctgct ttgtgtttag tgacgtggac ctcattccaa tgaatgacca taatgcgtac 780
aggtgttttt cacagccacg gcacatttcc gttgcaatgg ataagtttgg attcagccta 840
ccttatgttc agtattttgg aggtgtctct gctctaagta aacaacagtt tctaaccatc 900
aatggatttc ctaataatta ttggggctgg ggaggagaag atgatgacat ttttaacaga 960
ttagttttta gaggcatgtc tatatctcgc ccaaatgctg tggtcgggag gtgtcgcatg 1020
atccgccact caagagacaa gaaaaatgaa cccaatcctc agaggtttga ccgaattgca 1080
cacacaaagg agacaatgct ctctgatggt ttgaactcac tcacctacca ggtgctggat 1140
gtacagagat acccattgta tacccaaatc acagtggaca tcgggacacc gagctag 1197

<210> SEQ ID NO 2
<211> LENGTH: 398
<212> TYPE: PRT
<213> ORGANISM: Homo sapiens

<400> SEQUENCE: 2

```
Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395
```

<210> SEQ ID NO 3
<211> LENGTH: 1152
<212> TYPE: DNA

<213> ORGANISM: Artificial Sequence
<220> FEATURE:
<223> OTHER INFORMATION: hybrid enzyme; Arabidopsis Thaliana beta 1,4 xylT and human beta 1,4 galactosylT

<400> SEQUENCE: 3

```
atgagtaaac ggaatccgaa gattctgaag atttttctgt atatgttact tctcaactct     60

ctctttctca tcatctactt cgtttttcac tcatcgtcgt tttcaccgga gcagtcacag    120

cctcctcata tataccacgt ttcagtgaat aaccaatcgg cgatcgggca gtcctccggg    180

gagctccgga ccggaggggc ccggccgccg cctcctctag gcgcctcctc ccagccgcgc    240

ccgggtggcg actccagccc agtcgtggat tctggccctg gccccgctag caacttgacc    300

tcggtcccag tgccccacac caccgcactg tcgctgcccg cctgccctga ggagtccccg    360

ctgcttgtgg gccccatgct gattgagttt aacatgcctg tggacctgga gctcgtggca    420

aagcagaacc caaatgtgaa gatgggcggc cgctatgccc ccagggactg cgtctctcct    480

cacaaggtgg ccatcatcat tccattccgc aaccggcagg agcacctcaa gtactggcta    540

tattatttgc acccagtcct gcagcgccag cagctggact atggcatcta tgttatcaac    600

caggcgggag acactatatt caatcgtgct aagctcctca atgttggctt tcaagaagcc    660

ttgaaggact atgactacac ctgctttgtg tttagtgacg tggacctcat tccaatgaat    720

gaccataatg cgtacaggtg tttttcacag ccacggcaca tttccgttgc aatggataag    780

tttggattca gcctacctta tgttcagtat tttggaggtg tctctgctct aagtaaacaa    840

cagtttctaa ccatcaatgg atttcctaat aattattggg gctggggagg agaagatgat    900

gacattttta acagattagt ttttagaggc atgtctatat ctcgcccaaa tgctgtggtc    960

gggaggtgtc gcatgatccg ccactcaaga gacaagaaaa atgaacccaa tcctcagagg   1020

tttgaccgaa ttgcacacac aaaggagaca atgctctctg atggtttgaa ctcactcacc   1080

taccaggtgc tggatgtaca gagataccca ttgtataccc aaatcacagt ggacatcggg   1140

acaccgagct ag                                                        1152
```

<210> SEQ ID NO 4
<211> LENGTH: 383
<212> TYPE: PRT
<213> ORGANISM: Artificial Sequence
<220> FEATURE:
<223> OTHER INFORMATION: hybrid enzyme; Arabidopsis Thaliana beta 1,4 xylT and human beta 1,4 galT

<400> SEQUENCE: 4

```
Met Ser Lys Arg Asn Pro Lys Ile Leu Lys Ile Phe Leu Tyr Met Leu
1               5                   10                  15

Leu Leu Asn Ser Leu Phe Leu Ile Ile Tyr Phe Val Phe His Ser Ser
            20                  25                  30

Ser Phe Ser Pro Glu Gln Ser Gln Pro Pro His Ile Tyr His Val Ser
        35                  40                  45

Val Asn Asn Gln Ser Ala Ile Gly Gln Ser Ser Gly Glu Leu Arg Thr
    50                  55                  60

Gly Gly Ala Arg Pro Pro Pro Pro Leu Gly Ala Ser Ser Gln Pro Arg
65                  70                  75                  80

Pro Gly Gly Asp Ser Ser Pro Val Val Asp Ser Gly Pro Gly Pro Ala
                85                  90                  95

Ser Asn Leu Thr Ser Val Pro Val Pro His Thr Thr Ala Leu Ser Leu
            100                 105                 110

Pro Ala Cys Pro Glu Glu Ser Pro Leu Leu Val Gly Pro Met Leu Ile
```

```
        115                 120                 125

Glu Phe Asn Met Pro Val Asp Leu Glu Leu Val Ala Lys Gln Asn Pro
    130                 135                 140

Asn Val Lys Met Gly Gly Arg Tyr Ala Pro Arg Asp Cys Val Ser Pro
145                 150                 155                 160

His Lys Val Ala Ile Ile Ile Pro Phe Arg Asn Arg Gln Glu His Leu
                165                 170                 175

Lys Tyr Trp Leu Tyr Tyr Leu His Pro Val Leu Gln Arg Gln Gln Leu
            180                 185                 190

Asp Tyr Gly Ile Tyr Val Ile Asn Gln Ala Gly Asp Thr Ile Phe Asn
        195                 200                 205

Arg Ala Lys Leu Leu Asn Val Gly Phe Gln Glu Ala Leu Lys Asp Tyr
    210                 215                 220

Asp Tyr Thr Cys Phe Val Phe Ser Asp Val Asp Leu Ile Pro Met Asn
225                 230                 235                 240

Asp His Asn Ala Tyr Arg Cys Phe Ser Gln Pro Arg His Ile Ser Val
                245                 250                 255

Ala Met Asp Lys Phe Gly Phe Ser Leu Pro Tyr Val Gln Tyr Phe Gly
            260                 265                 270

Gly Val Ser Ala Leu Ser Lys Gln Gln Phe Leu Thr Ile Asn Gly Phe
        275                 280                 285

Pro Asn Asn Tyr Trp Gly Trp Gly Gly Glu Asp Asp Asp Ile Phe Asn
    290                 295                 300

Arg Leu Val Phe Arg Gly Met Ser Ile Ser Arg Pro Asn Ala Val Val
305                 310                 315                 320

Gly Arg Cys Arg Met Ile Arg His Ser Arg Asp Lys Lys Asn Glu Pro
                325                 330                 335

Asn Pro Gln Arg Phe Asp Arg Ile Ala His Thr Lys Glu Thr Met Leu
            340                 345                 350

Ser Asp Gly Leu Asn Ser Leu Thr Tyr Gln Val Leu Asp Val Gln Arg
        355                 360                 365

Tyr Pro Leu Tyr Thr Gln Ile Thr Val Asp Ile Gly Thr Pro Ser
    370                 375                 380
```

<210> SEQ ID NO 5
<211> LENGTH: 1642
<212> TYPE: DNA
<213> ORGANISM: Homo sapiens

<400> SEQUENCE: 5

```
ccatggtgat gagacgctac aagctctttc tcatgttctg tatggccggc ctgtgcctca      60

tctccttcct gcacttcttc aagaccctgt cctatgtcac cttcccccga gaactggcct     120

ccctcagccc taacctggtg tccagctttt tctggaacaa tgccccggtc acgccccagg     180

ccagccccga gccaggaggc cctgacctgc tgcgtacccc actctactcc cactcgcccc     240

tgctgcagcc gctgccgccc agcaaggcgg ccgaggagct ccaccgggtg gacttggtgc     300

tgcccgagga caccaccgag tatttcgtgc gcaccaaggc cggcggcgtc tgcttcaaac     360

ccggcaccaa gatgctggag aggccgcccc cgggacggcc ggaggagaag cctgaggggg     420

ccaacggctc ctcggcccgg cggccacccc ggtacctcct gagcgcccgg gagcgcacgg     480

ggggccgagg cgcccggcgc aagtgggtgg agtgcgtgtg cctgcccggc tggcacggac     540

ccagctgcgg cgtgcccact gtggtgcagt actccaacct gcccaccaag gagcggctgg     600

tgcccaggga ggtgccgcgc cgcgtcatca acgccatcaa cgtcaaccac gagttcgacc     660
```

```
tgctggacgt gcgcttccac gagctgggcg acgtggtgga cgcctttgtg gtgtgcgagt     720

ccaacttcac ggcttatggg gagccgcggc cgctcaagtt ccgggagatg ctgaccaatg     780

gcaccttcga gtacatccgc cacaaggtgc tctatgtctt cctggaccac ttcccgcccg     840

gcggccggca ggacggctgg atcgccgacg actacctgcg caccttcctc acccaggacg     900

gcgtctcgcg gctgcgcaac ctgcggcccg acgacgtctt catcattgac gatgcggacg     960

agatcccggc ccgtgacggc gtccttttcc tcaagctcta cgatggctgg accgagccct    1020

tcgccttcca catgcgcaag tcgctctacg gcttcttctg gaagcagccg ggcaccctgg    1080

aggtggtgtc aggctgcacg gtggacatgc tgcaggcagt gtatgggctg gacggcatcc    1140

gcctgcgccg ccgccagtac tacaccatgc ccaacttcag acagtatgag aaccgcaccg    1200

gccacatcct ggtgcagtgg tcgctgggca gccccctgca cttcgccggc tggcactgct    1260

cctggtgctt cacgcccgag ggcatctact tcaagctcgt gtccgcccag aatggcgact    1320

tcccacgctg gggtgactac gaggacaagc gggacctgaa ctacatccgc ggcctgatcc    1380

gcaccggggg ctggttcgac ggcacgcagc aggagtaccc gcctgcagac cccagcgagc    1440

acatgtatgc gcccaagtac ctgctgaaga actacgaccg gttccactac ctgctggaca    1500

acccctacca ggagcccagg agcacggcgg cgggcgggtg gcgccacagg ggtcccgagg    1560

gaaggccgcc cgcccggggc aaactggacg aggcggaagt cgaacaaaaa ctcatctcag    1620

aagaggatct gaattaggat cc                                             1642
```

```
<210> SEQ ID NO 6
<211> LENGTH: 544
<212> TYPE: PRT
<213> ORGANISM: Homo sapiens

<400> SEQUENCE: 6

Met Val Met Arg Arg Tyr Lys Leu Phe Leu Met Phe Cys Met Ala Gly
1               5                   10                  15

Leu Cys Leu Ile Ser Phe Leu His Phe Phe Lys Thr Leu Ser Tyr Val
            20                  25                  30

Thr Phe Pro Arg Glu Leu Ala Ser Leu Ser Pro Asn Leu Val Ser Ser
        35                  40                  45

Phe Phe Trp Asn Asn Ala Pro Val Thr Pro Gln Ala Ser Pro Glu Pro
    50                  55                  60

Gly Gly Pro Asp Leu Leu Arg Thr Pro Leu Tyr Ser His Ser Pro Leu
65                  70                  75                  80

Leu Gln Pro Leu Pro Pro Ser Lys Ala Ala Glu Glu Leu His Arg Val
                85                  90                  95

Asp Leu Val Leu Pro Glu Asp Thr Thr Glu Tyr Phe Val Arg Thr Lys
            100                 105                 110

Ala Gly Gly Val Cys Phe Lys Pro Gly Thr Lys Met Leu Glu Arg Pro
        115                 120                 125

Pro Pro Gly Arg Pro Glu Glu Lys Pro Glu Gly Ala Asn Gly Ser Ser
    130                 135                 140

Ala Arg Arg Pro Pro Arg Tyr Leu Leu Ser Ala Arg Glu Arg Thr Gly
145                 150                 155                 160

Gly Arg Gly Ala Arg Arg Lys Trp Val Glu Cys Val Cys Leu Pro Gly
                165                 170                 175

Trp His Gly Pro Ser Cys Gly Val Pro Thr Val Val Gln Tyr Ser Asn
            180                 185                 190

Leu Pro Thr Lys Glu Arg Leu Val Pro Arg Glu Val Pro Arg Arg Val
        195                 200                 205
```

```
Ile Asn Ala Ile Asn Val Asn His Glu Phe Asp Leu Leu Asp Val Arg
    210                 215                 220

Phe His Glu Leu Gly Asp Val Val Asp Ala Phe Val Val Cys Glu Ser
225                 230                 235                 240

Asn Phe Thr Ala Tyr Gly Glu Pro Arg Pro Leu Lys Phe Arg Glu Met
                245                 250                 255

Leu Thr Asn Gly Thr Phe Glu Tyr Ile Arg His Lys Val Leu Tyr Val
            260                 265                 270

Phe Leu Asp His Phe Pro Pro Gly Gly Arg Gln Asp Gly Trp Ile Ala
        275                 280                 285

Asp Asp Tyr Leu Arg Thr Phe Leu Thr Gln Asp Gly Val Ser Arg Leu
    290                 295                 300

Arg Asn Leu Arg Pro Asp Asp Val Phe Ile Ile Asp Asp Ala Asp Glu
305                 310                 315                 320

Ile Pro Ala Arg Asp Gly Val Leu Phe Leu Lys Leu Tyr Asp Gly Trp
                325                 330                 335

Thr Glu Pro Phe Ala Phe His Met Arg Lys Ser Leu Tyr Gly Phe Phe
            340                 345                 350

Trp Lys Gln Pro Gly Thr Leu Glu Val Val Ser Gly Cys Thr Val Asp
        355                 360                 365

Met Leu Gln Ala Val Tyr Gly Leu Asp Gly Ile Arg Leu Arg Arg Arg
    370                 375                 380

Gln Tyr Tyr Thr Met Pro Asn Phe Arg Gln Tyr Glu Asn Arg Thr Gly
385                 390                 395                 400

His Ile Leu Val Gln Trp Ser Leu Gly Ser Pro Leu His Phe Ala Gly
                405                 410                 415

Trp His Cys Ser Trp Cys Phe Thr Pro Glu Gly Ile Tyr Phe Lys Leu
            420                 425                 430

Val Ser Ala Gln Asn Gly Asp Phe Pro Arg Trp Gly Asp Tyr Glu Asp
        435                 440                 445

Lys Arg Asp Leu Asn Tyr Ile Arg Gly Leu Ile Arg Thr Gly Gly Trp
    450                 455                 460

Phe Asp Gly Thr Gln Gln Glu Tyr Pro Pro Ala Asp Pro Ser Glu His
465                 470                 475                 480

Met Tyr Ala Pro Lys Tyr Leu Leu Lys Asn Tyr Asp Arg Phe His Tyr
                485                 490                 495

Leu Leu Asp Asn Pro Tyr Gln Glu Pro Arg Ser Thr Ala Ala Gly Gly
            500                 505                 510

Trp Arg His Arg Gly Pro Glu Gly Arg Pro Pro Ala Arg Gly Lys Leu
        515                 520                 525

Asp Glu Ala Glu Val Glu Gln Lys Leu Ile Ser Glu Glu Asp Leu Asn
    530                 535                 540


<210> SEQ ID NO 7
<211> LENGTH: 10
<212> TYPE: PRT
<213> ORGANISM: Artificial Sequence
<220> FEATURE:
<223> OTHER INFORMATION: Synthetic myc epitope tag

<400> SEQUENCE: 7

Glu Gln Lys Leu Ile Ser Glu Glu Asp Leu
1               5                   10


<210> SEQ ID NO 8
<211> LENGTH: 31
```

<212> TYPE: PRT
<213> ORGANISM: Homo sapiens

<400> SEQUENCE: 8

```
Gln Glu Pro Arg Ser Thr Ala Ala Gly Gly Trp Arg His Arg Gly Pro
1               5                   10                  15

Glu Gly Arg Pro Pro Ala Arg Gly Lys Leu Asp Glu Ala Glu Val
            20                  25                  30
```

<210> SEQ ID NO 9
<211> LENGTH: 1614
<212> TYPE: DNA
<213> ORGANISM: Artificial Sequence
<220> FEATURE:
<223> OTHER INFORMATION: hybrid enzyme; plant TmxylT and human GntIII

<400> SEQUENCE: 9

```
catgagtaaa cggaatccga agattctgaa gatttttctg tatatgttac ttctcaactc     60
tctctttctc atcatctact tcgtttttca ctcatcgtcg ttttcaccgg agcagtcaca    120
gcctcctcat atataccacg tttcagtgaa taaccaatcg gcacatggag gccctgacct    180
gctgcgtacc ccactctact cccactcgcc cctgctgcag ccgctgccgc ccagcaaggc    240
ggccgaggag ctccaccggg tggacttggt gctgcccgag gacaccaccg agtatttcgt    300
gcgcaccaag gccggcggcg tctgcttcaa acccggcacc aagatgctgg agaggccgcc    360
cccgggacgg ccggaggaga agcctgaggg ggccaacggc tcctcggccc ggcggccacc    420
ccggtacctc ctgagcgccc gggagcgcac ggggggccga ggcgcccggc gcaagtgggt    480
ggagtgcgtg tgcctgcccg gctggcacgg acccagctgc ggcgtgccca ctgtggtgca    540
gtactccaac ctgcccacca aggagcggct ggtgcccagg gaggtgccgc gccgcgtcat    600
caacgccatc aacgtcaacc acgagttcga cctgctggac gtgcgcttcc acgagctggg    660
cgacgtggtg gacgcctttg tggtgtgcga gtccaacttc acggcttatg gggagccgcg    720
gccgctcaag ttccgggaga tgctgaccaa tggcaccttc gagtacatcc gccacaaggt    780
gctctatgtc ttcctggacc acttcccgcc cggcggccgg caggacggct ggatcgccga    840
cgactacctg cgcaccttcc tcacccagga cggcgtctcg cggctgcgca acctgcggcc    900
cgacgacgtc ttcatcattg acgatgcgga cgagatcccg gcccgtgacg gcgtcctttt    960
cctcaagctc tacgatggct ggaccgagcc cttcgccttc cacatgcgca agtcgctcta   1020
cggcttcttc tggaagcagc cgggcaccct ggaggtggtg tcaggctgca cggtggacat   1080
gctgcaggca gtgtatgggc tggacggcat ccgcctgcgc cgccgccagt actacaccat   1140
gcccaacttc agacagtatg agaaccgcac cggccacatc ctggtgcagt ggtcgctggg   1200
cagccccctg cacttcgccg gctggcactg ctcctggtgc ttcacgcccg agggcatcta   1260
cttcaagctc gtgtccgccc agaatggcga cttcccacgc tggggtgact acgaggacaa   1320
gcgggacctg aactacatcc gcggcctgat ccgcaccggg ggctggttcg acggcacgca   1380
gcaggagtac ccgcctgcag accccagcga gcacatgtat gcgcccaagt acctgctgaa   1440
gaactacgac cggttccact acctgctgga caacccctac caggagccca ggagcacggc   1500
ggcgggcggg tggcgccaca ggggtcccga gggaaggccg cccgcccggg gcaaactgga   1560
cgaggcggaa gtcgaacaaa aactcatctc agaagaggat ctgaattagg atcc         1614
```

<210> SEQ ID NO 10
<211> LENGTH: 535
<212> TYPE: PRT
<213> ORGANISM: Artificial Sequence

```
<220> FEATURE:
<223> OTHER INFORMATION: Hybrid enzyme;  plant TmxylT and human GntIII

<400> SEQUENCE: 10

Met Ser Lys Arg Asn Pro Lys Ile Leu Lys Ile Phe Leu Tyr Met Leu
1               5                   10                  15

Leu Leu Asn Ser Leu Phe Leu Ile Ile Tyr Phe Val Phe His Ser Ser
            20                  25                  30

Ser Phe Ser Pro Glu Gln Ser Gln Pro Pro His Ile Tyr His Val Ser
        35                  40                  45

Val Asn Asn Gln Ser Ala His Gly Gly Pro Asp Leu Leu Arg Thr Pro
    50                  55                  60

Leu Tyr Ser His Ser Pro Leu Leu Gln Pro Leu Pro Pro Ser Lys Ala
65                  70                  75                  80

Ala Glu Glu Leu His Arg Val Asp Leu Val Leu Pro Glu Asp Thr Thr
                85                  90                  95

Glu Tyr Phe Val Arg Thr Lys Ala Gly Gly Val Cys Phe Lys Pro Gly
            100                 105                 110

Thr Lys Met Leu Glu Arg Pro Pro Pro Gly Arg Pro Glu Glu Lys Pro
        115                 120                 125

Glu Gly Ala Asn Gly Ser Ser Ala Arg Arg Pro Pro Arg Tyr Leu Leu
    130                 135                 140

Ser Ala Arg Glu Arg Thr Gly Gly Arg Gly Ala Arg Arg Lys Trp Val
145                 150                 155                 160

Glu Cys Val Cys Leu Pro Gly Trp His Gly Pro Ser Cys Gly Val Pro
                165                 170                 175

Thr Val Val Gln Tyr Ser Asn Leu Pro Thr Lys Glu Arg Leu Val Pro
            180                 185                 190

Arg Glu Val Pro Arg Arg Val Ile Asn Ala Ile Asn Val Asn His Glu
        195                 200                 205

Phe Asp Leu Leu Asp Val Arg Phe His Glu Leu Gly Asp Val Val Asp
    210                 215                 220

Ala Phe Val Val Cys Glu Ser Asn Phe Thr Ala Tyr Gly Glu Pro Arg
225                 230                 235                 240

Pro Leu Lys Phe Arg Glu Met Leu Thr Asn Gly Thr Phe Glu Tyr Ile
                245                 250                 255

Arg His Lys Val Leu Tyr Val Phe Leu Asp His Phe Pro Pro Gly Gly
            260                 265                 270

Arg Gln Asp Gly Trp Ile Ala Asp Asp Tyr Leu Arg Thr Phe Leu Thr
        275                 280                 285

Gln Asp Gly Val Ser Arg Leu Arg Asn Leu Arg Pro Asp Asp Val Phe
    290                 295                 300

Ile Ile Asp Asp Ala Asp Glu Ile Pro Ala Arg Asp Gly Val Leu Phe
305                 310                 315                 320

Leu Lys Leu Tyr Asp Gly Trp Thr Glu Pro Phe Ala Phe His Met Arg
                325                 330                 335

Lys Ser Leu Tyr Gly Phe Phe Trp Lys Gln Pro Gly Thr Leu Glu Val
            340                 345                 350

Val Ser Gly Cys Thr Val Asp Met Leu Gln Ala Val Tyr Gly Leu Asp
        355                 360                 365

Gly Ile Arg Leu Arg Arg Arg Gln Tyr Tyr Thr Met Pro Asn Phe Arg
    370                 375                 380

Gln Tyr Glu Asn Arg Thr Gly His Ile Leu Val Gln Trp Ser Leu Gly
385                 390                 395                 400
```

```
Ser Pro Leu His Phe Ala Gly Trp His Cys Ser Trp Cys Phe Thr Pro
                405                 410                 415

Glu Gly Ile Tyr Phe Lys Leu Val Ser Ala Gln Asn Gly Asp Phe Pro
            420                 425                 430

Arg Trp Gly Asp Tyr Glu Asp Lys Arg Asp Leu Asn Tyr Ile Arg Gly
        435                 440                 445

Leu Ile Arg Thr Gly Gly Trp Phe Asp Gly Thr Gln Gln Glu Tyr Pro
    450                 455                 460

Pro Ala Asp Pro Ser Glu His Met Tyr Ala Pro Lys Tyr Leu Leu Lys
465                 470                 475                 480

Asn Tyr Asp Arg Phe His Tyr Leu Leu Asp Asn Pro Tyr Gln Glu Pro
                485                 490                 495

Arg Ser Thr Ala Ala Gly Gly Trp Arg His Arg Gly Pro Glu Gly Arg
            500                 505                 510

Pro Pro Ala Arg Gly Lys Leu Asp Glu Ala Glu Val Glu Gln Lys Leu
        515                 520                 525

Ile Ser Glu Glu Asp Leu Asn
    530                 535


<210> SEQ ID NO 11
<211> LENGTH: 13
<212> TYPE: DNA
<213> ORGANISM: Artificial Sequence
<220> FEATURE:
<223> OTHER INFORMATION: Synthetic myc epitope tag

<400> SEQUENCE: 11

aatacttcca ccc                                                          13


<210> SEQ ID NO 12
<211> LENGTH: 34
<212> TYPE: DNA
<213> ORGANISM: Artificial Sequence
<220> FEATURE:
<223> OTHER INFORMATION: Synthetic

<400> SEQUENCE: 12

ccacccgtta acaatgaaga tgagacgcta caag                                   34


<210> SEQ ID NO 13
<211> LENGTH: 29
<212> TYPE: DNA
<213> ORGANISM: Artificial Sequence
<220> FEATURE:
<223> OTHER INFORMATION: Synthetic

<400> SEQUENCE: 13

gggccatgga gatgagacgc tacaagctc                                         29


<210> SEQ ID NO 14
<211> LENGTH: 28
<212> TYPE: DNA
<213> ORGANISM: Artificial Sequence
<220> FEATURE:
<223> OTHER INFORMATION: Synthetic

<400> SEQUENCE: 14

ggatccaatg aagatgagac gctacaag                                          28


<210> SEQ ID NO 15
<211> LENGTH: 41
<212> TYPE: DNA
<213> ORGANISM: Artificial Sequence
```

<220> FEATURE:
<223> OTHER INFORMATION: Synthetic

<400> SEQUENCE: 15
gggcccggga gatcctaatt cagatcctct tctgagatga g 41

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
cccggatcct aattcagatc ctcttctgag atgag 35

<210> SEQ ID NO 17
<211> LENGTH: 38
<212> TYPE: DNA
<213> ORGANISM: Artificial Sequence
<220> FEATURE:
<223> OTHER INFORMATION: Synthetic

<400> SEQUENCE: 17
gggtctagat cctaattcag atcctcttct gagatgag 38

<210> SEQ ID NO 18
<211> LENGTH: 35
<212> TYPE: DNA
<213> ORGANISM: Artificial Sequence
<220> FEATURE:
<223> OTHER INFORMATION: Synthetic

<400> SEQUENCE: 18
ccacccgtta acaatgagta aacggaatcc gaaga 35

<210> SEQ ID NO 19
<211> LENGTH: 35
<212> TYPE: DNA
<213> ORGANISM: Artificial Sequence
<220> FEATURE:
<223> OTHER INFORMATION: Synthetic

<400> SEQUENCE: 19
gggccatggg taaacggaat ccgaagattc tgaag 35

<210> SEQ ID NO 20
<211> LENGTH: 34
<212> TYPE: DNA
<213> ORGANISM: Artificial Sequence
<220> FEATURE:
<223> OTHER INFORMATION: Synthetic

<400> SEQUENCE: 20
cccggatcca tgagtaaacg gaatccgaag attc 34

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
gcgccccggg acgctagctc ggtgtcccg 29

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
cccggatcca cgctagctcg gtgtc 25

<210> SEQ ID NO 23
<211> LENGTH: 31
<212> TYPE: DNA
<213> ORGANISM: Artificial Sequence
<220> FEATURE:
<223> OTHER INFORMATION: Synthetic

<400> SEQUENCE: 23
gggtctagat ccacgctagc tcggtgtccc g 31

<210> SEQ ID NO 24
<211> LENGTH: 39
<212> TYPE: DNA
<213> ORGANISM: Artificial Sequence
<220> FEATURE:
<223> OTHER INFORMATION: Synthetic

<400> SEQUENCE: 24
ccacccgtta acaatgaggc ttcgggagcc gctcctgag 39

<210> SEQ ID NO 25
<211> LENGTH: 31
<212> TYPE: DNA
<213> ORGANISM: Artificial Sequence
<220> FEATURE:
<223> OTHER INFORMATION: Synthetic

<400> SEQUENCE: 25
gggccatggg gcttcgggag ccgctcctga g 31

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26
cccggatcca tgaggcttcg ggagccgctc ctgag 35

<210> SEQ ID NO 27
<211> LENGTH: 7155
<212> TYPE: DNA
<213> ORGANISM: Artificial Sequence
<220> FEATURE:
<223> OTHER INFORMATION: cassette encoding the hybrid enzymes TmXyl-GalT plus TmGnTI-GnTII plus TmGnTI- ManII

<400> SEQUENCE: 27
ggcgcgcctc gaggcgatcg cagatctaat ctaaccaatt acgatacgct ttgggtacac 60
ttgatttttg tttcagtggt tacatatatc ttgttttata tgctatcttt aaggatctgc 120
acaaagatta tttgttgatg ttcttgatgg ggctcagaag atttgatatg atacactcta 180
atctttagga gataccagcc aggattatat tcagtaagac aatcaaattt tacgtgttca 240
aactcgttat cttttcattc aaaggatgag ccagaatctt tatagaatga ttgcaatcga 300

-continued

```
gaatatgttc ggccgatatg cctttgttgg cttcaatatt ctacatatca cacaagaatc    360
gaccgtattg taccctcttt ccataaagga aaacacaata tgcagatgct tttttcccac    420
atgcagtaac atataggtat tcaaaaatgg ctaaaagaag ttggataaca aattgacaac    480
tatttccatt tctgttatat aaatttcaca acacacaaaa gcccgtaatc aagagtctgc    540
ccatgtacga aataacttct attatttggt attgggccta agcccagctc agagtacgtg    600
ggggtaccac atataggaag gtaacaaaat actgcaagat agccccataa cgtaccagcc    660
tctccttacc acgaagagat aagatataag acccaccctg ccacgtgtca catcgtcatg    720
gtggttaatg ataagggatt acatccttct atgtttgtgg acatgatgca tgtaatgtca    780
tgagccacag gatccaatgg ccacaggaac gtaagaatgt agatagattt gattttgtcc    840
gttagatagc aaacaacatt ataaaaggtg tgtatcaata ggaactaatt cactcattgg    900
attcatagaa gtccattcct cctaagtatc tagaaaccat ggcgaggatc tcgtgtgact    960
tgagatttct tctcatcccg gcagctttca tgttcatcta catccagatg aggcttttcc   1020
agacgcaatc acagtatgca gatcgcctca gttccgctat cgaatctgag aaccattgca   1080
ctagtcaaat gcgaggcctc atagatgaag ttagcatcaa acagtcgcgg attgttgccc   1140
tcgaagatat gaagaaccgc caggacgaag aacttgtgca gcttaaggat ctaatccaga   1200
cgtttgaaaa aaaaggaata gcaaaactca ctcaaggtgg agccatggat tccaattcag   1260
gcgccgtcgt tgatatcaca actaaagatc tatacgatag gattgagttt cttgatacag   1320
atggtggtcc atggaaacaa ggttggagag ttacgtataa agacgatgag tgggagaaag   1380
agaagctcaa aatcttcgtt gttcctcatt ctcataacga tcctggttgg aaattgactg   1440
tagaggagta ttatcagaga caatccagac atattcttga caccattgtt gagactttat   1500
ctaaggtatg acgaaagttt ttgcttttgg ttttaatatt ttaattctct cccatggtta   1560
tcccgtgaac aatcttaaat gtcttaaaat tctcatgacg tcattaaact ctataaccaa   1620
acttctttgc tgggttctgt tttttttag tttcgtgatg aaacagagtt ctagaagttc   1680
gttcttttgg aaaatttgaa gtctttggag ctaaagtttg ttttttatt actgggtttt   1740
gagattgaag gatagctaga atcttatttg tgtgggggtt tgttttgaat atgtttaata   1800
ggattcaaga agaaagttta tatgggagga gatgtcatat ctggagagat ggtggagaga   1860
cgcttcacct aataaacaag aagctttgac taaattggtt aaggatgggc agctagagat   1920
tgttggaggt ggctgggtta tgaatgatga ggctaattca cattattttg ccataattga   1980
acagatagca gagggtaata tgtggctgaa tgacacaatt ggggttattc ctaagaattc   2040
ttgggctata gatccctttg gctattcatc aaccatggct tatcttctcc ggcgtatggg   2100
ttttgaaaac atgcttattc aaaggactca ttacgagctc aagaaagacc ttgcccagca   2160
taagaatctt gaatatattt ggcgtcagag ctgggatgct atggaaacca cagatatctt   2220
tgttcatatg atgccgtttt attcatacga tatcccacac acttgtggac cagagcctgc   2280
aatttgctgt cagtttgatt tcgctcggat gcggggattt aagtatgaac tttgtccatg   2340
gggaaagcac ccagtggaga ccacactaga aaatgtgcag gagagggcat taaagcttct   2400
ggatcaatac aggaaaaaat ccactctata tcgaactaat acacttctta tacctcttgg   2460
agatgatttt aggtacatta gtatcgatga agccgaggct cagttccgta actaccagat   2520
gttgtttgat cacatcaact ctaatcctag tctaaacgca gaagcaaagt ttggtacttt   2580
ggaggattat ttcagaacag tccgagaaga agcagacaga gtgaattatt ctcgtcctgg   2640
tgaggttggc tctggtcagg ttgttggttt cccttctctg tcaggtgact tctttacata   2700
```

-continued

```
tgcagatagg caacaagact attggagtgg ttattatgtt tcaagacctt tcttcaaagc   2760
tgttgatcgt gtgctcgagc atacccttcg tggagctgag atcatgatgt catttctgct   2820
aggttattgc catcgaattc aatgtgagaa atttccaaca agttttacgt ataagttgac   2880
tgctgcaaga agaaatctgg ctcttttcca gcaccatgat ggggtaactg gaactgctaa   2940
ggattatgtg gtacaagatt acggcacccg gatgcatact tcattgcaag accttcagat   3000
ctttatgtct aaagcaatcg aagttcttct tgggatccgc cacgagaaag aaaaatctga   3060
tcaatcccca tcatttttcg aggcagagca aatgagatca aagtatgatg ctcggccagt   3120
tcacaagcca attgctgccc gggaaggaaa ttcgcacaca gttatactct tcaatccatc   3180
agaacagacg agagaggagg tggtgacggt tgttgttaac cgcgctgaaa tctcggtttt   3240
ggactcaaac tggacttgtg tccctagcca aatttctcct gaagtgcagc atgacgatac   3300
caaactattc accggcagac atcgccttta ctggaaagct tccatcccag ctcttggtct   3360
gagaacatat ttcattgcta atgggaatgt cgagtgtgag aaagctactc cgtctaaact   3420
caaatacgct tctgagtttg acccatttcc ttgtcctcct ccatattcct gctccaaact   3480
ggacaacgac gttactgaga tccgaaatga acatcagact cttgtgtttg atgtgaagaa   3540
cggatcactg cggaagatag tccatagaaa cggatcagag actgttgtgg gagaagagat   3600
aggtatgtac tctagtccag agagtggagc ttacctgttc aaaccagatg gtgaagctca   3660
gccaattgtt caacctgatg gacatgtagt cacctctgag ggtctgctgg ttcaagaagt   3720
cttctcttac cctaaaacca aatgggagaa atcacccctc tctcagaaaa ctcgtcttta   3780
cactggaggt aatacgcttc aggatcaagt ggtcgagata gaatatcatg ttgagcttct   3840
tggtaatgat tttgatgacc gggaattgat tgtccggtac aagactgatg ttgacaacaa   3900
gaaggtcttc tattcagatc tcaatggttt ccaaatgagc aggagagaaa cttatgataa   3960
gatccctctt caaggaaact actacccaat gccatctctc gcatttatcc aaggatccaa   4020
tggtcagaga ttctccgtgc actctcgtca atctctcggt gttgcaagcc tcaaagaggg   4080
ttggttggag attatgctgg acagacggtt ggttcgtgat gacggacggg gtctagggca   4140
aggtgtgatg gataaccgcg caatgaccgt ggtatttcac cttcttgcgg aatctaacat   4200
ttctcaagca gaccctgctt ccaacactaa cccgaggaac ccttcgcttc tctctcacct   4260
cataggtgct cacttaaact accccataaa cacattcatt gccaagaaac cgcaagacat   4320
atctgtgcgt gttccacaat acggttcctt tgctccttta gccaaaccgt taccatgtga   4380
cctccacatt gtaaatttca aggttcctcg tccatccaaa tactctcagc aattggaaga   4440
agacaagcca aggttcgctc ttatcctcaa tagacgagct tgggattcag cttattgcca   4500
taaaggaaga caagtaaact gcacaagcat ggctaatgaa ccagtaaact tttccgacat   4560
gttcaaagat cttgcagctt caaaggtaaa accaacttca ctgaatctct tgcaagaaga   4620
tatggagatt cttgggtacg atgaccaaga gctacctcga gatagttcac agccacggga   4680
aggacgtgtc tcgatctctc ccatggaaat acgagcttat aagcttgaac tgcgacctca   4740
caagtgaacc tgctgaagat ccgctagagt ccgcaaaaat caccagtctc tctctacaaa   4800
tctatctctc tctatttttc tccagaataa tgtgtgagta gttcccagat aagggaatta   4860
gggttcttat agggtttcgc tcatgtgttg agcatataag aaacccttag tatgtatttg   4920
tatttgtaaa atacttctat caataaaatt tctaatccta aaaccaaaat cccgcgcgcg   4980
cctcgaggcg atcgcagatc tcattatacc gttagaagca tagttaaaat ctaaagcttg   5040
tcgttaattc tagtcatttt acattgttgg gttctacatt attaatgaat tttctaatgc   5100
```

```
aaatacagaa tttaaatcaa aattgttgaa ttatgctaaa catgtaacat acgtatatct   5160

ccgccttgtg tgttgtatta acttgaagtt atcataagaa ccacaaatac actagtaaat   5220

ctatgagaag gcaggtggca acacaaacaa gagtatctaa gattttcatt tgtgactata   5280

ggaatataat atctcttatc tgatttaatg aatccacatg ttcacttctc atttgtccac   5340

aagatcacaa ctttatcttc aatattcaca acttgttata tccaccacaa tttcattctt   5400

ttcacttagc cccacaaaat actttgtccc cttatttgcc accttttgta tttaatttat   5460

tcttgtggag ctaagtgttc atattattct tcttctcaaa aaaacaaaaa caaaaaaaaa   5520

gagaagaaaa ccatggcgag gatctcgtgt gacttgagat ttcttctcat cccggcagct   5580

ttcatgttca tctacatcca gatgaggctt ttccagacgc aatcacagta tgcagatcgc   5640

ctcagttccg ctatcgaatc tgagaaccat tgcactagtc aaatgcgagg cctcatagat   5700

gaagttagca tcaaacagtc gcggattgtt gccctcgaag atatgaagaa ccgccaggac   5760

gaagaacttg tgcagcttaa ggatctaatc cagacgtttg aaaaaaaagg aatagcaaaa   5820

ctcactcaag gtggagccat ggctctaagg ttgcatagaa ggaaccattt ttcgcctaga   5880

aatacggatc tgttcccgga tttggcaaaa gatcgtgtgg ttatcgtctt gtatgtgcat   5940

aatcgggctc agtattttcg agtcacagtg gaaagtttgt cgaaggttaa aggtataagt   6000

gagacattgt tgattgttag tcatgatggt tactttgaag agatgaatag gattgtggag   6060

agtattaagt tttgtcaagt gaaacagatt ttctcgcctt attcgcctca tatatatcgt   6120

actagcttcc cgggtgtgac cctgaatgat tgtaagaaca agggtgatga ggcaaagggg   6180

cattgtgaag gtaatcctga tcagtatggg aatcatcggt ctccgaagat tgtatctttg   6240

aagcatcact ggtggtggat gatgaacact gtatgggatg ggttggaaga gactaaagga   6300

catgaggggc atatcctttt cattgaagaa gatcattttc tgtttcctaa tgcctatcgt   6360

aacatacaga ctcttacgag gctgaaaccc gcaaagtgtc ctgactgttt tgctgctaat   6420

ttagcaccgt ctgatgtgaa gtcaagagga gaagggcttg aaagtttggt tgcagagaga   6480

atgggaaatg ttgggtattc ttttaataga agtgtgtggg agaatattca tcagaaggca   6540

agagagtttt gtttctttga tgattacaac tgggatataa cgatgtgggc aacggttttc   6600

ccgtcgtttg gttccccggt gtacacattg cgagggccta ggactagtgc ggtacacttt   6660

ggaaaatgtg ggttgcatca aggtagagga gatgagggtg attgcatcga taatggggtc   6720

gtaaacatag aagttaagga aacagataaa gttgtgaaca taaaagaagg atggggagtt   6780

cgggtgtata agcatcaagc gggttataaa gccggtttcg aaggttgggg aggttggggc   6840

gatgataggg accgacattt atgtttggat tttgccacta tgtatcgtta cagcagtagc   6900

agtgcatctc catgaaacgg atccgctaga gtccgcaaaa atcaccagtc tctctctaca   6960

aatctatctc tctctatttt tctccagaat aatgtgtgag tagttcccag ataagggaat   7020

tagggttctt atagggtttc gctcatgtgt tgagcatata agaaaccctt agtatgtatt   7080

tgtatttgta aaatacttct atcaataaaa tttctaatcc taaaaccaaa atcccgcgag   7140

agacctctta attaa                                                    7155
```

<210> SEQ ID NO 28
<211> LENGTH: 4993
<212> TYPE: DNA
<213> ORGANISM: Artificial Sequence
<220> FEATURE:
<223> OTHER INFORMATION: cassette encoding the hybrid enzyme TmGnTI-ManII with the RbcS1 promoter

<400> SEQUENCE: 28

```
ggcgcgcctc gaggcgatcg cagatctaat ctaaccaatt acgatacgct ttgggtacac     60
ttgatttttg tttcagtggt tacatatatc ttgttttata tgctatcttt aaggatctgc    120
acaaagatta tttgttgatg ttcttgatgg ggctcagaag atttgatatg atacactcta    180
atctttagga gataccagcc aggattatat tcagtaagac aatcaaattt tacgtgttca    240
aactcgttat cttttcattc aaaggatgag ccagaatctt tatagaatga ttgcaatcga    300
gaatatgttc ggccgatatg cctttgttgg cttcaatatt ctacatatca cacaagaatc    360
gaccgtattg taccctcttt ccataaagga aaacacaata tgcagatgct tttttcccac    420
atgcagtaac atataggtat tcaaaaatgg ctaaaagaag ttggataaca aattgacaac    480
tatttccatt tctgttatat aaatttcaca acacacaaaa gcccgtaatc aagagtctgc    540
ccatgtacga aataacttct attatttggt attgggccta agcccagctc agagtacgtg    600
ggggtaccac atataggaag gtaacaaaat actgcaagat agccccataa cgtaccagcc    660
tctccttacc acgaagagat aagatataag acccaccctg ccacgtgtca catcgtcatg    720
gtggttaatg ataagggatt acatccttct atgtttgtgg acatgatgca tgtaatgtca    780
tgagccacag gatccaatgg ccacaggaac gtaagaatgt agatagattt gattttgtcc    840
gttagatagc aaacaacatt ataaaaggtg tgtatcaata ggaactaatt cactcattgg    900
attcatagaa gtccattcct cctaagtatc tagaaaccat ggcgaggatc tcgtgtgact    960
tgagatttct tctcatcccg gcagctttca tgttcatcta catccagatg aggcttttcc   1020
agacgcaatc acagtatgca gatcgcctca gttccgctat cgaatctgag aaccattgca   1080
ctagtcaaat gcgaggcctc atagatgaag ttagcatcaa acagtcgcgg attgttgccc   1140
tcgaagatat gaagaaccgc caggacgaag aacttgtgca gcttaaggat ctaatccaga   1200
cgtttgaaaa aaaaggaata gcaaaactca ctcaaggtgg agccatggat tccaattcag   1260
gcgccgtcgt tgatatcaca actaaagatc tatacgatag gattgagttt cttgatacag   1320
atggtggtcc atggaaacaa ggttggagag ttacgtataa agacgatgag tgggagaaag   1380
agaagctcaa aatcttcgtt gttcctcatt ctcataacga tcctggttgg aaattgactg   1440
tagaggagta ttatcagaga caatccagac atattcttga caccattgtt gagactttat   1500
ctaaggtatg acgaaagttt ttgcttttgg ttttaatatt ttaattctct cccatggtta   1560
tcccgtgaac aatcttaaat gtcttaaaat tctcatgacg tcattaaact ctataaccaa   1620
acttctttgc tgggttctgt tttttttag tttcgtgatg aaacagagtt ctagaagttc   1680
gttcttttgg aaaatttgaa gtctttggag ctaaagtttg tttttttatt actgggtttt   1740
gagattgaag gatagctaga atcttatttg tgtgggggtt tgttttgaat atgtttaata   1800
ggattcaaga agaaagttta tatgggagga gatgtcatat ctggagagat ggtggagaga   1860
cgcttcacct aataaacaag aagctttgac taaattggtt aaggatgggc agctagagat   1920
tgttggaggt ggctgggtta tgaatgatga ggctaattca cattattttg ccataattga   1980
acagatagca gagggtaata tgtggctgaa tgacacaatt ggggttattc ctaagaattc   2040
ttgggctata gatccctttg gctattcatc aaccatggct tatcttctcc ggcgtatggg   2100
ttttgaaaac atgcttattc aaaggactca ttacgagctc aagaaagacc ttgcccagca   2160
taagaatctt gaatatattt ggcgtcagag ctgggatgct atggaaacca cagatatctt   2220
tgttcatatg atgccgtttt attcatacga tatcccacac acttgtggac cagagcctgc   2280
aatttgctgt cagtttgatt tcgctcggat gcggggattt aagtatgaac tttgtccatg   2340
gggaaagcac ccagtggaga ccacactaga aaatgtgcag gagagggcat taaagcttct   2400
```

```
ggatcaatac aggaaaaaat ccactctata tcgaactaat acacttctta tacctcttgg   2460
agatgatttt aggtacatta gtatcgatga agccgaggct cagttccgta actaccagat   2520
gttgtttgat cacatcaact ctaatcctag tctaaacgca gaagcaaagt ttggtacttt   2580
ggaggattat ttcagaacag tccgagaaga agcagacaga gtgaattatt ctcgtcctgg   2640
tgaggttggc tctggtcagg ttgttggttt cccttctctg tcaggtgact tctttacata   2700
tgcagatagg caacaagact attggagtgg ttattatgtt tcaagacctt tcttcaaagc   2760
tgttgatcgt gtgctcgagc atacccttcg tggagctgag atcatgatgt catttctgct   2820
aggttattgc catcgaattc aatgtgagaa atttccaaca agttttacgt ataagttgac   2880
tgctgcaaga agaaatctgg ctcttttcca gcaccatgat ggggtaactg gaactgctaa   2940
ggattatgtg gtacaagatt acggcacccg gatgcatact tcattgcaag accttcagat   3000
ctttatgtct aaagcaatcg aagttcttct tgggatccgc cacgagaaag aaaaatctga   3060
tcaatcccca tcatttttcg aggcagagca aatgagatca aagtatgatg ctcggccagt   3120
tcacaagcca attgctgccc gggaaggaaa ttcgcacaca gttatactct tcaatccatc   3180
agaacagacg agagaggagg tggtgacggt tgttgttaac cgcgctgaaa tctcggtttt   3240
ggactcaaac tggacttgtg tccctagcca aatttctcct gaagtgcagc atgacgatac   3300
caaactattc accggcagac atcgccttta ctggaaagct tccatcccag ctcttggtct   3360
gagaacatat ttcattgcta atgggaatgt cgagtgtgag aaagctactc cgtctaaact   3420
caaatacgct tctgagtttg acccatttcc ttgtcctcct ccatattcct gctccaaact   3480
ggacaacgac gttactgaga tccgaaatga acatcagact cttgtgtttg atgtgaagaa   3540
cggatcactg cggaagatag tccatagaaa cggatcagag actgttgtgg gagaagagat   3600
aggtatgtac tctagtccag agagtggagc ttacctgttc aaaccagatg gtgaagctca   3660
gccaattgtt caacctgatg gacatgtagt cacctctgag ggtctgctgg ttcaagaagt   3720
cttctcttac cctaaaacca aatgggagaa atcacccctc tctcagaaaa ctcgtcttta   3780
cactggaggt aatacgcttc aggatcaagt ggtcgagata gaatatcatg ttgagcttct   3840
tggtaatgat tttgatgacc gggaattgat tgtccggtac aagactgatg ttgacaacaa   3900
gaaggtcttc tattcagatc tcaatggttt ccaaatgagc aggagagaaa cttatgataa   3960
gatccctctt caaggaaact actacccaat gccatctctc gcatttatcc aaggatccaa   4020
tggtcagaga ttctccgtgc actctcgtca atctctcggt gttgcaagcc tcaaagaggg   4080
ttggttggag attatgctgg acagacggtt ggttcgtgat gacggacggg gtctagggca   4140
aggtgtgatg gataaccgcg caatgaccgt ggtatttcac cttcttgcgg aatctaacat   4200
ttctcaagca gaccctgctt ccaacactaa cccgaggaac ccttcgcttc tctctcacct   4260
cataggtgct cacttaaact accccataaa cacattcatt gccaagaaac cgcaagacat   4320
atctgtgcgt gttccacaat acggttcctt tgctccttta gccaaaccgt taccatgtga   4380
cctccacatt gtaaatttca aggttcctcg tccatccaaa tactctcagc aattggaaga   4440
agacaagcca aggttcgctc ttatcctcaa tagacgagct tgggattcag cttattgcca   4500
taaaggaaga caagtaaact gcacaagcat ggctaatgaa ccagtaaact tttccgacat   4560
gttcaaagat cttgcagctt caaaggtaaa accaacttca ctgaatctct tgcaagaaga   4620
tatggagatt cttgggtacg atgaccaaga gctacctcga gatagttcac agccacggga   4680
aggacgtgtc tcgatctctc ccatggaaat acgagcttat aagcttgaac tgcgacctca   4740
caagtgaacc tgctgaagat ccgctagagt ccgcaaaaat caccagtctc tctctacaaa   4800
```

tctatctctc tctatttttc tccagaataa tgtgtgagta gttcccagat aagggaatta 4860
gggttcttat agggtttcgc tcatgtgttg agcatataag aaacccttag tatgtatttg 4920
tatttgtaaa atacttctat caataaaatt tctaatccta aaaccaaaat cccgcgagag 4980
acctcttaat taa 4993

<210> SEQ ID NO 29
<211> LENGTH: 3825
<212> TYPE: DNA
<213> ORGANISM: Artificial Sequence
<220> FEATURE:
<223> OTHER INFORMATION: hybrid enzyme TmGnTI-ManII

<400> SEQUENCE: 29
ccatggcgag gatctcgtgt gacttgagat ttcttctcat cccggcagct ttcatgttca 60
tctacatcca gatgaggctt ttccagacgc aatcacagta tgcagatcgc ctcagttccg 120
ctatcgaatc tgagaaccat tgcactagtc aaatgcgagg cctcatagat gaagttagca 180
tcaaacagtc gcggattgtt gccctcgaag atatgaagaa ccgccaggac gaagaacttg 240
tgcagcttaa ggatctaatc cagacgtttg aaaaaaaagg aatagcaaaa ctcactcaag 300
gtggagccat ggattccaat tcaggcgccg tcgttgatat cacaactaaa gatctatacg 360
ataggattga gtttcttgat acagatggtg gtccatggaa acaaggttgg agagttacgt 420
ataaagacga tgagtgggag aaagagaagc tcaaaatctt cgttgttcct cattctcata 480
acgatcctgg ttggaaattg actgtagagg agtattatca gagacaatcc agacatattc 540
ttgacaccat tgttgagact ttatctaagg tatgacgaaa gtttttgctt ttggttttaa 600
tattttaatt ctctcccatg gttatcccgt gaacaatctt aaatgtctta aaattctcat 660
gacgtcatta aactctataa ccaaacttct ttgctgggtt ctgttttttt ttagtttcgt 720
gatgaaacag agttctagaa gttcgttctt ttggaaaatt tgaagtcttt ggagctaaag 780
tttgtttttt tattactggg ttttgagatt gaaggatagc tagaatctta tttgtgtggg 840
ggtttgtttt gaatatgttt aataggattc aagaagaaag tttatatggg aggagatgtc 900
atatctggag agatggtgga gagacgcttc acctaataaa caagaagctt tgactaaatt 960
ggttaaggat gggcagctag agattgttgg aggtggctgg gttatgaatg atgaggctaa 1020
ttcacattat tttgccataa ttgaacagat agcagagggt aatatgtggc tgaatgacac 1080
aattggggtt attcctaaga attcttgggc tatagatccc tttggctatt catcaaccat 1140
ggcttatctt ctccggcgta tgggttttga aaacatgctt attcaaagga ctcattacga 1200
gctcaagaaa gaccttgccc agcataagaa tcttgaatat atttggcgtc agagctggga 1260
tgctatggaa accacagata tctttgttca tatgatgccg ttttattcat acgatatccc 1320
acacacttgt ggaccagagc ctgcaatttg ctgtcagttt gatttcgctc ggatgcgggg 1380
atttaagtat gaactttgtc catggggaaa gcacccagtg gagaccacac tagaaaatgt 1440
gcaggagagg gcattaaagc ttctggatca atacaggaaa aaatccactc tatatcgaac 1500
taatacactt cttatacctc ttggagatga ttttaggtac attagtatcg atgaagccga 1560
ggctcagttc cgtaactacc agatgttgtt tgatcacatc aactctaatc ctagtctaaa 1620
cgcagaagca aagtttggta ctttggagga ttatttcaga acagtccgag aagaagcaga 1680
cagagtgaat tattctcgtc ctggtgaggt tggctctggt caggttgttg gtttcccttc 1740
tctgtcaggt gacttcttta catatgcaga taggcaacaa gactattgga gtggttatta 1800
tgtttcaaga cctttcttca aagctgttga tcgtgtgctc gagcataccc ttcgtggagc 1860

```
tgagatcatg atgtcatttc tgctaggtta ttgccatcga attcaatgtg agaaatttcc   1920

aacaagtttt acgtataagt tgactgctgc aagaagaaat ctggctcttt tccagcacca   1980

tgatggggta actggaactg ctaaggatta tgtggtacaa gattacggca cccggatgca   2040

tacttcattg caagaccttc agatctttat gtctaaagca atcgaagttc ttcttgggat   2100

ccgccacgag aaagaaaaat ctgatcaatc cccatcattt ttcgaggcag agcaaatgag   2160

atcaaagtat gatgctcggc cagttcacaa gccaattgct gcccgggaag gaaattcgca   2220

cacagttata ctcttcaatc catcagaaca gacgagagag gaggtggtga cggttgttgt   2280

taaccgcgct gaaatctcgg ttttggactc aaactggact tgtgtcccta gccaaatttc   2340

tcctgaagtg cagcatgacg ataccaaact attcaccggc agacatcgcc tttactggaa   2400

agcttccatc ccagctcttg gtctgagaac atatttcatt gctaatggga atgtcgagtg   2460

tgagaaagct actccgtcta aactcaaata cgcttctgag tttgacccat ttccttgtcc   2520

tcctccatat tcctgctcca aactggacaa cgacgttact gagatccgaa atgaacatca   2580

gactcttgtg tttgatgtga agaacggatc actgcggaag atagtccata gaaacggatc   2640

agagactgtt gtgggagaag agataggtat gtactctagt ccagagagtg gagcttacct   2700

gttcaaacca gatggtgaag ctcagccaat tgttcaacct gatggacatg tagtcacctc   2760

tgagggtctg ctggttcaag aagtcttctc ttaccctaaa accaaatggg agaaatcacc   2820

cctctctcag aaaactcgtc tttacactgg aggtaatacg cttcaggatc aagtggtcga   2880

gatagaatat catgttgagc ttcttggtaa tgattttgat gaccgggaat tgattgtccg   2940

gtacaagact gatgttgaca acaagaaggt cttctattca gatctcaatg gtttccaaat   3000

gagcaggaga gaaacttatg ataagatccc tcttcaagga aactactacc caatgccatc   3060

tctcgcattt atccaaggat ccaatggtca gagattctcc gtgcactctc gtcaatctct   3120

cggtgttgca agcctcaaag agggttggtt ggagattatg ctggacagac ggttggttcg   3180

tgatgacgga cggggtctag ggcaaggtgt gatggataac cgcgcaatga ccgtggtatt   3240

tcaccttctt gcggaatcta acatttctca agcagaccct gcttccaaca ctaacccgag   3300

gaacccttcg cttctctctc acctcatagg tgctcactta aactacccca taaacacatt   3360

cattgccaag aaaccgcaag acatatctgt gcgtgttcca caatacggtt cctttgctcc   3420

tttagccaaa ccgttaccat gtgacctcca cattgtaaat ttcaaggttc ctcgtccatc   3480

caaatactct cagcaattgg aagaagacaa gccaaggttc gctcttatcc tcaatagacg   3540

agcttgggat tcagcttatt gccataaagg aagacaagta aactgcacaa gcatggctaa   3600

tgaaccagta aacttttccg acatgttcaa agatcttgca gcttcaaagg taaaaccaac   3660

ttcactgaat ctcttgcaag aagatatgga gattcttggg tacgatgacc aagagctacc   3720

tcgagatagt tcacagccac gggaaggacg tgtctcgatc tctcccatgg aaatacgagc   3780

ttataagctt gaactgcgac ctcacaagtg aacctgctga agatc                  3825
```

<210> SEQ ID NO 30
<211> LENGTH: 2181
<212> TYPE: DNA
<213> ORGANISM: Artificial Sequence
<220> FEATURE:
<223> OTHER INFORMATION: hybrid enzyme TmGnTI-GntII

<400> SEQUENCE: 30

```
ggcgcgcctc gaggcgatcg cagatctcat tataccgtta gaagcatagt taaaatctaa     60

agcttgtcgt taattctagt cattttacat tgttgggttc tacattatta atgaattttc    120
```

```
taatgcaaat acagaattta aatcaaaatt gttgaattat gctaaacatg taacatacgt    180
atatctccgc cttgtgtgtt gtattaactt gaagttatca taagaaccac aaatacacta    240
gtaaatctat gagaaggcag gtggcaacac aaacaagagt atctaagatt ttcatttgtg    300
actataggaa tataatatct cttatctgat ttaatgaatc cacatgttca cttctcattt    360
gtccacaaga tcacaacttt atcttcaata ttcacaactt gttatatcca ccacaatttc    420
attcttttca cttagcccca caaaatactt tgtcccctta tttgccacct tttgtattta    480
atttattctt gtggagctaa gtgttcatat tattcttctt ctcaaaaaaa caaaaacaaa    540
aaaaaagaga agaaaaccat ggcgaggatc tcgtgtgact tgagatttct tctcatcccg    600
gcagctttca tgttcatcta catccagatg aggcttttcc agacgcaatc acagtatgca    660
gatcgcctca gttccgctat cgaatctgag aaccattgca ctagtcaaat gcgaggcctc    720
atagatgaag ttagcatcaa acagtcgcgg attgttgccc tcgaagatat gaagaaccgc    780
caggacgaag aacttgtgca gcttaaggat ctaatccaga cgtttgaaaa aaaaggaata    840
gcaaaactca ctcaaggtgg agccatggct ctaaggttgc atagaaggaa ccatttttcg    900
cctagaaata cggatctgtt cccggatttg gcaaaagatc gtgtggttat cgtcttgtat    960
gtgcataatc gggctcagta ttttcgagtc acagtggaaa gtttgtcgaa ggttaaaggt   1020
ataagtgaga cattgttgat tgttagtcat gatggttact ttgaagagat gaataggatt   1080
gtggagagta ttaagttttg tcaagtgaaa cagattttct cgccttattc gcctcatata   1140
tatcgtacta gcttcccggg tgtgaccctg aatgattgta agaacaaggg tgatgaggca   1200
aaggggcatt gtgaaggtaa tcctgatcag tatgggaatc atcggtctcc gaagattgta   1260
tctttgaagc atcactggtg gtggatgatg aacactgtat gggatgggtt ggaagagact   1320
aaaggacatg aggggcatat ccttttcatt gaagaagatc attttctgtt tcctaatgcc   1380
tatcgtaaca tacagactct tacgaggctg aaacccgcaa agtgtcctga ctgttttgct   1440
gctaatttag caccgtctga tgtgaagtca agaggagaag ggcttgaaag tttggttgca   1500
gagagaatgg gaaatgttgg gtattctttt aatagaagtg tgtgggagaa tattcatcag   1560
aaggcaagag agttttgttt ctttgatgat tacaactggg atataacgat gtgggcaacg   1620
gttttcccgt cgtttggttc cccggtgtac acattgcgag ggcctaggac tagtgcggta   1680
cactttggaa aatgtgggtt gcatcaaggt agaggagatg agggtgattg catcgataat   1740
ggggtcgtaa acatagaagt taaggaaaca gataaagttg tgaacataaa agaaggatgg   1800
ggagttcggg tgtataagca tcaagcgggt tataaagccg gtttcgaagg ttggggaggt   1860
tggggcgatg atagggaccg acatttatgt ttggattttg ccactatgta tcgttacagc   1920
agtagcagtg catctccatg aaacggatcc gctagagtcc gcaaaaatca ccagtctctc   1980
tctacaaatc tatctctctc tatttttctc cagaataatg tgtgagtagt tcccagataa   2040
gggaattagg gttcttatag ggtttcgctc atgtgttgag catataagaa acccttagta   2100
tgtatttgta tttgtaaaat acttctatca ataaaatttc taatcctaaa accaaaatcc   2160
cgcgagagac ctcttaatta a                                             2181
```

<210> SEQ ID NO 31
<211> LENGTH: 1394
<212> TYPE: DNA
<213> ORGANISM: Artificial Sequence
<220> FEATURE:
<223> OTHER INFORMATION: hybrid enzyme TmGnTI-GnTII

<400> SEQUENCE: 31

```
ccatggcgag gatctcgtgt gacttgagat ttcttctcat cccggcagct ttcatgttca     60

tctacatcca gatgaggctt ttccagacgc aatcacagta tgcagatcgc ctcagttccg    120

ctatcgaatc tgagaaccat tgcactagtc aaatgcgagg cctcatagat gaagttagca    180

tcaaacagtc gcggattgtt gccctcgaag atatgaagaa ccgccaggac gaagaacttg    240

tgcagcttaa ggatctaatc cagacgtttg aaaaaaaagg aatagcaaaa ctcactcaag    300

gtggagccat ggctctaagg ttgcatagaa ggaaccattt ttcgcctaga aatacggatc    360

tgttcccgga tttggcaaaa gatcgtgtgg ttatcgtctt gtatgtgcat aatcgggctc    420

agtattttcg agtcacagtg gaaagtttgt cgaaggttaa aggtataagt gagacattgt    480

tgattgttag tcatgatggt tactttgaag agatgaatag gattgtggag agtattaagt    540

tttgtcaagt gaaacagatt ttctcgcctt attcgcctca tatatatcgt actagcttcc    600

cgggtgtgac cctgaatgat tgtaagaaca agggtgatga ggcaaagggg cattgtgaag    660

gtaatcctga tcagtatggg aatcatcggt ctccgaagat tgtatctttg aagcatcact    720

ggtggtggat gatgaacact gtatgggatg ggttggaaga gactaaagga catgaggggc    780

atatcctttt cattgaagaa gatcattttc tgtttcctaa tgcctatcgt aacatacaga    840

ctcttacgag gctgaaaccc gcaaagtgtc ctgactgttt tgctgctaat ttagcaccgt    900

ctgatgtgaa gtcaagagga gaagggcttg aaagtttggt tgcagagaga atgggaaatg    960

ttgggtattc ttttaataga agtgtgtggg agaatattca tcagaaggca agagagtttt   1020

gtttctttga tgattacaac tgggatataa cgatgtgggc aacggttttc ccgtcgtttg   1080

gttccccggt gtacacattg cgagggccta ggactagtgc ggtacacttt ggaaaatgtg   1140

ggttgcatca aggtagagga gatgagggtg attgcatcga taatggggtc gtaaacatag   1200

aagttaagga aacagataaa gttgtgaaca taaaagaagg atggggagtt cgggtgtata   1260

agcatcaagc gggttataaa gccggtttcg aaggttgggg aggttggggc gatgataggg   1320

accgacattt atgtttggat tttgccacta tgtatcgtta cagcagtagc agtgcatctc   1380

catgaaacgg atcc                                                      1394
```

<210> SEQ ID NO 32
<211> LENGTH: 312
<212> TYPE: DNA
<213> ORGANISM: Arabidopsis thaliana

<400> SEQUENCE: 32

```
ccatggcgag gatctcgtgt gacttgagat ttcttctcat cccggcagct ttcatgttca     60

tctacatcca gatgaggctt ttccagacgc aatcacagta tgcagatcgc ctcagttccg    120

ctatcgaatc tgagaaccat tgcactagtc aaatgcgagg cctcatagat gaagttagca    180

tcaaacagtc gcggattgtt gccctcgaag atatgaagaa ccgccaggac gaagaacttg    240

tgcagcttaa ggatctaatc cagacgtttg aaaaaaaagg aatagcaaaa ctcactcaag    300

gtggagccat gg                                                         312
```

<210> SEQ ID NO 33
<211> LENGTH: 276
<212> TYPE: DNA
<213> ORGANISM: Arabidopsis thaliana

<400> SEQUENCE: 33

```
ccatggcgag agggagcaga tcagtgggta gcagcagcag caaatggagg tactgcaacc     60

cttcctatta cttgaagcgc ccaaagcgtc ttgctctgct cttcatcgtt ttcgtttgtg    120
```

```
tctctttcgt tttctgggac cgtcaaactc tcgtcagaga gcaccaggtt gaaatttctg    180

agctgcagaa agaagtgact gatttgaaaa atttggtgga tgatttaaat aacaaacaag    240

gtggtacctc tgggaaaact gacttgggga ccatgg                              276
```

<210> SEQ ID NO 34
<211> LENGTH: 9240
<212> TYPE: DNA
<213> ORGANISM: Artificial Sequence
<220> FEATURE:
<223> OTHER INFORMATION: triple cassette for hybrid enzymes

<400> SEQUENCE: 34

```
ggcgcgcctc gaggcgatcg cagatccgat ataacaaaat ttgaatcgca cagatcgatc     60

tctttggaga ttctatacct agaaaatgga gacgattttc aaatctctgt aaaaattctg    120

gtttcttctt gacggaagaa gacgacgact ccaatatttc ggttagtact gaaccggaaa    180

gtttgactgg tgcaaccaat ttaatgtacc gtacgtaacg caccaatcgg attttgtatt    240

caatgggcct tatctgtgag cccattaatt gatgtgacgg cctaaactaa atccgaacgg    300

tttatttcag cgatccgcga cggtttgtat tcagccaata gcaatcaatt atgtagcagt    360

ggtgatcctc gtcaaaccag taaagctaga tctggaccgt tgaattggtg caagaaagca    420

catgttgtga tatttttacc cgtacgatta gaaaacttga gaaacacatt gataatcgat    480

aaaaaccgtc cgatcatata aatccgcttt accatcgttg cctataaatt aatatcaata    540

gccgtacacg cgtgaagact gacaatatta tctttttcga attcggagct caagtttgaa    600

attcggagaa gctagagagt ttctgataa ccatggcgag agggagcaga tcagtgggta    660

gcagcagcag caaatggagg tactgcaacc cttcctatta cttgaagcgc ccaaagcgtc    720

ttgctctgct cttcatcgtt ttcgtttgtg tctctttcgt tttctgggac cgtcaaactc    780

tcgtcagaga gcaccaggtt gaaatttctg agctgcagaa agaagtgact gatttgaaaa    840

atttggtgga tgatttaaat aacaaacaag gtggtacctc tgggaaaact gacttgggga    900

ccatgggaca gatgcctgtg gctgctgtag tggttatggc ctgcagtcgt gcagactatc    960

ttgaaaggac tgttaaatca gttttaacat atcaaactcc cgttgcttca aaatatcctc   1020

tatttatatc tcaggatgga tctgatcaag ctgtcaagag caagtcattg agctataatc   1080

aattaacata tatgcagcac ttggattttg aaccagtggt cactgaaagg cctggcgaac   1140

tgactgcgta ctacaagatt gcacgtcact acaagtgggc actggaccag ttgttttaca   1200

aacacaaatt tagtcgagtg attatactag aagatgatat ggaaattgct ccagacttct   1260

ttgattactt tgaggctgca gctagtctca tggataggga taaaaccatt atggctgctt   1320

catcatggaa tgataatgga cagaagcagt ttgtgcatga tccctatgcg ctataccgat   1380

cagatttttt tcctggcctt gggtggatgc tcaagagatc gacttgggat gagttatcac   1440

caaagtggcc aaaggcttac tggggatgatt ggctgagact aaaggaaaac cataaaggcc   1500

gccaattcat tcgaccggaa gtctgtagaa catacaattt tggtgaacat gggtctagtt   1560

tgggacagtt tttcagtcag tatctggaac ctataaagct aaacgatgtg acggttgact   1620

ggaaagcaaa ggacctggga tacctgacag agggaaacta taccaagtac ttttctggct   1680

tagtgagaca agcacgacca attcaaggtt ctgaccttgt cttaaaggct caaaacataa   1740

aggatgatgt tcgtatccgg tataaagacc aagtagagtt tgaacgcatt gcaggggaat   1800

ttggtatatt tgaagaatgg aaggatggtg tgcctcgaac agcatataaa ggagtagtgg   1860

tgtttcgaat ccagacaaca agacgtgtat tcctggttgg gccagattct gtaatgcagc   1920
```

-continued

```
ttggaattcg aaattcctga tgcggatccg ctagagtccg caaaaatcac cagtctctct   1980
ctacaaatct atctctctct atttttctcc agaataatgt gtgagtagtt cccagataag   2040
ggaattaggg ttcttatagg gtttcgctca tgtgttgagc atataagaaa cccttagtat   2100
gtatttgtat ttgtaaaata cttctatcaa taaaatttct aatcctaaaa ccaaaatccc   2160
gcgcctcgag gcgatcgcag atctaatcta accaattacg atacgctttg ggtacacttg   2220
atttttgttt cagtggttac atatatcttg ttttatatgc tatctttaag gatctgcaca   2280
aagattattt gttgatgttc ttgatggggc tcagaagatt tgatatgata cactctaatc   2340
tttaggagat accagccagg attatattca gtaagacaat caaattttac gtgttcaaac   2400
tcgttatctt ttcattcaaa ggatgagcca gaatctttat agaatgattg caatcgagaa   2460
tatgttcggc cgatatgcct ttgttggctt caatattcta catatcacac aagaatcgac   2520
cgtattgtac cctctttcca taaaggaaaa cacaatatgc agatgctttt ttcccacatg   2580
cagtaacata taggtattca aaaatggcta aaagaagttg gataacaaat tgacaactat   2640
ttccatttct gttatataaa tttcacaaca cacaaaagcc cgtaatcaag agtctgccca   2700
tgtacgaaat aacttctatt atttggtatt gggcctaagc ccagctcaga gtacgtgggg   2760
gtaccacata taggaaggta acaaaatact gcaagatagc cccataacgt accagcctct   2820
ccttaccacg aagagataag atataagacc caccctgcca cgtgtcacat cgtcatggtg   2880
gttaatgata agggattaca tccttctatg tttgtggaca tgatgcatgt aatgtcatga   2940
gccacaggat ccaatggcca caggaacgta agaatgtaga tagatttgat tttgtccgtt   3000
agatagcaaa caacattata aaaggtgtgt atcaatagga actaattcac tcattggatt   3060
catagaagtc cattcctcct aagtatctag aaaccatggc gagagggagc agatcagtgg   3120
gtagcagcag cagcaaatgg aggtactgca acccttccta ttacttgaag cgcccaaagc   3180
gtcttgctct gctcttcatc gttttcgttt gtgtctcttt cgttttctgg gaccgtcaaa   3240
ctctcgtcag agagcaccag gttgaaattt ctgagctgca gaaagaagtg actgatttga   3300
aaaatttggt ggatgattta aataacaaac aaggtggtac ctctgggaaa actgacttgg   3360
ggaccatgga ttccaattca ggcgccgtcg ttgatatcac aactaaagat ctatacgata   3420
ggattgagtt tcttgataca gatggtggtc catggaaaca aggttggaga gttacgtata   3480
aagacgatga gtgggagaaa gagaagctca aaatcttcgt tgttcctcat tctcataacg   3540
atcctggttg gaaattgact gtagaggagt attatcagag acaatccaga catattcttg   3600
acaccattgt tgagacttta tctaaggtat gacgaaagtt tttgcttttg gttttaatat   3660
tttaattctc tcccatggtt atcccgtgaa caatcttaaa tgtcttaaaa ttctcatgac   3720
gtcattaaac tctataacca aacttctttg ctgggttctg ttttttttta gtttcgtgat   3780
gaaacagagt tctagaagtt cgttcttttg gaaaatttga agtctttgga gctaaagttt   3840
gtttttttat tactgggttt tgagattgaa ggatagctag aatcttattt gtgtgggggt   3900
ttgttttgaa tatgtttaat aggattcaag aagaaagttt atatgggagg agatgtcata   3960
tctggagaga tggtggagag acgcttcacc taataaacaa gaagctttga ctaaattggt   4020
taaggatggg cagctagaga ttgttggagg tggctgggtt atgaatgatg aggctaattc   4080
acattatttt gccataattg aacagatagc agagggtaat atgtggctga atgacacaat   4140
tggggttatt cctaagaatt cttgggctat agatcccttt ggctattcat caaccatggc   4200
ttatcttctc cggcgtatgg gttttgaaaa catgcttatt caaaggactc attacgagct   4260
caagaaagac cttgcccagc ataagaatct tgaatatatt tggcgtcaga gctgggatgc   4320
```

-continued

```
tatggaaacc acagatatct ttgttcatat gatgccgttt tattcatacg atatcccaca   4380
cacttgtgga ccagagcctg caatttgctg tcagtttgat ttcgctcgga tgcggggatt   4440
taagtatgaa ctttgtccat ggggaaagca cccagtggag accacactag aaaatgtgca   4500
ggagagggca ttaaagcttc tggatcaata caggaaaaaa tccactctat atcgaactaa   4560
tacacttctt atacctcttg gagatgattt taggtacatt agtatcgatg aagccgaggc   4620
tcagttccgt aactaccaga tgttgtttga tcacatcaac tctaatccta gtctaaacgc   4680
agaagcaaag tttggtactt tggaggatta tttcagaaca gtccgagaag aagcagacag   4740
agtgaattat tctcgtcctg gtgaggttgg ctctggtcag gttgttggtt tcccttctct   4800
gtcaggtgac ttctttacat atgcagatag gcaacaagac tattggagtg gttattatgt   4860
ttcaagacct ttcttcaaag ctgttgatcg tgtgctcgag catacccttc gtggagctga   4920
gatcatgatg tcatttctgc taggttattg ccatcgaatt caatgtgaga aatttccaac   4980
aagttttacg tataagttga ctgctgcaag aagaaatctg gctcttttcc agcaccatga   5040
tggggtaact ggaactgcta aggattatgt ggtacaagat tacggcaccc ggatgcatac   5100
ttcattgcaa gaccttcaga tctttatgtc taaagcaatc gaagttcttc ttgggatccg   5160
ccacgagaaa gaaaaatctg atcaatcccc atcatttttc gaggcagagc aaatgagatc   5220
aaagtatgat gctcggccag ttcacaagcc aattgctgcc cgggaaggaa attcgcacac   5280
agttatactc ttcaatccat cagaacagac gagagaggag gtggtgacgg ttgttgttaa   5340
ccgcgctgaa atctcggttt tggactcaaa ctggacttgt gtccctagcc aaatttctcc   5400
tgaagtgcag catgacgata ccaaactatt caccggcaga catcgccttt actggaaagc   5460
ttccatccca gctcttggtc tgagaacata tttcattgct aatgggaatg tcgagtgtga   5520
gaaagctact ccgtctaaac tcaaatacgc ttctgagttt gacccatttc cttgtcctcc   5580
tccatattcc tgctccaaac tggacaacga cgttactgag atccgaaatg aacatcagac   5640
tcttgtgttt gatgtgaaga acggatcact gcggaagata gtccatagaa acggatcaga   5700
gactgttgtg ggagaagaga taggtatgta ctctagtcca gagagtggag cttacctgtt   5760
caaaccagat ggtgaagctc agccaattgt tcaacctgat ggacatgtag tcacctctga   5820
gggtctgctg gttcaagaag tcttctctta ccctaaaacc aaatgggaga aatcacccct   5880
ctctcagaaa actcgtcttt acactggagg taatacgctt caggatcaag tggtcgagat   5940
agaatatcat gttgagcttc ttggtaatga ttttgatgac cgggaattga ttgtccggta   6000
caagactgat gttgacaaca agaaggtctt ctattcagat ctcaatggtt tccaaatgag   6060
caggagagaa acttatgata agatccctct tcaaggaaac tactacccaa tgccatctct   6120
cgcatttatc caaggatcca atggtcagag attctccgtg cactctcgtc aatctctcgg   6180
tgttgcaagc ctcaaagagg gttggttgga gattatgctg gacagacggt tggttcgtga   6240
tgacggacgg ggtctagggc aaggtgtgat ggataaccgc gcaatgaccg tggtatttca   6300
ccttcttgcg gaatctaaca tttctcaagc agaccctgct tccaacacta acccgaggaa   6360
cccttcgctt ctctctcacc tcataggtgc tcacttaaac taccccataa acacattcat   6420
tgccaagaaa ccgcaagaca tatctgtgcg tgttccacaa tacggttcct ttgctccttt   6480
agccaaaccg ttaccatgtg acctccacat tgtaaatttc aaggttcctc gtccatccaa   6540
atactctcag caattggaag aagacaagcc aaggttcgct cttatcctca atagacgagc   6600
ttgggattca gcttattgcc ataaaggaag acaagtaaac tgcacaagca tggctaatga   6660
accagtaaac ttttccgaca tgttcaaaga tcttgcagct tcaaaggtaa aaccaacttc   6720
```

```
actgaatctc ttgcaagaag atatggagat tcttgggtac gatgaccaag agctacctcg   6780
agatagttca cagccacggg aaggacgtgt ctcgatctct cccatggaaa tacgagctta   6840
taagcttgaa ctgcgacctc acaagtgaac ctgctgaaga tccgctagag tccgcaaaaa   6900
tcaccagtct ctctctacaa atctatctct ctctattttt ctccagaata atgtgtgagt   6960
agttcccaga taagggaatt agggttctta tagggtttcg ctcatgtgtt gagcatataa   7020
gaaaccctta gtatgtattt gtatttgtaa aatacttcta tcaataaaat ttctaatcct   7080
aaaaccaaaa tcccgcgcgc gcctcgaggc gatcgcagat ctcattatac cgttagaagc   7140
atagttaaaa tctaaagctt gtcgttaatt ctagtcattt tacattgttg ggttctacat   7200
tattaatgaa ttttctaatg caaatacaga atttaaatca aaattgttga attatgctaa   7260
acatgtaaca tacgtatatc tccgccttgt gtgttgtatt aacttgaagt tatcataaga   7320
accacaaata cactagtaaa tctatgagaa ggcaggtggc aacacaaaca agagtatcta   7380
agattttcat ttgtgactat aggaatataa tatctcttat ctgatttaat gaatccacat   7440
gttcacttct catttgtcca caagatcaca actttatctt caatattcac aacttgttat   7500
atccaccaca atttcattct tttcacttag ccccacaaaa tactttgtcc ccttatttgc   7560
caccttttgt atttaattta ttcttgtgga gctaagtgtt catattattc ttcttctcaa   7620
aaaaacaaaa acaaaaaaaa agagaagaaa accatggcga gagggagcag atcagtgggt   7680
agcagcagca gcaaatggag gtactgcaac ccttcctatt acttgaagcg cccaaagcgt   7740
cttgctctgc tcttcatcgt tttcgtttgt gtctctttcg ttttctggga ccgtcaaact   7800
ctcgtcagag agcaccaggt tgaaatttct gagctgcaga aagaagtgac tgatttgaaa   7860
aatttggtgg atgatttaaa taacaaacaa ggtggtacct ctgggaaaac tgacttgggg   7920
accatggctc taaggttgca tagaaggaac catttttcgc ctagaaatac ggatctgttc   7980
ccggatttgg caaaagatcg tgtggttatc gtcttgtatg tgcataatcg ggctcagtat   8040
tttcgagtca cagtggaaag tttgtcgaag gttaaaggta taagtgagac attgttgatt   8100
gttagtcatg atggttactt tgaagagatg aataggattg tggagagtat taagttttgt   8160
caagtgaaac agattttctc gccttattcg cctcatatat atcgtactag cttcccgggt   8220
gtgaccctga atgattgtaa gaacaagggt gatgaggcaa aggggcattg tgaaggtaat   8280
cctgatcagt atgggaatca tcggtctccg aagattgtat ctttgaagca tcactggtgg   8340
tggatgatga acactgtatg ggatgggttg gaagagacta aaggacatga ggggcatatc   8400
cttttcattg aagaagatca ttttctgttt cctaatgcct atcgtaacat acagactctt   8460
acgaggctga aacccgcaaa gtgtcctgac tgttttgctg ctaatttagc accgtctgat   8520
gtgaagtcaa gaggagaagg gcttgaaagt ttggttgcag agagaatggg aaatgttggg   8580
tattctttta atagaagtgt gtgggagaat attcatcaga aggcaagaga gttttgtttc   8640
tttgatgatt acaactggga tataacgatg tgggcaacgg ttttcccgtc gtttggttcc   8700
ccggtgtaca cattgcgagg gcctaggact agtgcggtac actttggaaa atgtgggttg   8760
catcaaggta gaggagatga gggtgattgc atcgataatg ggtcgtaaa catagaagtt    8820
aaggaaacag ataaagttgt gaacataaaa gaaggatggg gagttcgggt gtataagcat   8880
caagcgggtt ataaagccgg tttcgaaggt tggggaggtt ggggcgatga tagggaccga   8940
catttatgtt tggattttgc cactatgtat cgttacagca gtagcagtgc atctccatga   9000
aacggatccg ctagagtccg caaaaatcac cagtctctct ctacaaatct atctctctct   9060
atttttctcc agaataatgt gtgagtagtt cccagataag ggaattaggg ttcttatagg   9120
```

gtttcgctca tgtgttgagc atataagaaa cccttagtat gtatttgtat ttgtaaaata 9180
cttctatcaa taaaatttct aatcctaaaa ccaaaatccc gcgagagacc tcttaattaa 9240

<210> SEQ ID NO 35
<211> LENGTH: 2180
<212> TYPE: DNA
<213> ORGANISM: Artificial Sequence
<220> FEATURE:
<223> OTHER INFORMATION: expression cassette for for hybrid enzyme TmManI-GnTI

<400> SEQUENCE: 35
ggcgcgcctc gaggcgatcg cagatccgat ataacaaaat ttgaatcgca cagatcgatc 60
tctttggaga ttctatacct agaaaatgga gacgattttc aaatctctgt aaaaattctg 120
gtttcttctt gacggaagaa gacgacgact ccaatatttc ggttagtact gaaccggaaa 180
gtttgactgg tgcaaccaat ttaatgtacc gtacgtaacg caccaatcgg attttgtatt 240
caatgggcct tatctgtgag cccattaatt gatgtgacgg cctaaactaa atccgaacgg 300
tttatttcag cgatccgcga cggtttgtat tcagccaata gcaatcaatt atgtagcagt 360
ggtgatcctc gtcaaaccag taaagctaga tctggaccgt tgaattggtg caagaaagca 420
catgttgtga tatttttacc cgtacgatta gaaaacttga gaaacacatt gataatcgat 480
aaaaaccgtc cgatcatata aatccgcttt accatcgttg cctataaatt aatatcaata 540
gccgtacacg cgtgaagact gacaatatta tctttttcga attcggagct caagtttgaa 600
attcggagaa gctagagagt ttctgataa ccatggcgag agggagcaga tcagtgggta 660
gcagcagcag caaatggagg tactgcaacc cttcctatta cttgaagcgc ccaaagcgtc 720
ttgctctgct cttcatcgtt ttcgtttgtg tctctttcgt tttctgggac cgtcaaactc 780
tcgtcagaga gcaccaggtt gaaatttctg agctgcagaa agaagtgact gatttgaaaa 840
atttggtgga tgatttaaat aacaaacaag gtggtacctc tgggaaaact gacttgggga 900
ccatgggaca gatgcctgtg gctgctgtag tggttatggc ctgcagtcgt gcagactatc 960
ttgaaaggac tgttaaatca gttttaacat atcaaactcc cgttgcttca aaatatcctc 1020
tatttatatc tcaggatgga tctgatcaag ctgtcaagag caagtcattg agctataatc 1080
aattaacata tatgcagcac ttggattttg aaccagtggt cactgaaagg cctggcgaac 1140
tgactgcgta ctacaagatt gcacgtcact acaagtgggc actggaccag ttgttttaca 1200
aacacaaatt tagtcgagtg attatactag aagatgatat ggaaattgct ccagacttct 1260
ttgattactt tgaggctgca gctagtctca tggataggga taaaaccatt atggctgctt 1320
catcatggaa tgataatgga cagaagcagt ttgtgcatga tccctatgcg ctataccgat 1380
cagatttttt tcctggcctt gggtggatgc tcaagagatc gacttgggat gagttatcac 1440
caaagtggcc aaaggcttac tgggatgatt ggctgagact aaaggaaaac cataaaggcc 1500
gccaattcat tcgaccggaa gtctgtagaa catacaattt tggtgaacat gggtctagtt 1560
tgggacagtt tttcagtcag tatctggaac ctataaagct aaacgatgtg acggttgact 1620
ggaaagcaaa ggacctggga tacctgacag agggaaacta taccaagtac ttttctggct 1680
tagtgagaca agcacgacca attcaaggtt ctgaccttgt cttaaaggct caaaacataa 1740
aggatgatgt tcgtatccgg tataaagacc aagtagagtt tgaacgcatt gcaggggaat 1800
ttggtatatt tgaagaatgg aaggatggtg tgcctcgaac agcatataaa ggagtagtgg 1860
tgtttcgaat ccagacaaca agacgtgtat tcctggttgg gccagattct gtaatgcagc 1920

```
ttggaattcg aaattcctga tgcggatccg ctagagtccg caaaaatcac cagtctctct   1980

ctacaaatct atctctctct atttttctcc agaataatgt gtgagtagtt cccagataag   2040

ggaattaggg ttcttatagg gtttcgctca tgtgttgagc atataagaaa cccttagtat   2100

gtatttgtat ttgtaaaata cttctatcaa taaaatttct aatcctaaaa ccaaaatccc   2160

gcgagagacc tcttaattaa                                                2180
```

<210> SEQ ID NO 36
<211> LENGTH: 615
<212> TYPE: DNA
<213> ORGANISM: Arabidopsis thaliana

<400> SEQUENCE: 36

```
ggatccgata taacaaaatt tgaatcgcac agatcgatct ctttggagat tctataccta     60

gaaaatggag acgattttca aatctctgta aaaattctgg tttcttcttg acggaagaag    120

acgacgactc caatatttcg gttagtactg aaccggaaag tttgactggt gcaaccaatt    180

taatgtaccg tacgtaacgc accaatcgga ttttgtattc aatgggcctt atctgtgagc    240

ccattaattg atgtgacggc ctaaactaaa tccgaacggt ttatttcagc gatccgcgac    300

ggtttgtatt cagccaatag caatcaatta tgtagcagtg gtgatcctcg tcaaaccagt    360

aaagctagat ctggaccgtt gaattggtgc aagaaagcac atgttgtgat atttttaccc    420

gtacgattag aaaacttgag aaacacattg ataatcgata aaaaccgtcc gatcatataa    480

atccgcttta ccatcgttgc ctataaatta atatcaatag ccgtacacgc gtgaagactg    540

acaatattat ctttttcgaa ttcggagctc aagtttgaaa ttcggagaag ctagagagtt    600

ttctgataac catgg                                                     615
```

<210> SEQ ID NO 37
<211> LENGTH: 1319
<212> TYPE: DNA
<213> ORGANISM: Artificial Sequence
<220> FEATURE:
<223> OTHER INFORMATION: gene fusion of TmManI-TmGnTI

<400> SEQUENCE: 37

```
ccatggcgag agggagcaga tcagtgggta gcagcagcag caaatggagg tactgcaacc     60

cttcctatta cttgaagcgc ccaaagcgtc ttgctctgct cttcatcgtt ttcgtttgtg    120

tctctttcgt tttctgggac cgtcaaactc tcgtcagaga gcaccaggtt gaaatttctg    180

agctgcagaa agaagtgact gatttgaaaa atttggtgga tgatttaaat aacaaacaag    240

gtggtacctc tgggaaaact gacttgggga ccatgggaca gatgcctgtg gctgctgtag    300

tggttatggc ctgcagtcgt gcagactatc ttgaaaggac tgttaaatca gttttaacat    360

atcaaactcc cgttgcttca aaatatcctc tatttatatc tcaggatgga tctgatcaag    420

ctgtcaagag caagtcattg agctataatc aattaacata tatgcagcac ttggattttg    480

aaccagtggt cactgaaagg cctggcgaac tgactgcgta ctacaagatt gcacgtcact    540

acaagtgggc actggaccag ttgttttaca aacacaaatt tagtcgagtg attatactag    600

aagatgatat ggaaattgct ccagacttct ttgattactt tgaggctgca gctagtctca    660

tggataggga taaaaccatt atggctgctt catcatggaa tgataatgga cagaagcagt    720

ttgtgcatga tccctatgcg ctataccgat cagatttttt tcctggcctt gggtggatgc    780

tcaagagatc gacttgggat gagttatcac caaagtggcc aaaggcttac tgggatgatt    840

ggctgagact aaaggaaaac cataaaggcc gccaattcat tcgaccggaa gtctgtagaa    900
```

```
catacaattt tggtgaacat gggtctagtt tgggacagtt tttcagtcag tatctggaac    960
ctataaagct aaacgatgtg acggttgact ggaaagcaaa ggacctggga tacctgacag   1020
agggaaacta taccaagtac ttttctggct tagtgagaca agcacgacca attcaaggtt   1080
ctgaccttgt cttaaaggct caaaacataa aggatgatgt tcgtatccgg tataaagacc   1140
aagtagagtt tgaacgcatt gcaggggaat ttggtatatt tgaagaatgg aaggatggtg   1200
tgcctcgaac agcatataaa ggagtagtgg tgtttcgaat ccagacaaca agacgtgtat   1260
tcctggttgg gccagattct gtaatgcagc ttggaattcg aaattcctga tgcggatcc    1319
```

<210> SEQ ID NO 38
<211> LENGTH: 4957
<212> TYPE: DNA
<213> ORGANISM: Artificial Sequence
<220> FEATURE:
<223> OTHER INFORMATION: gene fusion TmManI-ManII with the RbcS1 promoter

<400> SEQUENCE: 38

```
ggcgcgcctc gaggcgatcg cagatctaat ctaaccaatt acgatacgct ttgggtacac     60
ttgatttttg tttcagtggt tacatatatc ttgttttata tgctatcttt aaggatctgc    120
acaaagatta tttgttgatg ttcttgatgg ggctcagaag atttgatatg atacactcta    180
atctttagga gataccagcc aggattatat tcagtaagac aatcaaattt tacgtgttca    240
aactcgttat cttttcattc aaaggatgag ccagaatctt tatagaatga ttgcaatcga    300
gaatatgttc ggccgatatg cctttgttgg cttcaatatt ctacatatca cacaagaatc    360
gaccgtattg taccctcttt ccataaagga aaacacaata tgcagatgct tttttcccac    420
atgcagtaac atataggtat tcaaaaatgg ctaaaagaag ttggataaca aattgacaac    480
tatttccatt tctgttatat aaatttcaca acacacaaaa gcccgtaatc aagagtctgc    540
ccatgtacga aataacttct attatttggt attgggccta agcccagctc agagtacgtg    600
ggggtaccac atataggaag gtaacaaaat actgcaagat agccccataa cgtaccagcc    660
tctccttacc acgaagagat aagatataag acccaccctg ccacgtgtca catcgtcatg    720
gtggttaatg ataagggatt acatccttct atgtttgtgg acatgatgca tgtaatgtca    780
tgagccacag gatccaatgg ccacaggaac gtaagaatgt agatagattt gattttgtcc    840
gttagatagc aaacaacatt ataaaaggtg tgtatcaata ggaactaatt cactcattgg    900
attcatagaa gtccattcct cctaagtatc tagaaaccat ggcgagaggg agcagatcag    960
tgggtagcag cagcagcaaa tggaggtact gcaacccttc ctattacttg aagcgcccaa   1020
agcgtcttgc tctgctcttc atcgttttcg tttgtgtctc tttcgttttc tgggaccgtc   1080
aaactctcgt cagagagcac caggttgaaa tttctgagct gcagaaagaa gtgactgatt   1140
tgaaaaattt ggtggatgat ttaaataaca aacaaggtgg tacctctggg aaaactgact   1200
tggggaccat ggattccaat tcaggcgccg tcgttgatat cacaactaaa gatctatacg   1260
ataggattga gtttcttgat acagatggtg gtccatggaa acaaggttgg agagttacgt   1320
ataaagacga tgagtgggag aaagagaagc tcaaaatctt cgttgttcct cattctcata   1380
acgatcctgg ttggaaattg actgtagagg agtattatca gagacaatcc agacatattc   1440
ttgacaccat tgttgagact ttatctaagg tatgacgaaa gtttttgctt ttggttttaa   1500
tattttaatt ctctcccatg gttatcccgt gaacaatctt aaatgtctta aaattctcat   1560
gacgtcatta aactctataa ccaaacttct ttgctgggtt ctgttttttt ttagtttcgt   1620
gatgaaacag agttctagaa gttcgttctt ttggaaaatt tgaagtcttt ggagctaaag   1680
```

```
tttgtttttt tattactggg ttttgagatt gaaggatagc tagaatctta tttgtgtggg   1740

ggtttgtttt gaatatgttt aataggattc aagaagaaag tttatatggg aggagatgtc   1800

atatctggag agatggtgga gagacgcttc acctaataaa caagaagctt tgactaaatt   1860

ggttaaggat gggcagctag agattgttgg aggtggctgg gttatgaatg atgaggctaa   1920

ttcacattat tttgccataa ttgaacagat agcagagggt aatatgtggc tgaatgacac   1980

aattggggtt attcctaaga attcttgggc tatagatccc tttggctatt catcaaccat   2040

ggcttatctt ctccggcgta tgggttttga aaacatgctt attcaaagga ctcattacga   2100

gctcaagaaa gaccttgccc agcataagaa tcttgaatat atttggcgtc agagctggga   2160

tgctatggaa accacagata tctttgttca tatgatgccg ttttattcat acgatatccc   2220

acacacttgt ggaccagagc ctgcaatttg ctgtcagttt gatttcgctc ggatgcgggg   2280

atttaagtat gaactttgtc catggggaaa gcacccagtg gagaccacac tagaaaatgt   2340

gcaggagagg gcattaaagc ttctggatca atacaggaaa aaatccactc tatatcgaac   2400

taatacactt cttatacctc ttggagatga ttttaggtac attagtatcg atgaagccga   2460

ggctcagttc cgtaactacc agatgttgtt tgatcacatc aactctaatc ctagtctaaa   2520

cgcagaagca aagtttggta ctttggagga ttatttcaga acagtccgag aagaagcaga   2580

cagagtgaat tattctcgtc ctggtgaggt tggctctggt caggttgttg gtttcccttc   2640

tctgtcaggt gacttcttta catatgcaga taggcaacaa gactattgga gtggttatta   2700

tgtttcaaga cctttcttca aagctgttga tcgtgtgctc gagcataccc ttcgtggagc   2760

tgagatcatg atgtcatttc tgctaggtta ttgccatcga attcaatgtg agaaatttcc   2820

aacaagtttt acgtataagt tgactgctgc aagaagaaat ctggctcttt tccagcacca   2880

tgatggggta actggaactg ctaaggatta tgtggtacaa gattacggca cccggatgca   2940

tacttcattg caagaccttc agatctttat gtctaaagca atcgaagttc ttcttgggat   3000

ccgccacgag aaagaaaaat ctgatcaatc cccatcattt ttcgaggcag agcaaatgag   3060

atcaaagtat gatgctcggc cagttcacaa gccaattgct gcccgggaag gaaattcgca   3120

cacagttata ctcttcaatc catcagaaca gacgagagag gaggtggtga cggttgttgt   3180

taaccgcgct gaaatctcgg ttttggactc aaactggact tgtgtcccta gccaaatttc   3240

tcctgaagtg cagcatgacg ataccaaact attcaccggc agacatcgcc tttactggaa   3300

agcttccatc ccagctcttg gtctgagaac atatttcatt gctaatggga atgtcgagtg   3360

tgagaaagct actccgtcta aactcaaata cgcttctgag tttgacccat ttccttgtcc   3420

tcctccatat tcctgctcca aactggacaa cgacgttact gagatccgaa atgaacatca   3480

gactcttgtg tttgatgtga agaacggatc actgcggaag atagtccata gaaacggatc   3540

agagactgtt gtgggagaag agataggtat gtactctagt ccagagagtg gagcttacct   3600

gttcaaacca gatggtgaag ctcagccaat tgttcaacct gatggacatg tagtcacctc   3660

tgagggtctg ctggttcaag aagtcttctc ttaccctaaa accaaatggg agaaatcacc   3720

cctctctcag aaaactcgtc tttacactgg aggtaatacg cttcaggatc aagtggtcga   3780

gatagaatat catgttgagc ttcttggtaa tgattttgat gaccgggaat tgattgtccg   3840

gtacaagact gatgttgaca acaagaaggt cttctattca gatctcaatg gtttccaaat   3900

gagcaggaga gaaacttatg ataagatccc tcttcaagga aactactacc caatgccatc   3960

tctcgcattt atccaaggat ccaatggtca gagattctcc gtgcactctc gtcaatctct   4020

cggtgttgca agcctcaaag agggttggtt ggagattatg ctggacagac ggttggttcg   4080
```

```
tgatgacgga cggggtctag ggcaaggtgt gatggataac cgcgcaatga ccgtggtatt   4140

tcaccttctt gcggaatcta acatttctca agcagaccct gcttccaaca ctaacccgag   4200

gaacccttcg cttctctctc acctcatagg tgctcactta aactacccca taaacacatt   4260

cattgccaag aaaccgcaag acatatctgt gcgtgttcca caatacggtt cctttgctcc   4320

tttagccaaa ccgttaccat gtgacctcca cattgtaaat ttcaaggttc ctcgtccatc   4380

caaatactct cagcaattgg aagaagacaa gccaaggttc gctcttatcc tcaatagacg   4440

agcttgggat tcagcttatt gccataaagg aagacaagta aactgcacaa gcatggctaa   4500

tgaaccagta aacttttccg acatgttcaa agatcttgca gcttcaaagg taaaaccaac   4560

ttcactgaat ctcttgcaag aagatatgga gattcttggg tacgatgacc aagagctacc   4620

tcgagatagt tcacagccac gggaaggacg tgtctcgatc tctcccatgg aaatacgagc   4680

ttataagctt gaactgcgac ctcacaagtg aacctgctga agatccgcta gagtccgcaa   4740

aaatcaccag tctctctcta caaatctatc tctctctatt tttctccaga ataatgtgtg   4800

agtagttccc agataaggga attagggttc ttatagggtt tcgctcatgt gttgagcata   4860

taagaaaccc ttagtatgta tttgtatttg taaaatactt ctatcaataa aatttctaat   4920

cctaaaacca aaatcccgcg agagacctct taattaa                            4957
```

<210> SEQ ID NO 39
<211> LENGTH: 921
<212> TYPE: DNA
<213> ORGANISM: Chrysanthemum x morifolium

<400> SEQUENCE: 39

```
agatctaatc taaccaatta cgatacgctt tgggtacact tgatttttgt ttcagtggtt     60

acatatatct tgttttatat gctatcttta aggatctgca caaagattat ttgttgatgt    120

tcttgatggg gctcagaaga tttgatatga tacactctaa tctttaggag ataccagcca    180

ggattatatt cagtaagaca atcaaatttt acgtgttcaa actcgttatc ttttcattca    240

aaggatgagc cagaatcttt atagaatgat tgcaatcgag aatatgttcg gccgatatgc    300

ctttgttggc ttcaatattc tacatatcac acaagaatcg accgtattgt accctctttc    360

cataaaggaa aacacaatat gcagatgctt ttttcccaca tgcagtaaca tataggtatt    420

caaaaatggc taaaagaagt tggataacaa attgacaact atttccattt ctgttatata    480

aatttcacaa cacacaaaag cccgtaatca agagtctgcc catgtacgaa ataacttcta    540

ttatttggta ttgggcctaa gcccagctca gagtacgtgg gggtaccaca tataggaagg    600

taacaaaata ctgcaagata gccccataac gtaccagcct ctccttacca cgaagagata    660

agatataaga cccaccctgc cacgtgtcac atcgtcatgg tggttaatga taagggatta    720

catccttcta tgtttgtgga catgatgcat gtaatgtcat gagccacagg atccaatggc    780

cacaggaacg taagaatgta gatagatttg attttgtccg ttagatagca aacaacatta    840

taaaaggtgt gtatcaatag gaactaattc actcattgga ttcatagaag tccattcctc    900

ctaagtatct agaaaccatg g                                              921
```

<210> SEQ ID NO 40
<211> LENGTH: 3789
<212> TYPE: DNA
<213> ORGANISM: Artificial Sequence
<220> FEATURE:
<223> OTHER INFORMATION: hybrid gene TmManI ManII

<400> SEQUENCE: 40

```
ccatggcgag agggagcaga tcagtgggta gcagcagcag caaatggagg tactgcaacc     60
cttcctatta cttgaagcgc ccaaagcgtc ttgctctgct cttcatcgtt ttcgtttgtg    120
tctctttcgt tttctgggac cgtcaaactc tcgtcagaga gcaccaggtt gaaatttctg    180
agctgcagaa agaagtgact gatttgaaaa atttggtgga tgatttaaat aacaaacaag    240
gtggtacctc tgggaaaact gacttgggga ccatggattc caattcaggc gccgtcgttg    300
atatcacaac taaagatcta tacgatagga ttgagtttct tgatacagat ggtggtccat    360
ggaaacaagg ttggagagtt acgtataaag acgatgagtg ggagaaagag aagctcaaaa    420
tcttcgttgt tcctcattct cataacgatc ctggttggaa attgactgta gaggagtatt    480
atcagagaca atccagacat attcttgaca ccattgttga gactttatct aaggtatgac    540
gaaagttttt gcttttggtt ttaatatttt aattctctcc catggttatc ccgtgaacaa    600
tcttaaatgt cttaaaattc tcatgacgtc attaaactct ataaccaaac ttctttgctg    660
ggttctgttt ttttttagtt tcgtgatgaa acagagttct agaagttcgt tcttttggaa    720
aatttgaagt ctttggagct aaagtttgtt tttttattac tgggttttga gattgaagga    780
tagctagaat cttatttgtg tgggggtttg ttttgaatat gtttaatagg attcaagaag    840
aaagtttata tgggaggaga tgtcatatct ggagagatgg tggagagacg cttcacctaa    900
taaacaagaa gctttgacta aattggttaa ggatgggcag ctagagattg ttggaggtgg    960
ctgggttatg aatgatgagg ctaattcaca ttattttgcc ataattgaac agatagcaga   1020
gggtaatatg tggctgaatg acacaattgg ggttattcct aagaattctt gggctataga   1080
tccctttggc tattcatcaa ccatggctta tcttctccgg cgtatgggtt ttgaaaacat   1140
gcttattcaa aggactcatt acgagctcaa gaaagacctt gcccagcata agaatcttga   1200
atatatttgg cgtcagagct gggatgctat ggaaaccaca gatatctttg ttcatatgat   1260
gccgttttat tcatacgata tcccacacac ttgtggacca gagcctgcaa tttgctgtca   1320
gtttgatttc gctcggatgc ggggatttaa gtatgaactt tgtccatggg gaaagcaccc   1380
agtggagacc acactagaaa atgtgcagga gagggcatta aagcttctgg atcaatacag   1440
gaaaaaatcc actctatatc gaactaatac acttcttata cctcttggag atgattttag   1500
gtacattagt atcgatgaag ccgaggctca gttccgtaac taccagatgt tgtttgatca   1560
catcaactct aatcctagtc taaacgcaga agcaaagttt ggtactttgg aggattattt   1620
cagaacagtc cgagaagaag cagacagagt gaattattct cgtcctggtg aggttggctc   1680
tggtcaggtt gttggtttcc cttctctgtc aggtgacttc tttacatatg cagataggca   1740
acaagactat tggagtggtt attatgtttc aagacctttc ttcaaagctg ttgatcgtgt   1800
gctcgagcat acccttcgtg gagctgagat catgatgtca tttctgctag gttattgcca   1860
tcgaattcaa tgtgagaaat ttccaacaag ttttacgtat aagttgactg ctgcaagaag   1920
aaatctggct cttttccagc accatgatgg ggtaactgga actgctaagg attatgtggt   1980
acaagattac ggcacccgga tgcatacttc attgcaagac cttcagatct ttatgtctaa   2040
agcaatcgaa gttcttcttg ggatccgcca cgagaaagaa aaatctgatc aatccccatc   2100
atttttcgag gcagagcaaa tgagatcaaa gtatgatgct cggccagttc acaagccaat   2160
tgctgcccgg gaaggaaatt cgcacacagt tatactcttc aatccatcag aacagacgag   2220
agaggaggtg gtgacggttg ttgttaaccg cgctgaaatc tcggttttgg actcaaactg   2280
gacttgtgtc cctagccaaa tttctcctga agtgcagcat gacgatacca aactattcac   2340
cggcagacat cgcctttact ggaaagcttc catcccagct cttggtctga gaacatattt   2400
```

```
cattgctaat gggaatgtcg agtgtgagaa agctactccg tctaaactca aatacgcttc   2460
tgagtttgac ccatttcctt gtcctcctcc atattcctgc tccaaactgg acaacgacgt   2520
tactgagatc cgaaatgaac atcagactct tgtgtttgat gtgaagaacg gatcactgcg   2580
gaagatagtc catagaaacg gatcagagac tgttgtggga gaagagatag gtatgtactc   2640
tagtccagag agtggagctt acctgttcaa accagatggt gaagctcagc caattgttca   2700
acctgatgga catgtagtca cctctgaggg tctgctggtt caagaagtct tctcttaccc   2760
taaaaccaaa tgggagaaat cacccctctc tcagaaaact cgtctttaca ctggaggtaa   2820
tacgcttcag gatcaagtgg tcgagataga atatcatgtt gagcttcttg gtaatgattt   2880
tgatgaccgg gaattgattg tccggtacaa gactgatgtt gacaacaaga aggtcttcta   2940
ttcagatctc aatggtttcc aaatgagcag gagagaaact tatgataaga tccctcttca   3000
aggaaactac tacccaatgc catctctcgc atttatccaa ggatccaatg gtcagagatt   3060
ctccgtgcac tctcgtcaat ctctcggtgt tgcaagcctc aaagagggtt ggttggagat   3120
tatgctggac agacggttgg ttcgtgatga cggacggggt ctagggcaag gtgtgatgga   3180
taaccgcgca atgaccgtgg tatttcacct tcttgcggaa tctaacattt ctcaagcaga   3240
ccctgcttcc aacactaacc cgaggaaccc ttcgcttctc tctcacctca taggtgctca   3300
cttaaactac cccataaaca cattcattgc caagaaaccg caagacatat ctgtgcgtgt   3360
tccacaatac ggttcctttg ctcctttagc caaaccgtta ccatgtgacc tccacattgt   3420
aaatttcaag gttcctcgtc catccaaata ctctcagcaa ttggaagaag acaagccaag   3480
gttcgctctt atcctcaata gacgagcttg ggattcagct tattgccata aaggaagaca   3540
agtaaactgc acaagcatgg ctaatgaacc agtaaacttt tccgacatgt tcaaagatct   3600
tgcagcttca aaggtaaaac caacttcact gaatctcttg caagaagata tggagattct   3660
tgggtacgat gaccaagagc tacctcgaga tagttcacag ccacgggaag gacgtgtctc   3720
gatctctccc atggaaatac gagcttataa gcttgaactg cgacctcaca agtgaacctg   3780
ctgaagatc                                                           3789
```

<210> SEQ ID NO 41
<211> LENGTH: 2145
<212> TYPE: DNA
<213> ORGANISM: Artificial Sequence
<220> FEATURE:
<223> OTHER INFORMATION: hybrid gene TmManI GnTII

<400> SEQUENCE: 41

```
ggcgcgcctc gaggcgatcg cagatctcat tataccgtta gaagcatagt taaaatctaa     60
agcttgtcgt taattctagt cattttacat tgttgggttc tacattatta atgaattttc    120
taatgcaaat acagaattta aatcaaaatt gttgaattat gctaaacatg taacatacgt    180
atatctccgc cttgtgtgtt gtattaactt gaagttatca taagaaccac aaatacacta    240
gtaaatctat gagaaggcag gtggcaacac aaacaagagt atctaagatt ttcatttgtg    300
actataggaa tataatatct cttatctgat ttaatgaatc cacatgttca cttctcattt    360
gtccacaaga tcacaacttt atcttcaata ttcacaactt gttatatcca ccacaatttc    420
attcttttca cttagcccca caaaatactt tgtcccctta tttgccacct tttgtattta    480
atttattctt gtggagctaa gtgttcatat tattcttctt ctcaaaaaaa caaaaacaaa    540
aaaaaagaga agaaaaccat ggcgagaggg agcagatcag tgggtagcag cagcagcaaa    600
tggaggtact gcaacccttc ctattacttg aagcgcccaa agcgtcttgc tctgctcttc    660
```

```
atcgttttcg tttgtgtctc tttcgttttc tgggaccgtc aaactctcgt cagagagcac    720

caggttgaaa tttctgagct gcagaaagaa gtgactgatt tgaaaaattt ggtggatgat    780

ttaaataaca aacaaggtgg tacctctggg aaaactgact tggggaccat ggctctaagg    840

ttgcatagaa ggaaccattt ttcgcctaga aatacggatc tgttcccgga tttggcaaaa    900

gatcgtgtgg ttatcgtctt gtatgtgcat aatcgggctc agtattttcg agtcacagtg    960

gaaagtttgt cgaaggttaa aggtataagt gagacattgt tgattgttag tcatgatggt   1020

tactttgaag agatgaatag gattgtggag agtattaagt tttgtcaagt gaaacagatt   1080

ttctcgcctt attcgcctca tatatatcgt actagcttcc cgggtgtgac cctgaatgat   1140

tgtaagaaca agggtgatga ggcaaagggg cattgtgaag gtaatcctga tcagtatggg   1200

aatcatcggt ctccgaagat tgtatctttg aagcatcact ggtggtggat gatgaacact   1260

gtatgggatg ggttggaaga gactaaagga catgaggggc atatcctttt cattgaagaa   1320

gatcattttc tgtttcctaa tgcctatcgt aacatacaga ctcttacgag gctgaaaccc   1380

gcaaagtgtc ctgactgttt tgctgctaat ttagcaccgt ctgatgtgaa gtcaagagga   1440

gaagggcttg aaagtttggt tgcagagaga atgggaaatg ttgggtattc ttttaataga   1500

agtgtgtggg agaatattca tcagaaggca agagagtttt gtttctttga tgattacaac   1560

tgggatataa cgatgtgggc aacggttttc ccgtcgtttg gttccccggt gtacacattg   1620

cgagggccta ggactagtgc ggtacacttt ggaaaatgtg ggttgcatca aggtagagga   1680

gatgagggtg attgcatcga taatggggtc gtaaacatag aagttaagga aacagataaa   1740

gttgtgaaca taaaagaagg atggggagtt cgggtgtata agcatcaagc gggttataaa   1800

gccggtttcg aaggttgggg aggttggggc gatgataggg accgacattt atgtttggat   1860

tttgccacta tgtatcgtta cagcagtagc agtgcatctc catgaaacgg atccgctaga   1920

gtccgcaaaa atcaccagtc tctctctaca aatctatctc tctctatttt tctccagaat   1980

aatgtgtgag tagttcccag ataagggaat tagggttctt atagggtttc gctcatgtgt   2040

tgagcatata agaaaccctt agtatgtatt tgtatttgta aaatacttct atcaataaaa   2100

tttctaatcc taaaaccaaa atcccgcgag agacctctta attaa                    2145
```

<210> SEQ ID NO 42
<211> LENGTH: 541
<212> TYPE: DNA
<213> ORGANISM: Solanum tuberosum

<400> SEQUENCE: 42

```
agatctcatt ataccgttag aagcatagtt aaaatctaaa gcttgtcgtt aattctagtc     60

attttacatt gttgggttct acattattaa tgaattttct aatgcaaata cagaatttaa    120

atcaaaattg ttgaattatg ctaaacatgt aacatacgta tatctccgcc ttgtgtgttg    180

tattaacttg aagttatcat aagaaccaca aatacactag taaatctatg agaaggcagg    240

tggcaacaca aacaagagta tctaagattt tcatttgtga ctataggaat ataatatctc    300

ttatctgatt taatgaatcc acatgttcac ttctcatttg tccacaagat cacaacttta    360

tcttcaatat tcacaacttg ttatatccac cacaatttca ttcttttcac ttagccccac    420

aaaatacttt gtccccttat ttgccacctt ttgtatttaa tttattcttg tggagctaag    480

tgttcatatt attcttcttc tcaaaaaaac aaaaacaaaa aaaaagagaa gaaaaccatg    540

g                                                                    541
```

<210> SEQ ID NO 43
<211> LENGTH: 1358
<212> TYPE: DNA
<213> ORGANISM: Artificial Sequence
<220> FEATURE:
<223> OTHER INFORMATION: hybrid gene TmManI GnTII

<400> SEQUENCE: 43

```
ccatggcgag agggagcaga tcagtgggta gcagcagcag caaatggagg tactgcaacc     60
cttcctatta cttgaagcgc ccaaagcgtc ttgctctgct cttcatcgtt ttcgtttgtg    120
tctctttcgt tttctgggac cgtcaaactc tcgtcagaga gcaccaggtt gaaatttctg    180
agctgcagaa agaagtgact gatttgaaaa atttggtgga tgatttaaat aacaaacaag    240
gtggtacctc tgggaaaact gacttgggga ccatggctct aaggttgcat agaaggaacc    300
atttttcgcc tagaaatacg gatctgttcc cggatttggc aaaagatcgt gtggttatcg    360
tcttgtatgt gcataatcgg gctcagtatt ttcgagtcac agtggaaagt ttgtcgaagg    420
ttaaaggtat aagtgagaca ttgttgattg ttagtcatga tggttacttt gaagagatga    480
ataggattgt ggagagtatt aagttttgtc aagtgaaaca gattttctcg ccttattcgc    540
ctcatatata tcgtactagc ttcccgggtg tgaccctgaa tgattgtaag aacaagggtg    600
atgaggcaaa ggggcattgt gaaggtaatc ctgatcagta tgggaatcat cggtctccga    660
agattgtatc tttgaagcat cactggtggt ggatgatgaa cactgtatgg gatgggttgg    720
aagagactaa aggacatgag ggcatatcc ttttcattga agaagatcat tttctgtttc     780
ctaatgccta tcgtaacata cagactctta cgaggctgaa acccgcaaag tgtcctgact    840
gttttgctgc taatttagca ccgtctgatg tgaagtcaag aggagaaggg cttgaaagtt    900
tggttgcaga gagaatggga aatgttgggt attcttttaa tagaagtgtg tgggagaata    960
ttcatcagaa ggcaagagag ttttgtttct ttgatgatta caactgggat ataacgatgt   1020
gggcaacggt tttcccgtcg tttggttccc cggtgtacac attgcgaggg cctaggacta   1080
gtgcggtaca ctttggaaaa tgtgggttgc atcaaggtag aggagatgag ggtgattgca   1140
tcgataatgg ggtcgtaaac atagaagtta aggaaacaga taaagttgtg aacataaaag   1200
aaggatgggg agttcgggtg tataagcatc aagcgggtta taaagccggt ttcgaaggtt   1260
ggggaggttg gggcgatgat agggaccgac atttatgttt ggattttgcc actatgtatc   1320
gttacagcag tagcagtgca tctccatgaa acggatcc                            1358
```

<210> SEQ ID NO 44
<211> LENGTH: 237
<212> TYPE: DNA
<213> ORGANISM: Artificial Sequence
<220> FEATURE:
<223> OTHER INFORMATION: Synthetic

<400> SEQUENCE: 44

```
ggatccgcta gagtccgcaa aaatcaccag tctctctcta caaatctatc tctctctatt     60
tttctccaga ataatgtgtg agtagttccc agataaggga attagggttc ttatagggtt    120
tcgctcatgt gttgagcata taagaaaccc ttagtatgta tttgtatttg taaaatactt    180
ctatcaataa aatttctaat cctaaaacca aaatcccgcg agagacctct taattaa       237
```

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
atactcgagt taacaatgag taaacggaat c 31

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
ttctcgatcg ccgattggtt attc 24

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
gccgccgcga tcgggcagtc ctcc 24

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
aacggatcca cgctagctcg gtgtcccgat 30

<210> SEQ ID NO 49
<211> LENGTH: 3327
<212> TYPE: DNA
<213> ORGANISM: Artificial Sequence
<220> FEATURE:
<223> OTHER INFORMATION: hybrid gene with the aminoterminal CTS region of an insect Mannosidase III gene replaced by a mouse signal peptide and a carboxyterminal ER retention signal (KDEL)

<400> SEQUENCE: 49
atgggcatca agatggagac acattctcag gtctttgtat acatgttgct gtggttgtct 60
ggtgtcgaca tgaagcactt caaatcttcc ctcactcaca ccgtcaagag ccgagacgag 120
ccaactccgg atcaatgccc tgcattgaag gaaagcgaag cggacatcga caccgtggcg 180
atatacccaa cttttgattt tcagccgagc tggttgcgta caaaggaatt ttgggacaag 240
tccttcgagg atcggtatga aagaattcat aacgacacta cacggcctag actgaaggta 300
atcgtggttc ctcactcaca caacgacccg ggatggctga agacgtttga acagtacttc 360
gagtggaaga ccaagaacat tatcaacaac atagtgaaca aactgcacca gtaccccaac 420
atgaccttca tttggaccga gatatcgttt ctgaatgcct ggtgggaaag gtcgcaccct 480
gtcaaacaaa aggcattgaa aaaacttatc aaagaaggtc gtctcgagat cacgacgggc 540
ggctgggtga tgccggacga agcctgcacg catatctatg cgctaattga ccagtttatt 600
gaaggacatc actgggtgaa aactaatctc ggcgtcatcc cgaagacagg atggtctatt 660
gaccccttcg gccacggggc cactgtgcct tacctgctag accagagcgg ccttgaggga 720
accattatac agagaatcca ttatgcgtgg aaacagtggc tggcggagcg acagattgag 780
gagttttact ggctggcgag ttgggctact acgaagccgt ccatgatagt gcacaatcag 840

```
ccgtttgata tttattcaat aaaaagcacg tgtggcccgc acccttcaat ttgtctcagt    900
ttcgacttca ggaagattcc cggcgaatat tctgaataca cagctaagca cgaagacatc    960
acggaacaca acttgcacag caaggcaaag actttgatag aggagtacga ccgtatcggg   1020
tccctgactc cacacaacgt ggtgctggtg ccgctcggag acgacttcag atacgagtac   1080
agcgtcgagt ttgatgccca atacgtcaat tatatgaaaa tgtttaacta catcaatgct   1140
cacaaggaaa tcttcaacgc tgacgtacag ttcggaactc ctctcgatta ctttaacgcc   1200
atgaaagaaa gacatcaaaa tatacccagc ttaaagggag atttcttcgt ttactccgat   1260
attttcagcg aaggtaaacc agcgtactgg tcaggttact acactactag accctaccaa   1320
aaaatcctcg cccgtcagtt cgaacaccaa ctgcgatcgg cagagatttt attcaccctt   1380
gtatcgaact acatcagaca gatgggtcgc caaggagagt tcggagcttc tgagaaaaag   1440
ttagaaaaat cttacgagca gcttatctat gctcgacgga acttgggtct gtttcaacat   1500
cacgatgcga ttactggaac atcaaagtcc agtgtgatgc aagattacgg aaccaaactg   1560
ttcacaagtc tgtatcactg catccgcctg caggaggccg cgctcaccac catcatgttg   1620
cctgaccagt cgttgcactc gcagagcatt atacaaagcg aggttgagtg ggaaacttac   1680
ggaaaaccgc ccaagaagct gcaagtgtcc ttcattgaca agaagaaagt tatacttttt   1740
aatccgttgg ctgagactcg aactgaagtg gtcacggtta gatccaacac gtccaacatc   1800
cgggtgtacg atacacacaa gaggaagcac gtcttgtatc agataatgcc cagcatcaca   1860
atccaagaca acggcaagag tatcgtaagc gacaccacgt tcgacataat gttcgtggcc   1920
accatcccgc ccctcacctc catctcgtac aagctgcagg agcacaccaa cacttcccac   1980
cactgcgtca ttttctgcaa caactgcgaa caataccaga aatccaatgt gttccaaatt   2040
aagaaaatga tgcctggtga catacaatta gaaaatgcag tgctaaaact tctcgttaat   2100
aggaacaccg gctttctgag acaagtctat agaaaggaca tccggaagag aactgtcgtt   2160
gacgtacaat tcggcgcata tcaaagtgcc caaagacatt ctggtgctta cctcttcatg   2220
cctcattacg actcacctga gaagaatgtt ctgcatccct acactaatca gaacaacatg   2280
caagatgata acataatcat agtgtccgga cctatttcta cggaaatcac gaccatgtac   2340
ttgcccttct tggtgcacac tattaggata tacaacgtgc cggacccggt actgtcgcgt   2400
gctattctat tagagaccga tgtagatttc gaggcgccac ctaagaacag agagactgag   2460
ttatttatga gattacagac tgatatacaa aacggtgaca ttcccgaatt ttacaccgat   2520
cagaacggat tccagtacca aaagagggtc aaagtgaata aactaggaat agaagctaat   2580
tactacccga tcactaccat ggcgtgcctg caagacgagg agacccggct cactctgctg   2640
acgaaccacg ctcaaggcgc tgctgcatac gaaccaggac gcttagaagt catgctcgat   2700
cgtcgaactc tttatgatga cttcagagga atcggtgaag gagtagtcga taacaaaccg   2760
acgactttcc agaactggat tttaattgaa tccatgccag gcgtgacgcg agccaagaga   2820
gacactagtg aaccaggttt caaatttgtt aatgaacgtc gttttggccc cggccagaag   2880
gaaagccctt accaagtacc gtcgcagact gcggactacc tgagcaggat gttcaattac   2940
ccggtgaacg tgtacctggt ggacactagc gaggttggcg agatcgaggt gaagccgtac   3000
cagtcgttcc tgcagagctt cccgcccggc atccacctgg tcaccctgcg caccatcacc   3060
gacgacgtgc tcgaactctt ccccagcaac gaaagctaca tggtactgca ccgaccagga   3120
tacagctgcg ctgtcggaga gaagccagtc gccaagtctc ccaagttttc gtccaaaacc   3180
aggttcaatg gtctgaacat tcagaacatc actgcagtca gcctgaccgg cctgaagtca   3240
```

```
ctccgacctc tcacaggtct gagtgacatc cacctgaacg ctatggaggt aaaaacttac   3300

aagatcaggt ttaaggacga gctttaa                                       3327


<210> SEQ ID NO 50
<211> LENGTH: 1108
<212> TYPE: PRT
<213> ORGANISM: Artificial Sequence
<220> FEATURE:
<223> OTHER INFORMATION: hybrid protein;  aminoterminal CTS region of an
      insect Mannosidase III gene replaced by a mouse signal peptide
      and a carboxyterminal ER retention signal (KDEL)

<400> SEQUENCE: 50

Met Gly Ile Lys Met Glu Thr His Ser Gln Val Phe Val Tyr Met Leu
1               5                   10                  15

Leu Trp Leu Ser Gly Val Asp Met Lys His Phe Lys Ser Ser Leu Thr
            20                  25                  30

His Thr Val Lys Ser Arg Asp Glu Pro Thr Pro Asp Gln Cys Pro Ala
        35                  40                  45

Leu Lys Glu Ser Glu Ala Asp Ile Asp Thr Val Ala Ile Tyr Pro Thr
    50                  55                  60

Phe Asp Phe Gln Pro Ser Trp Leu Arg Thr Lys Glu Phe Trp Asp Lys
65                  70                  75                  80

Ser Phe Glu Asp Arg Tyr Glu Arg Ile His Asn Asp Thr Thr Arg Pro
                85                  90                  95

Arg Leu Lys Val Ile Val Val Pro His Ser His Asn Asp Pro Gly Trp
            100                 105                 110

Leu Lys Thr Phe Glu Gln Tyr Phe Glu Trp Lys Thr Lys Asn Ile Ile
        115                 120                 125

Asn Asn Ile Val Asn Lys Leu His Gln Tyr Pro Asn Met Thr Phe Ile
    130                 135                 140

Trp Thr Glu Ile Ser Phe Leu Asn Ala Trp Trp Glu Arg Ser His Pro
145                 150                 155                 160

Val Lys Gln Lys Ala Leu Lys Lys Leu Ile Lys Glu Gly Arg Leu Glu
                165                 170                 175

Ile Thr Thr Gly Gly Trp Val Met Pro Asp Glu Ala Cys Thr His Ile
            180                 185                 190

Tyr Ala Leu Ile Asp Gln Phe Ile Glu Gly His His Trp Val Lys Thr
        195                 200                 205

Asn Leu Gly Val Ile Pro Lys Thr Gly Trp Ser Ile Asp Pro Phe Gly
    210                 215                 220

His Gly Ala Thr Val Pro Tyr Leu Leu Asp Gln Ser Gly Leu Glu Gly
225                 230                 235                 240

Thr Ile Ile Gln Arg Ile His Tyr Ala Trp Lys Gln Trp Leu Ala Glu
                245                 250                 255

Arg Gln Ile Glu Glu Phe Tyr Trp Leu Ala Ser Trp Ala Thr Thr Lys
            260                 265                 270

Pro Ser Met Ile Val His Asn Gln Pro Phe Asp Ile Tyr Ser Ile Lys
        275                 280                 285

Ser Thr Cys Gly Pro His Pro Ser Ile Cys Leu Ser Phe Asp Phe Arg
    290                 295                 300

Lys Ile Pro Gly Glu Tyr Ser Glu Tyr Thr Ala Lys His Glu Asp Ile
305                 310                 315                 320

Thr Glu His Asn Leu His Ser Lys Ala Lys Thr Leu Ile Glu Glu Tyr
                325                 330                 335
```

```
Asp Arg Ile Gly Ser Leu Thr Pro His Asn Val Val Leu Val Pro Leu
            340                 345                 350

Gly Asp Asp Phe Arg Tyr Glu Tyr Ser Val Glu Phe Asp Ala Gln Tyr
        355                 360                 365

Val Asn Tyr Met Lys Met Phe Asn Tyr Ile Asn Ala His Lys Glu Ile
    370                 375                 380

Phe Asn Ala Asp Val Gln Phe Gly Thr Pro Leu Asp Tyr Phe Asn Ala
385                 390                 395                 400

Met Lys Glu Arg His Gln Asn Ile Pro Ser Leu Lys Gly Asp Phe Phe
                405                 410                 415

Val Tyr Ser Asp Ile Phe Ser Glu Gly Lys Pro Ala Tyr Trp Ser Gly
            420                 425                 430

Tyr Tyr Thr Thr Arg Pro Tyr Gln Lys Ile Leu Ala Arg Gln Phe Glu
        435                 440                 445

His Gln Leu Arg Ser Ala Glu Ile Leu Phe Thr Leu Val Ser Asn Tyr
    450                 455                 460

Ile Arg Gln Met Gly Arg Gln Gly Glu Phe Gly Ala Ser Glu Lys Lys
465                 470                 475                 480

Leu Glu Lys Ser Tyr Glu Gln Leu Ile Tyr Ala Arg Arg Asn Leu Gly
                485                 490                 495

Leu Phe Gln His His Asp Ala Ile Thr Gly Thr Ser Lys Ser Ser Val
            500                 505                 510

Met Gln Asp Tyr Gly Thr Lys Leu Phe Thr Ser Leu Tyr His Cys Ile
        515                 520                 525

Arg Leu Gln Glu Ala Ala Leu Thr Thr Ile Met Leu Pro Asp Gln Ser
    530                 535                 540

Leu His Ser Gln Ser Ile Ile Gln Ser Glu Val Glu Trp Glu Thr Tyr
545                 550                 555                 560

Gly Lys Pro Pro Lys Lys Leu Gln Val Ser Phe Ile Asp Lys Lys Lys
                565                 570                 575

Val Ile Leu Phe Asn Pro Leu Ala Glu Thr Arg Thr Glu Val Val Thr
            580                 585                 590

Val Arg Ser Asn Thr Ser Asn Ile Arg Val Tyr Asp Thr His Lys Arg
        595                 600                 605

Lys His Val Leu Tyr Gln Ile Met Pro Ser Ile Thr Ile Gln Asp Asn
    610                 615                 620

Gly Lys Ser Ile Val Ser Asp Thr Thr Phe Asp Ile Met Phe Val Ala
625                 630                 635                 640

Thr Ile Pro Pro Leu Thr Ser Ile Ser Tyr Lys Leu Gln Glu His Thr
                645                 650                 655

Asn Thr Ser His His Cys Val Ile Phe Cys Asn Asn Cys Glu Gln Tyr
            660                 665                 670

Gln Lys Ser Asn Val Phe Gln Ile Lys Lys Met Met Pro Gly Asp Ile
        675                 680                 685

Gln Leu Glu Asn Ala Val Leu Lys Leu Leu Val Asn Arg Asn Thr Gly
    690                 695                 700

Phe Leu Arg Gln Val Tyr Arg Lys Asp Ile Arg Lys Arg Thr Val Val
705                 710                 715                 720

Asp Val Gln Phe Gly Ala Tyr Gln Ser Ala Gln Arg His Ser Gly Ala
                725                 730                 735

Tyr Leu Phe Met Pro His Tyr Asp Ser Pro Glu Lys Asn Val Leu His
            740                 745                 750

Pro Tyr Thr Asn Gln Asn Asn Met Gln Asp Asp Asn Ile Ile Ile Val
        755                 760                 765
```

```
Ser Gly Pro Ile Ser Thr Glu Ile Thr Thr Met Tyr Leu Pro Phe Leu
    770                 775                 780

Val His Thr Ile Arg Ile Tyr Asn Val Pro Asp Pro Val Leu Ser Arg
785                 790                 795                 800

Ala Ile Leu Leu Glu Thr Asp Val Asp Phe Glu Ala Pro Pro Lys Asn
                805                 810                 815

Arg Glu Thr Glu Leu Phe Met Arg Leu Gln Thr Asp Ile Gln Asn Gly
            820                 825                 830

Asp Ile Pro Glu Phe Tyr Thr Asp Gln Asn Gly Phe Gln Tyr Gln Lys
        835                 840                 845

Arg Val Lys Val Asn Lys Leu Gly Ile Glu Ala Asn Tyr Tyr Pro Ile
    850                 855                 860

Thr Thr Met Ala Cys Leu Gln Asp Glu Glu Thr Arg Leu Thr Leu Leu
865                 870                 875                 880

Thr Asn His Ala Gln Gly Ala Ala Ala Tyr Glu Pro Gly Arg Leu Glu
                885                 890                 895

Val Met Leu Asp Arg Arg Thr Leu Tyr Asp Asp Phe Arg Gly Ile Gly
            900                 905                 910

Glu Gly Val Val Asp Asn Lys Pro Thr Thr Phe Gln Asn Trp Ile Leu
        915                 920                 925

Ile Glu Ser Met Pro Gly Val Thr Arg Ala Lys Arg Asp Thr Ser Glu
    930                 935                 940

Pro Gly Phe Lys Phe Val Asn Glu Arg Arg Phe Gly Pro Gly Gln Lys
945                 950                 955                 960

Glu Ser Pro Tyr Gln Val Pro Ser Gln Thr Ala Asp Tyr Leu Ser Arg
                965                 970                 975

Met Phe Asn Tyr Pro Val Asn Val Tyr Leu Val Asp Thr Ser Glu Val
            980                 985                 990

Gly Glu Ile Glu Val Lys Pro Tyr  Gln Ser Phe Leu Gln  Ser Phe Pro
        995                 1000                1005

Pro Gly  Ile His Leu Val Thr  Leu Arg Thr Ile Thr  Asp Asp Val
    1010                1015                1020

Leu Glu  Leu Phe Pro Ser Asn  Glu Ser Tyr Met Val  Leu His Arg
    1025                1030                1035

Pro Gly  Tyr Ser Cys Ala Val  Gly Glu Lys Pro Val  Ala Lys Ser
    1040                1045                1050

Pro Lys  Phe Ser Ser Lys Thr  Arg Phe Asn Gly Leu  Asn Ile Gln
    1055                1060                1065

Asn Ile  Thr Ala Val Ser Leu  Thr Gly Leu Lys Ser  Leu Arg Pro
    1070                1075                1080

Leu Thr  Gly Leu Ser Asp Ile  His Leu Asn Ala Met  Glu Val Lys
    1085                1090                1095

Thr Tyr  Lys Ile Arg Phe Lys  Asp Glu Leu
    1100                1105
```

```
<210> SEQ ID NO 51
<211> LENGTH: 1068
<212> TYPE: DNA
<213> ORGANISM: Artificial Sequence
<220> FEATURE:
<223> OTHER INFORMATION: hybrid gene with aminoterminal CTS region of a
      human beta 1,4 GalT gene replaced with a mouse signal peptide and
      a c-terminal ER retention signal (KDEL)

<400> SEQUENCE: 51

atgggcatca agatggagac acattctcag gtctttgtat acatgttgct gtggttgtct      60
```

```
ggtgtcgaca tgcagtcctc cggggagctc cggaccggag gggcccggcc gccgcctcct    120

ctaggcgcct cctcccagcc gcgcccgggt ggcgactcca gcccagtcgt ggattctggc    180

cctggccccg ctagcaactt gacctcggtc ccagtgcccc acaccaccgc actgtcgctg    240

cccgcctgcc ctgaggagtc cccgctgctt gtgggcccca tgctgattga gtttaacatg    300

cctgtggacc tggagctcgt ggcaaagcag aacccaaatg tgaagatggg cggccgctat    360

gcccccaggg actgcgtctc tcctcacaag gtggccatca tcattccatt ccgcaaccgg    420

caggagcacc tcaagtactg gctatattat ttgcacccag tcctgcagcg ccagcagctg    480

gactatggca tctatgttat caaccaggcg ggagacacta tattcaatcg tgctaagctc    540

ctcaatgttg gctttcaaga agccttgaag gactatgact acacctgctt tgtgtttagt    600

gacgtggacc tcattccaat gaatgaccat aatgcgtaca ggtgtttttc acagccacgg    660

cacatttccg ttgcaatgga taagtttgga ttcagcctac cttatgttca gtattttgga    720

ggtgtctctg ctctaagtaa acaacagttt ctaaccatca atggatttcc taataattat    780

tggggctggg gaggagaaga tgatgacatt tttaacagat tagtttttag aggcatgtct    840

atatctcgcc caaatgctgt ggtcgggagg tgtcgcatga tccgccactc aagagacaag    900

aaaaatgaac ccaatcctca gaggtttgac cgaattgcac acacaaagga gacaatgctc    960

tctgatggtt tgaactcact cacctaccag gtgctggatg tacagagata cccattgtat   1020

acccaaatca cagtggacat cgggacaccg agcaaggacg agctttag                1068
```

<210> SEQ ID NO 52
<211> LENGTH: 355
<212> TYPE: PRT
<213> ORGANISM: Artificial Sequence
<220> FEATURE:
<223> OTHER INFORMATION: hybrid protein with aminoterminal CTS region of a human beta 1,4 GalT gene replaced with a mouse signal peptide and a c-terminal ER retention signal (KDEL)

<400> SEQUENCE: 52

```
Met Gly Ile Lys Met Glu Thr His Ser Gln Val Phe Val Tyr Met Leu
1               5                   10                  15

Leu Trp Leu Ser Gly Val Asp Met Gln Ser Ser Gly Glu Leu Arg Thr
            20                  25                  30

Gly Gly Ala Arg Pro Pro Pro Pro Leu Gly Ala Ser Ser Gln Pro Arg
        35                  40                  45

Pro Gly Gly Asp Ser Ser Pro Val Val Asp Ser Gly Pro Gly Pro Ala
    50                  55                  60

Ser Asn Leu Thr Ser Val Pro Val Pro His Thr Thr Ala Leu Ser Leu
65                  70                  75                  80

Pro Ala Cys Pro Glu Glu Ser Pro Leu Leu Val Gly Pro Met Leu Ile
                85                  90                  95

Glu Phe Asn Met Pro Val Asp Leu Glu Leu Val Ala Lys Gln Asn Pro
            100                 105                 110

Asn Val Lys Met Gly Gly Arg Tyr Ala Pro Arg Asp Cys Val Ser Pro
        115                 120                 125

His Lys Val Ala Ile Ile Ile Pro Phe Arg Asn Arg Gln Glu His Leu
    130                 135                 140

Lys Tyr Trp Leu Tyr Tyr Leu His Pro Val Leu Gln Arg Gln Gln Leu
145                 150                 155                 160

Asp Tyr Gly Ile Tyr Val Ile Asn Gln Ala Gly Asp Thr Ile Phe Asn
                165                 170                 175
```

```
Arg Ala Lys Leu Leu Asn Val Gly Phe Gln Glu Ala Leu Lys Asp Tyr
            180                 185                 190

Asp Tyr Thr Cys Phe Val Phe Ser Asp Val Asp Leu Ile Pro Met Asn
        195                 200                 205

Asp His Asn Ala Tyr Arg Cys Phe Ser Gln Pro Arg His Ile Ser Val
    210                 215                 220

Ala Met Asp Lys Phe Gly Phe Ser Leu Pro Tyr Val Gln Tyr Phe Gly
225                 230                 235                 240

Gly Val Ser Ala Leu Ser Lys Gln Gln Phe Leu Thr Ile Asn Gly Phe
                245                 250                 255

Pro Asn Asn Tyr Trp Gly Trp Gly Gly Glu Asp Asp Asp Ile Phe Asn
            260                 265                 270

Arg Leu Val Phe Arg Gly Met Ser Ile Ser Arg Pro Asn Ala Val Val
        275                 280                 285

Gly Arg Cys Arg Met Ile Arg His Ser Arg Asp Lys Lys Asn Glu Pro
    290                 295                 300

Asn Pro Gln Arg Phe Asp Arg Ile Ala His Thr Lys Glu Thr Met Leu
305                 310                 315                 320

Ser Asp Gly Leu Asn Ser Leu Thr Tyr Gln Val Leu Asp Val Gln Arg
                325                 330                 335

Tyr Pro Leu Tyr Thr Gln Ile Thr Val Asp Ile Gly Thr Pro Ser Lys
            340                 345                 350

Asp Glu Leu
        355
```

<210> SEQ ID NO 53
<211> LENGTH: 1119
<212> TYPE: DNA
<213> ORGANISM: Artificial Sequence
<220> FEATURE:
<223> OTHER INFORMATION: hybrid gene with N-teminal CTS region of an Arabidopsis thaliana GnTI gene replaced with a mouse signal peptide and a C-terminal ER retention signal (KDEL)

<400> SEQUENCE: 53

```
atgggcatca agatggagac acattctcag gtctttgtat acatgttgct gtggttgtct     60

ggtgtcgaca tgggacagat gcctgtggct gctgtagtgg ttatggcctg cagtcgtgca    120

gactatcttg aaaggactgt taaatcagtt ttaacatatc aaactcccgt tgcttcaaaa    180

tatcctctat ttatatctca ggatggatct gatcaagctg tcaagagcaa gtcattgagc    240

tataatcaat taacatatat gcagcacttg gattttgaac cagtggtcac tgaaaggcct    300

ggcgaactga ctgcgtacta caagattgca cgtcactaca agtgggcact ggaccagttg    360

ttttacaaac acaaatttag tcgagtgatt atactagaag atgatatgga aattgctcca    420

gacttctttg attactttga ggctgcagct agtctcatgg atagggataa aaccattatg    480

gctgcttcat catggaatga taatggacag aagcagtttg tgcatgatcc ctatgcgcta    540

taccgatcag atttttttcc tggccttggg tggatgctca agagatcgac ttgggatgag    600

ttatcaccaa agtggccaaa ggcttactgg gatgattggc tgagactaaa ggaaaaccat    660

aaaggccgcc aattcattcg accggaagtc tgtagaacat acaattttgg tgaacatggg    720

tctagtttgg gacagttttt cagtcagtat ctggaaccta taaagctaaa cgatgtgacg    780

gttgactgga aagcaaagga cctgggatac ctgacagagg gaaactatac caagtacttt    840

tctggcttag tgagacaagc acgaccaatt caaggttctg accttgtctt aaaggctcaa    900

aacataaagg atgatgttcg tatccggtat aaagaccaag tagagtttga acgcattgca    960
```

```
gggaatttg gtatatttga agaatggaag gatggtgtgc ctcgaacagc atataaagga   1020

gtagtggtgt ttcgaatcca gacaacaaga cgtgtattcc tggttgggcc agattctgta   1080

atgcagcttg gaattcgaaa ttccaaggac gagctttga                           1119


<210> SEQ ID NO 54
<211> LENGTH: 372
<212> TYPE: PRT
<213> ORGANISM: Artificial Sequence
<220> FEATURE:
<223> OTHER INFORMATION: hybrid protein with N-teminal CTS region of an
      Arabidopsis thaliana GnTI gene replaced with a mouse signal
      peptide and a C-terminal ER retention signal (KDEL)

<400> SEQUENCE: 54

Met Gly Ile Lys Met Glu Thr His Ser Gln Val Phe Val Tyr Met Leu
1               5                   10                  15

Leu Trp Leu Ser Gly Val Asp Met Gly Gln Met Pro Val Ala Ala Val
            20                  25                  30

Val Val Met Ala Cys Ser Arg Ala Asp Tyr Leu Glu Arg Thr Val Lys
        35                  40                  45

Ser Val Leu Thr Tyr Gln Thr Pro Val Ala Ser Lys Tyr Pro Leu Phe
    50                  55                  60

Ile Ser Gln Asp Gly Ser Asp Gln Ala Val Lys Ser Lys Ser Leu Ser
65                  70                  75                  80

Tyr Asn Gln Leu Thr Tyr Met Gln His Leu Asp Phe Glu Pro Val Val
                85                  90                  95

Thr Glu Arg Pro Gly Glu Leu Thr Ala Tyr Tyr Lys Ile Ala Arg His
            100                 105                 110

Tyr Lys Trp Ala Leu Asp Gln Leu Phe Tyr Lys His Lys Phe Ser Arg
        115                 120                 125

Val Ile Ile Leu Glu Asp Asp Met Glu Ile Ala Pro Asp Phe Phe Asp
    130                 135                 140

Tyr Phe Glu Ala Ala Ala Ser Leu Met Asp Arg Asp Lys Thr Ile Met
145                 150                 155                 160

Ala Ala Ser Ser Trp Asn Asp Asn Gly Gln Lys Gln Phe Val His Asp
                165                 170                 175

Pro Tyr Ala Leu Tyr Arg Ser Asp Phe Phe Pro Gly Leu Gly Trp Met
            180                 185                 190

Leu Lys Arg Ser Thr Trp Asp Glu Leu Ser Pro Lys Trp Pro Lys Ala
        195                 200                 205

Tyr Trp Asp Asp Trp Leu Arg Leu Lys Glu Asn His Lys Gly Arg Gln
    210                 215                 220

Phe Ile Arg Pro Glu Val Cys Arg Thr Tyr Asn Phe Gly Glu His Gly
225                 230                 235                 240

Ser Ser Leu Gly Gln Phe Phe Ser Gln Tyr Leu Glu Pro Ile Lys Leu
                245                 250                 255

Asn Asp Val Thr Val Asp Trp Lys Ala Lys Asp Leu Gly Tyr Leu Thr
            260                 265                 270

Glu Gly Asn Tyr Thr Lys Tyr Phe Ser Gly Leu Val Arg Gln Ala Arg
        275                 280                 285

Pro Ile Gln Gly Ser Asp Leu Val Leu Lys Ala Gln Asn Ile Lys Asp
    290                 295                 300

Asp Val Arg Ile Arg Tyr Lys Asp Gln Val Glu Phe Glu Arg Ile Ala
305                 310                 315                 320

Gly Glu Phe Gly Ile Phe Glu Glu Trp Lys Asp Gly Val Pro Arg Thr
                325                 330                 335
```

```
Ala Tyr Lys Gly Val Val Val Phe Arg Ile Gln Thr Thr Arg Arg Val
            340                 345                 350

Phe Leu Val Gly Pro Asp Ser Val Met Gln Leu Gly Ile Arg Asn Ser
        355                 360                 365

Lys Asp Glu Leu
    370


<210> SEQ ID NO 55
<211> LENGTH: 1158
<212> TYPE: DNA
<213> ORGANISM: Artificial Sequence
<220> FEATURE:
<223> OTHER INFORMATION: hybrid gene with N-terminal CTS region of an
      Arabidopsis thaliana GnTII gene replaced with a mouse signal
      peptide and a C-terminal ER retention signal (KDEL)

<400> SEQUENCE: 55

atgggcatca agatggagac acattctcag gtctttgtat acatgttgct gtggttgtct      60

ggtgtcgaca tggctctaag gttgcataga aggaaccatt tttcgcctag aaatacggat     120

ctgttcccgg atttggcaaa agatcgtgtg gttatcgtct tgtatgtgca taatcgggct     180

cagtattttc gagtcacagt ggaaagtttg tcgaaggtta aaggtataag tgagacattg     240

ttgattgtta gtcatgatgg ttactttgaa gagatgaata ggattgtgga gagtattaag     300

ttttgtcaag tgaaacagat ttctcgcct tattcgcctc atatatatcg tactagcttc     360

ccgggtgtga ccctgaatga ttgtaagaac aagggtgatg aggcaaaggg gcattgtgaa     420

ggtaatcctg atcagtatgg gaatcatcgg tctccgaaga ttgtatcttt gaagcatcac     480

tggtggtgga tgatgaacac tgtatgggat gggttggaag agactaaagg acatgagggg     540

catatccttt tcattgaaga agatcatttt ctgtttccta atgcctatcg taacatacag     600

actcttacga ggctgaaacc cgcaaagtgt cctgactgtt ttgctgctaa tttagcaccg     660

tctgatgtga agtcaagagg agaagggctt gaaagtttgg ttgcagagag aatgggaaat     720

gttgggtatt cttttaatag aagtgtgtgg gagaatattc atcagaaggc aagagagttt     780

tgtttctttg atgattacaa ctgggatata acgatgtggg caacggtttt cccgtcgttt     840

ggttccccgg tgtacacatt gcgagggcct aggactagtg cggtacactt tggaaaatgt     900

gggttgcatc aaggtagagg agatgagggt gattgcatcg ataatggggt cgtaaacata     960

gaagttaagg aaacagataa agttgtgaac ataaaagaag gatggggagt tcgggtgtat    1020

aagcatcaag cgggttataa agccggtttc gaaggttggg gaggttgggg cgatgatagg    1080

gaccgacatt tatgtttgga ttttgccact atgtatcgtt acagcagtag cagtgcatct    1140

ccaaaggacg agctttga                                                  1158


<210> SEQ ID NO 56
<211> LENGTH: 385
<212> TYPE: PRT
<213> ORGANISM: Artificial Sequence
<220> FEATURE:
<223> OTHER INFORMATION: hybrid protein; N-terminal CTS region of an
      Arabidopsis thaliana GnTII gene replaced with a mouse signal
      peptide and a C-terminal ER retention signal (KDEL)

<400> SEQUENCE: 56

Met Gly Ile Lys Met Glu Thr His Ser Gln Val Phe Val Tyr Met Leu
1               5                   10                  15

Leu Trp Leu Ser Gly Val Asp Met Ala Leu Arg Leu His Arg Arg Asn
            20                  25                  30
```

```
His Phe Ser Pro Arg Asn Thr Asp Leu Phe Pro Asp Leu Ala Lys Asp
        35                  40                  45

Arg Val Val Ile Val Leu Tyr Val His Asn Arg Ala Gln Tyr Phe Arg
    50                  55                  60

Val Thr Val Glu Ser Leu Ser Lys Val Lys Gly Ile Ser Glu Thr Leu
65                  70                  75                  80

Leu Ile Val Ser His Asp Gly Tyr Phe Glu Glu Met Asn Arg Ile Val
                85                  90                  95

Glu Ser Ile Lys Phe Cys Gln Val Lys Gln Ile Phe Ser Pro Tyr Ser
            100                 105                 110

Pro His Ile Tyr Arg Thr Ser Phe Pro Gly Val Thr Leu Asn Asp Cys
        115                 120                 125

Lys Asn Lys Gly Asp Glu Ala Lys Gly His Cys Glu Gly Asn Pro Asp
    130                 135                 140

Gln Tyr Gly Asn His Arg Ser Pro Lys Ile Val Ser Leu Lys His His
145                 150                 155                 160

Trp Trp Trp Met Met Asn Thr Val Trp Asp Gly Leu Glu Glu Thr Lys
                165                 170                 175

Gly His Glu Gly His Ile Leu Phe Ile Glu Glu Asp His Phe Leu Phe
            180                 185                 190

Pro Asn Ala Tyr Arg Asn Ile Gln Thr Leu Thr Arg Leu Lys Pro Ala
        195                 200                 205

Lys Cys Pro Asp Cys Phe Ala Ala Asn Leu Ala Pro Ser Asp Val Lys
    210                 215                 220

Ser Arg Gly Glu Gly Leu Glu Ser Leu Val Ala Glu Arg Met Gly Asn
225                 230                 235                 240

Val Gly Tyr Ser Phe Asn Arg Ser Val Trp Glu Asn Ile His Gln Lys
                245                 250                 255

Ala Arg Glu Phe Cys Phe Phe Asp Asp Tyr Asn Trp Asp Ile Thr Met
            260                 265                 270

Trp Ala Thr Val Phe Pro Ser Phe Gly Ser Pro Val Tyr Thr Leu Arg
        275                 280                 285

Gly Pro Arg Thr Ser Ala Val His Phe Gly Lys Cys Gly Leu His Gln
    290                 295                 300

Gly Arg Gly Asp Glu Gly Asp Cys Ile Asp Asn Gly Val Val Asn Ile
305                 310                 315                 320

Glu Val Lys Glu Thr Asp Lys Val Val Asn Ile Lys Glu Gly Trp Gly
                325                 330                 335

Val Arg Val Tyr Lys His Gln Ala Gly Tyr Lys Ala Gly Phe Glu Gly
            340                 345                 350

Trp Gly Gly Trp Gly Asp Asp Arg Asp Arg His Leu Cys Leu Asp Phe
        355                 360                 365

Ala Thr Met Tyr Arg Tyr Ser Ser Ser Ser Ala Ser Pro Lys Asp Glu
    370                 375                 380

Leu
385


<210> SEQ ID NO 57
<211> LENGTH: 1152
<212> TYPE: DNA
<213> ORGANISM: Homo sapiens

<400> SEQUENCE: 57

atgctgaaga agcagtctgc agggcttgtg ctgtggggcg ctatcctctt tgtggcctgg      60

aatgccctgc tgctcctctt cttctggacg cgcccagcac ctggcaggcc accctcagtc     120
```

```
agcgctctcg atggcgaccc cgccagcctc acccgggaag tcgacatgca gtcctccggg    180

gagctccgga ccggaggggc ccggccgccg cctcctctag gcgcctcctc ccagccgcgc    240

ccgggtggcg actccagccc agtcgtggat tctggccctg gccccgctag caacttgacc    300

tcggtcccag tgccccacac caccgcactg tcgctgcccg cctgccctga ggagtccccg    360

ctgcttgtgg gccccatgct gattgagttt aacatgcctg tggacctgga gctcgtggca    420

aagcagaacc caaatgtgaa gatgggcggc cgctatgccc ccagggactg cgtctctcct    480

cacaaggtgg ccatcatcat tccattccgc aaccggcagg agcacctcaa gtactggcta    540

tattatttgc acccagtcct gcagcgccag cagctggact atggcatcta tgttatcaac    600

caggcgggag acactatatt caatcgtgct aagctcctca atgttggctt tcaagaagcc    660

ttgaaggact atgactacac ctgctttgtg tttagtgacg tggacctcat tccaatgaat    720

gaccataatg cgtacaggtg tttttcacag ccacggcaca tttccgttgc aatggataag    780

tttggattca gcctacctta tgttcagtat tttggaggtg tctctgctct aagtaaacaa    840

cagtttctaa ccatcaatgg atttcctaat aattattggg gctggggagg agaagatgat    900

gacattttta acagattagt ttttagaggc atgtctatat ctcgcccaaa tgctgtggtc    960

gggaggtgtc gcatgatccg ccactcaaga gacaagaaaa atgaacccaa tcctcagagg   1020

tttgaccgaa ttgcacacac aaaggagaca atgctctctg atggtttgaa ctcactcacc   1080

taccaggtgc tggatgtaca gagataccca ttgtataccc aaatcacagt ggacatcggg   1140

acaccgagct ag                                                       1152
```

<210> SEQ ID NO 58
<211> LENGTH: 383
<212> TYPE: PRT
<213> ORGANISM: Homo sapiens

<400> SEQUENCE: 58

```
Met Leu Lys Lys Gln Ser Ala Gly Leu Val Leu Trp Gly Ala Ile Leu
1               5                   10                  15

Phe Val Ala Trp Asn Ala Leu Leu Leu Leu Phe Phe Trp Thr Arg Pro
            20                  25                  30

Ala Pro Gly Arg Pro Pro Ser Val Ser Ala Leu Asp Gly Asp Pro Ala
        35                  40                  45

Ser Leu Thr Arg Glu Val Asp Met Gln Ser Ser Gly Glu Leu Arg Thr
    50                  55                  60

Gly Gly Ala Arg Pro Pro Pro Pro Leu Gly Ala Ser Ser Gln Pro Arg
65                  70                  75                  80

Pro Gly Gly Asp Ser Ser Pro Val Val Asp Ser Gly Pro Gly Pro Ala
                85                  90                  95

Ser Asn Leu Thr Ser Val Pro Val Pro His Thr Thr Ala Leu Ser Leu
            100                 105                 110

Pro Ala Cys Pro Glu Glu Ser Pro Leu Leu Val Gly Pro Met Leu Ile
        115                 120                 125

Glu Phe Asn Met Pro Val Asp Leu Glu Leu Val Ala Lys Gln Asn Pro
    130                 135                 140

Asn Val Lys Met Gly Gly Arg Tyr Ala Pro Arg Asp Cys Val Ser Pro
145                 150                 155                 160

His Lys Val Ala Ile Ile Ile Pro Phe Arg Asn Arg Gln Glu His Leu
                165                 170                 175

Lys Tyr Trp Leu Tyr Tyr Leu His Pro Val Leu Gln Arg Gln Gln Leu
            180                 185                 190
```

```
Asp Tyr Gly Ile Tyr Val Ile Asn Gln Ala Gly Asp Thr Ile Phe Asn
        195                 200                 205

Arg Ala Lys Leu Leu Asn Val Gly Phe Gln Glu Ala Leu Lys Asp Tyr
    210                 215                 220

Asp Tyr Thr Cys Phe Val Phe Ser Asp Val Asp Leu Ile Pro Met Asn
225                 230                 235                 240

Asp His Asn Ala Tyr Arg Cys Phe Ser Gln Pro Arg His Ile Ser Val
                245                 250                 255

Ala Met Asp Lys Phe Gly Phe Ser Leu Pro Tyr Val Gln Tyr Phe Gly
            260                 265                 270

Gly Val Ser Ala Leu Ser Lys Gln Gln Phe Leu Thr Ile Asn Gly Phe
        275                 280                 285

Pro Asn Asn Tyr Trp Gly Trp Gly Gly Glu Asp Asp Asp Ile Phe Asn
    290                 295                 300

Arg Leu Val Phe Arg Gly Met Ser Ile Ser Arg Pro Asn Ala Val Val
305                 310                 315                 320

Gly Arg Cys Arg Met Ile Arg His Ser Arg Asp Lys Lys Asn Glu Pro
                325                 330                 335

Asn Pro Gln Arg Phe Asp Arg Ile Ala His Thr Lys Glu Thr Met Leu
            340                 345                 350

Ser Asp Gly Leu Asn Ser Leu Thr Tyr Gln Val Leu Asp Val Gln Arg
        355                 360                 365

Tyr Pro Leu Tyr Thr Gln Ile Thr Val Asp Ile Gly Thr Pro Ser
    370                 375                 380


<210> SEQ ID NO 59
<211> LENGTH: 400
<212> TYPE: PRT
<213> ORGANISM: Homo sapiens

<400> SEQUENCE: 59

Met Arg Leu Arg Glu Pro Leu Leu Ser Gly Ala Ala Met Pro Gly Ala
1               5                   10                  15

Ser Leu Gln Arg Ala Cys Arg Leu Leu Val Ala Val Cys Ala Leu His
            20                  25                  30

Leu Gly Val Thr Leu Val Tyr Tyr Leu Ala Gly Arg Asp Leu Ser Arg
        35                  40                  45

Leu Pro Gln Leu Val Gly Val Ser Thr Pro Leu Gln Gly Gly Ser Asn
    50                  55                  60

Ser Ala Ala Ala Ile Gly Gln Ser Ser Gly Glu Leu Arg Thr Gly Gly
65                  70                  75                  80

Ala Arg Pro Pro Pro Pro Leu Gly Ala Ser Ser Gln Pro Arg Pro Gly
                85                  90                  95

Gly Asp Ser Ser Pro Val Val Asp Ser Gly Pro Gly Pro Ala Ser Asn
            100                 105                 110

Leu Thr Ser Val Pro Val Pro His Thr Thr Ala Leu Ser Leu Pro Ala
        115                 120                 125

Cys Pro Glu Glu Ser Pro Leu Leu Val Gly Pro Met Leu Ile Glu Phe
    130                 135                 140

Asn Met Pro Val Asp Leu Glu Leu Val Ala Lys Gln Asn Pro Asn Val
145                 150                 155                 160

Lys Met Gly Gly Arg Tyr Ala Pro Arg Asp Cys Val Ser Pro His Lys
                165                 170                 175

Val Ala Ile Ile Ile Pro Phe Arg Asn Arg Gln Glu His Leu Lys Tyr
            180                 185                 190
```

```
Trp Leu Tyr Tyr Leu His Pro Val Leu Gln Arg Gln Gln Leu Asp Tyr
        195                 200                 205

Gly Ile Tyr Gly Ile Tyr Val Ile Asn Gln Ala Gly Asp Thr Ile Phe
    210                 215                 220

Asn Arg Ala Lys Leu Leu Asn Val Gly Phe Gln Glu Ala Leu Lys Asp
225                 230                 235                 240

Tyr Asp Tyr Thr Cys Phe Val Phe Ser Asp Val Asp Leu Ile Pro Met
                245                 250                 255

Asn Asp His Asn Ala Tyr Arg Cys Phe Ser Gln Pro Arg His Ile Ser
            260                 265                 270

Val Ala Met Asp Lys Phe Gly Phe Ser Leu Pro Tyr Val Gln Tyr Phe
        275                 280                 285

Gly Gly Val Ser Ala Leu Ser Lys Gln Gln Phe Leu Thr Ile Asn Gly
    290                 295                 300

Phe Pro Asn Asn Tyr Trp Gly Trp Gly Gly Glu Asp Asp Asp Ile Phe
305                 310                 315                 320

Asn Arg Leu Val Phe Arg Gly Met Ser Ile Ser Arg Pro Asn Ala Val
                325                 330                 335

Val Gly Arg Cys Arg Met Ile Arg His Ser Arg Asp Lys Lys Asn Glu
            340                 345                 350

Pro Asn Pro Gln Arg Phe Asp Arg Ile Ala His Thr Lys Glu Thr Met
        355                 360                 365

Leu Ser Asp Gly Leu Asn Ser Leu Thr Tyr Gln Val Leu Asp Val Gln
    370                 375                 380

Arg Tyr Pro Leu Tyr Thr Gln Ile Thr Val Asp Ile Gly Thr Pro Ser
385                 390                 395                 400
```